US012462919B1

(12) United States Patent
Gunduz et al.

(10) Patent No.: US 12,462,919 B1
(45) Date of Patent: Nov. 4, 2025

(54) CHILD EVALUATION SYSTEM AND METHOD OF USE

(71) Applicants: Susan O. Gunduz, Northport, NY (US); Stephanie Anne Denton, Birmingham, AL (US)

(72) Inventors: Susan O. Gunduz, Northport, NY (US); Stephanie Anne Denton, Birmingham, AL (US)

(73) Assignees: Susan O. Gunduz, Northport, NY (US); Stephanie Anne Denton, NY Birmingham (AL)

(*) Notice: Subject to any disclaimer, the term of this patent is extended or adjusted under 35 U.S.C. 154(b) by 0 days.

(21) Appl. No.: 18/768,976

(22) Filed: Jul. 10, 2024

(51) Int. Cl.

| | |
|---|---|
| ***G16H 20/70*** | (2018.01) |
| ***A61B 5/00*** | (2006.01) |
| ***A61B 5/11*** | (2006.01) |
| ***A61B 5/12*** | (2006.01) |

(52) U.S. Cl.
CPC ........... *G16H 20/70* (2018.01); *A61B 5/1124* (2013.01); *A61B 5/123* (2013.01); *A61B 5/4803* (2013.01)

(58) Field of Classification Search
CPC . G16H 20/70; G09B 3/00; G09B 7/00; A61B 5/1124; A61B 5/123; A61B 5/4803; A61B 5/165; A61B 5/168; A61B 5/1125; A61B 2503/06
See application file for complete search history.

(56) References Cited

U.S. PATENT DOCUMENTS

2021/0133509 A1* 5/2021 Wall ...................... G06F 18/285
2021/0290468 A1* 9/2021 Wortman-Jutt ......... G06F 3/011
2022/0309945 A1* 9/2022 Duffy .................. G06F 3/04883

* cited by examiner

*Primary Examiner* — Devin B Henson
(74) *Attorney, Agent, or Firm* — Sorell, Lenna & Schmidt, LLP

(57) ABSTRACT

Systems and methods for the diagnosis and treatment of developmental delay and/or disorders in children for the purpose of early diagnosis and treatment of children to promote the development of at least one of fine motor skills, gross motor skills, sound articulation and sound discrimination skills, receptive language, expressive language, phonological awareness, phonological processing to prevent reading failure, academic underachievement, color blindness, attention issues and social emotional dysregulation. The systems and methods resulting in the generation of a referral of the individual for services in areas where the evaluation results were deficient to promote at least one of fine motor skills, gross motor skills, sound articulation, and sound discrimination skills.

10 Claims, 220 Drawing Sheets

SoundWise Dx™
Pediatric Neurodevelopmental Assessment
Developed by Pediatricians

Parental Questionnaire
3 Year Old: Form A or B

Child:________________________________DOB________________

Parent Part - Completed by: ____________________________________________

1. Do you have concerns about your child's vision? ☐ Yes ☐ No ☐ Sometimes
2. Do you have concerns about your child's hearing? ☐ Yes ☐ No ☐ Sometimes
3. Did your child ever need ear tubes? ☐ Yes ☐ No 4. Do strangers understand most of what your child says? ☐ Yes ☐ No ☐ Sometimes
5. Can your child name 1-2 colors and name simple objects? ☐ Yes ☐ No ☐ Sometimes
6. Does your child speak in 3-5 word sentences? ☐ Yes ☐ No ☐ Sometimes
7. Can your child learn simple songs and nursery rhymes? ☐ Yes ☐ No ☐ Sometimes
8. Can your child follow 2-3 simple step commands at a time? ☐ Yes ☐ No ☐ Sometimes
9. Is your child in preschool? ☐ Yes ☐ No 10. Does your child ask "who", "what", "where" and "why" Questions? ☐ Yes ☐ No ☐ Sometimes
11. Does your child know their name and age? ☐ Yes ☐ No ☐ Sometimes
12. Does your child play with other children? ☐ Yes ☐ No ☐ Sometimes
13. Does your child express when they are happy or sad? ☐ Yes ☐ No ☐ Sometimes
14. Can your child use a spoon and fork? ☐ Yes ☐ No ☐ Sometimes
15. Can your child pedal a riding toy? ☐ Yes ☐ No ☐ Sometimes
16. Can your child walk up and down stairs unassisted? ☐ Yes ☐ No ☐ Sometimes Copyright © 2024 All Rights Reserved

SoundWise Dx™
Pediatric Neurodevelopmental Assessment
Developed by Pediatricians Parental Questionnaire
3 Year Old: Form A or B

Child:____________________________________DOB____________________

Parent Part - Completed by: ____________________________________________

| | | | |
|---|---|---|---|
| 1. Do you have concerns about your child's vision? | □ Yes | □ No | □ Sometimes |
| 2. Do you have concerns about your child's hearing? | □ Yes | □ No | □ Sometimes |
| 3. Did your child ever need ear tubes? | □ Yes | □ No | |
| 4. Do strangers understand most of what your child says? | □ Yes | □ No | □ Sometimes |
| 5. Can your child name 1-2 colors and name simple objects? | □ Yes | □ No | □ Sometimes |
| 6. Does your child speak in 3-5 word sentences? | □ Yes | □ No | □ Sometimes |
| 7. Can your child learn simple songs and nursery rhymes? | □ Yes | □ No | □ Sometimes |
| 8. Can your child follow 2-3 simple step commands at a time? | □ Yes | □ No | □ Sometimes |
| 9. Is your child in preschool? | □ Yes | □ No | |
| 10. Does your child ask "who", "what", "where" and "why" Questions? | □ Yes | □ No | □ Sometimes |
| 11. Does your child know their name and age? | □ Yes | □ No | □ Sometimes |
| 12. Does your child play with other children? | □ Yes | □ No | □ Sometimes |
| 13. Does your child express when they are happy or sad? | □ Yes | □ No | □ Sometimes |
| 14. Can your child use a spoon and fork? | □ Yes | □ No | □ Sometimes |
| 15. Can your child pedal a riding toy? | □ Yes | □ No | □ Sometimes |
| 16. Can your child walk up and down stairs unassisted? | □ Yes | □ No | □ Sometimes |

Fig. 1

Copyright © 2024 All Rights Reserved

SoundWise Dx™
Pediatric Neurodevelopmental Assessment
Developed by Pediatricians 3 year old: Form A or B Name: ______________________ DOB: ____________ Date: ____________

| | |
|---|---|
| | *Draw the shape*  |
| | |

Copyright © 2024 All Rights Reserved

SoundWise Dx™
Pediatric Neurodevelopmental Assessment
Developed by Pediatricians 3 Year Form A

3 year old: Form A

Name: ______________________ □ M □ F DOB:____________ Date:________________

*Administer in a quiet one-on-one setting with limited distractions.*

For Fine Motor skill have the child do the following the following:
1. Draw a straight line. □ Yes □ No *(You may show them how to draw the straight line and circle first)*
   - Correct Pencil Grip: □ Yes □ No
2. Draw a circle. □ Yes □ No
   - Correct Pencil Grip: □ Yes □ No

For Gross Motor Planning and Receptive Language.
3. Can you smile real big? □ Yes □ No
4. Touch your finger to your nose? □ Yes □ No *(Do not show them how, verbal commands only)*
5. Now touch your other finger to your nose. □ Yes □ No
6. Now touch one finger to another finger.. □ Yes □ No

Sound Articulation
*(when written like this /d/, it means the "d" sound not the letter "d")*

Can you say /d/ as in "dog" □ Yes □ No Can you say the sound /m/ □ Yes □ No Can you say /w/ as in "win" □ Yes □ No Can you say sound /t/ □ Yes □ No Can you say /ng/ as in "sing" □ Yes □ No Can you say the sound /h/ □ Yes □ No Can you say /b/ as in "bat" □ Yes □ No Can you say the sound /ee/ □ Yes □ No

Sound discrimination
*Do these sound the same or different?*

| | | | |
|---|---|---|---|
| /m/ /m/ /m/ | □ same | □ different | (same) |
| /b/ /b/ /d/ | □ same | □ different | (different) |
| /f/ /h/ /f/ | □ same | □ different | (different) |
| /p/ /p/ /p/ | □ same | □ different | (same) |
| /o/ /o/ /o/ | □ same | □ different | (same) |
| /i/ /i/ /o/ | □ same | □ different | (different) |
| /k/ /d/ /k/ | □ same | □ different | (different) |
| /g/ /g/ /g/ | □ same | □ different | (same) |

Engagement: Please note the the child's demeanor during testing:

□ Cooperative □ Smiling □ Shy □ Happy and engaged
□ Uncooperative □ Crying □ Distractible □ English Language Learner
□ Refusal to Interact □ Tired □ Anxious □ Difficult to motivate
□ Completed Independently □ Needed Redirection for completion
□ poor eye contact □ wouldn't engage □ Child's speech wasn't understandable
□ Other____________________________________________

Fig. 3

Copyright © 2024 All Rights Reserved

SoundWise Dx™
Pediatric Neurodevelopmental Assessment
Developed by Pediatricians Form B

3 year old: Form B

Name: ______________________ □ M □ F DOB:____________ Date:________________

*Administer in a quiet one-on-one setting with limited distractions.*

For Fine Motor skill have the child do the following the following:

1. Draw a straight line. □ Yes □ No *(You may show them how to draw the straight line and circle first)*
   - Correct Pencil Grip: □ Yes □ No
2. Draw a circle. □ Yes □ No
   - Correct Pencil Grip: □ Yes □ No

For Gross Motor Planning and Receptive Language.

3. Can you smile real big? □ Yes □ No
4. Touch your finger to your nose? □ Yes □ No *(Do not show them how, verbal commands only)*
5. Now touch your other finger to your nose. □ Yes □ No
6. Now touch both hands on top of your head. □ Yes □ No

Sound Articulation *(when written like this /d/, it means the "d" sound not the letter "d")*

| | | | | | |
|---|---|---|---|---|---|
| Can you say /l/ as in "log" | □ Yes | □ No | Can you say the sound /b/ | □ Yes | □ No |
| Can you say /f/ as in "fun" | □ Yes | □ No | Can you say the sound /t/ as | □ Yes | □ No |
| Can you say /p/ as in "pop" | □ Yes | □ No | Can you say the sound /m/ | □ Yes | □ No |
| Can you say /c/ as in "cat" | □ Yes | □ No | Can you say the sound /h/ | □ Yes | □ No |

Sound discrimination
Do these sound the same or different?

| | | | |
|---|---|---|---|
| /n/ /n/ /n/ | □ same | □ different | (same) |
| /b/ /d/ /d/ | □ same | □ different | (different) |
| /t/ /t/ /v/ | □ same | □ different | (different) |
| /a/ /a/ /a/ | □ same | □ different | (same) |
| /k/ /k/ /p/ | □ same | □ different | (different) |
| /h/ /h/ /h/ | □ same | □ different | (same) |
| /p/ /p/ /p/ | □ same | □ different | (same) |
| /e/ /e/ /o/ | □ same | □ different | (different) |

Behavioral Observations: Please note the the child's demeanor during testing:

□ Cooperative □ Smiling □ Shy □ Happy and engaged
□ Uncooperative □ Crying □ Distractible □ English Language Learner
□ Refusal to Interact □ Tired □ Anxious □ Difficult to motivate
□ Completed Independently □ Needed Redirection for completion
□ poor eye contact □ wouldn't engage □ Child's speech wasn't understandable □ Other______________________________________________

Fig. 4

Copyright © 2024 All Rights Reserved

SoundWise Dx™
Pediatric Neurodevelopmental Assessment
Developed by Pediatricians 3 Year Form A

Scoring Yearly vision screening is medically indicated and hearing if necessary

Fine Motor Skills: If unable to do numbers 1-2 or
- If fisted pencil grip( nl age 3,) Have parent practice 3 point grip of pencil
- Give OT Referral if has difficulty performing drawing circle and/or straight line

Gross Motor Planning: Unable to do any of numbers 3-6, Do at home exercises with directions
- PT/OT referral if significant Fine motor/Gross motor concerns during assessment

Receptive Language Skills: If difficulty understanding language or following directions for #3-6
- Refer for speech therapy working with receptive language mainly/expressive language as well
- If the primary language spoken is not English, need extra exposure to English therefore order Speech therapy for Receptive language Language exposure

Sound Articulation Skills:
- If no misses - strong skills, no extra emphasis on these skills needed
- If miss 1-3, give have parent develop these skills further
- If miss 4 or more (50% or greater), work on these skills and MUST start speech therapy for articulation/receptive/expressive speech

Sound Discrimination Skills: 4 or more sound discrimination questions wrong (50% or more)
- If no misses - strong skills, no extra emphasis on these skills needed
- If miss 1-3, give help parent develop these skills further and/or speech therapy
- If miss 4 or more (50% or greater), work on these skills and MUST start speech therapy for articulation/receptive/expressive speech

Parent questionnaire:If any yes to items 1-3 refer, If any No to items 4-16 decide intervention.

Engagement: If any concerns for Autism like lack of wanting to engage, poor eye contact/lack of joint attention, and sensory dysregulation MUST refer for Speech, OT, PT and a referral for Autism evaluation

Attention symptoms can be appreciated at age 4 and above for consideration of ADHD/ADD diagnosis. Attention deficit may be due to speech/language impairment and fine motor delay. When children are unable to focus, easily distracted, unable to sustain Attention for 6-8 minutes, consider re-evaluation in 1 to 2 months after receiving speech/language/OT services. Children who are inattentive and also exhibit staring spells, need to be evaluated for Absence seizures. SoundWise DX will offer RX or pediatrician/provider for neurology referral.

If there are any concerns about Anxiety, frustration with performance, thinking that they can not do well, crying, saying that they always fail every test,etc. Consider doing SCARED, and Columbia Screen or other screens for anxiety/depression.

Fig. 5A

Copyright © 2024 All Rights Reserved

SoundWise Dx™
Pediatric Neurodevelopmental Assessment
Developed by Pediatricians 3 Year Form A

Concerns present:
- ☐ None - Perfect Score
- ☐ Engagement Concerns (Based of evaluator's behavioral Observations)
- ☐ Fine Motor Concerns (#'s 1-2)
- ☐ Gross Motor Planning (#'s 3-6 or directions in general)
- ☐ Receptive Language Concerns
- ☐ Sound Articulation Concerns
- ☐ Sound Discrimination Concerns

Discuss parental Questionnaire and decide what intervention is necessary and list here:

Interventional Response:

- ☐ General 3 Year Old Milestone Information Sheet
  - Provides general understanding of what a 3 year should be able to do
- ☐ Specific Information Sheet for Opportunity and Development of Individual Skills
  - Based upon Neurodevelopmental Foundational Model and Treatment Approach
  - Includes Recommended Suggestions for opportunities and activities to grow
  - Expand Opportunities and Suggestions available through SoundWise DX platform and other recommended Sites.
  - Increased Academic Focused Instruction on Broad areas of Concern including Engagement, Fine Motor, Gross Motor Planning, Receptive Language, Sound Articulation & Discrimination
  - Parental questionnaire referral:

Follow up if concerns present: ☐ 3-6 months later ☐ Yearly at the next well child Visit

Fig 5B

Copyright © 2024 All Rights Reserved

SoundWise Dx™
Pediatric Neurodevelopmental Assessment
Developed by Pediatricians Form B

Scoring Yearly vision screening is medically indicated and hearing if necessary

Parent questionnaire:If any yes to items1-3,refer, If any no to items 4-16 decide intervention
Fine Motor Skills: Unable to do numbers 1-2
- If fisted pencil grip nl age 3, however must teach correct grip
- OT Referral if has difficulty with fine motor skills/pencil grip

Gross Motor Planning: Unable to do any of numbers 3-6, At home do like exercises
- PT/OT referral if significant Fine motor/Gross motor concerns

Receptive Language Skills: If difficulty understanding language or following directions: #3-6
- Refer for speech therapy working with receptive language/expressive language
- If the primary language spoken in the home is not English, more exposure to English and order Speech therapy for Receptive/language Language

Sound Articulation Skills:
- If no misses - strong skills, no extra emphasis on these skills needed
- If miss 1-3, give opportunities to develop these skills further with caretaker/teacher and/or with speech therapy
- If miss 4 or more (50% or greater), work on the skills and MUST start speech therapy for articulation/receptive/expressive speech

Sound Discrimination Skills: 4 or more sound discrimination questions wrong (50% or more)
- If no misses - strong skills, no extra emphasis on these skills needed
- If miss 1-3, give opportunities to develop these skills further and/or speech therapy
- If miss 4 or more (50% or greater), work on the skills needed and MUST start speech therapy for articulation/receptive/expressive speech

Parent questionnaire:If any yes to items 1-3 refer, If any No to items 4-16 decide intervention.

Engagement:

If any concerns for Autism like lack of wanting to engage, poor eye contact/lack of joint attention, and sensory dysregulation MUST refer for Speech, OT, PT and a referral for Autism evaluation

Attention symptoms can be appreciated at age 4 and above for consideration of ADHD/ADD diagnosis. Attention deficit may be due to speech/language impairment and fine motor delay. When children are unable to focus, easily distracted, unable to sustain Attention for 6-8 minutes, consider re-evaluation in 1 to 2 months after receiving speech/language/OT services. Children who are inattentive and also exhibit staring spells, need to be evaluated for Absence seizures. SoundWise DX will offer RX or pediatrician/provider for neurology referral.

If there are any concerns about Anxiety, frustration with performance, thinking that they can not do well, crying, saying that they always fail every test,etc. Consider doing SCARED, and Columbia Screen or other screens for anxiety/depression.

Fig. 6A

Copyright © 2024 All Rights Reserved

SoundWise Dx™
Pediatric Neurodevelopmental Assessment
Developed by Pediatricians Form B

Concerns present: □ None - Perfect Score

□ Engagement Concerns (Based of evaluator's behavioral Observations)
□ Fine Motor Concerns (#'s 1-2)
□ Gross Motor Planning (#'s 3-6 or directions in general)
□ Receptive Language Concerns
□ Sound Articulation Concerns
□ Sound Discrimination Concerns

Discuss parental Questionnaire and decide what intervention is necessary and list here:

Interventional Response:

□ General 3 Year Old Milestone Information Sheet
- Provides general understanding of what a 3 year should be able to do □ Specific Information Sheet for Opportunity and Development of Individual Skills
- Based upon Neurodevelopmental Foundational Model and Treatment Approach
- Includes Recommended Suggestions for opportunities and activities to grow
- Expand Opportunities and Suggestions available through SoundWise DX platform and other recommended Sites.
- Increased Academic Focused Instruction on Broad areas of Concern including Engagement, Fine Motor, Gross Motor Planning, Receptive Language, Sound Articulation & Discrimination
- Parental Questionnaire referral:

Follow up if concerns present: □ 3-6 months later □ Yearly at the next well child Visit

Fig. 6B

Copyright © 2024 All Rights Reserved

SoundWise Dx™
Pediatric Neurodevelopmental Assessment
Developed by Pediatricians

3 Year Old Developmental Milestone Information Sheet 3 year olds are excited to communicate their interests, are curious to explore the world, and have great imaginations! They ask a lot of questions. The WHO, the WHAT, the Why! This opens up a new world of social interaction and exploration for them. They are proud to show off their independence by dressing themselves, negotiating their nap time, deciding what they want to eat, and even what they want to wear. They are very interactive, always wanting to show what they know. Most are potty trained during the day.

Learning is through exploration, trial and error. By allowing them to make simple choices on their own, this allows them to learn and build new skills. They want to demonstrate self-care skills they have learned. They are learning to identify the world around them, can identify their gender, and know the use of common objects such as crayon, fork, ball etc. They are able to identify most colors and are excited to engage in interactive imaginative play with others Understanding how your child plays, learns, speaks, acts, and moves offer important clues about his or her development.

SoundWise DX allows each child the opportunity to do the age appropriate skills very important for their future.

What a typical 3 year old should be able to do.

| Language Communication Milestones | Social Emotional Milestones |
|---|---|
| • Asks "who", "what", "where", and "why" questions<br>• Have a conversation with at least 2 back and forth exchanges<br>• Is able to say what actions are happening in a book like "eating", "running", or "sleeping"<br>• When asked, will say their first name<br>• Talks well enough for others to understand, most of the time<br>• Speaks in conversation with 2 or 3 sentences spoken together<br>• Sentences are typical 4-5 words.<br>• Say around 450 words.<br>• Use plurals and pronouns | • Settles down within 10 minutes after you leave, like at a school drop off<br>• Notices and interacts with other children<br>• Plays with other children |

Fig 7A

Copyright © 2024 All Rights Reserved

SoundWise Dx™
Pediatric Neurodevelopmental Assessment
Developed by Pediatricians

| | |
|---|---|
| • Name simple things like a friend, a pet, or objects | |
| | |
| Cognitive Milestones (Learning, Thinking, Problem-Solving)<br>• Draws a circle if you show them how<br>• Follows simple 2 step commands<br>• Understand Opposites | Gross Motor Movement/Physical Milestones<br>• Ride a tricycle<br>• Throw a ball overhead<br>• Walk up stairs alternating feet<br>• Build a tower of cubes<br>• Balance on one foot for one second |
| | |
| Fine Motor Milestones<br>• Can string items together like beads<br>• Puts on clothes by his or herself, like loose pants or a jacket<br>• Use a fork/spoon<br>• Brush their teeth<br>• Able to draw a person with two body parts | |
| Should be toilet trained during the day! | |

How to help your child build stronger skills.

Developing healthy communication skills such as learning to speak, understanding language, and eventually learning to read are key milestones that your child needs to reach so that they enjoy and engage in play, and become successful in school.

Babies learn language through simple exposure by listening and watching you speak to them. They quickly learn how sounds are put together in different ways and can have different meanings. This exposure to sounds is building two major language skills:

1. Receptive language (input) - what you understand.
2. Expressive language (output) - what you can say.

Fig 7B

Copyright © 2024 All Rights Reserved

SoundWise Dx™
Pediatric Neurodevelopmental Assessment
Developed by Pediatricians A child's exposure to language starts in utero. As babies, they then start to babble and observe how we speak by looking at our faces and how we move our mouth, lips, and tongue to make sounds. They quickly understand that sounds have meaning and they start to acquire language at an amazing pace. When they are 5 years old, they will present to kindergarten to learn higher level language skills, like reading, writing, spelling, and math. The strength of your child's early language foundation will directly relate to their future academic success. Help them build a strong foundation for later scholastic and emotional success.

There are lots of simple things you can do that are fun and help build language skills;

- Sings songs
- Read to your child
  - Let them also point out pictures and name things on the page
  - Let them turn the pages of the book. Books with texture or are interactive in some way liking make sounds are fun
  - Let them understand that the words or symbols on the page mean something
  - Ask questions about the things you read about
  - Let them use their own imagination and create their own stories too
- Work on identifying objects within their world and building language vocabulary
- Play games with sounds:
  - Like identifying how sounds are different or the same
  - Play rhyming games
  - Play repetition games with sounds
  - Identifying placement of sounds in words
    - "What's the 1st sound, what's the middle sound, what's the last sound in a word?
  - No need to associate the letters with the sounds at first. Just have fun with figuring out how to make different sounds. Look in a mirror. Watch how your mouth moves differently when you make different sounds.
  - Pick a sound a week. Play games where you point to or think of things that start with that same sound.
  - Only after your child really understands the sound will you add the letter. The sounds are actually more important than the letter at this age.
- Talk to your child.
  - TV's and screens are not good substitutes. Limit screen time to 2 hours per day and do not put TV or computer devices in the bedroom
  - Talk about what you are doing as you are doing it
  - Repeat key concepts. For example: I'm putting toothpaste on your toothbrush. Toothpaste ON the toothbrush.
- Tell children what you are doing and why. Talk, Talk, talk!

Fig 7C

Copyright © 2024 All Rights Reserved

SoundWise Dx™
Pediatric Neurodevelopmental Assessment
Developed by Pediatricians

- Teach and show at the same time
  - For instance, point to red flower as you are talking about the red flower
  - Flip the light switch as you say on and off
  - Have fun as learning can be one great adventure and game
  - Children love to move, incorporate movement into exploration of their world
- Let your child draw with a pencil or crayon. Sometimes larger ones are easier for them to hold. Show them how you properly hold a pencil.
- Let children see your face as you are speaking
  - They need to know how the mouth moves to make different sounds
- Let your child tell the story in their own words. Their imaginations are entertaining!
- Ask your child questions as you tell a story. See if they are making a mental movie or picture while listening to the books or stories that you read to them.
- Let your child explore and use their imaginations.
- Teach language concepts with games.
  - Play hide & seek or find
  - Play with objects and place them around the room. Then give the child directions to follow with spatial concepts to find the items. For example: Find the toy under the chair. Find the toy beside the chair.
  - Focus on one or two words or concepts at a time and then practice multiple times a day to really learn those words or concepts.
- Teach math concepts with games.
  - Quantify/Comparative concepts (small, medium, large, most/least, same/different, young/old, wet/dry, etc.)
  - Play games using blocks to build towers of different sizes and compare.
  - Compare the size of your hands and your child's hands, your shoes to theirs, etc.
  - Play with different numbers of things like food, blocks, or toys. Compare and contrast different amounts so your child starts to learn counting and math concepts.
- Let your child have opportunities to play with other children.
  - Interactive games allow them to learn about sharing, taking turns and following simple directions.
- Use music as an opportunity to sing, dance together, and express their feelings.
- Allow outside playtime to promote exercise and the understanding of their environment like naming objects around them.
- Allow them to experience what the wind feels like or what happens when you jump in a puddle of water, smell a flower, etc.
- Allowing your child to make choices, such as places to go or what to wear, encourages independence and development of their language skills.
- Encourage affection in your family and reinforce positive behavior.

Fig 7D

Copyright © 2024 All Rights Reserved

SoundWise Dx™
Pediatric Neurodevelopmental Assessment
Developed by Pediatricians

- Set limits on behaviors that are not appropriate
- Resolve disagreements and disputes.
- Children need a structured loving environment. They also need to feel safe and loved.
- Encourage bedtime routines such as reading to your child.

What do sounds have to do with words in print, letters, and reading?

Learn those sounds! Practicing one new sound per week will strengthen your child's ability to eventually sound out words (decode). Decoding enables your child to sound out words so they do not have to guess. Accurate decoding is critically important tofuture reading success. It is the skill that separates good readers from poor readers.

Whenever you can, point out words wherever you go or in books so that your child recognizes that letters actually mean something. You can point to the print while you read. Play games like finding signs on buildings or street signs, or words on boxes at the supermarket. Reading to your child and pointing out words boosts vocabulary and advances knowledge.

Why does all this matter?

A person learns by experience and play. Give your child every opportunity to grow and learn. A strong grasp of language will give your child the ability to thrive in school and later in life. For it is the foundation that you build before 5 years of age that will be the platform from which learning will take place later on.

A strong foundation is built using the ability to play with, manipulate, hold onto, and retrieve sounds in words. That critical skill is called "sound processing." It is the skill that "good readers" do well and "poor readers" do not. So help your child accelerate into scholastic success and build a strong language foundation. And remember, those magical ingredients are sounds so play with them and have fun!

Fig 7E

Copyright © 2024 All Rights Reserved

SoundWise Dx™
Pediatric Neurodevelopmental Assessment
Developed by Pediatricians

3 year old Assessment Guided Treatment Flow Chart: Form A or B

Vision and Hearing Assessments: should be done on all children yearly.

SoundWise DX will perform a Vision Snell chart (or any other standardized screen) and a colorblind test (The Ishihara, EnChroma, or any other standardized color blind assessment or screen) before every assessment.) The colorblind tests can be done as early as when a child is able to recognize numbers, shapes, or animals.

*Color blindness (color vision deficiency, or CVD) affects approximately 1 in 12 men (8%) and 1 in 200 women. This is an important thing to know for all children as colors are frequently used on computer academic assessments and inability to discern colors can negatively impact learning.*

*Concern for possible color blindness: If a child misses questions with red and/or green they will be tested for color blindness as soon as they are able to identify the common shapes used in testing books like numbers, shapes, or animals.*

*Parental Questionnaire: If parents answer "yes" to any questions 1-3, visual and/or hearing assessments are recommended. If the parent answers "No" to any items 4 to 16, this information should be used in conjunction with the results of the child portion to factor into the medical decision making process of the physician. The entirety of the information acquired will be used to determine if referral for speech, fine motor, gross motor delay exists thus necessitating a need for referral and/or intervention.*

Fine Motor Skills: Items 1 and 2

- If a perfect score on Fine Motor items 1 & 2 with correct pencil grip, as determined by SoundWise DX computer program AI grader, pediatrician, or authorized personnel,
  Recommend the child use SoundWise DX AI/AI-Generative occupational therapy modules for enrichment activities (Modules are preceded by a short video explaining the lesson to be learned followed by AI/AI-Generative Online recommendation algorithm) and/or worksheets for learning advanced skills.

- Concerns or Fail: Unable to draw straight line (item 1) and/or circle (item 2) , and/or incorrect (fisted) pencil grip
  - Caregiver/teacher works with the child on drawing lines and circles with a correct pencil grip using SoundWise DX 3 Year Old Developmental Milestone Information Sheet (DMIS) for guidance.
  - Fine motor skills listed in items 1 and 2 includes, for example, the equivalent of the following (but not limited to): drawing line, drawing circle, and correct pencil grip (which can be expanded to other skills in the future).
  - START SoundWise DX AI/AI-Generative Online 3 year old Occupational Therapy modules ( Modules are preceded by a short video explaining the lesson to be learned followed by AI/AI-Generative Online recommendation algorithm) and/or worksheets that guides the child how to draw line, circle

Fig. 7F

SoundWise Dx™
Pediatric Neurodevelopmental Assessment
Developed by Pediatricians

3 year old Assessment Guided Treatment Flow Chart: Form A or B and development of correct pencil grip with AI grader determining for stroke/direction/pressure/speed, accuracy, and skill.

- Start In person Occupational Therapy. Automatic Prescription will be given through SoundWise DX or reach out to your Pediatrician/provider.
- Some children will wear gloves where computer will analyze proper technique with digitized feedback

- Multiple SoundWise DX modules and/or worksheets will be performed until the child is able to demonstrate proficiency or the child is confident to move on to learning advanced skills as determined by an SoundWise DX computer program AI grader,pediatrician, or authorized personnel.

Gross Motor Planning and Receptive Language: items 3 -6

We take into account AI algorithms to recognize, transcribe a child's letter sound/word pronunciation, analyze context/structure where pronunciation varies due to accents/dialects and word/sentence structure comprehension and fluency.

- If perfect score on items (Items # 3-6) as determined by SoundWise DX computer program AI grader, pediatrician, or authorized personnel, recommend the child use enrichment activities SoundWise DX AI/AI-Generative modules (Modules are preceded by a short video explaining the lesson to be learned followed by AI/AI-Generative Online recommendation algorithm) and/or worksheets for learning advanced skills.
- Concerns or Fail: Gross motor skills listed in items 3 -6 includes, for example, the equivalent of the following (but not limited to): big smile,touch finger to nose, other finger to nose, one finger to another finger, or both hands on top of head (which can be expanded to other skills in the future).
- If in items 3-6 unable to follow commands and/or properly demonstrate ability to perform and understand directions and /if child from English as second language home.
    - Caregiver/teacher work on Gross Motor Planning and Receptive language by using SoundWise DX 3 Year Old Developmental Milestone Information Sheet (DMIS)
- START SoundWise DX AI/AI-Generative Online 3 yr old Gross Motor Planning and Receptive/Expressive Language Modules (Modules are preceded by a short video explaining the lesson to be learned followed by AI/AI-Generative Online recommendation algorithm) and/or worksheets on following directions, upper extremity movement and coordination, and proprioceptive work, strengthening Receptive/ Expressive Language skills. Those from English second language homes use AI/AI-Generative modules and/or worksheets with emphasis on building English vocabulary.

Fig. 7G

SoundWise Dx™
Pediatric Neurodevelopmental Assessment
Developed by Pediatricians

3 year old Assessment Guided Treatment Flow Chart: Form A or B

- In English second language homes, modules should be done in both English and their primary language until the child is able to demonstrate proficiency to move on to learning advanced skills as determined by an SoundWise DX computer program AI grader, pediatrician, or authorized personnel.
- Start in person Occupational therapy focusing on motor integration, oral motor kinesthetics, and proprioceptive skills. Prescriptions will be given through SoundWise DX or reach out to your Pediatrician/provider.
- Start in person Speech and Language Referral focusing on building strong receptive/expressive language skills. Prescriptions will be given through SoundWise DX or reach out to your Pediatrician/provider.
- Some children will wear glove where computer will analyze proper technique with digitized feedback
- Multiple SoundWise DX modules will be performed until the child is able to demonstrate proficiency to move on to learning advanced skills as determined by an SoundWise DX computer program AI grader, pediatrician, or authorized personnel.

Sound Articulation Skills:

The ability to pronounce correctly some English sounds in words that are located at the beginning, middle, or end of a word. The ability to play and manipulate sounds in words is a foundational building block needed to later read well.

We use AI algorithms to recognize, transcribe a child's letter sound/word pronunciation, analyze context/structure where pronunciation varies due to accents/dialects and word/sentence structure comprehension and fluency.

- If a perfect score as determined by SoundWise DX computer program AI grader, pediatrician, or authorized personnel, then recommend the child do enrichment activities with SoundWise DX AI/AI-Generative modules (Modules are preceded by a short video explaining the lesson to be learned followed by AI/AI-Generative Online recommendation algorithm) for learning advanced skills.
- Concerns: Unable to do 1-3 items. SoundWise DX score is determined by SoundWise DX computer program AI grader, pediatrician, or authorized personnel, (less than 50% wrong on sound articulation items) then
  - Caregiver/teacher works with Phonological awareness and Expressive Language skills using SoundWise DX 3 Year Old Developmental Milestone Information Sheet (DMIS)
  - START SoundWise DX AI/AI-Generative Online 3 year old Expressive/Phonological Language modules (Modules are preceded by a short video explaining the lesson to be learned followed by AI/AI-Generative Online recommendation algorithms) and/or worksheets that focus specifically on Sound Articulation, and improving phonological awareness

Fig. 7H

SoundWise Dx™
Pediatric Neurodevelopmental Assessment
Developed by Pediatricians

3 year old Assessment Guided Treatment Flow Chart: Form A or B

- and phonological processing to build the foundational skills needed for reading
- Multiple SoundWise DX modules and/or worksheets will be performed until the child is able to demonstrate proficiency as determined by SoundWise DX computer program, pediatrician, or authorized personnel.

- Fail: If misses 4 or more (50% or greater on sound articulation items) then Caregiver/teacher works with Phonological awareness and Expressive Language skills using SoundWise DX 3 Year Old Developmental Milestone Information Sheet (DMIS)

- START SoundWise DX AI/AI-Generative Online 3 year old Expressive/Phonological Language modules (Modules are preceded by a short video explaining the lesson to be learned followed by AI/AI-Generative Online recommendation algorithm) and/or worksheets that focus on Expressive language specifically on Sound Articulation, but also on improving phonological awareness and phonological processing (Building foundational skills for reading) In addition:
  - Start in person Speech and Language Therapy focusing on improving Expressive Language specifically on Sound Articulation, but also on improving phonological awareness and phonological processing (Building foundational skills for reading)
  - Prescriptions will be given through SoundWise DX or reach out to your Pediatrician/provider.
  - Multiple SoundWise DX AI/AI-Gen modules and/or worksheets will be performed until the child is able to demonstrate proficiency as determined by the SoundWise DX computer program, pediatrician, or authorized personnel.

Sound Discrimination Skills:

We take into account AI algorithms to recognize, transcribe a child's letter sound/word pronunciation, analyze context/structure where pronunciation varies due to accents/dialects and word/sentence structure comprehension and fluency.

Sound discrimination is the ability to simply tell if sounds are similar or different. Understanding differences in sounds is part of phonological (sound) awareness which is a skill that must be mastered well to later learn how to accurately decode (sound out) words. Phonological awareness is more than just knowing if sounds are different; it is actually a complicated brain skill of the combined ability of discriminating, manipulating, and changing sounds in words.

How you process and understand sounds is what actually makes language meaningful. Phonological processing (the process of understanding sounds in words) is part manipulation and awareness but also the ability to hold on to and retrieve sounds in words. Phonological processing is the single most important skill that separates good readers from poor readers and can be tested as early as 4 years old. Phonological processing is a combination of visual processing (seeing), auditory processing (hearing), and knowledge of oral motor mouth movements (feeling.)

- If perfect score as determined by SoundWise DX computer program AI grader, pediatrician, or authorized personnel, then recommend the child use enrichment activities with SoundWise DX AI/AI-Generative receptive

Fig. 7I

SoundWise Dx™
Pediatric Neurodevelopmental Assessment
Developed by Pediatricians

3 year old Assessment Guided Treatment Flow Chart: Form A or B language/expressive/sound discrimination modules (Modules are preceded by a short video explaining the lesson to be learned followed by AI/AI-Generative Online recommendation algorithm) and/or worksheets for learning advanced skills.

- Concerns: Unable to do 1-3 items (less than 50% wrong on sound discrimination items) then
  - Caregiver/teacher works on Phonological awareness skills using SoundWise DX 3 Year Old Developmental Milestone Information Sheet (DMIS)
  - START SoundWise DX AI/AI-Generative Online 3 year old Receptive/Expressive/Sound Discrimination Language Modules (Modules are preceded by a short video explaining the lesson to be learned followed by AI/AI-Generative Online recommendation algorithm) and/or worksheets for learning Phonological Awareness and Receptive/Expressive language skills
  - Multiple SoundWise DX modules and/or worksheets will be performed until the child is able to demonstrate proficiency or the child is confident to move on to learning advanced skills as determined by an AI grader, pediatrician, or authorized personnel.

- Fail: If misses 4 or more (50% or greater on sound discrimination items),
  - Caregiver/teacher works on Phonological awareness skills using SoundWise DX 3 Year Old Developmental Milestone Information Sheet (DMIS)
  - START SoundWise DX AI/AI-Generative Online 3 year old Receptive/Expressive/Sound Discrimination Language Modules (Modules are preceded by a short video explaining the lesson to be learned followed by AI/AI-Generative Online recommendation algorithm) and/or worksheets for learning Phonological Awareness skills In addition:
  - Start In person Speech and Language Therapy focusing on improving phonological awareness and phonological processing/Sound Discrimination/Receptive/Expressive language. Prescriptions will be given through SoundWise DX or reach out to your Pediatrician/provider.
  - Multiple SoundWise DX modules will be performed until the child is able to demonstrate proficiency or the child is confident to move on to learning advanced skills as determined by an SoundWise DX computer program AI grader, pediatrician, or authorized personnel.

Engagement:

*Any and all diagnoses of psychiatric/behavioral disorders (ADHD, Autism, Anxiety, depression etc, will follow and change accordingly with the most current medical guidelines determined by the latest version of the Diagnostic and Statistical Manual of Mental Disorders which is currently the DSM-V. As new versions are published, SoundWise DX concerns identified and diagnostic criteria will adapt and be changed to match the most current diagnostic criteria.*

Perfect score:

- Able to demonstrate social communication, interaction , eye contact and able to demonstrate joint attention back and forth with assessment tasks. Not showing restrictive and repetitive behaviors, such as flapping their hands, spinning a lot, only interested in lining up toys or objects, sensory issues such as upset with loud noises, and difficulty with change of routine during the assessment.

Fig. 7J

SoundWise Dx™
Pediatric Neurodevelopmental Assessment
Developed by Pediatricians

3 year old Assessment Guided Treatment Flow Chart: Form A or B

- Able to sustain attention, not easily distracted, following directions on Assessment tasks.
- Attending the SoundWise DX assessment without crying and worrying about how they are doing with each task.
- Engagement evaluation is determined by SoundWise DX computer program AI grader, pediatrician, or authorized personnel.

A concern or fail for this section:

- Autism Concern:
  - The child has challenges with social communication and interaction. Has poor eye contact, refusal to engage in tasks, and/or lack of joint attention back and forth while doing assessment tasks.
  - The child demonstrates restrictive/repetitive behaviors, interests, and activities such as, but not limited to, flapping hands, spinning, lining up toys/objects, sensory issues (upset by loud noises/smell/touch), and challenges with change of routine during tasks.
- ADHD/ADD/attention deficits: Please note that ADHD diagnosis is made at age 4
  - The child is unable to keep their attention and/or unable to follow directions while completing Assessment without being distracted and/or unable to sit still long enough to complete assessment at age 3 years old, note that a formal diagnosis is not made at age 3, rather only a concern. Children who are inattentive and also exhibit staring spells, need to be evaluated for Absence seizures. SoundWise DX will offer RX or pediatrician/provider for Neurology referral.
    - Norm values:
      - 3 years old: 6-8 minutes
      - 4 years old: 8-12 minutes
      - 5 and 6 years old: 12-18 minutes
      - 7 and 8 years old: 16-24 minutes
      - 9 and 10 years old: 20-30 minutes
- Anxiety, panic attacks, or Post Traumatic Stress Disorder (PTSD) Concern or Fail:
  - The child is showing emotions of frustration with or without crying and/or demonstrating worry about their performance while completing the assessment.
  - Elevated heart rate and/or blood pressure measured by all digital devices
  - Avoidance behaviors when tasks are hard such as:
    - Child complains or somatic (body) complaints to end or get out of a task like:
      - Headaches
      - Nausea, stomach aches, vomiting
      - Tiredness, yawning, falling asleep
      - Tense posture, clenched shoulders or muscles, clenched teeth
      - Pulling on eyelashes, biting fingers or fingernails
      - Arguing, throwing the materials, leaving the test environment
      - Saying they are thirsty, hungry, tired, sleepy, or having to all of a sudden got to go to the bathroom
      - Complains of their heart racing
      - Child is unable to attempt assessment in part or at all.
      - Any other related complaints by the child not listed above.

Fig. 7K

SoundWise Dx™
Pediatric Neurodevelopmental Assessment
Developed by Pediatricians

3 year old Assessment Guided Treatment Flow Chart: Form A or B

- Children who do not attempt Assessment will need to to start SoundWise DX AI/AI-Gen engagement modules and a reassessment will be attempted in 1 to 3 months time as per SoundWise DX AI/AI-Gen grader.
- Engagement results are determined by SoundWise DX AI/AI-Gen computer program AI grader, Pediatrician, or authorized personnel.
- Engagement modules cover issues regarding attention , anxiety, autism, or other disorders as discussed below.
  - START SoundWise DX AI/AI-Generative Online 3 year old online Module for lack of engagement (Modules are preceded by a short video explaining the lesson to be learned followed by AI/AI-Generative Online recommendation algorithm) and/or worksheets. The Lack of Engagement modules deliver Speech & Language, Occupational Therapy, Physical Therapy and Behavioral Modification suggestions for building engagement.
  - As the child attends the Lack of Engagement modules, SoundWise DX AI/AI-Gen grader will determine the correct SoundWise DX modules for each individual child.
    - Lack of Engagement SoundWise DX modules include:
      1. Autism diagnostic evaluation through SoundWise DX and/or referral for autism diagnoses through a child's local medical services
      2. Attention Deficit/ADHD behavioral concerns/anxiety
         a. Continue to follow closely, make learning activities fun/engaging, limit activities to short segments.
         b. If severe behavioral issues or anxiety present: referral to child psychologist or for Play Therapy.
         c. Age 4 and older, refer to specific for ADHD module for further recommendations
      3. Modules for other recognized disorders such as post traumatic stress disorder, genetic disorders associated with learning disabilities, environment exposure to lead, fetal alcohol syndrome, Adoption and/or foster care population, proper nutrition, developmental delay, sensory issues, and other situations resulting in childhood developmental delay in need of intervention.
      4. Along with participating in Engagement modules, the following will be provided:
         - Refer for a in-person Speech and Language Evaluation focusing on building strong receptive/expressive language skill
         - Refer for an in person Sensory Integration Focused Occupational Therapy Evaluation focusing on motor integration, oral motor kinesthetics, proprioceptive skills, and sensory regulation..
         - Refer for an in person Physical therapy focusing on building strong gross motor skills.
         - Refer for in person evaluation for Autism
         - Refer for Genetics evaluation
         - Prescriptions for the above services will be provided by SoundWise DX or local health care facility.

- Specific SoundWise DX modules for Autism, ADHD/ADD, and Anxiety:

Fig. 7L

SoundWise Dx™
Pediatric Neurodevelopmental Assessment
Developed by Pediatricians

3 year old Assessment Guided Treatment Flow Chart: Form A or B

1. Autism: Autism presents challenges with social communication and interaction. They do not talk a lot because they are not motivated to socially interact. They have challenges with eye contact and are unable to demonstrate joint attention, not able to play a back and forth game or do SoundWise DX assessment tasks. They show restrictive and repetitive behaviors, such as flapping their hands, spinning a lot, only interested in lining up toys or objects, sensory issues such as being upset with loud noises, wanting to smell things and not wanting to play pretend. Children with Autism also have difficulty with change of routine for example, having a new teacher, or driving a new route home and difficulty changing tasks during the SoundWise DX assessment.
    - Determination of Autism by SoundWise DX computer program AI grader, pediatrician, or authorized personnel will recommend the following:
    - Recommended activities and/or worksheets generated in the modules will address the specific concerns of lack of engagement/ language delay affecting social interaction, high concerns for Autistic Spectrum Disorder (ASD), or ASD confirmed by meeting the diagnostic criteria for ASD as per the most current version of the DSM which is currently the DSM-V. This will includes activities that focus on but or not limited to the following:
        - To strengthen receptive, expressive, and pragmatic language skills
            - Specific games and activities addressing language goals
        - To improve sensory regulation
            - Specific games and activities to decrease sensory triggers whether they be hypo(low) or hyper(high) sensory
            - Recommendation to address sensory seeking behaviors and/or sensory avoidance behaviors
            - Occupational Therapy (OT) like play activities with OT therapy goals addressing visual/motor integration, sensory regulation, visual perceptual skills, executive function, and primitive reflex integration)
        - To improve fine motor skills
            - Specific games and activities to improve any fine motor skills or hand skill ability like but not limited to the following (handwriting, cutting, folding, stringing beads, coloring, drawing, gluing, buttoning, using utensils, etc.
        - To improve gross motor skills
            - Specific games and activities to strengthen gross motor movements that includes focusing on balance, coordination, ball skills (dribbling, throwing,catching, etc.), hand eye coordination, same side and alternating side body movements, body schema activities (proprioceptive, vestibular, tactile, and body awareness)
            - Physical Therapy (PT) therapy like activities with PT gross motor goals
        - To improve social and pragmatic language skills
            - Specific group play therapy along with games and activities promoting opportunity for improved and guided social interaction
                - Group play therapy
                - Applied Behavioral Analysis Therapy

Fig. 7M

SoundWise Dx™
Pediatric Neurodevelopmental Assessment
Developed by Pediatricians

3 year old Assessment Guided Treatment Flow Chart: Form A or B

- Increased peer group interactions.
- In situations where anxiety or family connections are more calming, the avatar (computer generated face and/or voice used) could be that of a person familiar to the individual) when the assessment or enrichment activities are delivered on the SoundWise DX platform.
- SoundWise DX modules can be used to treat and strengthen skills along with in person therapy especially when waiting for in person therapy. Using SoundWise DX modules will start therapeutic advancement of identified skill deficits while at home when awaiting in person therapies. They can also be used to augment and reinforce the actual future or current therapies in place like medically delivered Speech and Language Therapy, OT, Cognitive Behavioral Therapy, and PT.
- Engagement modules and/or worksheets allow Early Intervention to immediately start while a child awaits for in person evaluation and/or in person autism specific therapy.
- SoundWise DX modules and/or worksheets will improve skills and reassessment will allow progress. Children should continue using the modules and/or worksheets even after starting in-person therapy.
- Referral when indicated per AI/AI generated Algorithm
    - Refer for a in person Speech and Language Evaluation
    - Refer for a in person Sensory Integration Focused Occupational Therapy Evaluation
    - Refer for an in person Diagnostic Evaluation for Autism
    - Refer for in person Child Play Therapy

- Pursue all therapies covered by medical insurance while at the same time caregivers/ teachers work on language skills, social interaction, developmental milestones, and sensory regulation using SoundWise DX 3 Year Old Developmental Milestone Information Sheet (DMIS) for age appropriate activities.
- Recommendations will include prescriptions for in person services generated through SoundWise DX.
- Suggestions to seek specialized diagnostic evaluations when indicated by SoundWise DX AI/AI-Gen Grader will include follow up with the child's primary care medical provider, and specialty referrals.
- As part of the diagnostic process, SoundWise DX will administer and score standardized validated screeners as age appropriate such as but not limited to the MCHAT, ASQ, PEDS Form, Vanderbilts, Denver Developmental assessments, Conners Forms, Scat etc)
- While Autism may be the primary diagnosis or concern, other coexisting conditions like anxiety or ADHD and/or genetic disorders may exist. If a validated screening as discussed above elicits concerns for other disorders, the appropriate referral will be done through SoundWise DX.

2. For Attention Deficit Hyperactivity Disorder Concerns (ADHD/ADD):
3. While ADHD is not diagnosed until age 4 years or older, a behavioral modifications SoundWise DX module for 3 year old Behavioral Basics will be given that focuses tips on a structured environment, making learning activities fun, multisensory activities, and short but repetitive opportunities for learning.

Fig. 7N

SoundWise Dx™
Pediatric Neurodevelopmental Assessment
Developed by Pediatricians

3 year old Assessment Guided Treatment Flow Chart: Form A or B

- If engagement is appropriate, but focus/attention to a task cannot be maintained for the age expected time for this age (6-8 minutes), then refer to SoundWise ADHD/ADD age specific questions and holistic consideration of all factors that can affect attention and sustained focus.
- Children with ADHD/ADD have a hard time paying attention, daydreaming and often do not seem to listen. They are easily distracted from work and play and often do not pay attention to details/disorganization and do not follow through on directions. Prone to losing a lot of important things/forgetting things and avoids doing things that require mental effort. Having the hyperactivity component makes them prone not being able to stay seated, squirming a lot, talking too much, unable to play quietly and will jump, run and climb when not permitted to do so. They will demonstrate impulsivity, calling out without question being complete, Acts or speaks without thinking, Interrupting others often, trouble taking turns, cannot wait for things and may run onto street without looking out for traffic.
  - SoundWise DX AI/AI Gen grader will administer and score a Vanderbilt screen for parent and teacher if applicable. At age 3 years old usually Vanderbilt screens are not used. Vanderbilt screens are diagnostic of ADHD/ADD.
      - Visual attention and focus: SoundWise RX AI/Gen AI computer grader will derive objective and quantitative results for example gaze direction, dwell time, and glance frequency off the assessment site to other objects and locations. While monitoring eye tracking, we will measure where and for how long an individual looks in a certain direction or at a certain target, it is not a measure of actual visual attention However, this information can be used to necessitate further exploration into attention or focus disorders like ADHD/ADD. The SoundWise RX screen eye tracking will be used to assess student attention while taking the test. Just as eye tracking is the go-to method when determining driver distraction via glance target classification it can be used to assess attention to the assessment attention engagement in the test itself, or also suggest more analysis of visual tracking/perception/or processing is warranted.
- When above condition concerns are found, AI/AI-Gen computer program modules and/or worksheets for evaluation and guidance/ for ADHD/ADD will be generated. Further informational sheets on factors that can impact attention will be generated and given to the caregivers.
- Modules for scholastic accommodations such IEP, 504 and not limited to will also be given that can be effectively be used within a child's Individual Educational Plan (IEP) or 504 Plan.

Fig. 7O

SoundWise Dx™
Pediatric Neurodevelopmental Assessment
Developed by Pediatricians

3 year old Assessment Guided Treatment Flow Chart: Form A or B

- When formal diagnosis of ADHD for age 4 years old and older has been given, then information regarding evaluation for behavioral modification will be given.
- Starting at age 4 or older, medication for ADHD/ADD when indicated by SoundWise DX AI/AI-Gen and/or caregiver/teacher. Blood pressure. Pulse, EKG rhythm strip will be administered through all digital devices, along with telemedicine visit with SoundWise DX before medication is given.. Pathways towards diagnostic evaluation will be done according to the specific laws in each state.
- Classroom modifications and accommodation recommendations would be produced via SoundWise DX module via AI/AI-Gen and given via SoundWise DX according to the specific laws in each state.

3. Anxiety:
   - A diagnosis of Anxiety is when a child is worried or scared and it interferes with their everyday activities such as refusing to go to school, playing with friends,especially at recess or at social gatherings, getting to sleep and/or not being able to sleep alone in their bed. They may say their heart is beating too fast, or they have a stomach ache and shaking, maybe having trouble breathing, start to sweat and suddenly are unable to sustain attention and want to find a safe place, like home or a caregiver. See specific symptoms that were listed above in "what constitutes a fail". Anxiety may have been exhibited itself as shyness during the child's early years, or occur after a traumatic event experienced/ witnessed by the child or the child may be a victim of abuse by a caregiver or other.
   - There are 4 types of Anxiety present in children;
     - Social Anxiety-Difficulty playing or being with others, especially in school, will speak softly not wanting to be heard and will not volunteer to raise hand in school or participate in group activities.
     - Separation Anxiety- Unable to separate from the caregiver, wanting to always be in their presence, not wanting to go to school or be on a playdate.
     - Selective Mutism- severe anxiety-speaks at home but not anywhere else. Has early onset.
     - Generalized Anxiety-Strives to be perfect,worries about the past, current events and the future a lot and worries about what may happen in school in their school work or other activities. They may get diagnosed with ADHD, however this child can not pay attention due to worry, rather than attention.
   - The child may demonstrate Anxiety during SoundWise DX by being concerned about getting the assessment tasks correct or simply not speaking. They may cry and turn away and say they are afraid to continue.
   - SoundWise DX AI/Gen-AI will determine through an anxiety algorithm module and/or caregiver/teacher or authorized personnel to start Anxiety SoundWise DX modules as well to start arranged telemedicine visits through SoundWise DX and/or in person therapy.
   - Also the Caregiver/teacher will work on language development, social interaction, and sensory regulation by using SoundWise DX 3 Year Old Developmental Milestone Information Sheet (DMIS) for age appropriate activities.
   - SoundWiseDX will administer and score a diagnostic screen such as PHQ-9/SCARED/Columbia/Hamilton/GAD-7 for Anxiety that is appropriate for age.
   - Based on SoundWiseDX AI/AI-Gen Children will also be started on telemedicine services through SoundWise DX for anxiety.

Fig. 7P

SoundWise Dx™
Pediatric Neurodevelopmental Assessment
Developed by Pediatricians

3 year old Assessment Guided Treatment Flow Chart: Form A or B

- Reasons for indications for medicine management for Anxiety is determined by SoundWise DX AI/AI-Gen, physician, and input from caregiver/teacher. Pulse, Blood Pressure and EKG will be obtained by digital devices and are medically necessary before starting medication. Telemedicine services for anxiety though SoundWise DX must also be initiated and continued while the child is on medication for anxiety.
- All children diagnosed with Anxiety through SoundWise DX AI/AI-Gen will also be evaluated for ADHD/ADD and/or Autism

4. Low Self Esteem

- Self esteem should always be monitored closely in a child as this can lead to depression or other mental health disparities in the future.
- Low self esteem can arise from a variety of reasons.
- A soundWise DX Module AI/AI-Gen will be given that addresses building self esteem and confidence in a child.
- Telemedicine visits will be recommended via SoundWise DX or their local provider

- Reassessments SoundWise DX:
    - SoundWise DX will offer reassessments (Form B's) after 3 months of module implementation. Initial assessments are Form A.
    - In 3 months or less depending upon the discretion of SoundWise DX AI/AI-Gen computer program AI grader, pediatrician, and/or authorized personnel, the child will retake an assessment
        - If the child is still the same age, they will then take that age years Form B
        - If they have aged up and are now 1 year older, then they will take the next year's assessment Form A.
        - If a child is able to pass some, but not all, or if unable to pass the repeat pediatric assessment, they must follow through with the same algorithm as above until proficiency is determined by SoundWise DX computer program AI grader, pediatrician, or authorized personnel.
        - If the child is able to pass all parts of the new assessment, they should do SoundWise DX enrichment modules based on age group.

Fig. 7Q

SoundWise Dx™
Pediatric Neurodevelopmental Assessment
Developed by Pediatricians
Parental Questionnaire Age 4 years: Form A or B

Child:________________________________________DOB_________________

Parent Part - Completed by: ____________________________________________

1. Does your child seem to hear ok? ☐ Yes ☐ No ☐ Sometimes
2. Is your child in preschool? ☐ Yes ☐ No ☐ Sometimes
3. Does your child understand what you say? ☐ Yes ☐ No ☐ Sometimes
4. Can your child name some of their letters? ☐ Yes ☐ No ☐ Sometimes
5. Can your child play a game or do a task with you for 10 minutes? ☐ Yes ☐ No ☐ Sometimes 6. Does your child eat well with a spoon and fork? ☐ Yes ☐ No ☐ Sometimes
7. Can your child pedal a riding toy? ☐ Yes ☐ No ☐ Sometimes
8. Is your child able to rhyme? ☐ Yes ☐ No ☐ Sometimes
9. Can you understand your child when they speak? ☐ Yes ☐ No ☐ Sometimes 10. Does your child mix up sounds in words? ☐ Yes ☐ No ☐ Sometimes
11. Did your child ever need ear tubes? ☐ Yes ☐ No
12. Does anyone in your family struggle with spelling? ☐ Yes ☐ No ☐ Sometimes
13. Does anyone in your family struggle with reading, have dyslexia, or does not read for fun? ☐ Yes ☐ No ☐ Sometimes

Fig. 8

Copyright © 2024 All Rights Reserved

SoundWise Dx™
Pediatric Neurodevelopmental Assessment
Developed by Pediatricians
Name: ______________________ DOB: ______________ Date:__________
Age 4 years: Form A
Name: ______________________________________________
*-Draw a cat with three or more parts.*
*Copy the shape.*
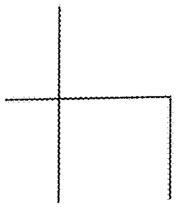
*Trace the line within the box.*
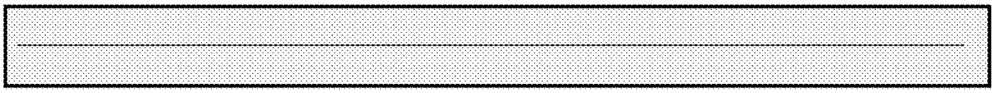
| | |
|---|---|
| D | S |
| M | C |
| P | R |
| A | E |
Fig. 9A
Copyright © 2024 All Rights Reserved

SoundWise Dx™
Pediatric Neurodevelopmental Assessment
Developed by Pediatricians

Age 4 years: Form A

Copyright © 2024 All Rights Reserved

SoundWise Dx™
Pediatric Neurodevelopmental Assessment
Developed by Pediatricians

Age 4 years: Form A

SoundWise Dx™
Pediatric Neurodevelopmental Assessment
Developed by Pediatricians
Name: ______________________ DOB: ______________ Date:__________
Age 4 years: Form B
Name: ________________________________________
*-Draw a dog with three or more parts.*
*Copy the shape.*
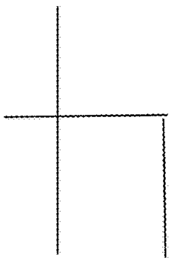
*Trace the line within the box.*
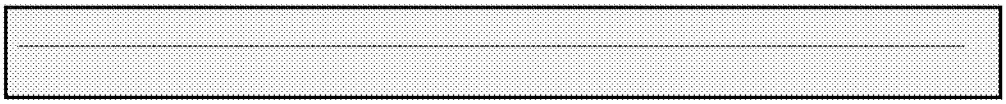
| | |
|---|---|
| B | N |
| O | P |
| T | U |
| V | F |
Fig. 10A
Copyright © 2024 All Rights Reserved

SoundWise Dx™
Pediatric Neurodevelopmental Assessment
Developed by Pediatricians

Age 4 years: Form B

Copyright © 2024 All Rights Reserved

SoundWise Dx™
Pediatric Neurodevelopmental Assessment
Developed by Pediatricians

Age 4 years: Form B

Copyright © 2024 All Rights Reserved

SoundWise Dx™
Pediatric Neurodevelopmental Assessment
Developed by Pediatricians

4 year old Assessment Form A

Name: ____________________ □ M □ F DOB:____________ Date:________________

*Administer in a quiet one-on-one setting with limited distractions.*

Yearly hearing and vision screen screening is medically indicated

Receptive Language: (Have the child pick the picture that fits best)

- Show me the blue circle. □ Yes □ No
- Point to the yellow square. □ Yes □ No
- Show me a green square □ Yes □ No
- Show me a red triangle. □ Yes □ No

Sound Discrimination (ask the child if the sounds are same or different?

- /r/ /t/ /t/ □ Same □ different
- /l/ /l/ /l/ □ Same □ different
- /b/ /d/ /d/ □ Same □ different
- /i/ /i/ /a/ □ Same □ different
- /f/ /f/ /f/ □ Same □ different
- /s/ /t/ /s/ □ Same □ different
- /t/ /t/ /v/ □ Same □ different
- /a/ /a/ /a/ □ Same □ different

Sound Order Awareness (ask the child if they can answer the following questions?

- Can you say the first sound in the word "apple" □ yes □ no (answer is /a/)
- Can you say the last sound in the word "me" □ yes □ no (answer is /ee/)
- Can you say the 2nd sound in the word "pin" □ yes □ no (answer is /i/
- Can you say the first sound in the word "bat" □ yes □ no (answer is /b/)
- Can you say the first sound in the word "mine" □ yes □ no (answer is /m/)
- Can you say the middle sound in the word "pan" □ yes □ no (answer is /a/)
- Can you say the last sound in the word "fun" □ yes □ no (answer is /n/)
- Can you say the last sound in the word "dog" □ yes □ no (answer is /g?)

Fine Motor *(Please have the child do the following)*

| | Done Correctly |
|---|---|
| **Typical 3 point pencil grip present** | □ Yes □ No |
| **Draw a cat with 3 or more parts** | □ Yes □ No |
| **Copies shape correctly** | □ Yes □ No |
| **Trace the line within the box** | □ Yes □ No |

Fig. 11A

Copyright © 2024 All Rights Reserved

SoundWise Dx™
Pediatric Neurodevelopmental Assessment
Developed by Pediatricians

4 year old Assessment Form A

Letter Name & Letter Sound Identification:

| | Say Letter Name | Say Letter Sound |
|---|---|---|
| D | □ Yes □ No | □ Yes □ No |
| M | □ Yes □ No | □ Yes □ No |
| P | □ Yes □ No | □ Yes □ No |
| A | □ Yes □ No | □ Yes □ No |
| S | □ Yes □ No | □ Yes □ No |
| C | □ Yes □ No | □ Yes □ No |
| R | □ Yes □ No | □ Yes □ No |
| E | □ Yes □ No | □ Yes □ No |

Phoneme Elision (Deletion - Taking away a sound or sounds)
Directions: Say, *Let's play a game* .
Example: *Say "raindrop". Now say raindrop without saying "drop"* ............................
If correct, say, *That's right. Let's try the next one.*
If incorrect, say. *That's not quite right. Raindrop without saying drop is rain.*

1. *You say Spaceship. Say Spaceship again, without saying "space"* (ship) □ Yes □ No
2. *You say Snowflake. Say Snowflake again, without saying "flake"* (snow) □ Yes □ No
3. *You say ladybug. Say ladybug again, without saying "bug"* (lady) □ Yes □ No
4. You say sidewalk . Say sidewalk again, without saying "walk" (side) □ Yes □ No
5. You say map. Now say map again, without the /m/ sound (ap) □ Yes □ No
6. You say pen. Now say pen again, without the /p/ sound (en) □ Yes □ No
7. *You say Bat. Now say Bat again, without the /b/ sound (at)* □ Yes □ No
8, *You say box. Say Box again, without the /b/ sound (ox)* □ Yes □ No

Behavioral/Engagement (Observations): Please note the the child's demeanor during testing:

□ Cooperative □ Smiling □ Shy □ Happy and engaged
□ Uncooperative □ Crying □ Distractible □ English Language Learner
□ Refusal to Interact □ Tired □ Anxious □ Difficult to motivate
□ Completed Independently □ Needed Redirection for completion
□ Other________________________________

Fig. 11B

Copyright © 2024 All Rights Reserved

SoundWise Dx™
Pediatric Neurodevelopmental Assessment
Developed by Pediatricians

4 year old Assessment Form A

Scoring Yearly vision screen screening is medically indicated and hearing if necessary Receptive Language Skills:

- 2 or more wrong-Does not understand directions-refer for speech Receptive/expressive/phonological awareness/processing skills .
- If the primary language at home is not English, refer to speech therapy for English Receptive/Expressive language/Phonological awareness/processing skills

Sound Discrimination Skills:

- If no misses - strong skills
- If miss 1, practice at home with parent/teacher/tutor/librarian
- If miss 2 or more - work on these skills at home and Start speech therapy on phonological awareness/processing/articulation/Receptive/Expressive Language skills

Sound Order Awareness Skills:

- If no misses - strong skills
- If misses 1, work on skills further with parent/teacher/tutor/Librarian
- If miss 2 or more (50% or greater), work on skills with parent/teacher/tutor/librarian and speech therapy referral for phonemic awareness/processing/articulation skills/Receptive/Expressive language skills

Fine Motor Skills:

- If no misses - strong skills
- If misses 1 work on skills further with parent/teacher/tutor/Librarian
- If misses 2 or more work on skills with Parent/teacher/tutor/Librarian and OT referral for pencil grip and life skills.

Letter & Sound Identification Skills:

- If no misses - strong skills.
- If misses 1-3, work on skills with parent/teacher/Librarian/tutor
- If misses 4 or more work on skills with Parent/teacher/tutor/Librarian and Speech therapist for letter sounds/letter Identification/phonological awareness/processing skills. Lively letters APP/Youtube tutorials on letter sounds and identification

Phonemic Elision (Sound Deletion) Skills:

- If no misses - strong skills
- If misses any,work on these skills with parent/teacher/tutor/librarian
- If miss 2 or more work on the skills with parent/teacher/tutor/Librarian and order speech therapy referral for Phonemic Elision/Articulation/Expressive/Receptive language/Phonological awareness/processing

Engagement: If any concerns for Autism like poor eye contact/lack of joint attention, lack of wanting to engage, and sensory dysregulation refer for Speech, OT, PT and a referral for ASD evaluation If there are any concerns for ADHD/ADD, for example, unable to focus, easily distracted, unable to sustain attention for 8-12 minutes, consider speaking to parents about Vanderbilt screen. Children who are inattentive and also exhibit staring spells, need to be evaluated for Absence seizures. SoundWise DX will offer RX or pediatrician/provider for neurology referral.

Fig. 11C

Copyright © 2024 All Rights Reserved

SoundWise Dx™
Pediatric Neurodevelopmental Assessment
Developed by Pediatricians

4 year old Assessment Form A

If there are any concerns about Anxiety, frustration with performance, thinking that they can not do well, crying, saying that they always fail every test,etc. Consider doing SCARED, and Columbia Screen or other screens for anxiety/depression.

Concerns present:
- ☐ None - Perfect Score
- ☐ Engagement Concerns (Based of Evaluator's Behavioral Observations)
- ☐ Receptive Language Concerns
- ☐ Sound Discrimination Concerns
- ☐ Sound OrderAwareness Concerns
- ☐ Fine Motor Concerns
- ☐ Letter & Sound Identification Concerns
- ☐ Sound Articulation Concerns
- ☐ Letter & Sound Identification Concerns
- ☐ Phonemic Elision (Sound Deletion) Concerns

Interventional Response:

☐ General 4 Year Old Milestone Information Sheet
- Provides general understanding of what a 4 year should be able to do ☐ Specific Information Sheet for Opportunity and Development of Individual Skills
- Based upon Neurodevelopmental Foundational Model and Treatment Approach
- Includes Recommended Suggestions for opportunities and activities to grow skills
- Expand Opportunities and Suggestions available through SoundWise DX platform and other recommended sites.
- Increased Academic Focused Instruction on Broad areas of Concern (Engagement, Receptive Language, Sound Order awareness,Sound Discrimination, Fine Motor, Letter & Sound Identification, and Phonemic Elision)
- Start Speech Therapy and/or Occupational Therapy based on score

Follow up if concerns present: ☐ 3-6 months later ☐ Yearly at the next Well Child Visit

Fig. 11D

Copyright © 2024 All Rights Reserved

SoundWise Dx™
Pediatric Neurodevelopmental Assessment
Developed by Pediatricians

4 year old Form B

Name: ______________________ □ M □ F DOB:_____________ Date:__________________

*Administer in a quiet one-on-one setting with limited distractions.*

Receptive Language: (Have the child pick the picture that fits best)

- Show me the red circle. □ Yes □ No
- Point to the blue square □ Yes □ No
- Show me a yellow square □ Yes □ No
- Show me green triangle □ Yes □ No

Sound discrimination (ask the child if the sounds are same or different?

| | | | | | | |
|---|---|---|---|---|---|---|
| ○ | /p/ | /p/ | /d/ | □ Same | □ different | **(Different)** |
| ○ | /s/ | /s/ | /s/ | □ Same | □ different | **(Same)** |
| ○ | /m/ | /m/ | /n/ | □ Same | □ different | **(Different)** |
| ○ | /e/ | /i/ | /e/ | □ Same | □ different | **(Different)** |
| ○ | /r/ | /r/ | /l/ | □ Same | □ different | **(Different)** |
| ○ | /b/ | /b/ | /d/ | □ Same | □ different | **(Different)** |
| ○ | /t/ | /p/ | /p/ | □ Same | □ different | **(Different)** |
| ○ | /i/ | /i/ | /i/ | □ Same | □ different | **(Same)** |

Sound Awareness (ask the child if they can answer the following questions?

- Can you say the last sound in the word "foot" □ yes □ no (answer is /t/)
- Can you say the 2nd sound in the word "feet" □ yes □ no (answer is /ee/)
- Can you say the first sound in the word "hut" □ yes □ no (answer is /h/)
- Can you say the last sound in the word "boat" □ yes □ no (answer /t/)
- Can you say the first sound in the word "blue" □ yes □ no (answer /b/)
- Can you say the first sound in the word "snake" □ yes □ no (answer is /s/)
- Can you say the last sound "dog" □ yes □ no (answer is /g/)
- Can you say the middle sound "cat" □ yes □ no (answer is /a/)

Fine Motor *(Please have the child do the following)*

| | Done Correctly |
|---|---|
| **Typical 3 point pencil grip present** | □ Yes □ No |
| **Draw a dog with 3 or more parts** | □ Yes □ No |
| **Copies shape correctly** | □ Yes □ No |
| **Trace the line within the box** | □ Yes □ No |

Fig. 12A

Copyright © 2024 All Rights Reserved

SoundWise Dx™
Pediatric Neurodevelopmental Assessment
Developed by Pediatricians

4 year old Form B

Letter Naming & Letter Sound

| | Say Letter Name | Say Letter Sound |
|---|---|---|
| **B** | □ Yes □ No | □ Yes □ No |
| **O** | □ Yes □ No | □ Yes □ No |
| **T** | □ Yes □ No | □ Yes □ No |
| **V** | □ Yes □ No | □ Yes □ No |
| **N** | □ Yes □ No | □ Yes □ No |
| **P** | □ Yes □ No | □ Yes □ No |
| **U** | □ Yes □ No | □ Yes □ No |
| **F** | □ Yes □ No | □ Yes □ No |

Phoneme Elision (Deletion - Taking away a sound or sounds)

Directions: Say, *Let's play a game* .

Example: *Say "raindrop". Now say raindrop without saying "drop"* ............................

If correct, say, *That's right. Let's try the next one.*

If incorrect, say. *That's not quite right. Raindrop without saying drop is rain.*

1. *You say peanut. Say peanut again, without saying "pea"* (nut) □ Yes □ No
2. *You say snowman. Say snowman again, without saying 'snow" (man)* □ Yes □ No
3. You say pineapple. Say pineapple again, without saying "pine" (apple) □ Yes □ No
4. You say applesauce. Say applesauce again, without saying "sauce" (apple) □ Yes □ No
5. *You say seek. Now say seek again, without the /s/ sound* (eek) □ Yes □ No
6. You say pin. Now say pin again, without the /p/ sound (in) □ Yes □ No
7. *You say mint. Now say mint again, without the /t/ sound* (min) □ Yes □ No
8. *You say feet. Now say feet again, without the /t/ sound* (fee) □ Yes □ No

Behavioral Observations: Please note the the child's demeanor during testing:

□ Cooperative □ Smiling □ Shy □ Happy and engaged

□ Uncooperative □ Crying □ Distractible □ English Language Learner

□ Refusal to Interact □ Tired □ Anxious □ Difficult to motivate

□ Completed Independently □ Needed Redirection for completion

□ Other________________________________

Fig. 12B

Copyright © 2024 All Rights Reserved

SoundWise Dx™
Pediatric Neurodevelopmental Assessment
Developed by Pediatricians

4 year old Form B

Scoring Yearly vision screen screening is medically indicated and hearing if necessary Receptive Language Skills:

- 2 or more wrong-Does not understand directions-refer for speech Receptive/expressive/phonological awareness/processing skills .
- If the primary language at home is not English, refer to speech therapy for English Receptive/Expressive language/Phonological awareness/processing skills

Sound Discrimination Skills:

- If no misses - strong skills
- If miss 1, practice at home with parent/teacher/tutor/librarian
- If miss 2 or more - work on these skills at home and Start speech therapy on phonological awareness/processing/articulation/Receptive/Expressive Language skills

Sound Order Awareness Skills:

- If no misses - strong skills
- If misses 1, work on skills further with parent/teacher/tutor/Librarian
- If miss 2 or more (50% or greater), work on skills with parent/teacher/tutor/librarian and speech therapy referral for phonemic awareness/processing/articulation skills/Receptive/Expressive language skills

Fine Motor Skills:

- If no misses - strong skills
- If misses 1 work on skills further with parent/teacher/tutor/Librarian
- If misses 2 or more work on skills with Parent/teacher/tutor/Librarian and OT referral for pencil grip and life skills.

Letter & Sound Identification Skills:

- If no misses - strong skills.
- If misses 1-3, work on skills with parent/teacher/Librarian/tutor
- If misses 4 or more work on skills with Parent/teacher/tutor/Librarian and Speech therapist for letter sounds/letter Identification/phonological awareness/processing skills. Lively letters APP/Youtube tutorials on letter sounds and identification

Phonemic Elision (Sound Deletion) Skills:

- If no misses - strong skills
- If misses any,work on these skills with parent/teacher/tutor/librarian
- If miss 2 or more work on the skills with parent/teacher/tutor/Librarian and order speech therapy referral for Phonemic Elision/Articulation/Expressive/Receptive language/Phonological awareness/processing

Engagement: If any concerns for Autism like poor eye contact/lack of joint attention, lack of wanting to engage, and sensory dysregulation refer for Speech, OT, PT and a referral for ASD evaluation If there are any concerns for ADHD/ADD, for example, unable to focus, easily distracted, unable to sustain attention for 8-12 minutes, consider speaking to parents about Vanderbilt screen. Children who are inattentive and also exhibit staring spells, need to be evaluated for Absence seizures. SoundWise DX will offer RX or pediatrician/provider for neurology referral.

If there are any concerns about Anxiety, frustration with performance, thinking that they can not do well, crying, saying that they always fail every test,etc. Consider doing SCARED, and Columbia Screen or other screens for anxiety/depression.

Fig. 12C

Copyright © 2024 All Rights Reserved

SoundWise Dx™
Pediatric Neurodevelopmental Assessment
Developed by Pediatricians

4 year old Form B

Concerns present:
- □ None - Perfect Score
- □ Engagement Concerns (Based of Evaluator's Behavioral Observations)
- □ Receptive Language Concerns
- □ Sound Discrimination Concerns
- □ Sound OrderAwareness Concerns
- □ Fine Motor Concerns
- □ Letter & Sound Identification Concerns
- □ Sound Articulation Concerns
- □ Letter & Sound Identification Concerns
- □ Phonemic Elision (Sound Deletion) Concerns

Interventional Response:

□ General 4 Year Old Milestone Information Sheet
- Provides general understanding of what a 4 year should be able to do □ Specific Information Sheet for Opportunity and Development of Individual Skills
- Based upon Neurodevelopmental Foundational Model and Treatment Approach
- Includes Recommended Suggestions for opportunities and activities to grow skills
- Expand Opportunities and Suggestions available through SoundWise DX platform and other recommended sites.
- Increased Academic Focused Instruction on Broad areas of Concern (Engagement, Receptive Language, Sound Order awareness,Sound Discrimination, Fine Motor, Letter & Sound Identification, and Phonemic Elision)
- Start Speech Therapy and/or Occupational Therapy based on score

Follow up if concerns present: □ 3-6 months later □ Yearly at the next Well Child Visit

Fig. 12D

Copyright © 2024 All Rights Reserved

SoundWise Dx™
Pediatric Neurodevelopmental Assessment
Developed by Pediatricians

4 year old Assessment Guided Treatment Flow Chart Form A or B

Vision and Hearing Assessments: should be done on all children yearly.

SoundWise DX will perform vision and color blindness screening before every assessment.

SoundWise DX will perform a Vision Snell chart (or any other standardized screen) and a colorblind test (The Ishihara, EnChroma, or any other standardized color blind assessment or screen) before every assessment.) The colorblind tests can be done as early as when a child is able to recognize numbers, shapes, or animals.

*Color blindness (color vision deficiency, or CVD) affects approximately 1 in 12 men (8%) and 1 in 200 women. This is an important thing to know for all children as colors are frequently used on computer academic assessments and inability to discern colors can negatively impact learning.*

*Concern for possible color blindness: If a child misses questions with red and/or green they will be tested for color blindness as soon as they are able to identify the common shapes used in testing books like numbers, shapes, or animals.*

Receptive Language Skills:

We take into account AI algorithms to recognize, transcribe a child's letter sound/word pronunciation, analyze context/structure where pronunciation varies due to accents/dialects and word/sentence structure comprehension and fluency.

- Perfect score on items of Receptive Language items/understood all directions of all tasks, then recommend the child use SoundWise DX AI/AI-Generative for 4 year old Receptive Language modules enrichment activities( Modules are preceded by a short video explaining the lesson to be learned followed by AI/AI-Generative Online recommendation algorithm) and/or worksheets for learning advanced skills.

- If unable to follow and/or properly demonstrate ability to perform and understand directions and /if child from English as a second language home, as determined by SoundWise DX computer program AI grader, pediatrician, or authorized personnel,
    - Caregiver/ teacher work on receptive language by using SoundWise DX 4 Year Old Developmental Milestone Information Sheet (DMIS)
- START SoundWise DX AI/AI-Generative Online 4 year old Receptive/Expressive/phonological processing/awareness Language modules (Modules are preceded by a short video explaining the lesson to be learned followed by AI/AI-Generative Online recommendation algorithm) and/or worksheets with respect to following directions, strengthening Receptive/ Expressive Language skills, with emphasis on building English vocabulary.
- In addition SoundWise DX recommends:
- In person Speech/ Language Therapy focusing on improving Receptive language/ Expressive/phonological processing/awareness Language with emphasis on vocabulary building

Fig. 13A

SoundWise Dx™
Pediatric Neurodevelopmental Assessment
Developed by Pediatricians

4 year old Assessment Guided Treatment Flow Chart Form A or B

- Prescriptions for speech and language will be given through SoundWise DX and or Pediatrician/provider.
- Multiple SoundWise DX modules will be performed until the child is able to demonstrate proficiency to move on to learning advanced skills as determined by the SoundWise DX computer program AI grader, pediatrician, or authorized personnel.
- If from an English second language home, then these modules should be done in both English and their primary language until the child is able to demonstrate proficiency as determined by the SoundWise DX computer program AI grader, pediatrician, or authorized personnel.

Sound Discrimination Skills:

We take into account AI algorithms to recognize, transcribe a child's letter sound/word pronunciation, analyze context/structure where pronunciation varies due to accents/dialects and word/sentence structure comprehension and fluency.

Sound discrimination is the ability to simply tell if sounds are similar or different. Understanding differences in sounds is part of phonological (sound) awareness which is a skill that must be mastered well to later learn how to accurately decode (sound out) words. Phonological awareness is more than just knowing if sounds are different; it is actually a complicated brain skill of the combined ability of discriminating, manipulating, and changing sounds in words.

How you process and understand sounds is what actually makes language meaningful. Phonological processing (the process of understanding sounds in words) is part manipulation and awareness but also the ability to hold on to and retrieve sounds in words. Phonological processing is the single most important skill that separates good readers from poor readers and can be tested as early as 4 years old. Phonological processing is a combination of visual processing (seeing), auditory processing (hearing), and knowledge of oral motor mouth movements (feeling.)

- If a perfect score ( all 8 items correct) as determined by SoundWise DX computer program AI grader, pediatrician, or authorized personnel, then recommend the child use enrichment activities with SoundWise DX AI/AI-Generative 4 year old Receptive/Expressive language/sound discrimination modules (Modules are preceded by a short video explaining the lesson to be learned followed by AI/AI-Generative Online recommendation algorithm) and/or worksheets for learning advanced skills
- Concern or Fail:: Unable to do 1 to 3 items (less than 50% wrong on sound discrimination items) SoundWise DX score is determined by SoundWise DX computer program AI grader, pediatrician, or authorized personnel,
  - Caregiver/teacher works on Phonological awareness skills using SoundWise DX 4 Year Old Developmental Milestone Information Sheet (DMIS)
  - START SoundWise DX AI/AI-Generative Online 4 year old Receptive/Expressive language/Sound discrimination/phonological processing/expressive modules (Modules are preceded by a short video explaining the lesson to be learned followed by AI/AI-Generative Online

Fig. 13B

SoundWise Dx™
Pediatric Neurodevelopmental Assessment
Developed by Pediatricians

4 year old Assessment Guided Treatment Flow Chart Form A or B recommendation algorithm)and/or worksheets that focus on Phonological Awareness/processing and receptive/expressive language skills.

- Multiple SoundWise DX modules will be performed until the child is able to demonstrate proficiency as determined by SoundWise DX computer program AI grader, pediatrician, or authorized personnel.
- If unable to pass the skill using the SoundWise DX modules and/or worksheets after 3 months of actively working on this skill then continued work with modules but also
  - Start in person Speech and Language Therapy focusing on improving phonological awareness/ processing/sound discrimination
  - Prescriptions for speech and language will be given through SoundWise DX or Pediatrician/Provider

- Fail: If misses 4 or more (50% or greater on sound discrimination items), SoundWise DX score is determined by SoundWise DX computer program AI grader, pediatrician, or authorized personnel,
  - Caregiver/teacher/authorized personnel works on Phonological awareness skills using SoundWise DX 4 Year Old Developmental Milestone Information Sheet (DMIS)
  - START SoundWise DX AI/AI-Generative Online 4 year old Receptive/Expressive Language/Sound discrimination modules that focus on Phonological Awareness/processing/sound discrimination skills and Receptive/Expressive language skills.
  - Multiple SoundWise DX modules will be performed until the child is able to demonstrate proficiency as determined by SoundWise DX computer program AI grader,Pediatrician, or authorized personnel. In Addition:
  - Start in person Speech and Language Therapy focusing on improving receptive/expressive/phonological awareness/Sound Discrimination
  - Prescriptions for speech and language will be given through SoundWise DX or reach to your Pediatrician/Provider.
  - SoundWise DX will administer or recommend local referral for an assessment that looks at early literacy skills such as the Comprehensive Test of Phonological Processing CTOPP-2 or Test of Preschool Literacy Skills (TOPEL), or any other standardized assessment (most current version) that measures awareness and/or phonological processing.
  - Multiple SoundWise DX modules will be performed until the child is able to demonstrate proficiency as determined by SoundWise DX computer program AI grader, Pediatrician, or authorized personnel

Sound Order Awareness Skills:

Fig. 13C

SoundWise Dx™
Pediatric Neurodevelopmental Assessment
Developed by Pediatricians

4 year old Assessment Guided Treatment Flow Chart Form A or B

The ability to recognize the sound order in words specifically looking at which sounds are first, middle, or last.

We take into account AI algorithms to recognize, transcribe a child's letter sound/word pronunciation, analyze context/structure where pronunciation varies due to accents/dialects and word/sentence structure comprehension and fluency.

- If a perfect score (all 8 items correct) as determined by SoundWise DX computer program AI grader, pediatrician, or authorized personnel, then recommend the child use SoundWise DX AI/AI-Generative 4 year old Receptive/Expressive language/ sound order awareness/phonological processing/awareness modules (Modules are preceded by a short video explaining the lesson to be learned followed by AI/AI-Generative Online recommendation algorithm) and/or worksheets for learning advanced skills

- Concerns or Fail: Unable to do 1-3 or more (less than 50% wrong on sound order awareness items) SoundWise DX score is determined by SoundWise DX computer program AI grader, pediatrician, or authorized personnel,
  - Caregiver/teacher/or authorized personnel work on Phonological awareness with using SoundWise DX 4 Year Old Developmental Milestone Information Sheet (DMIS)
  - START SoundWise DX AI/AI-Generative Online 4 year old Receptive/Expressive/phonological processing/awareness Language/Sound order Awareness modules(Modules are preceded by a short video explaining the lesson to be learned followed by AI/AI-Generative Online recommendation algorithm) that focus on phonological awareness and phonological processing/Receptive/Expressive Language to build stronger foundational skills for reading
  - Multiple SoundWise DX modules will be performed until the child is able to demonstrate proficiency as determined by SoundWise DX computer program AI grader, Pediatrician, or authorized personnel.
  - If unable to pass the skill using the SoundWise DX modules with 3 months of actively working on this skill then along with modules,
    - Start in person Speech and Language Therapy focusing on Receptive/Expressive language/improving phonological awareness and phonological processing. Prescriptions for speech and language will be given through SoundWise DX or reach out to your Pediatrician/Provider

- Fail :If misses 4 or more (50% or greater on sound articulation items), SoundWise DX score is determined by SoundWise DX computer program AI grader, pediatrician, or authorized personnel,
  - Caregiver/teacher/or authorized personnel work on Phonological awareness skills using SoundWise DX 4 Year Old Developmental Milestone Information Sheet (DMIS)

Fig. 13D

SoundWise Dx™
Pediatric Neurodevelopmental Assessment
Developed by Pediatricians

4 year old Assessment Guided Treatment Flow Chart Form A or B

- START SoundWise DX AI/AI-Generative Online 4 year old Receptive/Expressive Language/Sound order Awareness/phonological awareness/processing modules (Modules are preceded by a short video explaining the lesson to be learned followed by AI/AI-Generative Online recommendation algorithm) that focus on phonological awareness and phonological processing
- Start in person Speech and Language Therapy focusing on improving Receptive/Expressive/ phonological awareness and phonological processing to build stronger foundational skills for reading
- Prescriptions for speech and language will be given through SoundWise DX or local health care facility
- SoundWise DX will administer or local referral for an assessment that looks at early pre literacy skills such as the Comprehensive Test of Phonological Processing CTOPP-2 or Test of Preschool Literacy Skills (TOPEL), or any other standardized assessment (most current version) that measures awareness and/or phonological processing.
- Multiple SoundWise DX modules will be performed until the child is able to demonstrate proficiency as determined by SoundWise DX computer program AI grader, Pediatrician, or authorized personnel

Fine Motor Skills:

SoundWise DX will use AI determination of correct stroke/direction/pressure, speed, accuracy, and skill.

(4 total scored items that include correct pencil grip (no fisted grip), drawing animal either cat or dog, copies shape, and traces line):

- If a perfect score on Fine Motor with correct pencil grip, as determined by SoundWise DX computer program AI grader, pediatrician, or authorized personnel,
then recommend the child use enrichment Occupational Therapy modules with SoundWise DX AI/AI-Generative 4 yr old occupational therapy modules) and/or worksheets for learning advanced skills. SoundWise DX will use AI determination of correct stroke/direction/pressure, speed, accuracy, and skill.

Fine motor skills listed include, for example,the equivalent of the following (but not limited to) drawing animals, copying shapes, drawing line and correct pencil grip (which can be expanded to other skills in the future)

Fig. 13E

SoundWise Dx™
Pediatric Neurodevelopmental Assessment
Developed by Pediatricians

4 year old Assessment Guided Treatment Flow Chart Form A or B

- Concerns or Fail: Unable to draw item 1 (< 50% completed incorrectly) SoundWise DX score is determined by SoundWise DX computer program AI grader, pediatrician, or authorized personnel,
  - Caregiver/teacher/or authorized personnel will work on drawing with correct pencil grip using SoundWise DX 4 Year Old Developmental Milestone Information Sheet (DMIS)
  - Fine motor skills listed includes, for example, the equivalent of the following (but not limited to):draw cat with 3 or more parts, copies shape,trace the line within the box and demonstrates pencil grip (which can be expanded to other skills in the future).
- START SoundWise DX AI/AI-Generative Online 4 year old Occupational Therapy modules (Modules are preceded by a short video explaining the lesson to be learned followed by AI/AI-Generative Online recommendation algorithm) and/or worksheets on how to draw figures, copy shapes, trace lines, and use of correct pencil grip with AI determination of correct stroke/direction/pressure, speed, accuracy, and skill.
- Start in person OT services
  - Prescriptions for speech and language will be given through SoundWise DX or a child's Pediatrician/Provider.
  - Some children will wear gloves where computer will analyze proper technique with digitized feedback
- Multiple SoundWise DX modules will be performed until the child is able to demonstrate proficiency as determined by SoundWise DX computer program AI grader, Pediatrician, or authorized personnel.

Letter Naming/Letter Sound:

Knowing basic phonic rules of how a specific sound relates to a specific letter is an important part of mastering the alphabetic code.

We take into account AI algorithms to recognize, transcribe a child's letter sound/word pronunciation, analyze context/structure where pronunciation varies due to accents/dialects and word/sentence structure comprehension and fluency.

SoundWise DX will use AI determination of correct stroke/direction/pressure, speed, accuracy, and skill.

- If a perfect score (all 16 letter and sound identification items correct) as determined by SoundWise DX computer program AI grader, pediatrician, or authorized personnel, then recommend the child use enrichment modules with SoundWise DX AI/AI-Generative 4 year old letter naming and letter sound identification/letter sound skill modules (Modules are preceded by a short video explaining the lesson to be learned followed by AI/AI-Generative Online recommendation algorithm) and/or worksheets for learning advanced skills

Fig. 13F

SoundWise Dx™
Pediatric Neurodevelopmental Assessment
Developed by Pediatricians

4 year old Assessment Guided Treatment Flow Chart Form A or B

- Concerns or Failure to do 1-3 items (less than 50% wrong on letter names or letter sounds) SoundWise DX score is determined by SoundWise DX computer program AI grader, pediatrician, or authorized personnel,
  - Caretaker/teacher/ or authorized personnel work on letter naming/letter sound skills using SoundWise DX 4 Year Old Developmental Milestone Information Sheet (DMIS)
  - START SoundWise DX AI/AI-Generative Online 4 year old letter naming/letter sound modules/phonological processing/awareness (Modules are preceded by a short video explaining the lesson to be learned followed by AI/AI-Generative Online recommendation algorithm) and/or worksheets that focus on letter naming and letter sound identification skills along with phonological awareness skills
  - Multiple SoundWise DX modules will be performed until the child is able to demonstrate proficiency as determined by SoundWise DX computer program AI grader, Pediatrician, or authorized personnel.
  - If unable to pass the skill using SoundWise DX modules within 3 months of actively working on this skill then include along with modules
    - Start in person Speech and Language Therapy focusing on improving phonological awareness/ processing/letter identification/sounds as needed
    - Prescriptions for speech and language will be given through SoundWise DX or Pediatrician/provider.

- Fail:If misses 4 or more items (greater than 50% wrong) on either letter names or on letter sounds, SoundWise DX score is determined by SoundWise DX computer program AI grader, pediatrician, or authorized personnel,
  - Caregiver/teacher/ or authorized personnel work on letter naming/letter sound using SoundWise DX 4 Year Old Developmental Milestone Information Sheet (DMIS)
  - START SoundWise DX AI/AI-Generative Online 4 year old letter naming/letter sound/Phonological Awareness/processing modules (Modules are preceded by a short video explaining the lesson to be learned followed by AI/AI-Generative Online recommendation algorithm) and/or worksheets that focus on letter naming and letter sound identification skills along with phonological Processing/awareness skills
  - Start in person Speech and Language Therapy focusing on improving phonological awareness and processing is needed along with letter sounds/naming
  - Prescriptions for speech and language will be given through SoundWise DX or Pediatrician/Provider
  - SoundWise DX will administer or local referral for an assessment that looks at early pre literacy skills such as the Comprehensive Test of Phonological Processing CTOPP-2 or Test of Preschool Literacy Skills (TOPEL), or any other standardized assessment (most current version) that measures awareness and/or phonological processing.

Fig. 13G

SoundWise Dx™
Pediatric Neurodevelopmental Assessment
Developed by Pediatricians

4 year old Assessment Guided Treatment Flow Chart Form A or B

- Multiple SoundWise DX modules will be performed until the child is able to demonstrate proficiency as determined by SoundWise DX computer program AI grader, Pediatrician, or authorized personnel.

Phoneme Elision (sound deletion):

Phoneme Elision means to take away a sound and is one of the strongest predictors that a child will go on to struggle in reading. It can be tested as early as 4 years old.

We take into account AI algorithms to recognize, transcribe a child's letter sound/word pronunciation, analyze context/structure where pronunciation varies due to accents/dialects and word/sentence structure comprehension and fluency.

- If a perfect score as determined by SoundWise DX computer program AI grader, pediatrician, or authorized personnel, then recommend the child do enrichment with SoundWise DX AI/AI-Generative 4 year old Phonemic elision/Receptive/Expressive language skill modules (Modules are preceded by a short video explaining the lesson to be learned followed by AI/AI-Generative Online recommendation algorithm) and/or worksheets for learning advanced skills
- Concerns or Fail :Failure to do 1 to 3 items only (less than 50% wrong on phoneme elision) SoundWise DX score is determined by SoundWise DX computer program AI grader, pediatrician, or authorized personnel,
    - Work on Phonological awareness/Receptive/Expressive language skills with a caregiver/ teacher using SoundWise DX 4 Year Old Developmental Milestone Information Sheet (DMIS)
    - START SoundWise DX AI/AI-Generative Online 4 year old phoneme elision/Receptive/Expressive/phonological processing/awareness language modules (Modules are preceded by a short video explaining the lesson to be learned followed by AI/AI-Generative Online recommendation algorithm) and/or worksheets that focus on Phonological Awareness/processing/phonemic elision skills
    - Multiple SoundWise DX modules will be performed until the child is able to demonstrate proficiency as determined by SoundWise DX computer program AI grader ,Pediatrician, or authorized personnel.
    - If unable to pass the skill using the SoundWise DX modules with 3 months of actively working on this skill then include along with modules,
        - In person Speech and Language Therapy focusing on improving phonological awareness and phonological processing/receptive/expressive language skills
        - Prescriptions for speech and language will be given through SoundWise DX or Pediatrician/Provider

Fig. 13H

SoundWise Dx™
Pediatric Neurodevelopmental Assessment
Developed by Pediatricians

4 year old Assessment Guided Treatment Flow Chart Form A or B

- Multiple SoundWise DX modules will be performed until the child is able to demonstrate proficiency as determined by SoundWise DX computer program AI grader, Pediatrician, or authorized personnel.

- Fail:If misses 4 or more (50% or greater on phoneme elision items): SoundWise DX score is determined by SoundWise DX computer program AI grader, pediatrician, or authorized personnel,
  - Caregiver/teacher work on Phonological awareness skills using SoundWise DX 4 Year Old Developmental Milestone Information Sheet (DMIS)
  - START SoundWise DX AI/AI-Generative Online 4 year old on Phoneme Elision/Receptive/Expressive language/phonological processing/awareness(Modules are preceded by a short video explaining the lesson to be learned followed by AI/AI-Generative Online recommendation algorithm) and/or worksheets modules on phoneme elision that focus on Phonological Awareness/processing skills
  - In person Speech and Language Therapy focusing on improving phonological awareness and phonological processing
  - Prescriptions for speech and language will be given through SoundWise DX or Pediatrician/Provider.
  - SoundWise DX will administer or local referral for an assessment that looks at early pre literacy skills such as the Comprehensive Test of Phonological Processing CTOPP-2 or Test of Preschool Literacy Skills (TOPEL), or any other standardized assessment (most current version) that measures awareness and/or phonological processing.
  - Multiple SoundWise DX modules will be performed until the child is able to demonstrate proficiency as determined by SoundWise DX computer program AI grader, Pediatrician, or authorized personnel.

Engagement:

*Any and all diagnoses of psychiatric/behavioral disorders (ADHD, Autism, Anxiety, depression etc, will follow and change accordingly with the most current medical guidelines determined by the latest version of the Diagnostic and Statistical Manual of Mental Disorders which is currently the DSM-V. As new versions are published, SoundWise DX concerns identified and diagnostic criteria will adapt and be changed to match the most current diagnostic criteria.*

Perfect score:

- Able to demonstrate social communication, interaction , eye contact and able to demonstrate joint attention back and forth with assessment tasks. Not showing restrictive and repetitive behaviors, such as flapping their hands, spinning a lot, only interested in lining up toys or objects, sensory issues such as upset with loud noises, and difficulty with change of routine during the assessment.
- Able to sustain attention, not easily distracted, following directions on Assessment tasks.

Fig. 13I

SoundWise Dx™
Pediatric Neurodevelopmental Assessment
Developed by Pediatricians

4 year old Assessment Guided Treatment Flow Chart Form A or B

- Attending the SoundWise DX assessment without crying and worrying about how they are doing with each task.
- Engagement evaluation is determined by SoundWise DX computer program AI grader, pediatrician, or authorized personnel.

A concern or fail for this section:

- Autism Concern:
  - The child has challenges with social communication and interaction. Has poor eye contact, refusal to engage in tasks, and/or lack of joint attention back and forth while doing assessment tasks.
  - The child demonstrates restrictive/repetitive behaviors, interests, and activities such as, but not limited to, flapping hands, spinning, lining up toys/objects, sensory issues (upset by loud noises/smell/touch), and challenges with change of routine during tasks.
- ADHD/ADD/attention deficits: Please note that ADHD diagnosis is made at age 4
  - The child is unable to keep their attention and/or unable to follow directions while completing Assessment without being distracted and/or unable to sit still long enough to complete assessment at age 3 years old, note that a formal diagnosis is not made at age 3, rather only a concern. Children who are inattentive and also exhibit staring spells, need to be evaluated for Absence Seizures. SoundWise DX will offer RX or pediatrician/provider for Neurology referral.
    - Norm values:
      - 3 years old: 6-8 minutes
      - 4 years old: 8-12 minutes
      - 5 and 6 years old: 12-18 minutes
      - 7 and 8 years old: 16-24 minutes
      - 9 and 10 years old: 20-30 minutes
- Anxiety, panic attacks, or Post Traumatic Stress Disorder (PTSD) Concern or Fail:
  - The child is showing emotions of frustration with or without crying and/or demonstrating worry about their performance while completing the assessment.
  - Elevated heart rate and/or blood pressure measured by all digital devices
  - Avoidance behaviors when tasks are hard such as:
    - Child complains or somatic (body) complaints to end or get out of a task like:
      - Headaches
      - Nausea, stomach aches, vomiting
      - Tiredness, yawning, falling asleep
      - Tense posture, clenched shoulders or muscles, clenched teeth
      - Pulling on eyelashes, biting fingers or fingernails
      - Arguing, throwing the materials, leaving the test environment
      - Saying they are thirsty, hungry, tired, sleepy, or having to all of a sudden got to go to the bathroom
      - Complains of their heart racing
      - Child is unable to attempt assessment in part or at all.
      - Any other related complaints by the child not listed above.

Fig. 13J

SoundWise Dx™
Pediatric Neurodevelopmental Assessment
Developed by Pediatricians

4 year old Assessment Guided Treatment Flow Chart Form A or B

- Children who do not attempt Assessment will need to to start SoundWise DX AI/AI-Gen engagement modules and a reassessment will be attempted in 1 to 3 months time as per SoundWise DX AI/AI-Gen grader.
- Engagement results are determined by SoundWise DX AI/AI-Gen computer program AI grader, Pediatrician, or authorized personnel.
- Engagement modules cover issues regarding attention, anxiety, autism, or other disorders as discussed below.
    - START SoundWise DX AI/AI-Generative Online 4 year old online Module for lack of engagement (Modules are preceded by a short video explaining the lesson to be learned followed by AI/AI-Generative Online recommendation algorithm) and/or worksheets. The Lack of Engagement modules deliver Speech & Language, Occupational Therapy, Physical Therapy and Behavioral Modification suggestions for building engagement.
    - As the child attends the Lack of Engagement modules, SoundWise DX AI/AI-Gen grader will determine the correct SoundWise DX modules for each individual child.
        - Lack of Engagement SoundWise DX modules include:
            1. Autism diagnostic evaluation through SoundWise DX and/or referral for autism diagnoses through a child's local medical services
            2. Attention Deficit/ADHD behavioral concerns/anxiety
                a. Continue to follow closely, make learning activities fun/engaging, limit activities to short segments.
                b. If severe behavioral issues or anxiety present: referral to child psychologist or for Play Therapy.
                c. Age 4 and older, refer to specific for ADHD module for further recommendations
            3. Modules for other recognized disorders such as post traumatic stress disorder, genetic disorders associated with learning disabilities, environment exposure to lead, fetal alcohol syndrome, Adoption and/or foster care population, proper nutrition, developmental delay, sensory issues, and other situations resulting in childhood developmental delay in need of intervention.
            4. Along with participating in Engagement modules, the following will be provided:
                - Refer for a in-person Speech and Language Evaluation focusing on building strong receptive/expressive language skill
                - Refer for an in person Sensory Integration Focused Occupational Therapy Evaluation focusing on motor integration, oral motor kinesthetics, proprioceptive skills, and sensory regulation..
                - Refer for an in person Physical therapy focusing on building strong gross motor skills.
                - Refer for in person evaluation for Autism
                - Refer for Genetics evaluation
                - Prescriptions for the above services will be provided by SoundWise DX or local health care facility.

- Specific SoundWise DX modules for Autism, ADHD/ADD, and Anxiety:

Fig. 13K

SoundWise Dx™
Pediatric Neurodevelopmental Assessment
Developed by Pediatricians

4 year old Assessment Guided Treatment Flow Chart Form A or B

1. Autism: Autism presents challenges with social communication and interaction. They do not talk a lot because they are not motivated to socially interact. They have challenges with eye contact and are unable to demonstrate joint attention, not able to play a back and forth game or do SoundWise DX assessment tasks. They show restrictive and repetitive behaviors, such as flapping their hands, spinning a lot, only interested in lining up toys or objects, sensory issues such as being upset with loud noises, wanting to smell things and not wanting to play pretend. Children with Autism also have difficulty with change of routine for example, having a new teacher, or driving a new route home and difficulty changing tasks during the SoundWise DX assessment.
    - Determination of Autism by SoundWise DX computer program AI grader, pediatrician, or authorized personnel will recommend the following:
    - Recommended activities and/or worksheets generated in the modules will address the specific concerns of lack of engagement/ language delay affecting social interaction, high concerns for Autistic Spectrum Disorder (ASD), or ASD confirmed by meeting the diagnostic criteria for ASD as per the most current version of the DSM which is currently the DSM-V. This will includes activities that focus on but or not limited to the following:
        - To strengthen receptive, expressive, and pragmatic language skills
            - Specific games and activities addressing language goals
        - To improve sensory regulation
            - Specific games and activities to decrease sensory triggers whether they be hypo(low) or hyper(high) sensory
            - Recommendation to address sensory seeking behaviors and/or sensory avoidance behaviors
            - Occupational Therapy (OT) like play activities with OT therapy goals addressing visual/motor integration, sensory regulation, visual perceptual skills, executive function, and primitive reflex integration)
        - To improve fine motor skills
            - Specific games and activities to improve any fine motor skills or hand skill ability like but not limited to the following (handwriting, cutting, folding, stringing beads, coloring, drawing, gluing, buttoning, using utensils, etc.
        - To improve gross motor skills
            - Specific games and activities to strengthen gross motor movements that includes focusing on balance, coordination, ball skills (dribbling, throwing,catching, etc.), hand eye coordination, same side and alternating side body movements, body schema activities (proprioceptive, vestibular, tactile, and body awareness)
            - Physical Therapy (PT) therapy like activities with PT gross motor goals
        - To improve social and pragmatic language skills
            - Specific group play therapy along with games and activities promoting opportunity for improved and guided social interaction
                - Group play therapy
                - Applied Behavioral Analysis Therapy

Fig. 13L

SoundWise Dx™
Pediatric Neurodevelopmental Assessment
Developed by Pediatricians

4 year old Assessment Guided Treatment Flow Chart Form A or B

- Increased peer group interactions.

- In situations where anxiety or family connections are more calming, the avatar (computer generated face and/or voice used) could be that of a person familiar to the individual) when the assessment or enrichment activities are delivered on the SoundWise DX platform.
- SoundWise DX modules can be used to treat and strengthen skills along with in person therapy especially when waiting for in person therapy. Using SoundWise DX modules will start therapeutic advancement of identified skill deficits while at home when awaiting in person therapies. They can also be used to augment and reinforce the actual future or current therapies in place like medically delivered Speech and Language Therapy, OT, Cognitive Behavioral Therapy, and PT.
- Engagement modules and/or worksheets allow Early Intervention to immediately start while a child awaits for in person evaluation and/or in person autism specific therapy.
- SoundWise DX modules and/or worksheets will improve skills and reassessment will allow progress. Children should continue using the modules and/or worksheets even after starting in-person therapy.
- Referral when indicated per AI/AI generated Algorithm
  - Refer for a in person Speech and Language Evaluation
  - Refer for a in person Sensory Integration Focused Occupational Therapy Evaluation
  - Refer for an in person Diagnostic Evaluation for Autism
  - Refer for in person Child Play Therapy

- Pursue all therapies covered by medical insurance while at the same time caregivers/ teachers work on language skills, social interaction, developmental milestones, and sensory regulation using SoundWise DX 4 Year Old Developmental Milestone Information Sheet (DMIS) for age appropriate activities.
- Recommendations will include prescriptions for in person services generated through SoundWise DX.
- Suggestions to seek specialized diagnostic evaluations when indicated by SoundWise DX AI/AI-Gen Grader will include follow up with the child's primary care medical provider, and specialty referrals.
- As part of the diagnostic process, SoundWise DX will administer and score standardized validated screeners as age appropriate such as but not limited to the MCHAT, ASQ, PEDS Form, Vanderbilts, Denver Developmental assessments, Conners Forms, Scat etc)
- While Autism may be the primary diagnosis or concern, other coexisting conditions like anxiety or ADHD and/or genetic disorders may exist. If a validated screening as discussed above elicits concerns for other disorders, the appropriate referral will be done through SoundWise DX.

2. For Attention Deficit Hyperactivity Disorder Concerns (ADHD/ADD):
   - While ADHD is not diagnosed until age 4 years or older, a behavioral modifications SoundWise DX module for 4 year old Behavioral Basics will be given that focuses tips on a structured environment, making learning

Fig. 13M

SoundWise Dx™
Pediatric Neurodevelopmental Assessment
Developed by Pediatricians

4 year old Assessment Guided Treatment Flow Chart Form A or B activities fun, multisensory activities, and short but repetitive opportunities for learning.

- If engagement is appropriate, but focus/attention to a task cannot be maintained for the age expected time for this age (8-12 minutes), then refer to SoundWise ADHD/ADD age specific questions and holistic consideration of all factors that can affect attention and sustained focus.
- Children with ADHD/ADD have a hard time paying attention, daydreaming and often do not seem to listen. They are easily distracted from work and play and often do not pay attention to details/disorganization and do not follow through on directions. Prone to losing a lot of important things/forgetting things and avoids doing things that require mental effort. Having the hyperactivity component makes them prone not being able to stay seated, squirming a lot, talking too much, unable to play quietly and will jump, run and climb when not permitted to do so. They will demonstrate impulsivity, calling out without question being complete, Acts or speaks without thinking, Interrupting others often, trouble taking turns, cannot wait for things and may run onto street without looking out for traffic.
    - SoundWise DX AI/AI Gen grader will administer and score a Vanderbilt screen for parent and teacher if applicable). These screens are diagnostic of ADHD/ADD.
        - Visual attention and focus: SoundWise RX AI/Gen AI computer grader will derive objective and quantitative results for example gaze direction, dwell time, and glance frequency off the assessment site to other objects and locations. While monitoring eye tracking, we will measure where and for how long an individual looks in a certain direction or at a certain target, it is not a measure of actual visual attention However, this information can be used to necessitate further exploration into attention or focus disorders like ADHD/ADD. The SoundWise RX screen eye tracking will be used to assess student attention while taking the test. Just as eye tracking is the go-to method when determining driver distraction via glance target classification it can be used to assess attention to the assessment attention engagement in the test itself, or also suggest more analysis of visual tracking/perception/or processing is warranted.
- When above condition concerns are found, AI/AI-Gen computer program modules and/or worksheets for evaluation and guidance/ for ADHD/ADD will be generated. Further informational sheets on factors that can impact attention will be generated and given to the caregivers.
- Modules for scholastic accommodations such IEP, 504 and not limited to will also be given that can be effectively be used within a child's Individual Educational Plan (IEP) or 504 Plan.

Fig. 13N

SoundWise Dx™
Pediatric Neurodevelopmental Assessment
Developed by Pediatricians

4 year old Assessment Guided Treatment Flow Chart Form A or B

- When formal diagnosis of ADHD for age 4 years old and older has been given, then information regarding evaluation for behavioral modification will be given.
- Starting at age 4 or older, medication for ADHD/ADD when indicated by SoundWise DX AI/AI-Gen and/or caregiver/teacher. Blood pressure. Pulse, EKG rhythm strip will be administered through all digital devices, along with telemedicine visit with SoundWise DX before medication is given.. Pathways towards diagnostic evaluation will be done according to the specific laws in each state.
- Classroom modifications and accommodation recommendations would be produced via SoundWise DX module via AI/AI-Gen and given via SoundWise DX according to the specific laws in each state.

3. Anxiety:
   - A diagnosis of Anxiety is when a child is worried or scared and it interferes with their everyday activities such as refusing to go to school, playing with friends,especially at recess or at social gatherings, getting to sleep and/or not being able to sleep alone in their bed. They may say their heart is beating too fast, or they have a stomach ache and shaking, maybe having trouble breathing, start to sweat and suddenly are unable to sustain attention and want to find a safe place, like home or a caregiver. See specific symptoms that were listed above in "what constitutes a fail". Anxiety may have been exhibited itself as shyness during the child's early years, or occur after a traumatic event experienced/ witnessed by the child or the child may be a victim of abuse by a caregiver or other.
   - There are 4 types of Anxiety present in children;
     - Social Anxiety-Difficulty playing or being with others, especially in school, will speak softly not wanting to be heard and will not volunteer to raise hand in school or participate in group activities.
     - Separation Anxiety- Unable to separate from the caregiver, wanting to always be in their presence, not wanting to go to school or be on a playdate.
     - Selective Mutism- severe anxiety-speaks at home but not anywhere else. Has early onset.
     - Generalized Anxiety-Strives to be perfect,worries about the past, current events and the future a lot and worries about what may happen in school in their school work or other activities. They may get diagnosed with ADHD, however this child can not pay attention due to worry, rather than attention.
   - The child may demonstrate Anxiety during SoundWise DX by being concerned about getting the assessment tasks correct or simply not speaking. They may cry and turn away and say they are afraid to continue.
   - SoundWise DX AI/Gen-AI will determine through an anxiety algorithm module and/or caregiver/teacher or authorized personnel to start Anxiety SoundWise DX modules as well to start arranged telemedicine visits through SoundWise DX and/or in person therapy.
   - Also the Caregiver/teacher will work on language development, social interaction, and sensory regulation by using SoundWise DX 3 Year Old Developmental Milestone Information Sheet (DMIS) for age appropriate activities.
   - SoundWiseDX will administer and score a diagnostic screen such as PHQ-9/SCARED/Columbia/Hamilton/GAD-7 for Anxiety that is appropriate for age.
   - Based on SoundWiseDX AI/AI-Gen Children will also be started on telemedicine services through SoundWise DX for anxiety.

Fig. 13O

SoundWise Dx™
Pediatric Neurodevelopmental Assessment
Developed by Pediatricians

4 year old Assessment Guided Treatment Flow Chart Form A or B

- Reasons for indications for medicine management for Anxiety is determined by SoundWise DX AI/AI-Gen, physician, and input from caregiver/teacher. Pulse, Blood Pressure and EKG will be obtained by digital devices and are medically necessary before starting medication. Telemedicine services for anxiety though SoundWise DX must also be initiated and continued while the child is on medication for anxiety.
- All children diagnosed with Anxiety through SoundWise DX AI/AI-Gen will also be evaluated for ADHD/ADD and/or Autism

4. Low Self Esteem

- Self esteem should always be monitored closely in a child as this can lead to depression or other mental health disparities in the future.
- Low self esteem can arise from a variety of reasons.
- A soundWise DX Module AI/AI-Gen will be given that addresses building self esteem and confidence in a child.
- Telemedicine visits will be recommended via SoundWise DX or their local provider

- Reassessments SoundWise DX:
  - SoundWise DX will offer reassessments (Form B's) after 3 months of module implementation. Initial assessments are Form A.
  - In 3 months or less depending upon the discretion of SoundWise DX AI/AI-Gen computer program AI grader, pediatrician, and/or authorized personnel, the child will retake an assessment
    - If the child is still the same age, they will then take that age years Form B
    - If they have aged up and are now 1 year older, then they will take the next year's assessment Form A.
    - If a child is able to pass some, but not all, or if unable to pass the repeat pediatric assessment, they must follow through with the same algorithm as above until proficiency is determined by SoundWise DX computer program AI grader, pediatrician, or authorized personnel.
    - If the child is able to pass all parts of the new assessment, they should do SoundWise DX enrichment modules based on age group.

Fig. 13P

SoundWise Dx™
Pediatric Neurodevelopmental Assessment
Developed by Pediatricians

4 Year Old Developmental Milestone Information Sheet 4 year olds are enthusiastic explorers. They happily will tell you what they are thinking. They display boundless energy and a curiosity that does not cease. A 4 year old starts to show the ability to feel and express emotion, experience the joy of friendship, and the discovery of make believe along with "magical thinking." They enjoy telling a story, often interrupting a conversation without realizing it. Often they demand to know what, when, why and how about everything. It is also not uncommon for a 4 year old to lie or fail to take responsibility for their actions. They often test the limits of their parents or siblings.

They look forward to the opportunities of social interaction at preschool along with experiential learning. Navigating and understanding how to respond to conflict can be challenging at times especially as they are learning to regulate their emotions. They respond very well to praise and will be more emotionally regulated when boundaries are clearly stated. As they learn to navigate and feel comfortable with "the rules of different situations", they develop the confidence to become more independent.

A typical 4 year old asks lots of questions. It is important to answer them in short simple answers. Understand that at this age they are very sensitive, want to please, are easily encouraged, but can also become hurt by others actions. Show them how to navigate social situations by demonstrating appropriate behaviors like apologizing if someone has been hurt, good sportsmanship like congratulating a person who makes a good move during a game, and praising the ability to understand others feelings.

SoundWise DX guides parents to prepare their children to be school ready. It is important to enroll your 4 year old in structured learning experiences with other children their age like preschool, community programs, playgroups, or other social activities. School readiness starts from birth and develops from every past experience, social interaction, learning about the world around them.

Fig. 14A

SoundWise Dx™
Pediatric Neurodevelopmental Assessment
Developed by Pediatricians

What a typical 4 year old should be able to do.

Language Communication Milestones

- Asks a lot of When and How questions.
- Able to say 4 word sentences with multiple sentences together
- Typically 1500+ word vocabulary
- When speaking, over 95% percent is understandable to strangers
- Follows simple directions, especially when playing board games or navigating environments
- Identifies basic shapes and colors
- They know their first name, discover their gender
- Has an interest in words
- Is able to point out letters and separate the first letter from the beginning of a word; for example, This is P like in Pet.
- Can play with sounds in words by rhyming or making up words that start with the same sounds.
- Stuttering can be normal as long as it doesn't frustrate them or persist longer than 6 months

Important Tip

Limit television and mobile devices no more

Social Emotional Milestones

- Able to pretend play (be a dog, be a painter, be a teacher)
- Asks to play with others
- Comforts others who are hurt or sad like giving a crying friend a hug.
- Avoids dangerous things like jumping from a tall height on a playgrounds
- Loves to be a "helper"
- Can change behavior based on where they are (like being quiet in a library, sitting in a place of worship, actively exploring equipment on a playground)

Tips for play and learning!

- Be interactive
- Use your environment
- Let it be multisensory (touch, feel, say, smell, see, and hear)
  Listen to sounds of the ocean birds, busy city streets, feel the fur of your pet, tree bark see the sunrise, and how the clouds in the sky are in different shapes
- Learning is fun!

Fig. 14B

SoundWise Dx™
Pediatric Neurodevelopmental Assessment
Developed by Pediatricians than 3 hrs per day.

- Every opportunity to play is an opportunity to learn
- Keep learning at 10 minutes multiple times during the day Cognitive Milestones
(Learning, Thinking, Problem-Solving)

- Draws a person with 3 or more body parts
- Begins to be able to play board games.
- Begins to know what might come next in a story
- Know what to do in certain situations like if they are cold or hungry
- Identify a few colors
- Should be able to pay attention to a task for 8-12 minutes Gross Motor Movement/Physical Milestones

- Catches an easily thrown ball most of the time
- Serves themselves food or pours water, with adult supervision
- Walks up and down stairs on their own alternating feet
- Hopping on each foot and balance on each foot for 2 seconds
- Skip
- Kick a ball
- Throw a ball overhand easily
- Able to ride a bicycle with training wheels
- Build an 8 block tower Fine Motor Milestones

- Draw a square
- Can cut out a picture using scissors & string items together like beads
- Putting on clothes properly
- Manage a spoon and for neatly while eating a fork/spoon

Fig. 14C

SoundWise Dx™
Pediatric Neurodevelopmental Assessment
Developed by Pediatricians

- Unbuttons some buttons
- Hold a crayon or pencil between fingers and thumb (not with a fist grip)
- Brushes own teeth
- Copies a cross
- Traces a line within a path
- Draws pictures you recognize

How to help your child build stronger skills.

Developing healthy communication skills such as learning to speak, understanding language, and eventually learning to read are key milestones that your child needs to reach so that they enjoy and engage in play, and become successful in school.

Babies learn language through simple exposure by listening and watching you speak to them. They quickly learn how sounds are put together in different ways and have a different meaning. This exposure to sounds is building two major language skills:

1. Receptive language (input) - what you understand.
2. Expressive language (output) - what you can say.

A child's exposure to language starts in utero. As babies, they then start to babble and observe how we speak by looking at our faces and how we move our mouth, lips, and tongue to make sounds. They quickly understand that sounds have meaning and they start to acquire language at an amazing pace. When they are 5 years old, they will present to kindergarten to learn higher level language skills, like reading, writing, spelling, and math. The strength of your child's early language foundation will directly relate to their future academic success and overall psychological well-being. Help them build a strong foundation for later scholastic and emotional success.

There are lots of simple things you can do that are fun and help build language skills;

- Sings songs
- Read to your child
  - Let them also point out pictures and name things on the page
  - Let them turn the pages of the book. Books with texture or that are interactive in some way can make things more interesting
  - Let them understand that the words or symbols on the page mean something
  - Ask questions about the things you read or talk about

Fig. 14D

SoundWise Dx™
Pediatric Neurodevelopmental Assessment
Developed by Pediatricians

- Let them use their own imagination and create their own stories too
- Work on identifying objects within their world and building language vocabulary
- Play games with sounds:
    - Like identifying how sounds are different or the same
    - Play rhyming games
    - Play repetition games with sounds
        - Like naming all the words that start with a similar sound
    - Identifying placement of sounds in words
        - "What's the 1st sound, what's the middle sound, what's the last sound in a word?
    - No need to associate the letters with the sounds at first. Just have fun with figuring out how to make different sounds. Look in a mirror. Watch how your mouth moves differently when you make different sounds.
    - Pick a sound a week. Play games where you point to or think of things that start with that same sound.
    - Only after your child really understands the sound will you add the letter. The sounds are actually more important than the letter at this age.
    - Let your child start to recognize the look of the letters that make up their first name.
- Talk to your child.
    - TV's and screens are not good substitutes. Limit screen time to 2 hours per day and do not put TV or computer devices in the bedroom
    - Talk about what you are doing as you are doing it
    - Repeat key concepts especially directional terms. For example: Let's find the BLUE shoes UNDER your bed.
- Tell children what you are doing and why. Talk, Talk, talk!
- Teach and show at the same time
    - For instance, here is the RED crayon, here is the yellow book
    - Play movement games like jumping UP and jumping down
    - Have fun as learning can be one great adventure and game
    - Children love to move, incorporate movement into exploration of their world
- Let children see your face as you are speaking
    - They need to know how the mouth moves to make different sounds
- Let your child tell the story in their own words. Their imaginations are entertaining!
- Ask your child questions as you tell a story. See if they are making a mental movie or picture while listening to the books or stories that you read to them.
- Let your child explore and use their imaginations.
- Teach language concepts with games.
    - Play hide & seek or find

Fig. 14E

SoundWise Dx™
Pediatric Neurodevelopmental Assessment
Developed by Pediatricians

- Play with objects and place them around the room. Then give the child directions to follow with spatial concepts to find the items. For example: Find the BLUE toy ON TOP of the BROWN chair. Find the toy UNDER the table.
    - Focus on one or two words or concepts at a time and then practice multiple times a day to really learn those words or concepts.
- Teach math concepts with games.
    - Quantify/Comparative concepts (small, medium, large, most/least, same/different, young/old, wet/dry, etc.)
    - Play games using blocks to build towers of different sizes and compare.
    - Compare the size of your hands and your child's hands, your shoes to theirs, etc.
    - Play with different numbers of things like food, blocks, or toys. Compare and contrast different amounts so your child starts to learn counting and math concepts.
- Let your child have opportunities to play with other children.
    - Interactive games allow them to learn about sharing, taking turns and following simple directions.
- Use music as an opportunity to sing, dance together, and express their feelings.
- Allow outside playtime to promote exercise and the understanding of their environment like naming objects around them.
- Allow them to experience what the wind feels like or what happens when you jump in a puddle of water, smell a flower, press on a squishy object, etc.
- Allowing your child to make choices, such as places to go or what to wear, encourages independence and development of their language skills.
- Encourage affection in your family and reinforce positive behavior.
- Set limits on behaviors that are not appropriate
- Resolve disagreements and disputes.
- Children need a structured loving environment. They also need to feel safe and loved.
- Encourage bedtime routines such as reading to your child.

What do sounds have to do with words in print, letters, and reading?

Learn those sounds! Practicing one new sound per week will strengthen your child's ability to eventually sound out words (decode). Decoding enables your child to sound out words so they do not have to guess. Accurate decoding is critically important tofuture reading success. It is the skill that separates good readers from poor readers.

Whenever you can, point out words wherever you go or in books so that your child recognizes that letters actually mean something. You can point to the print while you

Fig. 14F

SoundWise Dx™
Pediatric Neurodevelopmental Assessment
Developed by Pediatricians read. Play games like finding signs on buildings or street signs, or words on boxes at the supermarket. Reading to your child and pointing out words boosts vocabulary and advances knowledge.

You can teach letters but always teach the sound association with it.

Why does all this matter?

A person learns by experience and play. Give your child every opportunity to grow and learn. A strong grasp of language will give your child the ability to thrive in school and later in life. For it is the foundation that you build before 5 years of age that will be the platform from which learning will take place later on.

A strong foundation is built using the ability to play with, manipulate, hold onto, and retrieve sounds in words. That critical skill is called "sound processing." It is the skill that "good readers" do well and "poor readers" do not. So help your child accelerate into scholastic success and build a strong language foundation. And remember, those magical ingredients are sounds so play with them and have fun!

Fig. 14G

SoundWise Dx™
Pediatric Neurodevelopmental Assessment
Developed by Pediatricians

Age 5 years: Form A or B

Child:________________________________________DOB__________

Parent Part Completed By:______________________________________

1. Can you understand your child when they speak? □ Yes □ No □ Sometimes
2. Is your child able to rhyme well? □ Yes □ No □ Sometimes
3. Does your child follow simple directions well? □ Yes □ No □ Sometimes
4. Can your child name all their letters? □ Yes □ No □ Sometimes
5. Does your child attend a school? □ Yes □ No
6. Can your child play a game or do a task with you for 10 minutes? □ Yes □ No □ Sometimes
7. Does your child seem to hear ok? □ Yes □ No □ Sometimes 8. Does your child brush teeth on their own with toothpaste? □ Yes □ No □ Sometimes
9. Does your child walk down steps switching feet (no rail)? □ Yes □ No □ Sometimes
10. Does your child mix up sounds in words? □ Yes □ No □ Sometimes
11. Does your child have a hard time with sight words? □ Yes □ No □ Sometimes 12. Did your child ever need ear tubes? □ Yes □ No
13. Does anyone in your family have a hard time spelling? □ Yes □ No □ Sometimes
14. Does anyone in your family struggle with reading, have dyslexia, or does not read for fun? □ Yes □ No □ Sometimes

Fig. 15A

Copyright © 2024 All Rights Reserved

SoundWise Dx™

Pediatric Neurodevelopmental Assessment

Developed by Pediatricians

5 year old Assessment Form A

Age 5 yrs: Form A

Name: ______________________ DOB: ______________ Date:__________

*Administer in a quiet one-on-one setting with limited distractions.*

Receptive Language: (Have the child pick the picture that fits best)

- Show me the green circle on top of a red square ☐ Yes ☐ No
- Point to two small red circles ☐ Yes ☐ No
- Show me the blue triangle inside the yellow circle ☐ Yes ☐ No
- Show me the pink circle under the dark blue square. ☐ Yes ☐ No

Fine Motor: Please have the child do the following:

| | Done Correctly | |
|---|---|---|
| **Typical 3 point pencil grip** | ☐ Yes | ☐ No |
| **Colors circle within lines** | ☐ Yes | ☐ No |
| **Copies square** | ☐ Yes | ☐ No |
| **Draws line within rectangle** | ☐ Yes | ☐ No |

Letter Naming & Letter Sound

| | Say Letter Name | | Say Letter Sound | |
|---|---|---|---|---|
| S | ☐ Yes | ☐ No | ☐ Yes | ☐ No |
| O | ☐ Yes | ☐ No | ☐ Yes | ☐ No |
| V | ☐ Yes | ☐ No | ☐ Yes | ☐ No |
| N | ☐ Yes | ☐ No | ☐ Yes | ☐ No |
| B | ☐ Yes | ☐ No | ☐ Yes | ☐ No |
| H | ☐ Yes | ☐ No | ☐ Yes | ☐ No |
| E | ☐ Yes | ☐ No | ☐ Yes | ☐ No |
| K | ☐ Yes | ☐ No | ☐ Yes | ☐ No |

Fig. 15B

Copyright © 2024 All Rights Reserved

SoundWise Dx™

Pediatric Neurodevelopmental Assessment
Developed by Pediatricians

5 year old Assessment Form A

Age 5 yrs: Form A

Phoneme Elision (deletion) (Taking away a sound or sounds)

Directions: Say, *Let's play a game .*

Example: *Say "raindrop". Now say raindrop without saying "drop"* ............................

If correct, say, *That's right. Let's try the next one.*

If incorrect, say. *That's not quite right. Raindrop without saying drop is rain.*

1. *You say snowshoes. Say Snowshoes again,without saying "snow"* (shoes) ☐ Yes ☐ No
2. *You say Firefly. Say Firefly again, without saying "fire"* (fly) ☐ Yes ☐ No
3. *You say Hairbrush. Say Hairbrush again, without saying brush* (hair) ☐ Yes ☐ No
4. *You say heartbeat. Say Heartbeat again, without saying heart* (beat) ☐ Yes ☐ No
5. *You say box. Say Box again, without the /b/ sound (ox)* ☐ Yes ☐ No
6. You say *snug. Say snug again, without the /n/ sound* (sug) ☐ Yes ☐ No
7. *You say list. Say List again, without the /s/ sound (lit)* ☐ Yes ☐ No
8. You say *couch. Say couch again, without the /c/sound* (ouch) ☐ Yes ☐ No

Rhyming exercise

Do these words rhyme? (sound the same) *(For example, Sun and fun rhyme but sun and sat do not)*

1. met, let ☐ Yes ☐ No
2. rink, rock ☐ Yes ☐ No
3. cake, lake ☐ Yes ☐ No
4. list, mist ☐ Yes ☐ No
5. greet, grate ☐ Yes ☐ No
6. train, trip ☐ Yes ☐ No
7. twister, sister ☐ Yes ☐ No
8. spoon, small ☐ Yes ☐ No

Behavioral Observations: Please note the the child's demeanor during testing:

☐ Cooperative ☐ Smiling ☐ Shy ☐ Happy and engaged

☐ Uncooperative ☐ Crying ☐ Distractible ☐ English Language Learner

☐ Refusal to Interact ☐ Tired ☐ Anxious ☐ Difficult to motivate

☐ Completed Independently ☐ Needed Redirection for completion

☐ poor eye contact ☐ wouldn't engage ☐ Child's speech wasn't understandable

☐ Other____________________________________________

Fig. 15C

Copyright © 2024 All Rights Reserved

SoundWise Dx™
Pediatric Neurodevelopmental Assessment
Developed by Pediatricians

Age 5 Yrs: Form B

Name: ______________________ DOB: ______________ Date:__________

Administer in a quiet one-on-one setting with limited distractions.

Receptive Language: (Have the child pick the picture that fits best)

- Show me the yellow circle on top of a red square □ Yes □ No
- Point to two large blue circles □ Yes □ No
- Show me green triangle inside the red circle □ Yes □ No
- Show me the orange circle under the green triangle. □ Yes □ No

Fine Motor: Please have the child do the following:

| | Done Correctly | |
|---|---|---|
| **Typical 3 point pencil grip** | □ Yes | □ No |
| **Colors circle within lines** | □ Yes | □ No |
| **Copies square** | □ Yes | □ No |
| **Draws line within the rectangle** | □ Yes | □ No |

Letter Naming & Letter Sound

| | Say Letter Name | | Say Letter Sound | |
|---|---|---|---|---|
| R | □ Yes | □ No | □ Yes | □ No |
| A | □ Yes | □ No | □ Yes | □ No |
| M | □ Yes | □ No | □ Yes | □ No |
| T | □ Yes | □ No | □ Yes | □ No |
| S | □ Yes | □ No | □ Yes | □ No |
| L | □ Yes | □ No | □ Yes | □ No |
| U | □ Yes | □ No | □ Yes | □ No |
| D | □ Yes | □ No | □ Yes | □ No |

Fig. 16A

Copyright © 2024 All Rights Reserved

SoundWise Dx™
Pediatric Neurodevelopmental Assessment
Developed by Pediatricians

Age 5 Yrs: Form B

Phoneme Elision (deletion) (Taking away a sound or sounds)

Directions: Say, *Let's play a game* .

Example: *Say "raindrop". Now say raindrop without saying "drop"* ..........................

If correct, say, *That's right. Let's try the next one.*

If incorrect, say. *That's not quite right. Raindrop without saying drop is rain.*

1. *You say hairbrush. Say hairbrush again, without saying "brush"* (hair) ☐ Yes ☐ No
2. *You say Moonbeam. Say Moonbeam again, without saying "beam"* (moon) ☐ Yes ☐ No
3. *You say Gumdrop. Say Gumdrop again, without saying gum* (drop) ☐ Yes ☐ No
4. *You say Friendship. Say Friendship again, without saying friend* (ship) ☐ Yes ☐ No
5. *You say Pat. Say Pat again, without the /p/ sound (at)* ☐ Yes ☐ No
6. You say *sleep. Say sleep again, without the /l/ sound* (seep) ☐ Yes ☐ No
7. *You say ring. Say Ring again, without the /r/ sound (ing)* ☐ Yes ☐ No
8. You say *whisper. Say whisper again, without the "per"* (whis) ☐ Yes ☐ No

Rhyming exercise

Do these words rhyme? (sound the same) *(For example, Sun and fun rhyme but sun and sat do not)*

1. fin, tin ☐ Yes ☐ No
2. lap, fog ☐ Yes ☐ No
3. list, mist ☐ Yes ☐ No
4. meet, greet ☐ Yes ☐ No
5. book, bank ☐ Yes ☐ No
6. track, trick ☐ Yes ☐ No
7. Sink, drink ☐ Yes ☐ No
8. Zig, zag ☐ Yes ☐ No

Behavioral Observations: Please note the the child's demeanor during testing:

☐ Cooperative ☐ Smiling ☐ Shy ☐ Happy and engaged

☐ Uncooperative ☐ Crying ☐ Distractible ☐ English Language Learner

☐ Refusal to Interact ☐ Tired ☐ Anxious ☐ Difficult to motivate

☐ Completed Independently ☐ Needed Redirection for completion

☐ poor eye contact ☐ wouldn't engage ☐ Child's speech wasn't understandable

☐ Other______________________________________________

Fig. 16B

Copyright © 2024 All Rights Reserved

SoundWise Dx™

Pediatric Neurodevelopmental Assessment
Developed by Pediatricians

5 year old Assessment Form A

Scoring Yearly vision screening is medically indicated and hearing if necessary

Receptive Language Skills:
- 2 or more wrong -does not understanding directions Refer to speech therapist for receptive/expressive language/phonological awareness/processing therapy
- If language spoken at home is not English, Give exposure to English Receptive/expressive/phonological awareness/processing Language Skills. Consider speech therapy.

Fine Motor Skills:
- If no misses - strong skills
- If misses 1, have parent/teacher/tutor help develop these skills further
- If miss 2 or more work on pencil grip/drawing skills with Parent//teacher/tutor/Librarian and Occupational Therapy referral to work on pencil grip/life skills

Letter & Sound Identification Skills:
- If no misses - strong skills,
- If misses 1-3, work on these skills with parent/teacher/tutor
- If miss 4 or more, work on these skills with parent/teacher/tutor/librarian
- Start Speech therapist for letter sound/identification/articulation/phonological awareness/processing
- Use Lively letters APP/or any Youtube letter sound/letter Identification

Phonemic Elision (Sound Deletion) Skills:
- If no misses - strong skills
- If misses any, work on skills these with caretaker/teacher/tutor/librarian
- If miss 2 or more, work on the skills with caretaker/teacher/tutor/librarian and start Speech therapy referral for phonemic elision/phonemic awareness/processing along with articulation/receptive/expressive language skills

Rhyming is a phonological awareness skill. It is the ability to create a repetition of similar sounds in two or more words. It requires the ability to know if sounds are the same or different.
- If perfect score then no treatment needed
- Failure to do 1-3 item (less than 50% wrong on rhyming items) then
  - Work with Phonological awareness/processing skills with caregiver/ teacher/tutor and consider speech therapy referral
  - If more than 3 wrong, work on rhyming with caregiver/teacher/tutor/librarian and must do Speech Therapy for rhyming/phonemic awareness/processing/articulation
  - Hearing screen if indicated

Nonsense words:

- If perfect score, no treatment
- Failure to do 1-3 items
  - Work with phonological awareness/processing with parent/teacher/tutor/librarian and consider speech therapy referral
  - If more than 3 are wrong, work with nonsense words and rhyming with caregiver/teacher/tutor/ Librarian.Also, start Speech Therapy for nonsense words/phonemic awareness/processing/articulation/receptive/expressive language skills
  - Hearing screen if indicated

Engagement: If any concerns for autism like poor eye contact/lack of joint attention, lack of wanting to engage, and sensory dysregulation refer for Speech, OT, PT and a referral for Autism evaluation

If any concerns for ADHD/ADD, like unable to focus, easily distracted, unable to sustain attention for 12-18 minutes consider speaking to parents about Vanderbilt screen. Children who are inattentive and also exhibit staring spells, need to be evaluated for Absence seizures. SoundWise DX will offer RX or pediatrician/provider for neurology referral.

Fig. 17A

Copyright © 2024 All Rights Reserved

SoundWise Dx™

Pediatric Neurodevelopmental Assessment
Developed by Pediatricians

5 year old Assessment Form A

If there are any concerns about Anxiety, frustration with performance, thinking that they can not do well, crying, saying that they always fail every test,etc. Consider doing SCARED, and Columbia Screen or other screens for anxiety/depression.

Concerns present:
- □ None - Perfect Score
- □ Engagement Concerns (Based of Evaluator's Behavioral Observations)
- □ Receptive Language Concerns
- □ Sound Discrimination Concerns
- □ Sound OrderAwareness Concerns
- □ Fine Motor Concerns
- □ Letter & Sound Identification Concerns
- □ Sound Articulation Concerns
- □ Letter & Sound Identification Concerns
- □ Phonemic Elision (Sound Deletion) Concerns

Interventional Response:

□ General 4 Year Old Milestone Information Sheet
- Provides general understanding of what a 4 year should be able to do □ Specific Information Sheet for Opportunity and Development of Individual Skills
- Based upon Neurodevelopmental Foundational Model and Treatment Approach
- Includes Recommended Suggestions for opportunities and activities to grow skills
- Expand Opportunities and Suggestions available through SoundWise DX platform and other recommended sites.
- Increased Academic Focused Instruction on Broad areas of Concern (Engagement, Receptive Language, Sound Order awareness,Sound Discrimination, Fine Motor, Letter & Sound Identification, and Phonemic Elision)

Follow up if concerns present: □ 3-6 months later □ Yearly at the next Well Child Visit

Fig. 17B

Copyright © 2024 All Rights Reserved

SoundWise Dx™
Pediatric Neurodevelopmental Assessment
Developed by Pediatricians Age 5 years:Form A
5 year old Screens: Form A
Name: ______________________ DOB: ______________ Date:__________
Name: ______________________________________
*Color circle within the lines.*
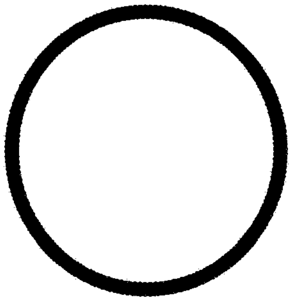
*Copy the square.*
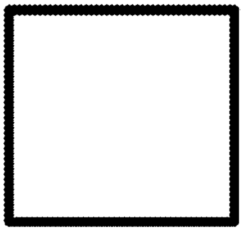
*Draw a straight line through the rectangle.*
| | |
|---|---|
| S | B |
| O | H |
| V | E |
| N | K |
Copyright © 2024 All Rights Reserved
Fig. 17C

SoundWise Dx™
Pediatric Neurodevelopmental Assessment
Developed by Pediatricians

Age 5 yrs: Form A

Copyright © 2024 All Rights Reserved

SoundWise Dx™
Pediatric Neurodevelopmental Assessment
Developed by Pediatricians

Age 5 yrs: Form A

Copyright © 2024 All Rights Reserved

SoundWise Dx™
Pediatric Neurodevelopmental Assessment
Developed by Pediatricians Age 5 years:Form A
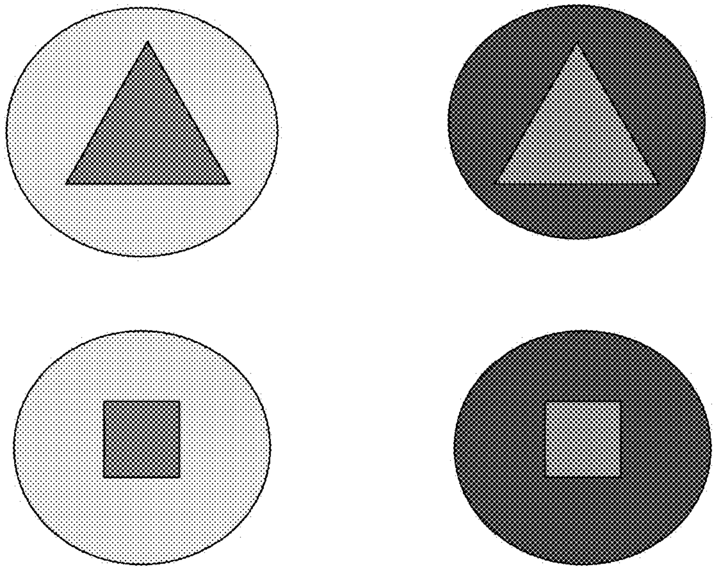
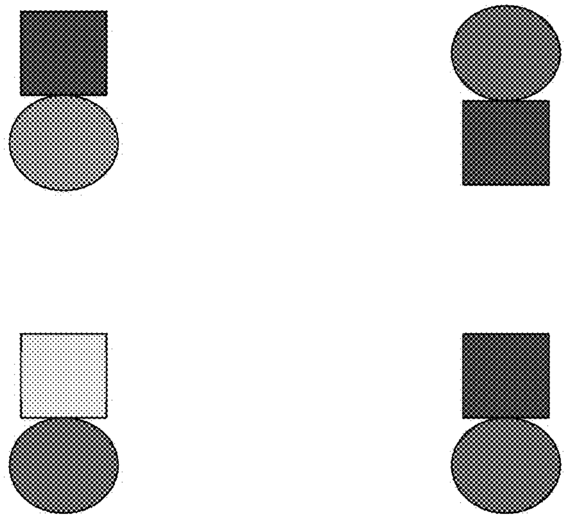
Copyright © 2024 All Rights Reserved
Fig. 17F

SoundWise Dx™
Pediatric Neurodevelopmental Assessment
Developed by Pediatricians

Age 5 Yrs: Form B

Scoring: Yearly vision screening is medically indicated and hearing if necessary.

Receptive Language Skills:

- 2 or more wrong (50% or more) due to not understanding directions or what is being said- Refer to speech therapist for receptive/expressive language therapy
- If language spoken at home is not English, Give exposure to English Receptive/expressive Language Skills. Consider speech therapy.

Fine Motor Skills:

- If no misses - strong skills, no treatment
- If misses 1, have parent/teacher/tutor help develop these skills further
- If miss 2 or more (50% or greater), work on pencil grip/drawing skills with Parent//teacher/tutor/Librarian and Occupational Therapy referral to work on pencil grip/life skills

Letter & Sound Identification Skills:

- If no misses - strong skills, no treatment
- If misses 1-3, work these skills with parent/teacher/tutor
- If miss 4 or more (50% or greater), work on these skills with parent/teacher/tutor/librarian
- Start Speech therapist for letter sound/identification/articulation
- Use Lively letters APP/or any youtube letter sound/letter Identification

Phonemic Elision (Sound Deletion) Skills:

- If no misses - strong skills, no treatment
- If misses any, work on skills these with caretaker/teacher/tutor/librarian
- If miss 2 or more (50% or greater), work on the skills with caretaker/teacher/tutor/librarian
- Start Speech therapy referral for phonemic elision/phonemic awareness/processing along with articulation/receptive/expressive language skills

Rhyming is a phonological awareness skill. It is the ability to create a repetition of similar sounds in two or more words. It requires the ability to know if sounds are the same or different.

- If perfect score then no treatment needed
- Failure to do 1-3 item (less than 50% wrong on rhyming items) then
  - Work with Phonological awareness/processing skills with caregiver/ teacher/tutor and consider speech therapy referral
  - If more than 3 wrong,work with phonological awareness/processing/rhyming/articulation with caregiver/teacher/tutor/librarian
  - Hearing screen to access hearing indicated
  - Speech Therapy for rhyming/phonemic awareness/processing/articulation

Engagement:

If any concerns for autism like poor eye contact/lack of joint attention, lack of wanting to engage, and sensory dysregulation refer for Speech, OT, PT and a referral for Autism evaluation

If any concerns for ADHD/ADD, like unable to focus, easily distracted, unable to sustain attention for 12-18 minutes consider speaking to parent about Vanderbilt screen. Children who are inattentive and also exhibit staring spells, need to be evaluated for Absence seizures. SoundWise DX will offer RX or pediatrician/provider for neurology referral.

Fig. 18A

Copyright © 2024 All Rights Reserved

SoundWise Dx™
Pediatric Neurodevelopmental Assessment
Developed by Pediatricians

Age 5 Yrs: Form B

If there are any concerns about Anxiety, frustration with performance, thinking that they can not do well, crying, saying that they always fail every test,etc. Consider doing SCARED, and Columbia Screen or other screens for anxiety/depression.

Concerns present:
- ☐ None - Perfect Score
- ☐ Engagement Concerns (Based of Evaluator's Behavioral Observations)
- ☐ Receptive Language Concerns
- ☐ Sound Discrimination Concerns
- ☐ Sound OrderAwareness Concerns
- ☐ Fine Motor Concerns
- ☐ Letter & Sound Identification Concerns
- ☐ Sound Articulation Concerns
- ☐ Letter & Sound Identification Concerns
- ☐ Phonemic Elision (Sound Deletion) Concerns

Interventional Response:

☐ General 4 Year Old Milestone Information Sheet
- Provides general understanding of what a 4 year should be able to do ☐ Specific Information Sheet for Opportunity and Development of Individual Skills
- Based upon Neurodevelopmental Foundational Model and Treatment Approach
- Includes Recommended Suggestions for opportunities and activities to grow skills
- Expand Opportunities and Suggestions available through SoundWise DX platform and other recommended sites.
- Increased Academic Focused Instruction on Broad areas of Concern (Engagement, Receptive Language, Sound Order awareness,Sound Discrimination, Fine Motor, Letter & Sound Identification, and Phonemic Elision)

Follow up if concerns present: ☐ 3-6 months later ☐ Yearly at the next Well Child Visit

Fig. 18B

Copyright © 2024 All Rights Reserved

SoundWise Dx™
Pediatric Neurodevelopmental Assessment
Developed by Pediatricians
Age 5 years: Form B
Name: ______________________ DOB: ______________ Date:__________
Name: ______________________________________
*Color circle within the lines.*
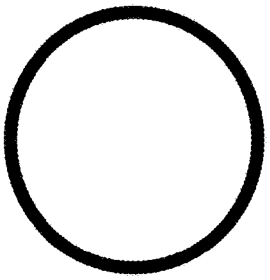
*Copy the square.*
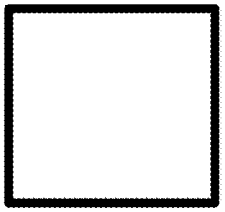
*Draw a straight line through the rectangle.*
| | |
|---|---|
| R | S |
| A | L |
| M | U |
| T | D |
Copyright © 2024 All Rights Reserved
Fig. 18C

SoundWise Dx™
Pediatric Neurodevelopmental Assessment
Developed by Pediatricians

Age 5 yrs: Form B

Copyright © 2024 All Rights Reserved

SoundWise Dx™
Pediatric Neurodevelopmental Assessment
Developed by Pediatricians

Age 5 yrs: Form B

Copyright © 2024 All Rights Reserved

SoundWise Dx™
Pediatric Neurodevelopmental Assessment
Developed by Pediatricians
Age 5 yrs: Form B
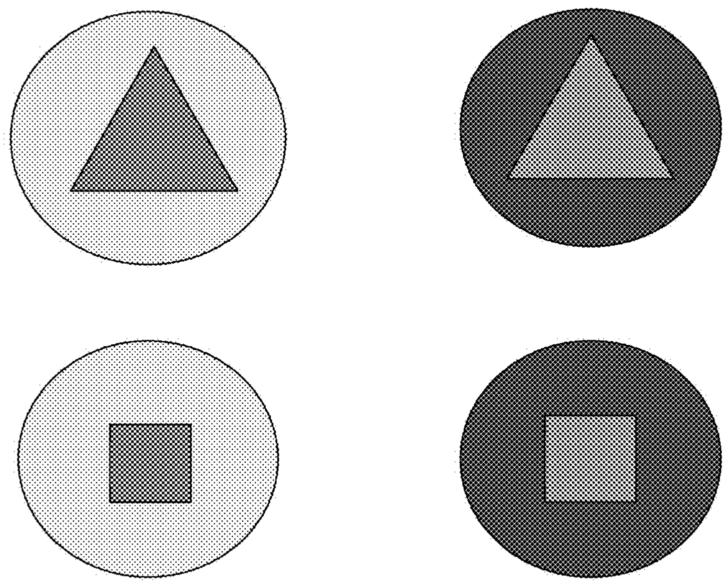
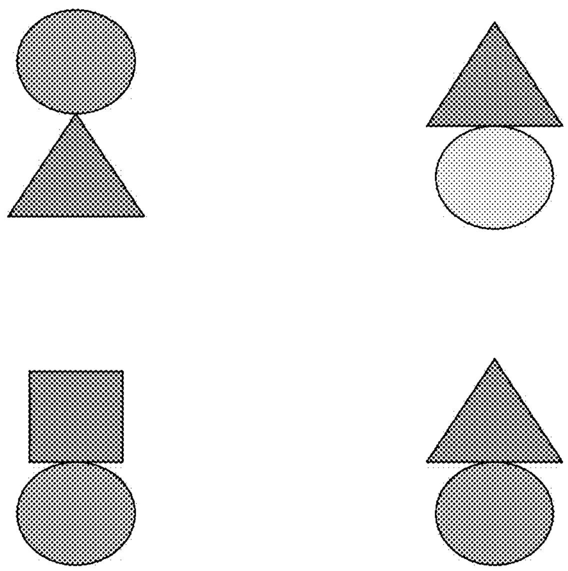
Copyright © 2024 All Rights Reserved
Fig. 18F

Pediatric Neurodevelopmental Assessment
Developed by Pediatricians

5 year old Assessment Guided Treatment flow chart Form A or B

Vision and Hearing Assessments: should be done on all children yearly.

SoundWise DX will perform vision and colorblind testing before every assessment.

SoundWise DX will perform a Vision Snell chart (or any other standardized screen) and a colorblind test (The Ishihara, EnChroma, or any other standardized color blind assessment or screen) before every assessment.) The colorblind tests can be done as early as when a child is able to recognize numbers, shapes, or animals.

> *Color blindness (color vision deficiency, or CVD) affects approximately 1 in 12 men (8%) and 1 in 200 women. This is an important thing to know for all children as colors are frequently used on computer academic assessments and inability to discern colors can negatively impact learning.*
>
> *Concern for possible color blindness: If a child misses questions with red and/or green they will be tested for color blindness as soon as they are able to identify the common shapes used in testing books like numbers, shapes, or animals.*

Receptive Language Skills:

> We take into account AI algorithms to recognize, transcribe a child's letter sound/word pronunciation, analyze context/structure where pronunciation varies due to accents/dialects and word/sentence structure comprehension and fluency.

- Perfect score on items of Receptive Language items/understood all directions of all tasks, then recommend the child use enrichment with SoundWise DX AI/AI-Generative for 5 year old Receptive Language modules( Modules are preceded by a short video explaining the lesson to be learned followed by AI/AI-Generative Online recommendation algorithm)and/or worksheets for learning advanced skills.

- If unable to follow and/or properly demonstrate ability to perform and understand directions and if child from English as a second language home, as determined by SoundWise DX computer program AI grader, pediatrician, or authorized personnel,
  - Caregiver/ teacher work on receptive language by using SoundWise DX 5 Year Old Developmental Milestone Information Sheet (DMIS)
- START SoundWise DX AI/AI-Generative Online 5 year old Receptive/Expressive Language modules (Modules are preceded by a short video explaining the lesson to be learned followed by AI/AI-Generative Online recommendation algorithm) and/or worksheets with respect to following directions, strengthening Receptive/ Expressive Language skills, with emphasis on building English vocabulary.
- In addition SoundWise DX recommends:
- In person Speech/ Language Therapy focusing on improving Receptive language and English Expressive Language vocabulary building.
- Prescriptions for speech/ language will be given through SoundWise DX or Pediatrician/Provider
- Multiple SoundWise DX modules will be performed until the child is able to demonstrate proficiency to move on to learning advanced skills as determined by the SoundWise DX computer program AI grader, pediatrician, or authorized personnel.

Fig. 19A

SoundWise Dx™
Pediatric Neurodevelopmental Assessment
Developed by Pediatricians

5 year old Assessment Guided Treatment flow chart Form A or B

- If from an English second language home, then these modules should be done in both English and their primary language until the child is able to demonstrate proficiency as determined by the SoundWise DX computer program AI grader, pediatrician, or authorized personnel.
- If Child still demonstrates difficulty, SoundWise DX will administer or recommend local referral for an assessment that looks at early literacy skills such as the Comprehensive Test of Phonological Processing CTOPP-2 or Test of Preschool Literacy Skills (TOPEL), or any other standardized assessment (most current version) that measures awareness and/or phonological processing.

Fine Motor Skills:

SoundWise DX will use AI determination of correct stroke/direction/pressure, speed, accuracy, and skill.

(4 total scored items that include correct pencil grip (no fisted grip), drawing animal either cat or dog, copies shape, and traces line):

- If a perfect score on Fine Motor items with correct pencil grip, as determined by SoundWise DX computer program AI grader, pediatrician, or authorized personnel, then recommend the child do Enrichment modules with SoundWise DX AI/AI-Generative 5 yr old occupational therapy modules (Modules are preceded by a short video explaining the lesson to be learned followed by AI/AI-Generative Online recommendation algorithm) and/or worksheets for learning advanced skills. SoundWise DX will use AI determination of correct stroke/direction/pressure, speed, accuracy, and skill.

Fine motor skills listed include, for example,the equivalent of the following (but not limited to) drawing animals, copying shapes, trace line, and correct pencil grip (which can be expanded to other skills in the future)

- Concerns or Fail: unable to do 1 item (< 50% completed incorrectly)
  - Caregiver/teacher/or authorized personnel will work on drawing with correct pencil grip using SoundWise DX 5 Year Old Developmental Milestone Information Sheet (DMIS)
  - Fine motor skills listed includes, for example, the equivalent of the following (but not limited to):draw cat with 3 or more parts, copies shape,trace the line within the box and demonstrates pencil grip (which can be expanded to other skills in the future).
- START SoundWise DX AI/AI-Generative Online 5 year old Occupational Therapy modules (Modules are preceded by a short video explaining the lesson to be learned followed by AI/AI-Generative Online recommendation algorithm) and/or worksheets on how to draw figures, copy shapes, trace lines, and use of correct pencil grip with AI determination of correct stroke/direction/pressure, speed, accuracy, and skill.
- Start in person Occupational Therapy services for correct pencil grip/life skills

FIG. 19B

SoundWise Dx™
Pediatric Neurodevelopmental Assessment
Developed by Pediatricians

5 year old Assessment Guided Treatment flow chart Form A or B

- Prescriptions for speech and language will be given through SoundWise DX or Pediatrician/Provider

- Some children will wear gloves where computer will analyze proper technique with digitized feedback
- Multiple SoundWise DX modules will be performed until the child is able to demonstrate proficiency as determined by SoundWise DX computer program AI grader, Pediatrician, or authorized personnel.

Letter Naming/Letter Sound:

Knowing basic phonic rules of how a specific sound relates to a specific letter is an important part of mastering the alphabetic code.

We take into account AI algorithms to recognize, transcribe a child's letter sound/word pronunciation, analyze context/structure where pronunciation varies due to accents/dialects and word/sentence structure comprehension and fluency.

- If a perfect score (all 16 letter and sound identification items correct) as determined by SoundWise DX computer program AI grader, pediatrician, or authorized personnel, then recommend the child do enrichment with SoundWise DX AI/AI-Generative 5 year old letter naming and letter sound identification/letter sound skill modules (Modules are preceded by a short video explaining the lesson to be learned followed by AI/AI-Generative Online recommendation algorithm) and/or worksheets for learning advanced skills

- Concerns or Failure: Fail to do 1-3 items (less than 50% wrong on letter names or on letter sounds) then
  - Caretaker/teacher/ or authorized personnel work on letter naming/letter sound skills using SoundWise DX 5 Year Old Developmental Milestone Information Sheet (DMIS)
  - START SoundWise DX AI/AI-Generative Online 5 year old letter naming/letter sound modules (Modules are preceded by a short video explaining the lesson to be learned followed by AI/AI-Generative Online recommendation algorithm) and/or worksheets that focus on letter naming/ letter sound identification/phonological processing/awareness skills.
  - Multiple SoundWise DX modules will be performed until the child is able to demonstrate proficiency as determined by SoundWise DX computer program AI grader, Pediatrician, or authorized personnel.
  - If unable to pass the skill using SoundWise DX modules within 3 months of actively working on this skill then include along with modules
    - Start in person Speech and Language Therapy focusing on improving phonological awareness/ processing/Letter name/sounds as needed
    - Prescriptions for speech and language will be given through SoundWise DX or Pediatrician/Provider

- Fail: If misses 4 or more items (greater than 50% wrong) on either letter names or on letter sounds then

FIG. 19C

SoundWise Dx™
Pediatric Neurodevelopmental Assessment
Developed by Pediatricians

5 year old Assessment Guided Treatment flow chart Form A or B

Caregiver/teacher/ or authorized personnel work on letter naming/letter sound using SoundWise DX 5 Year Old Developmental Milestone Information Sheet (DMIS)

START SoundWise DX AI/AI-Generative Online 5 year old letter naming/letter sound modules (Modules are preceded by a short video explaining the lesson to be learned followed by AI/AI-Generative Online recommendation algorithm) and/or worksheets that focus on letter naming and letter sound identification skills along with phonological processing/awareness skills

- Start in person Speech and Language Therapy focusing on improving letter sound/identification and phonological awareness/ processing
- Prescriptions for speech and language will be given through SoundWise DX or Pediatrician/Provider.
- Multiple SoundWise DX modules will be performed until the child is able to demonstrate proficiency as determined by SoundWise DX computer program AI grader, Pediatrician, or authorized personnel.

- If child still having difficulty with Assessments, SoundWise DX will administer or local referral for an assessment that looks at early pre literacy skills such as the Comprehensive Test of Phonological Processing CTOPP-2 or Test of Preschool Literacy Skills (TOPEL), or any other standardized assessment (most current version) that measures awareness and/or phonological processing.

Phoneme Elision (sound deletion):

Phoneme Elision means to take away a sound and is one of the strongest predictors that a child will go on to struggle in reading. It can be tested as early as 4 years old.

We take into account AI algorithms to recognize, transcribe a child's letter sound/word pronunciation, analyze context/structure where pronunciation varies due to accents/dialects and word/sentence structure comprehension and fluency.

- If a perfect score as determined by SoundWise DX computer program AI grader, pediatrician, or authorized personnel, then recommend the child do enrichment with SoundWise DX AI/AI-Generative 5 year old letter naming and letter sound identification/letter sound skill modules (Modules are preceded by a short video explaining the lesson to be learned followed by AI/AI-Generative Online recommendation algorithm) and/or worksheets for learning advanced skills

- Concerns or Fail: If unable to do 1 to 3 items only (less than 50% wrong on phoneme elision)
  - Work on Phonological awareness/processing/phonemic elision/receptive/expressive language skills with a caregiver/ teacher using SoundWise DX 5 Year Old Developmental Milestone Information Sheet (DMIS)
  - START SoundWise DX AI/AI-Generative Online 5 year old phoneme elision/receptive/expressive language/phonological

FIG. 19D

SoundWise Dx™
Pediatric Neurodevelopmental Assessment
Developed by Pediatricians

5 year old Assessment Guided Treatment flow chart Form A or B awareness/processing modules (Modules are preceded by a short video explaining the lesson to be learned followed by AI/AI-Generative Online recommendation algorithm) and/or worksheets that focus on Phonological Awareness/processing/Receptive/Expressive language/phonemic elision skills

- Multiple SoundWise DX modules will be performed until the child is able to demonstrate proficiency as determined by SoundWise DX computer program AI grader ,Pediatrician, or authorized personnel.
- If unable to pass the skill using the SoundWise DX modules with 3 months of actively working on this skill then include along with modules,
    - Must start In person Speech and Language Therapy focusing on improving phonological awareness/ processing/phonemic elision/receptive/expressive language skills
    - Prescriptions for speech and language will be given through SoundWise DX or Pediatrician/Provider.
    - Multiple SoundWise DX modules will be performed until the child is able to demonstrate proficiency as determined by SoundWise DX computer program AI grader, Pediatrician, or authorized personnel.

- Fail: If misses 4 or more (50% or greater on phoneme elision items), then
    - Caregiver/teacher work on Phonological awareness skills using SoundWise DX 5 Year Old Developmental Milestone Information Sheet (DMIS)
    - START SoundWise DX AI/AI-Generative Online 5 year old on Phonological awareness/processing/expressive and receptive language/phonemic elision (Modules are preceded by a short video explaining the lesson to be learned followed by AI/AI-Generative Online recommendation algorithm) and/or worksheets modules on phoneme elision that focus on PhonologicalAwareness/processing/receptive/expressive language skills
    - Must start In person Speech and Language Therapy focusing on improving phonological awareness/ processing/phonemic elision/receptive/expressive language skills
    - Prescriptions for speech and language will be given through SoundWise DX or Pediatrician/Provider
    - Multiple SoundWise DX modules will be performed until the child is able to demonstrate proficiency as determined by SoundWise DX computer program AI grader, Pediatrician, or authorized personnel.
    - If still presents with difficulty, SoundWise DX will administer or local referral for an assessment that looks at early pre literacy skills such as the Comprehensive Test of Phonological Processing CTOPP-2 or Test of Preschool Literacy Skills (TOPEL), or any other standardized assessment (most current version) that measures awareness and/or phonological processing.

FIG. 19E

SoundWise Dx™
Pediatric Neurodevelopmental Assessment
Developed by Pediatricians

5 year old Assessment Guided Treatment flow chart Form A or B

Rhyming exercise:

Rhyming is a phonological awareness skill. It is the ability to create a repetition of similar sounds in two or more words. It requires the ability to know if sounds are the same or different.

We take into account AI algorithms to recognize, transcribe a child's letter sound/word pronunciation, analyze context/structure where pronunciation varies due to accents/dialects and word/sentence structure comprehension and fluency.

- If a perfect score as determined by SoundWise DX computer program AI grader, pediatrician, or authorized personnel, then recommend the child do enrichment with SoundWise DX AI/AI-Generative 5 year old phonological awareness skill modules (Modules are preceded by a short video explaining the lesson to be learned followed by AI/AI-Generative Online recommendation algorithm) and/or worksheets for learning advanced skills

- Concerns or Fail: Failure to do 1 to 3 items only (less than 50% wrong on rhyming)
  - Work on Phonological awareness/processing skills with a caregiver/ teacher using SoundWise DX 5 Year Old Developmental Milestone Information Sheet (DMIS)
  - START SoundWise DX AI/AI-Generative Online 5 year old rhyming/phonological awareness/processing modules/receptive/expressive language (Modules are preceded by a short video explaining the lesson to be learned followed by AI/AI-Generative Online recommendation algorithm) and/or worksheets that focus on Phonological Awareness/processing skills/rhyming/receptive/expressive language
  - Multiple SoundWise DX modules will be performed until the child is able to demonstrate proficiency as determined by SoundWise DX computer program AI grader ,Pediatrician, or authorized personnel.
  - If unable to pass the skill using the SoundWise DX modules with 3 months of actively working on this skill then include along with modules,
    - Must Start In person Speech and Language Therapy focusing on improving phonological awareness/ processing/rhyming/receptive/expressive language skills.
    - Prescriptions for speech and language will be given through SoundWise DX or Pediatrician/Provider.
    - Multiple SoundWise DX modules will be performed until the child is able to demonstrate proficiency as determined by SoundWise DX computer program AI grader, Pediatrician, or authorized personnel.

- Fail: If misses 4 or more (50% or greater on rhyming items), then
  - Caregiver/teacher work on Phonological awareness/processing skills with caregiver and/or teacher using SoundWise DX 5 Year Old Developmental Milestone Information Sheet (DMIS)
  - START SoundWise DX AI/AI-Generative Online 5 year old modules on rhyming/phonological awareness/processing/receptive/expressive language skills (Modules are preceded by a short video explaining the lesson to be learned followed by AI/AI-Generative Online recommendation

FIG. 19F

SoundWise Dx™
Pediatric Neurodevelopmental Assessment
Developed by Pediatricians

5 year old Assessment Guided Treatment flow chart Form A or B algorithm) and/or worksheets modules on rhyming/ that focus on Phonological Awareness/process/expressive/receptive language skills.

- Start In person Speech and Language Therapy focusing on improving rhyming/phonological awareness and phonological processing/receptive/expressive language skills.
- Prescriptions for speech and language will be given through SoundWise DX or Pediatrician/provider.
- Multiple SoundWise DX modules will be performed until the child is able to demonstrate proficiency as determined by SoundWise DX computer program AI grader, Pediatrician, or authorized personnel
- If still having difficulty,.SoundWise DX will administer or local referral for an assessment that looks at early pre literacy skills such as the Comprehensive Test of Phonological Processing CTOPP-2 or Test of Preschool Literacy Skills (TOPEL), or any other standardized assessment (most current version) that measures awareness and/or phonological processing.

Engagement:

*Any and all diagnoses of psychiatric/behavioral disorders (ADHD, Autism, Anxiety, depression etc, will follow and change accordingly with the most current medical guidelines determined by the latest version of the Diagnostic and Statistical Manual of Mental Disorders which is currently the DSM-V. As new versions are published, SoundWise DX concerns identified and diagnostic criteria will adapt and be changed to match the most current diagnostic criteria.*

Perfect score:

- Able to demonstrate social communication, interaction , eye contact and able to demonstrate joint attention back and forth with assessment tasks. Not showing restrictive and repetitive behaviors, such as flapping their hands, spinning a lot, only interested in lining up toys or objects, sensory issues such as upset with loud noises, and difficulty with change of routine during the assessment.
- Able to sustain attention, not easily distracted, following directions on Assessment tasks.
- Attending the SoundWise DX assessment without crying and worrying about how they are doing with each task.
- Engagement evaluation is determined by SoundWise DX computer program AI grader, pediatrician, or authorized personnel.

A concern or fail for this section:

- Autism Concern:
  - The child has challenges with social communication and interaction. Has poor eye contact, refusal to engage in tasks, and/or lack of joint attention back and forth while doing assessment tasks.
  - The child demonstrates restrictive/repetitive behaviors, interests, and activities such as, but not limited to, flapping hands, spinning, lining up toys/objects, sensory issues (upset by loud noises/smell/touch), and challenges with change of routine during tasks.

FIG. 19G

SoundWise Dx™
Pediatric Neurodevelopmental Assessment
Developed by Pediatricians

5 year old Assessment Guided Treatment flow chart Form A or B

- ADHD/ADD/attention deficits:
  - The child is unable to keep their attention and/or unable to follow directions while completing Assessment without being distracted and/or unable to sit still long enough to complete assessment at age 3 years old, note that a formal diagnosis is not made at age 3, rather only a concern.
  - Children who are inattentive and also exhibit staring spells, need to be evaluated for Absence Seizures. SoundWise DX will offer RX or pediatrician/provider for Neurology referral.
    - Norm values:
      - 3 years old: 6-8 minutes
      - 4 years old: 8-12 minutes
      - 5 and 6 years old: 12-18 minutes
      - 7 and 8 years old: 16-24 minutes
      - 9 and 10 years old: 20-30 minutes
- Anxiety, panic attacks, or Post Traumatic Stress Disorder (PTSD) Concern or Fail:
  - The child is showing emotions of frustration with or without crying and/or demonstrating worry about their performance while completing the assessment.
  - Elevated heart rate and/or blood pressure measured by all digital devices
  - Avoidance behaviors when tasks are hard such as:
    - Child complains or somatic (body) complaints to end or get out of a task like:
      - Headaches
      - Nausea, stomach aches, vomiting
      - Tiredness, yawning, falling asleep
      - Tense posture, clenched shoulders or muscles, clenched teeth
      - Pulling on eyelashes, biting fingers or fingernails
      - Arguing, throwing the materials, leaving the test environment
      - Saying they are thirsty, hungry, tired, sleepy, or having to all of a sudden got to go to the bathroom
      - Complains of their heart racing
      - Child is unable to attempt assessment in part or at all.
      - Any other related complaints by the child not listed above.

- Children who do not attempt Assessment will need to to start SoundWise DX AI/AI-Gen engagement modules and a reassessment will be attempted in 1 to 3 months time as per SoundWise DX AI/AI-Gen grader.
- Engagement results are determined by SoundWise DX AI/AI-Gen computer program AI grader, Pediatrician, or authorized personnel.
- Engagement modules cover issues regarding attention, anxiety, autism, or other disorders as discussed below.
  - START SoundWise DX AI/AI-Generative Online 5 year old online Module for lack of engagement (Modules are preceded by a short video explaining the lesson to be learned followed by AI/AI-Generative Online recommendation algorithm) and/or worksheets. The Lack of Engagement modules deliver Speech & Language, Occupational Therapy, Physical Therapy and Behavioral Modification suggestions for building engagement.
  - As the child attends the Lack of Engagement modules, SoundWise DX AI/AI-Gen grader will determine the correct SoundWise DX modules for each individual child.
    - Lack of Engagement SoundWise DX modules include:
      1. Autism diagnostic evaluation through SoundWise DX and/or referral for autism diagnoses through a child's local medical services

FIG. 19H

SoundWise Dx™
Pediatric Neurodevelopmental Assessment
Developed by Pediatricians

5 year old Assessment Guided Treatment flow chart Form A or B

2. Attention Deficit/ADHD behavioral concerns/anxiety
    a. Continue to follow closely, make learning activities fun/engaging, limit activities to short segments.
    b. If severe behavioral issues or anxiety present: referral to child psychologist or for Play Therapy.
    c. Age 4 and older, refer to specific for ADHD module for further recommendations
3. Modules for other recognized disorders such as post traumatic stress disorder, genetic disorders associated with learning disabilities, environment exposure to lead, fetal alcohol syndrome, Adoption and/or foster care population, proper nutrition, developmental delay, sensory issues, and other situations resulting in childhood developmental delay in need of intervention.
4. Along with participating in Engagement modules, the following will be provided:
    - Refer for a in-person Speech and Language Evaluation focusing on building strong receptive/expressive language skill
    - Refer for an in person Sensory Integration Focused Occupational Therapy Evaluation focusing on motor integration, oral motor kinesthetics, proprioceptive skills, and sensory regulation..
    - Refer for an in person Physical therapy focusing on building strong gross motor skills.
    - Refer for in person evaluation for Autism
    - Refer for Genetics evaluation
    - Prescriptions for the above services will be provided by SoundWise DX or local health care facility.

- Specific SoundWise DX modules for Autism, ADHD/ADD, and Anxiety:

1. Autism: Autism presents challenges with social communication and interaction. They do not talk a lot because they are not motivated to socially interact. They have challenges with eye contact and are unable to demonstrate joint attention, not able to play a back and forth game or do SoundWise DX assessment tasks. They show restrictive and repetitive behaviors, such as flapping their hands, spinning a lot, only interested in lining up toys or objects, sensory issues such as being upset with loud noises, wanting to smell things and not wanting to play pretend. Children with Autism also have difficulty with change of routine for example, having a new teacher, or driving a new route home and difficulty changing tasks during the SoundWise DX assessment.
    - Determination of Autism by SoundWise DX computer program AI grader, pediatrician, or authorized personnel will recommend the following:
    - Recommended activities and/or worksheets generated in the modules will address the specific concerns of lack of engagement/ language delay affecting social interaction, high concerns for Autistic Spectrum Disorder (ASD), or ASD confirmed by meeting the diagnostic criteria for ASD as per the most current version of the DSM which is currently the DSM-V. This will includes activities that focus on but or not limited to the following:
        - To strengthen receptive, expressive, and pragmatic language skills

FIG. 19I

SoundWise Dx™
Pediatric Neurodevelopmental Assessment
Developed by Pediatricians

5 year old Assessment Guided Treatment flow chart Form A or B

- Specific games and activities addressing language goals
    - To improve sensory regulation
        - Specific games and activities to decrease sensory triggers whether they be hypo(low) or hyper(high) sensory
        - Recommendation to address sensory seeking behaviors and/or sensory avoidance behaviors
        - Occupational Therapy (OT) like play activities with OT therapy goals addressing visual/motor integration, sensory regulation, visual perceptual skills, executive function, and primitive reflex integration)
    - To improve fine motor skills
        - Specific games and activities to improve any fine motor skills or hand skill ability like but not limited to the following (handwriting, cutting, folding, stringing beads, coloring, drawing, gluing, buttoning, using utensils, etc.
    - To improve gross motor skills
        - Specific games and activities to strengthen gross motor movements that includes focusing on balance, coordination, ball skills (dribbling, throwing,catching, etc.), hand eye coordination, same side and alternating side body movements, body schema activities (proprioceptive, vestibular, tactile, and body awareness)
        - Physical Therapy (PT) therapy like activities with PT gross motor goals
    - To improve social and pragmatic language skills
        - Specific group play therapy along with games and activities promoting opportunity for improved and guided social interaction
            - Group play therapy
            - Applied Behavioral Analysis Therapy
            - Increased peer group interactions.
- In situations where anxiety or family connections are more calming, the avatar (computer generated face and/or voice used) could be that of a person familiar to the individual) when the assessment or enrichment activities are delivered on the SoundWise DX platform.
- SoundWise DX modules can be used to treat and strengthen skills along with in person therapy especially when waiting for in person therapy. Using SoundWise DX modules will start therapeutic advancement of identified skill deficits while at home when awaiting in person therapies. They can also be used to augment and reinforce the actual future or current therapies in place like medically delivered Speech and Language Therapy, OT, Cognitive Behavioral Therapy, and PT.
- Engagement modules and/or worksheets allow Early Intervention to immediately start while a child awaits for in person evaluation and/or in person autism specific therapy.
- SoundWise DX modules and/or worksheets will improve skills and reassessment will allow progress. Children should continue using the modules and/or worksheets even after starting in-person therapy.
- Referral when indicated per AI/AI generated Algorithm
    - Refer for a in person Speech and Language Evaluation

FIG. 19J

SoundWise Dx™
Pediatric Neurodevelopmental Assessment
Developed by Pediatricians

5 year old Assessment Guided Treatment flow chart Form A or B

- Refer for a in person Sensory Integration Focused Occupational Therapy Evaluation
- Refer for an in person Diagnostic Evaluation for Autism
- Refer for in person Child Play Therapy

- Pursue all therapies covered by medical insurance while at the same time caregivers/ teachers work on language skills, social interaction, developmental milestones, and sensory regulation using SoundWise DX 5 Year Old Developmental Milestone Information Sheet (DMIS) for age appropriate activities.
- Recommendations will include prescriptions for in person services generated through SoundWise DX.
- Suggestions to seek specialized diagnostic evaluations when indicated by SoundWise DX AI/AI-Gen Grader will include follow up with the child's primary care medical provider, and specialty referrals.
- As part of the diagnostic process, SoundWise DX will administer and score standardized validated screeners as age appropriate such as but not limited to the MCHAT, ASQ, PEDS Form, Vanderbilts, Denver Developmental assessments, Conners Forms, Scat etc)
- While Autism may be the primary diagnosis or concern, other coexisting conditions like anxiety or ADHD and/or genetic disorders may exist. If a validated screening as discussed above elicits concerns for other disorders, the appropriate referral will be done through SoundWise DX.

2. For Attention Deficit Hyperactivity Disorder Concerns (ADHD/ADD):
   - Behavioral modifications SoundWise DX module for 5 year old Behavioral Basics will be given that focuses tips on a structured environment, making learning activities fun, multisensory activities, and short but repetitive opportunities for learning.
   - If engagement is appropriate, but focus/attention to a task cannot be maintained for the age expected time for this age (12-18 minutes), then refer to SoundWise ADHD/ADD age specific questions and holistic consideration of all factors that can affect attention and sustained focus.
   - Children with ADHD/ADD have a hard time paying attention, daydreaming and often do not seem to listen. They are easily distracted from work and play and often do not pay attention to details/disorganization and do not follow through on directions. Prone to losing a lot of important things/forgetting things and avoids doing things that require mental effort. Having the hyperactivity component makes them prone not being able to stay seated, squirming a lot, talking too much, unable to play quietly and will jump, run and climb when not permitted to do so. They will demonstrate impulsivity, calling out without question being complete, Acts or speaks without thinking, Interrupting others often, trouble taking turns, cannot wait for things and may run onto street without looking out for traffic.
     - SoundWise DX AI/AI Gen grader will administer and score a Vanderbilt screen for parent and teacher if applicable). These screens are diagnostic of ADHD/ADD.
       - Visual attention and focus: SoundWise RX AI/Gen AI computer grader will derive objective and

FIG. 19K

SoundWise Dx™
Pediatric Neurodevelopmental Assessment
Developed by Pediatricians

5 year old Assessment Guided Treatment flow chart Form A or B quantitative results for example gaze direction, dwell time, and glance frequency off the assessment site to other objects and locations. While monitoring eye tracking, we will measure where and for how long an individual looks in a certain direction or at a certain target, it is not a measure of actual visual attention However, this information can be used to necessitate further exploration into attention or focus disorders like ADHD/ADD. The SoundWise RX screen eye tracking will be used to assess student attention while taking the test. Just as eye tracking is the go-to method when determining driver distraction via glance target classification it can be used to assess attention to the assessment attention engagement in the test itself, or also suggest more analysis of visual tracking/perception/or processing is warranted.

- When above condition concerns are found, AI/AI-Gen computer program modules and/or worksheets for evaluation and guidance/ for ADHD/ADD will be generated. Further informational sheets on factors that can impact attention will be generated and given to the caregivers.
- Modules for scholastic accommodations such IEP, 504 and not limited to will also be given that can be effectively be used within a child's Individual Educational Plan (IEP) or 504 Plan.
- When formal diagnosis of ADHD for age 5 years old and older has been given, then information regarding evaluation for behavioral modification will be given.
- Starting at age 5 or older, medication for ADHD/ADD when indicated by SoundWise DX AI/AI-Gen and/or caregiver/teacher. Blood pressure. Pulse, EKG rhythm strip will be administered through all digital devices, along with telemedicine visit with SoundWise DX before medication is given. Pathways towards diagnostic evaluation will be done according to the specific laws in each state.
- Classroom modifications and accommodation recommendations would be produced via SoundWise DX module via AI/AI-Gen and given via SoundWise DX according to the specific laws in each state.

3. Anxiety:

- A diagnosis of Anxiety is when a child is worried or scared and it interferes with their everyday activities such as refusing to go to school, playing with friends,especially at recess or at social gatherings, getting to sleep and/or not being able to sleep alone in their bed. They may say their heart is beating too fast, or they have a stomach ache and shaking, maybe having trouble breathing, start to sweat and suddenly are unable to sustain attention and want to find a safe place, like home or a caregiver. See specific symptoms that were listed above in "what constitutes a fail". Anxiety may have been exhibited itself as shyness during the child's early years, or occur after a traumatic event experienced/ witnessed by the child or the child may be a victim of abuse by a caregiver or other.
- There are 4 types of Anxiety present in children;

FIG. 19L

SoundWise Dx™
Pediatric Neurodevelopmental Assessment
Developed by Pediatricians

5 year old Assessment Guided Treatment flow chart Form A or B

- Social Anxiety-Difficulty playing or being with others, especially in school, will speak softly not wanting to be heard and will not volunteer to raise hand in school or participate in group activities.
- Separation Anxiety- Unable to separate from the caregiver, wanting to always be in their presence, not wanting to go to school or be on a playdate.
- Selective Mutism- severe anxiety-speaks at home but not anywhere else. Has early onset.
- Generalized Anxiety-Strives to be perfect,worries about the past, current events and the future a lot and worries about what may happen in school in their school work or other activities. They may get diagnosed with ADHD, however this child can not pay attention due to worry, rather than attention.

- The child may demonstrate Anxiety during SoundWise DX by being concerned about getting the assessment tasks correct or simply not speaking. They may cry and turn away and say they are afraid to continue.
- SoundWise DX AI/Gen-AI will determine through an anxiety algorithm module and/or caregiver/teacher or authorized personnel to start Anxiety SoundWise DX modules as well to start arranged telemedicine visits through SoundWise DX and/or in person therapy.
- Also the Caregiver/teacher will work on language development, social interaction, and sensory regulation by using SoundWise DX 5 Year Old Developmental Milestone Information Sheet (DMIS) for age appropriate activities.
- SoundWiseDX will administer and score a diagnostic screen such as PHQ-9/SCARED/Columbia/Hamilton/GAD-7 for Anxiety that is appropriate for age.
- Based on SoundWiseDX AI/AI-Gen Children will also be started on telemedicine services through SoundWise DX for anxiety.
- Reasons for indications for medicine management for Anxiety is determined by SoundWise DX AI/AI-Gen, physician, and input from caregiver/teacher. Pulse, Blood Pressure and EKG will be obtained by digital devices and are medically necessary before starting medication. Telemedicine services for anxiety though SoundWise DX must also be initiated and continued while the child is on medication for anxiety.
- All children diagnosed with Anxiety through SoundWise DX AI/AI-Gen will also be evaluated for ADHD/ADD and/or Autism

4. Low Self Esteem

- Self esteem should always be monitored closely in a child as this can lead to depression or other mental health disparities in the future.
- Low self esteem can arise from a variety of reasons.
- A soundWise DX Module AI/AI-Gen will be given that addresses building self esteem and confidence in a child.
- Telemedicine visits will be recommended via SoundWise DX or their local provider

Reassessments SoundWise DX:

- SoundWise DX will offer reassessments (Form B's) after 3 months of module implementation. Initial assessments are Form A.

FIG. 19M

SoundWise Dx™
Pediatric Neurodevelopmental Assessment
Developed by Pediatricians

5 year old Assessment Guided Treatment flow chart Form A or B

- In 3 months or less depending upon the discretion of SoundWise DX AI/AI-Gen computer program AI grader, pediatrician, and/or authorized personnel, the child will retake an assessment
  - If the child is still the same age, they will then take that age years Form B
  - If they have aged up and are now 1 year older, then they will take the next year's assessment Form A.
  - If a child is able to pass some, but not all, or if unable to pass the repeat pediatric assessment, they must follow through with the same algorithm as above until proficiency is determined by SoundWise DX computer program AI grader, pediatrician, or authorized personnel.
  - If the child is able to pass all parts of the new assessment, they should do SoundWise DX enrichment modules based on age group.

FIG. 19N

SoundWise Dx™
Pediatric Neurodevelopmental Assessment
Developed by Pediatricians 5 Year Old Neurodevelopmental Milestone Information Sheet When children reach 5 years, they discover they can communicate well with their peers as their language skills allow them to understand the back and forth of conversations as well as pick up social cues. They are great at following directions most of the time.They experiment with their strong physical skills in running, climbing and playing games outdoors. More importantly they are ready to attend school and typically have the necessary foundational skills to perform successfully at school. Experienced based learning is always happening as they learn how to work in groups, learn how to follow directions, are able to take turns in the classroom/recess, and adjust to new routines like eating lunch at school. Very quickly, children learn to adapt and adjust to numerous environments and situations, however, some may have problems with the school routines for a variety of reasons.

At ages 5-6 years old, expect tricky emotions, independence, friendships and social play, plenty of talk, improved coordination and more. It is good for a child's development to play with you, do simple choses, practice classroom behavior, have play dates, and to talk about their feelings and emotions. Play and opportunities to learn and practice these skills are critically important.

Recognizing early that a child is struggling in the classroom is very important for their willingness to go to school every day, their self esteem, and over future scholastic success. Most children enjoy learning and going to school. If a child does not, the reasons why should be explored.

When a child is not able to follow directions in the classroom and/or they have trouble with assignments, school can be a distressing and frustrating place. Many children are often aware that the difficulty is happening but do not know what to do to help. Not being able to understand directions in the classroom, adapt to changing situations, or respond appropriately to their peers in social situations can be most distressing to a child.

SoundWise DX recognizes the importance of each child being school ready. We recognize and embrace the role that the parent and family relationships play in a child's development and future scholastic success. Parents want to help their children succeed in every situation. SoundWise DX wants to work together with you to help strengthen the foundational skills necessary for your child's overall success. We want children to thrive in school! They should feel both strong and confident in their ability to learn.

Fig. 20A

Copyright © 2024 All Rights Reserved

SoundWise Dx™
Pediatric Neurodevelopmental Assessment
Developed by Pediatricians

What a typical 5 year old should be able to do.

Language Communication Milestones

- Speaks very clear, using sentences of 5 or more words.
- Tells a story in complete sentences.
- Recognize and name 10 or more letters
- Sings songs and rhymes well
- Blends parts of words to gether like "cup" and "cake" to make 1 word
- Identifies some rhyming words like "cat" and "mat".
- Tell a story with at least 2 events
- Answer simple questions about a story or book
- Keep a conversation going with more than 3 back-and-forth exchanges
- Follow multistep directions
- Understand and combine words to for active sentences
- Speech should be 90-100% intelligible to a stranger without any context of the topic being discussed
- Use the future tense , such as "I will go there"
- Identify their name and where they live.

Important Tip

Limit television and mobile devices no more than 3 hrs per day.

Social Emotional Milestones

- Able to pretend play (be a dog, be a painter, be a teacher)
- Likes to sing, dance, and act
- Knows the difference between fantasy and reality
- Wants to please and play others others
- Agrees to rules more easily
- Knows who is a boy a girl
- Expresses likes and dislikes
- Shows increasing independence
- Seeks new experiences
- Demonstrates both demanding and cooperative behaviors.
- Understands about other people's feeling and needs
- Can share and take turns at least some of the time

Cognitive Milestones

Gross Motor

Copyright © 2024 All Rights Reserved

Fig. 20B

SoundWise Dx™
Pediatric Neurodevelopmental Assessment
Developed by Pediatricians (Learning, Thinking, Problem-Solving)

- Imitates reading and writing from left to right
- Count to 10
- Know at least 4 colors
- Understand items used every day such as food or money
- Draws a person at least 6 body parts
- Copy a triangle, circle, and square
- Understand the concept of time like today, yesterday, and tomorrow
- Recognizes some letters and numbers.
- Recognizes their name in print
- Attention span should be 12-18 minutes
- Able to play board games.
- Begins to know what might come next in a story
- Know what to do in most situations like if they are cold or hungry
- Should be able to pay attention to a task for 15 minutes Movement/Physical Milestones

- Hops on 1 foot
- Skips on alternate feet
- Walk along a line
- Jump over an object and land with both feet together
- Stands on one foot for at least 10 seconds
- Do a somersault
- Uses the toilet independently
- Can swing and climb
- Runs very well
- Throw a ball overhead and underhand
- Catches a ball reliably
- Walks down steps switching feet without using a rail
- Able to ride a bicycle with or without training wheels
- Build block tower with more than 10 blocks
- Jumps rope Fine Motor Milestones

- Writes their own name
- Copy a circle, cross and square
- Hold a pencil with a tripod grasp (3 point grasp)
- Color inside the lines
- Draws square & triangle, circle
- Draw a person with 6 or more body parts
- Tracing on a line with control
- Cut on a line continuously
- Copies numbers 1-5 and letters
- Has a preferred hand for most activities
- Opens zip lock bags, containers, and lunch boxes
- Completes 8-12 piece interlocking puzzle
- Dress and undress on their own (excluding shoes laces)
- Brushes their teeth on their own with toothpaste Copyright © 2024 All Rights Reserved

Fig. 20C

SoundWise Dx™
Pediatric Neurodevelopmental Assessment
Developed by Pediatricians

- Use a fork and spoon, and sometimes a table knife
- Able to tie a knot

Tips for play and learning!

- Be interactive
- Use your environment
- Name all objects around you
- Let it be multisensory
  (touch, feel, say, smell, see, and hear)
  Listen to the sound of the ocean,bird sounds
  Feel the softness of your pets fur and roughness of a trees bark
  Jump into puddles after a rainstorm and celebrate the various sounds of a busy city street.
  Learning is fun
- Every opportunity to play is an opportunity to learn.
- Keep learning activities around 15 minutes multiple times throughout the day

How to help your child build stronger language skills.

Developing healthy communication skills such as learning to speak, understanding language, and eventually learning to read are key milestones that your child needs to reach so that they enjoy and engage in play, and become successful in school.

Babies learn language through simple exposure by listening and watching you speak to them. They quickly learn how sounds are put together in different ways and have a different meaning. This exposure to sounds is building two major language skills:

1. Receptive language (input) - what you understand.
2. Expressive language (output) - what you can say.

A child's exposure to language starts in utero. As babies, they then start to babble and observe how we speak by looking at our faces and how we move our mouth, lips, and tongue to make sounds. They quickly understand that sounds have meaning and they start to acquire language at an amazing pace. When they are 5 years old, they will present to kindergarten to learn higher level language skills, like reading, writing, Copyright © 2024 All Rights Reserved

Fig. 20D

SoundWise Dx™
Pediatric Neurodevelopmental Assessment
Developed by Pediatricians spelling, and math. The strength of your child's early language foundation will directly relate to their future academic success and overall psychological well-being. Help them build a strong foundation for later scholastic and emotional success.

There are lots of simple things you can do that are fun and help build language skills;

- Sings songs
- Read to your child
  - Build their vocabulary
  - Ask questions about the things you read or talk about
  - Let them use their own imagination and create their own stories too
- Work on identifying objects within their world and building language vocabulary
- Play games with sounds:
  - Like identifying how sounds are different or the same
  - Play rhyming games
  - Play repetition games with sounds
    - Like naming all the words that start with a similar sound
  - Identifying placement of sounds in words
    - "What's the 1st sound, what's the middle sound, what's the last sound in a word?
  - Associate the letters with the sounds but the sounds are more important. Just have fun with figuring out how to play and manipulate sounds like with rhyming. Look in a mirror. Learn that the mouth moves in different ways to make different sounds. Play games where you try to lip-read to guess what sound was make.
  - Let children see your face as you are speaking
    - They need to know how the mouth moves to make different sounds
  - Pick 1-2 sounds and letter to focus on in a week. Play games where you point to or think of things that start with that same sound.
  - The sounds are actually more important than the letter at this age.
- Talk to your child.
  - TV's and screens are not good substitutes. Limit screen time to 2 hours per day and do not put TV or computer devices in the bedroom
  - Talk about what you are doing as you are doing it
  - Repeat key concepts, especially directional terms. For example: Let's find the BLUE shoes UNDER your bed. Play games like "Simon Says" where practising directions can be fun.
- Tell children what you are doing and why. Talk, Talk, talk!
- Teach and show at the same time
  - For instance, when introducing new vocabulary say "here is the BRIGHT RED crayon, here is the PALE YELLOW book"
  - Play movement games like jumping UP and jumping DOWN
  - Have fun as learning can be one great adventure and game Copyright © 2024 All Rights Reserved

Fig. 20E

SoundWise Dx™
Pediatric Neurodevelopmental Assessment
Developed by Pediatricians

- Children love to move, incorporate movement into exploration of their world
- Let your child tell the story in their own words. Their imaginations are entertaining!
- Ask your child questions as you tell a story. See if they are making a mental movie or picture while listening to the books or stories that you read to them.
- Let your child explore and use their imaginations.
- Teach language concepts with games.
    - Play hide & seek or find
    - Play with objects and place them around the room. Then give the child directions to follow with spatial concepts to find the items. For example: Find the BLUE toy ON TOP of the BROWN chair. Find the toy UNDER the table.
    - Focus on one or two words or concepts at a time and then practice multiple times a day to really learn those words or concepts.
- Teach math concepts with games.
    - Quantify/Comparative concepts (small, medium, large, most/least, same/different, young/old, wet/dry, etc.)
    - Play games using blocks to build towers of different sizes and compare.
    - Compare the size of your hands and your child's hands, your shoes to theirs, etc.
    - Play with different numbers of things like food, blocks, or toys. Compare and contrast different amounts so your child starts to learn counting and math concepts.
- Let your child have opportunities to play with other children.
    - Interactive games allow them to learn about sharing, taking turns and following simple directions.
- Use music as an opportunity to sing, dance together, and express their feelings.
- Allow outside playtime to promote exercise and the understanding of their environment like naming objects around them.
- Allow them to experience what the wind feels like or what happens when you jump in a puddle of water, smell a flower, press on a squishy object, etc.
- Allowing your child to make choices, such as places to go or what to wear, encourages independence and development of their language skills.
- Encourage affection in your family and reinforce positive behavior.
- Set limits on behaviors that are not appropriate
- Resolve disagreements and disputes peacefully.
- Children need a structured loving environment. They also need to feel safe and loved.
- Encourage a bedtime routines such as reading to your child.
- Make sure that your child gets enough sleep to wake up well rested.

Copyright © 2024 All Rights Reserved

Fig. 20F

SoundWise Dx™
Pediatric Neurodevelopmental Assessment
Developed by Pediatricians What do sounds have to do with words in print, letters, and reading?

Learn those sounds! Practicing one new sound per week will strengthen your child's ability to eventually sound out words (decode). Decoding enables your child to sound out words so they do not have to guess. Accurate decoding is critically important to future reading success. It is the skill that separates good readers from poor readers.

Whenever you can, point out words wherever you go or in books so that your child recognizes that letters actually mean something. You can point to the print while you read. Play games like finding signs on buildings or street signs, or words on boxes at the supermarket. Reading to your child and pointing out words boosts vocabulary and advances knowledge.

You can teach letters but always teach the sound association with it.

Why does all this matter?

A person learns by experience and play. Give your child every opportunity to grow and learn. A strong grasp of language will give your child the ability to thrive in school and later in life. For it is the foundation that you build before 5 years of age that will be the platform from which learning will take place later on.

A strong foundation is built using the ability to play with, manipulate, hold onto, and retrieve sounds in words. That critical skill is called "sound processing." It is the skill that "good readers" do well and "poor readers" do not. So help your child accelerate into scholastic success and build a strong language foundation. And remember, those magical ingredients are sounds so play with them and have fun!

Fig. 20G

Copyright © 2024 All Rights Reserved

SoundWise Dx™
Pediatric Neurodevelopmental Assessment
Developed by Pediatricians Parental Questionnaire

Age 6 yrs: Form A or B

Child:________________________________DOB________________

Parent Part Completed By: ______________________________

1. Can you understand your child when they speak? □ Yes □ No □ Sometimes
2. Is your child able to rhyme well? □ Yes □ No □ Sometimes
3. Does your child follow simple directions well? □ Yes □ No □ Sometimes
4. Can your child name all their letters? □ Yes □ No □ Sometimes
5. Can your child play a game or do a task with you for 10 minutes? □ Yes □ No
6. Does your child brush teeth on their own with toothpaste? □ Yes □ No □ Sometimes
7. Does your child walk down steps switching feet (no rail)? □ Yes □ No □ Sometimes 8. Does your child attend a school? □ Yes □ No
9. Does your child hear ok? □ Yes □ No □ Sometimes 10. Does your child mix up sounds in words? □ Yes □ No □ Sometimes
11. Does your child have a hard time with sight words? □ Yes □ No □ Sometimes
12. Did your child ever need ear tubes? □ Yes □ No
13. Does anyone in your family have a hard time spelling? □ Yes □ No □ Sometimes
14. Does anyone in your family struggle with reading, have dyslexia, or doesn't read for fun? □ Yes □ No □ Sometimes

Fig. 21

Copyright © 2024 All Rights Reserved

SoundWise Dx™
Pediatric Neurodevelopmental Assessment
Developed by Pediatricians Age 6: Form A

Name: ______________ ☐ M ☐ F DOB:__________ Date:______________

*Administer in a quiet one-on-one setting with limited distractions.*

Receptive Language: (Have the child pick the picture that fits best)

- Show me 3 red circles ☐ Yes ☐ No
- Show me a red arrow on top of a blue square ☐ Yes ☐ No
- Show me two red hearts and 1 orange triangle ☐ Yes ☐ No
- Show me a red number 7 inside a yellow circle ☐ Yes ☐ No

Fine Motor: Please have the child do the following:

| | | |
|---|---|---|
| **Typical three-point pencil grip?** | ☐ Yes | ☐ No |
| **Draws a dog with 6+ body parts** | ☐ Yes | ☐ No |
| **Copies numbers 1-6** | ☐ Yes | ☐ No |
| **Writes first name correctly** | ☐ Yes | ☐ No |
| **Draws a triangle and circle** | ☐ Yes | ☐ No |

Letter//Sound naming

| | Say the Letter Name | Say the Letter Sound |
|---|---|---|
| **s** | ☐ **Yes** ☐ **No** | ☐ **Yes** ☐ **No** |
| **a** | ☐ **Yes** ☐ **No** | ☐ **Yes** ☐ **No** |
| **b** | ☐ **Yes** ☐ **No** | ☐ **Yes** ☐ **No** |
| **f** | ☐ **Yes** ☐ **No** | ☐ **Yes** ☐ **No** |
| **t** | ☐ **Yes** ☐ **No** | ☐ **Yes** ☐ **No** |
| **q** | ☐ **Yes** ☐ **No** | ☐ **Yes** ☐ **No** |
| **o** | ☐ **Yes** ☐ **No** | ☐ **Yes** ☐ **No** |
| **r** | ☐ **Yes** ☐ **No** | ☐ **Yes** ☐ **No** |

Phoneme Elision (deletion) (Taking away a sound or sounds)

Directions: Say, *Let's play a game* .

Example: *Say "raindrop". Now say raindrop without saying "drop"* ...........................

If correct, say, *That's right. Let's try the next one.*

If incorrect, say. *That's not quite right. Raindrop without saying drop is rain.*

| | | |
|---|---|---|
| *1. Say football, now you say football without saying "ball"* (foot) | ☐ Yes | ☐ No |
| *2. Say outside, now you say outside without saying "out"* (side) | ☐ Yes | ☐ No |
| *3. Say sunshine, now you say sunshine without saying "sun"* (shine) | ☐ Yes | ☐ No |
| *4. Say softball, now you say softball without saying "ball"* (soft) | ☐ Yes | ☐ No |
| *5. Say stop, now you say stop without saying /s/* (top) | ☐ Yes | ☐ No |
| *6. Say three, now you say three with the /r/ sound* (thee) | ☐ Yes | ☐ No |
| *7. Say gold, now you say gold with the /g/ sound* (old) | ☐ Yes | ☐ No |
| *8. Say spill, now you say spill without saying /s/* (pill) | ☐ Yes | ☐ No |

Copyright © 2024 All Rights Reserved

Fig. 22A

SoundWise Dx™
Pediatric Neurodevelopmental Assessment
Developed by Pediatricians Age 6: Form A

Rhyming exercise

Do these words rhyme? (sound the same) *(For example, Sun and fun rhyme but sun and sat do not)*

| | | | |
|---|---|---|---|
| 1. | **rope, hope** | □ **Yes** | □ **No** |
| 2. | **fog, log** | □ **Yes** | □ **No** |
| 3. | **hit, hip** | □ **Yes** | □ **No** |
| 4. | **bank, tank** | □ **Yes** | □ **No** |
| 5. | **knee, know** | □ **Yes** | □ **No** |
| 6. | **train, trip** | □ **Yes** | □ **No** |
| 7. | **fry, sky** | □ **Yes** | □ **No** |
| 8. | **feast, fast** | □ **Yes** | □ **No** |

Reading Nonsense Words (ask child to read each word)

| | | | | | |
|---|---|---|---|---|---|
| 1. | fim | □ Yes | □ No | /f/ /i/ /m/ | (rhymes with him) |
| 2. | sab | □ Yes | □ No | /s/ /a/ /b/ | (rhymes with tab) |
| 3. | wug | □ Yes | □ No | /w/ /u/ /g/ | (rhymes with hug) |
| 4. | bast | □ Yes | □ No | /b/ /a/ /s/ /t/ | (rhymes with last) |
| 5. | zink | □ Yes | □ No | /z/ /i/ /n/ /k/ | (rhymes with rink) |
| 6. | nib | □ Yes | □ No | /n/ /i/ /b/ | (rhymes with bib) |
| 7. | lood | □ Yes | □ No | /l/ /oo/ /d/ | (rhymes with mood) |
| 8. | blee | □ Yes | □ No | /b/ /l/ /ee/ | (rhymes with see) |

Behavioral Observations: Please note the the child's demeanor during testing:

□ Cooperative □ Smiling □ Shy □ Happy and engaged

□ Uncooperative □ Crying □ Distractible □ English Language Learner

□ Refusal to Interact □ Tired □ Anxious □ Difficult to motivate

□ Completed Independently □ Needed Redirection for completion

□ poor eye contact □ wouldn't engage □ Child's speech wasn't understandable

□ Attention and ability to focus on task asked was difficult

□ Other________________________________________

Fig. 22B

Copyright © 2024 All Rights Reserved

SoundWise Dx™
Pediatric Neurodevelopmental Assessment
Developed by Pediatricians Age 6: Form A

Scoring Yearly vision screening is medically indicated and hearing if necessary

Receptive Language Skills:
- 2 or more wrong -does not understanding directions Refer to speech therapist for receptive/expressive language/phonological awareness/processing therapy
- If language spoken at home is not English, Give exposure to English Receptive/expressive/phonological awareness/processing Language Skills. Consider speech therapy.

Fine Motor Skills:
- If no misses - strong skills
- If misses 1, have parent/teacher/tutor help develop these skills further
- If miss 2 or more work on pencil grip/drawing skills with Parent//teacher/tutor/Librarian and Occupational Therapy referral to work on pencil grip/life skills

Letter & Sound Identification Skills:
- If no misses - strong skills,
- If misses 1-3, work on these skills with parent/teacher/tutor
- If miss 4 or more, work on these skills with parent/teacher/tutor/librarian
- Start Speech therapist for letter sound/identification/articulation/phonological awareness/processing
- Use Lively letters APP/or any Youtube letter sound/letter Identification

Phonemic Elision (Sound Deletion) Skills:
- If no misses - strong skills
- If misses any, work on skills these with caretaker/teacher/tutor/librarian
- If miss 2 or more, work on the skills with caretaker/teacher/tutor/librarian and start Speech therapy referral for phonemic elision/phonemic awareness/processing along with articulation/receptive/expressive language skills

Rhyming is a phonological awareness skill. It is the ability to create a repetition of similar sounds in two or more words. It requires the ability to know if sounds are the same or different.
- If perfect score then no treatment needed
- Failure to do 1-3 item (less than 50% wrong on rhyming items) then
  - Work with Phonological awareness/processing skills with caregiver/ teacher/tutor and consider speech therapy referral
  - If more than 3 wrong, work on rhyming with caregiver/teacher/tutor/librarian and must do Speech Therapy for rhyming/phonemic awareness/processing/articulation
  - Hearing screen if indicated

Nonsense words:

- If perfect score, no treatment
- Failure to do 1-3 items
  - Work with phonological awareness/processing with parent/teacher/tutor/librarian and consider speech therapy referral
  - If more than 3 are wrong, work with nonsense words and rhyming with caregiver/teacher/tutor/ Librarian.Also, start Speech Therapy for nonsense words/phonemic awareness/processing/articulation/receptive/expressive language skills
  - Hearing screen if indicated

Engagement: If any concerns for autism like poor eye contact/lack of joint attention, lack of wanting to engage, and sensory dysregulation refer for Speech, OT, PT and a referral for Autism evaluation

If any concerns for ADHD/ADD, like unable to focus, easily distracted, unable to sustain attention for 12-18 minutes consider speaking to parents about Vanderbilt screen. Children who are inattentive and also exhibit staring spells, need to be evaluated for Absence seizures. SoundWise DX will offer RX or pediatrician/provider for neurology referral.

Fig. 22C

Copyright © 2024 All Rights Reserved

SoundWise Dx™
Pediatric Neurodevelopmental Assessment
Developed by Pediatricians Age 6: Form A

If there are any concerns about Anxiety, frustration with performance, thinking that they can not do well, crying, saying that they always fail every test,etc. Consider doing SCARED, and Columbia Screen or other screens for anxiety/depression.

Concerns present:
- □ None - Perfect Score
- □ Engagement Concerns (Based of Evaluator's Behavioral Observations)
- □ Receptive Language Concerns
- □ Sound Discrimination Concerns
- □ Sound OrderAwareness Concerns
- □ Fine Motor Concerns
- □ Letter & Sound Identification Concerns
- □ Sound Articulation Concerns
- □ Letter & Sound Identification Concerns
- □ Phonemic Elision (Sound Deletion) Concerns

Interventional Response:

□ General 4 Year Old Milestone Information Sheet
- Provides general understanding of what a 4 year should be able to do □ Specific Information Sheet for Opportunity and Development of Individual Skills
- Based upon Neurodevelopmental Foundational Model and Treatment Approach
- Includes Recommended Suggestions for opportunities and activities to grow skills
- Expand Opportunities and Suggestions available through SoundWise DX platform and other recommended sites.
- Increased Academic Focused Instruction on Broad areas of Concern (Engagement, Receptive Language, Sound Order awareness,Sound Discrimination, Fine Motor, Letter & Sound Identification, and Phonemic Elision)

Follow up if concerns present: □ 3-6 months later □ Yearly at the next Well Child Visit

Fig. 22D

Copyright © 2024 All Rights Reserved

SoundWise Dx™
Pediatric Neurodevelopmental Assessment
Developed by Pediatricians

Age 6 years: Form A

Name: ____________________ □ M □ F DOB:______________ Date:________________

*Have the child write their first name.*

Name: ______________________________________________

| | |
|---|---|
| *Draw a dog with 6 + body parts.* | *Draw a triangle and circle.*  |

| | |
|---|---|
| *Copy the Numbers.* *1 2 3 4 5 6* | *fim* *sab*<br>*wug* *bast*<br>*zink* *nib*<br>*lood* *blee* |
| s | t |
| a | q |
| b | o |
| f | r |

Copyright © 2024 All Rights Reserved

SoundWise Dx™
Pediatric Neurodevelopmental Assessment
Developed by Pediatricians

Age 6 years: Form A

Copyright © 2024 All Rights Reserved

SoundWise Dx™
Pediatric Neurodevelopmental Assessment
Developed by Pediatricians

Age 6 years: Form A

Copyright © 2024 All Rights Reserved

SoundWise Dx™
Pediatric Neurodevelopmental Assessment
Developed by Pediatricians

Age 6 years: Form A

Copyright © 2024 All Rights Reserved

SoundWise Dx™
Pediatric Neurodevelopmental Assessment
Developed by Pediatricians

Age 6 years: Form A

Copyright © 2024 All Rights Reserved

SoundWise Dx™
Pediatric Neurodevelopmental Assessment
Developed by Pediatricians Age 6: Form B

Name: ______________ □ M □ F DOB: ________ Date: ____________

*Administer in a quiet one-on-one setting with limited distractions.*

Please note the child's demeanor during testing:

Receptive Language: (Have the child pick the picture that fits best)

- Show me 2 red circles □ Yes □ No
- Show me a blue arrow on top of a red square □ Yes □ No
- Show me two green hearts and 1 orange triangle □ Yes □ No
- Show me a red number 7 inside a green circle □ Yes □ No

Fine Motor: Please have the child do the following:

| | | |
|---|---|---|
| Typical three-point pencil grip? | □ Yes | □ No |
| Draws a cat with 6+ body parts | □ Yes | □ No |
| Draws a triangle and a circle | □ Yes | □ No |
| Copies numbers 1-6 | □ Yes | □ No |
| Writes first name correctly | □ Yes | □ No |

Letter/Sound Naming

| | Say the Letter Name | Say the Letter Sound |
|---|---|---|
| l | □ Yes □ No | □ Yes □ No |
| p | □ Yes □ No | □ Yes □ No |
| d | □ Yes □ No | □ Yes □ No |
| c | □ Yes □ No | □ Yes □ No |
| v | □ Yes □ No | □ Yes □ No |
| i | □ Yes □ No | □ Yes □ No |
| m | □ Yes □ No | □ Yes □ No |
| u | □ Yes □ No | □ Yes □ No |

Phoneme Elision (deletion) (Taking away a sound or sounds)

**Directions: Say, *Let's play a game*.**
**Example: *Say "raindrop". Now say raindrop without saying "drop"* ............................**
**If correct, say, *That's right. Let's try the next one.***
**If incorrect, say. *That's not quite right. Raindrop without saying drop is rain.***

| | | |
|---|---|---|
| *1. Say sunflower, now you say Sunflower without saying "flower"* (sun) | □ Yes | □ No |
| *2. Say outside, now you say outside without saying "side"* (out) | □ Yes | □ No |
| *3. Say haystack, now you say haystack without saying "hay"* (stack) | □ Yes | □ No |
| *4. Say football, now you say football without saying "ball"* (foot) | □ Yes | □ No |
| *5. Say neat, now you say neat without saying /n/* (eat) | □ Yes | □ No |
| *6. Say tanks, now you say tanks without the /s/ sound* (tank) | □ Yes | □ No |
| *7. Say halt, now you say halt with the /l/ sound* (hat) | □ Yes | □ No |
| *8. Say feel, now you say feel without saying /l/* (fee) | □ Yes | □ No |

Copyright © 2024 All Rights Reserved

Fig. 23A

SoundWise Dx™
Pediatric Neurodevelopmental Assessment
Developed by Pediatricians Age 6: Form B

Rhyming exercise

Do these words rhyme? (sound the same)

*(For example, Sun and fun rhyme but sun and sat do not)*

| | | |
|---|---|---|
| 1. | **dog, fog** | □ **Yes** □ **No** |
| 2. | **drip, drop** | □ **Yes** □ **No** |
| 3. | **neat, seat** | □ **Yes** □ **No** |
| 4. | **gold, fold** | □ **Yes** □ **No** |
| 5. | **thru, three** | □ **Yes** □ **No** |
| 6. | **rain, road** | □ **Yes** □ **No** |
| 7. | **fry, spy** | □ **Yes** □ **No** |
| 8. | **great, greet** | □ **Yes** □ **No** |

Reading Nonsense Words (ask child to read each word)

| | | | | | |
|---|---|---|---|---|---|
| 1. | lim | □ Yes | □ No | /l/ /i/ /m/ | (rhymes with him) |
| 2. | pab | □ Yes | □ No | /p/ /a/ /b/ | (rhymes with tab) |
| 3. | vug | □ Yes | □ No | /v/ /u/ /g/ | (rhymes with hug) |
| 4. | bist | □ Yes | □ No | /b/ /i/ /s/ /t/ | (rhymes with list) |
| 5. | bink | □ Yes | □ No | /b/ /i/ /n/ /k/ | (rhymes with rink) |
| 6. | nab | □ Yes | □ No | /n/ /a/ /b/ | (rhymes with cab) |
| 7. | nood | □ Yes | □ No | /l/ /oo/ /d/ | (rhymes with mood) |
| 8. | pree | □ Yes | □ No | /p/ /r/ /ee/ | (rhymes with tree) |

Behavioral Observations: Please note the the child's demeanor during testing:

□ Cooperative □ Smiling □ Shy □ Happy and engaged

□ Uncooperative □ Crying □ Distractible □ English Language Learner

□ Refusal to Interact □ Tired □ Anxious □ Difficult to motivate

□ Completed Independently □ Needed Redirection for completion

□ poor eye contact □ wouldn't engage □ Child's speech wasn't understandable

□ Attention and ability to focus on task asked was difficult

□ Other____________________________________________

Copyright © 2024 All Rights Reserved

Fig. 23B

SoundWise Dx™
Pediatric Neurodevelopmental Assessment
Developed by Pediatricians Age 6: Form B

Scoring Yearly vision screening is medically indicated and hearing if necessary

Receptive Language Skills:
- 2 or more wrong -does not understanding directions Refer to speech therapist for receptive/expressive language/phonological awareness/processing therapy
- If language spoken at home is not English, Give exposure to English Receptive/expressive/phonological awareness/processing Language Skills. Consider speech therapy.

Fine Motor Skills:
- If no misses - strong skills
- If misses 1, have parent/teacher/tutor help develop these skills further
- If miss 2 or more work on pencil grip/drawing skills with Parent//teacher/tutor/Librarian and Occupational Therapy referral to work on pencil grip/life skills

Letter & Sound Identification Skills:
- If no misses - strong skills,
- If misses 1-3, work on these skills with parent/teacher/tutor
- If miss 4 or more, work on these skills with parent/teacher/tutor/librarian
- Start Speech therapist for letter sound/identification/articulation/phonological awareness/processing
- Use Lively letters APP/or any Youtube letter sound/letter Identification

Phonemic Elision (Sound Deletion) Skills:
- If no misses - strong skills
- If misses any, work on skills these with caretaker/teacher/tutor/librarian
- If miss 2 or more, work on the skills with caretaker/teacher/tutor/librarian and start Speech therapy referral for phonemic elision/phonemic awareness/processing along with articulation/receptive/expressive language skills

Rhyming is a phonological awareness skill. It is the ability to create a repetition of similar sounds in two or more words. It requires the ability to know if sounds are the same or different.
- If perfect score then no treatment needed
- Failure to do 1-3 item (less than 50% wrong on rhyming items) then
  - Work with Phonological awareness/processing skills with caregiver/ teacher/tutor and consider speech therapy referral
  - If more than 3 wrong, work on rhyming with caregiver/teacher/tutor/librarian and must do Speech Therapy for rhyming/phonemic awareness/processing/articulation
  - Hearing screen if indicated

Nonsense words:
- If perfect score, no treatment
- Failure to do 1-3 items
  - Work with phonological awareness/processing with parent/teacher/tutor/librarian and consider speech therapy referral
  - If more than 3 are wrong, work with nonsense words and rhyming with caregiver/teacher/tutor/ Librarian.Also, start Speech Therapy for nonsense words/phonemic awareness/processing/articulation/receptive/expressive language skills
  - Hearing screen if indicated

Engagement: If any concerns for autism like poor eye contact/lack of joint attention, lack of wanting to engage, and sensory dysregulation refer for Speech, OT, PT and a referral for Autism evaluation

If any concerns for ADHD/ADD, like unable to focus, easily distracted, unable to sustain attention for 12-18 minutes consider speaking to parents about Vanderbilt screen. Children who are inattentive and also exhibit staring spells, need to be evaluated for Absence seizures. SoundWise DX will offer RX or pediatrician/provider for neurology referral.

Copyright © 2024 All Rights Reserved

Fig. 23C

SoundWise Dx™
Pediatric Neurodevelopmental Assessment
Developed by Pediatricians Age 6: Form B

If there are any concerns about Anxiety, frustration with performance, thinking that they can not do well, crying, saying that they always fail every test,etc. Consider doing SCARED, and Columbia Screen or other screens for anxiety/depression.

Concerns present:
- □ None - Perfect Score
- □ Engagement Concerns (Based of Evaluator's Behavioral Observations)
- □ Receptive Language Concerns
- □ Sound Discrimination Concerns
- □ Sound OrderAwareness Concerns
- □ Fine Motor Concerns
- □ Letter & Sound Identification Concerns
- □ Sound Articulation Concerns
- □ Letter & Sound Identification Concerns
- □ Phonemic Elision (Sound Deletion) Concerns

Interventional Response:

□ General 4 Year Old Milestone Information Sheet
- Provides general understanding of what a 4 year should be able to do □ Specific Information Sheet for Opportunity and Development of Individual Skills
- Based upon Neurodevelopmental Foundational Model and Treatment Approach
- Includes Recommended Suggestions for opportunities and activities to grow skills
- Expand Opportunities and Suggestions available through SoundWise DX platform and other recommended sites.
- Increased Academic Focused Instruction on Broad areas of Concern (Engagement, Receptive Language, Sound Order awareness,Sound Discrimination, Fine Motor, Letter & Sound Identification, and Phonemic Elision)

Follow up if concerns present: □ 3-6 months later □ Yearly at the next Well Child Visit Copyright © 2024 All Rights Reserved

Fig. 23D

SoundWise Dx™
Pediatric Neurodevelopmental Assessment
Developed by Pediatricians

Age 6 years: Form B

Name: ______________________ □ M □ F DOB:____________ Date:_________________

*Have the child write their first name.*

Name: ________________________________________________

| *Draw a cat with 6 + body parts.* | *Draw a Triangle and circle.* |
|---|---|
| |  |

| *Copy the Numbers.* | |
|---|---|
| 1 2 3 4 5 6 | lim bink<br>pab nab<br>vug nood<br>bist pree |

| | |
|---|---|
| l | v |
| p | i |
| d | m |
| c | u |

Copyright © 2024 All Rights Reserved

SoundWise Dx™
Pediatric Neurodevelopmental Assessment
Developed by Pediatricians

Age 6 years: Form B

Copyright © 2024 All Rights Reserved

SoundWise Dx™
Pediatric Neurodevelopmental Assessment
Developed by Pediatricians

Age 6 years: Form B

Copyright © 2024 All Rights Reserved

SoundWise Dx™
Pediatric Neurodevelopmental Assessment
Developed by Pediatricians

Age 6 years: Form B

Copyright © 2024 All Rights Reserved

SoundWise Dx™
Pediatric Neurodevelopmental Assessment
Developed by Pediatricians

Age 6 years: Form B

Copyright © 2024 All Rights Reserved

SoundWise Dx™
Pediatric Neurodevelopmental Assessment
Developed by Pediatricians
6 year old Assessment Guided Treatment flow chart Form A or B

Vision and Hearing Assessments: should be done on all children yearly.

SoundWise DX will perform vision and colorblind testing before every assessment.

SoundWise DX will perform a Vision Snell chart (or any other standardized screen) and a colorblind test (The Ishihara, EnChroma, or any other standardized color blind assessment or screen) before every assessment.) The colorblind tests can be done as early as when a child is able to recognize numbers, shapes, or animals.

*Color blindness (color vision deficiency, or CVD) affects approximately 1 in 12 men (8%) and 1 in 200 women. This is an important thing to know for all children as colors are frequently used on computer academic assessments and inability to discern colors can negatively impact learning.*

*Concern for possible color blindness: If a child misses questions with red and/or green they will be tested for color blindness as soon as they are able to identify the common shapes used in testing books like numbers, shapes, or animals.*

Receptive Language Skills:

- Perfect score on items of Receptive Language items/understood all directions of all tasks,then recommend the child do enrichment with SoundWise DX AI/AI-Generative for 6 year old Receptive Language modules( Modules are preceded by a short video explaining the lesson to be learned followed by AI/AI-Generative Online recommendation algorithm) and/or worksheets for learning advanced skills.
- If unable to follow and/or properly demonstrate ability to perform and understand directions and if child from English as a second language home, as determined by SoundWise DX computer program AI grader, pediatrician, or authorized personnel,
    - Caregiver/ teacher work on receptive language by using SoundWise DX 6 Year Old Developmental Milestone Information Sheet (DMIS)

- START SoundWise DX AI/AI-Generative Online 6 year old Receptive/expressive Language modules (Modules are preceded by a short video explaining the lesson to be learned followed by AI/AI-Generative Online
- recommendation algorithm) and/or worksheets with respect to following directions, strengthening Receptive and Expressive Language skills, with emphasis on building English vocabulary.
- In addition SoundWise DX recommends:
- In person Speech and Language Therapy focusing on improving Receptive/
- Expressive language/phonological awareness/processing and English Language vocabulary building.
- Prescriptions for speech and language will be given through SoundWise DX or Pediatrician/Provider.
- Multiple SoundWise DX modules will be performed until the child is able to demonstrate proficiency to move on to learning advanced skills as determined by the SoundWise DX computer program AI grader, pediatrician, or authorized personnel.
- If from an English second language home, then these modules should be done in both English and their primary language until the child is able to demonstrate proficiency as determined by the SoundWise DX computer program AI grader, pediatrician, or authorized personnel.

Fig. 24A

SoundWise Dx™
Pediatric Neurodevelopmental Assessment
Developed by Pediatricians
6 year old Assessment Guided Treatment flow chart Form A or B

- If Child still demonstrates difficulty, SoundWise DX will administer or recommend local referral for an assessment that looks at early literacy skills such as the Comprehensive Test of Phonological Processing CTOPP-2 or Test of Preschool Literacy Skills (TOPEL), or any other standardized assessment (most current version) that measures awareness and/or phonological processing.

Fine Motor Skills:

SoundWise DX will use AI determination of correct stroke/direction/pressure, speed, accuracy, and skill.

(6 total scored items that include correct pencil grip (no fisted grip), drawing animal either cat, Using hands to do school related tasks. Between 4-6 years of age a child will begin to use the most mature grasp which is the dynamic tripod. They will use the tips of their fingers on the writing utensil and hold the utensil at more of an angle rather than vertical. or dog, writes numbers correctly 1-6, writes first name, draws a triangle and a circle):

- If a perfect score on Fine Motor items with correct pencil grip, as determined by SoundWise DX computer program AI grader, pediatrician, or authorized personnel, then recommend the child use enrichment with SoundWise DX AI/AI-Generative 6 yr old occupational therapy modules) and/or worksheets for learning advanced skills SoundWise DX will use AI determination of correct stroke/direction/pressure, speed, accuracy, and skill.

Fine motor skills listed include, for example,the equivalent of the following (but not limited to) drawing animals, copying shapes and writing numbers and correct pencil grip (which can be expanded to other skills in the future)

- Concerns or Fail: unable to do 1 item (< 50% completed incorrectly)
  - Caregiver/teacher/or authorized personnel will work on drawing with correct pencil grip using SoundWise DX 6 Year Old Developmental Milestone Information Sheet (DMIS)
  - Fine motor skills listed includes, for example, the equivalent of the following (but not limited to):draw cat with 3 or more parts, copies shape,trace the line within the box and demonstrates pencil grip (which can be expanded to other skills in the future).
- Must START SoundWise DX AI/AI-Generative Online 6 year old Occupational Therapy modules (Modules are preceded by a short video explaining the lesson to be learned followed by AI/AI-Generative Online recommendation algorithm) and/or worksheets on how to draw figures, copy shapes, trace lines, and use of correct pencil grip with AI determination of correct stroke/direction/pressure, speed, accuracy, and skill.
- Must Start in person Occupational Therapy services
  - Prescriptions for speech and language will be given through SoundWise DX or Pediatrician/Provider.

- Some children will wear gloves where computer will analyze proper technique with digitized feedback
- Multiple SoundWise DX modules will be performed until the child is able to demonstrate proficiency as determined by SoundWise DX computer program AI grader, Pediatrician, or authorized personnel.

Fig. 24B

SoundWise Dx™
Pediatric Neurodevelopmental Assessment
Developed by Pediatricians
6 year old Assessment Guided Treatment flow chart Form A or B

Letter Identification/Letter Sound:

Knowing basic phonic rules of how a specific sound relates to a specific letter is an important part of mastering the alphabetic code.

We take into account AI algorithms to recognize, transcribe a child's letter sound/word pronunciation, analyze context/structure where pronunciation varies due to accents/dialects and word/sentence structure comprehension and fluency.

- If a perfect score (all 16 letter and sound identification items correct) as determined by SoundWise DX computer program AI grader, pediatrician, or authorized personnel, then recommend the child do enrichment with SoundWise DX AI/AI-Generative 6 year old letter identification /letter sound skill modules (Modules are preceded by a short video explaining the lesson to be learned followed by AI/AI-Generative Online recommendation algorithm) and/or worksheets for learning advanced skills

- Concerns or Fail: Unable to do 1-3 items (less than 50% wrong on letter names or on letter sounds) then

- Caretaker/teacher/ or authorized personnel work on letter naming/letter sound skills using SoundWise DX 6 Year Old Developmental Milestone Information Sheet (DMIS)
    - START SoundWise DX AI/AI-Generative Online 6 year old letter naming/letter sound modules (Modules are preceded by a short video explaining the lesson to be learned followed by AI/AI-Generative Online recommendation algorithm) and/or worksheets that focus on letter identification/letter sound skills along with phonological awareness/processing skills
    - Multiple SoundWise DX modules will be performed until the child is able to demonstrate proficiency as determined by SoundWise DX computer program AI grader, Pediatrician, or authorized personnel.
    - If unable to pass the skill using SoundWise DX modules within 3 months of actively working on this skill then include along with modules
        - Start in person Speech and Language Therapy focusing on improving phonological awareness/processing and letter identification/letter sounds
        - Prescriptions for speech and language will be given through SoundWise DX or Pediatrician/Provider for letter identification/sounds

- Fail: If misses 4 or more items (greater than 50% wrong) on either letter names or on letter sounds:

Work with Caregiver/teacher/ or authorized personnel work on letter identification /letter sound using SoundWise DX 6 Year Old Developmental Milestone Information Sheet (DMIS)

Fig. 24C

SoundWise Dx™
Pediatric Neurodevelopmental Assessment
Developed by Pediatricians
6 year old Assessment Guided Treatment flow chart Form A or B START SoundWise DX AI/AI-Generative Online 6 year old letter identification/letter sound modules (Modules are preceded by a short video explaining the lesson to be learned followed by AI/AI-Generative Online recommendation algorithm) and/or worksheets that focus on letter identification/ letter sound skills along with phonological awareness/processing skills

- Start in person Speech and Language Therapy focusing on improving phonological awareness/processing and letter identification/letter sounds.
- Prescriptions for speech and language will be given through SoundWise DX or Pediatrician/provider.
- Multiple SoundWise DX modules will be performed until the child is able to demonstrate proficiency as determined by SoundWise DX computer program AI grader, Pediatrician, or authorized personnel.

- If proficiency is not reached after 3 months, SoundWise DX will administer or give a local referral for an assessment that diagnoses a Specific Learning Disorder with Impairment in Reading (dyslexia). This assessment at the least should include a standardized measure of receptive language (including a cognitive measure if receptive language assessment is a deficit), reading and spelling measures, phonological processing assessments (for example that include but not limited to the CTOPP-2), and simple handwriting assessments. At the same time, a diagnostic assessment for ADHD should be done. If an intellectual disability is suspected, a standardized cognitive measure like an IQ test should also be given. All standardized assessments will be the most current versions of the test available. Results of diagnostic testing will be reviewed by SoundWise DX and/or either an in person licensed psychologist or physician to make the appropriate medical diagnosis. This can be done through SoundWise DX or the child's local care network.

Phoneme Elision (sound deletion):

Phoneme Elision means to take away a sound and is one of the strongest predictors that a child will go on to struggle in reading. It can be tested as early as 4 years old.

We take into account AI algorithms to recognize, transcribe a child's letter sound/word pronunciation, analyze context/structure where pronunciation varies due to accents/dialects and word/sentence structure comprehension and fluency.

- If a perfect score as determined by SoundWise DX computer program AI grader, pediatrician, or authorized personnel, then recommend the child do enrichment with SoundWise DX AI/AI-Generative 6 year old phoneme Elision skill modules (Modules are preceded by a short video explaining the lesson to be learned followed by AI/AI-Generative Online recommendation algorithm) and/or worksheets for learning advanced skills
- Concerns or Fail: Unable to do 1 to 3 items only (less than 50% wrong on phoneme elision) then
  - Work on Phonological awareness/processing skills with a caregiver/ teacher using SoundWise DX 6 Year Old Developmental Milestone Information Sheet (DMIS)
  - START SoundWise DX AI/AI-Generative Online 6 year old phoneme elision/receptive/expressive/articulation/phonological processing/awareness modules (Modules are preceded by a short video

Fig. 24D

SoundWise Dx™
Pediatric Neurodevelopmental Assessment
Developed by Pediatricians
6 year old Assessment Guided Treatment flow chart Form A or B explaining the lesson to be learned followed by AI/AI-Generative Online recommendation algorithm) and/or worksheets that focus on Phonological Awareness/Processing/phonemic elision skills

- Multiple SoundWise DX modules will be performed until the child is able to demonstrate proficiency as determined by SoundWise DX computer program AI grader ,Pediatrician, or authorized personnel.

- If unable to pass the skill using the SoundWise DX modules with 3 months of actively working on this skill then include along with modules,
  - In person Speech and Language Therapy focusing on improving phonological awareness and phonological processing
  - Prescriptions for speech and language will be given through SoundWise DX or Pediatrician/provider..
  - Multiple SoundWise DX modules will be performed until the child is able to demonstrate proficiency as determined by SoundWise DX computer program AI grader, Pediatrician, or authorized personnel.

- Fail: If misses 4 or more (50% or greater on phoneme elision items), then
  - Caregiver/teacher work on Phonological awareness/processing/phonemic elision skills using SoundWise DX 6 Year Old Developmental Milestone Information Sheet (DMIS)
  - START SoundWise DX AI/AI-Generative Online 6 year old (Modules are preceded by a short video explaining the lesson to be learned followed by AI/AI-Generative Online recommendation algorithm) and/or worksheets modules on phoneme elision/phonemic processing/awareness/receptive/expressive language skills that focus on Phonological Awareness/processing/phonemic elision/receptive/expressive language skills
  - Start In person Speech/Language Therapy focusing on improving phonological awareness/processing/phonemic elision/receptive/expressive language skills
  - Prescriptions for speech and language will be given through SoundWise DX or Pediatrician/provider..
  - Multiple SoundWise DX modules will be performed until the child is able to demonstrate proficiency as determined by SoundWise DX computer program AI grader, Pediatrician, or authorized personnel.

- If proficiency is not reached after 3 months,SoundWise DX will administer or give a local referral for an assessment that diagnoses a Specific Learning Disorder with Impairment in Reading (dyslexia). This assessment at the least should include a standardized measure of receptive language (including a cognitive measure if receptive language assessment is a deficit), reading and spelling measures, phonological processing assessments (for example that include but not limited to the CTOPP-2), and simple handwriting assessments. At the same time, a diagnostic assessment for ADHD should be done. If an intellectual disability is suspected, a standardized cognitive measure like an IQ test should also be given. All standardized assessments will be the most current versions of the test available. Results of diagnostic testing will be reviewed by SoundWise DX and/or either an in person licensed psychologist or physician to make the appropriate medical diagnosis. This can be done through SoundWise DX or the child's local care network.

Fig. 24E

SoundWise Dx™
Pediatric Neurodevelopmental Assessment
Developed by Pediatricians
6 year old Assessment Guided Treatment flow chart Form A or B

Rhyming Exercises:

Rhyming is a phonological awareness skill. It is the ability to create a repetition of similar sounds in two or more words. It requires the ability to know if sounds are the same or different.

We take into account AI algorithms to recognize, transcribe a child's letter sound/word pronunciation, analyze context/structure where pronunciation varies due to accents/dialects and word/sentence structure comprehension and fluency.

- If a perfect score as determined by SoundWise DX computer program AI grader, pediatrician, or authorized personnel, then recommend the child do enrichment with SoundWise DX AI/AI-Generative 6 year old phonological awareness skill modules (Modules are preceded by a short video explaining the lesson to be learned followed by AI/AI-Generative Online recommendation algorithm) and/or worksheets for learning advanced skills
- Concern or Fail: Unable to do 1 to 3 items only (less than 50% wrong on rhyming) then
  - Work on Phonological awareness/processing skills with a caregiver/ teacher using SoundWise DX 6 Year Old Developmental Milestone Information Sheet (DMIS)
  - START SoundWise DX AI/AI-Generative Online 6 year old rhyming/phonological awareness/processing/rhyming modules (Modules are preceded by a short video explaining the lesson to be learned followed by AI/AI-Generative Online recommendation algorithm) and/or worksheets that focus on Phonological Awareness/processing/rhyming skills
  - Multiple SoundWise DX modules will be performed until the child is able to demonstrate proficiency as determined by SoundWise DX computer program AI grader, Pediatrician, or authorized personnel.
  - If unable to pass the skill using the SoundWise DX modules with 3 months of actively working on this skill then include along with modules,
    - Start In person Speech/Language Therapy focusing on improving phonological awareness/processing/rhyming/receptive/expressive language skills.
    - Prescriptions for speech and language will be given through SoundWise DX or Pediatrician/provider.
    - Multiple SoundWise DX modules will be performed until the child is able to demonstrate proficiency as determined by SoundWise DX computer program AI grader, Pediatrician, or authorized personnel.
- Fail: If misses 4 or more (50% or greater on rhyming items), then
  - Work with Phonological awareness/processing skills with caregiver and/or teacher. See SoundWise DX 6 Year Old Developmental Milestone Information Sheet (DMIS)
  - START SoundWise DX AI/AI-Generative Online 6 year old modules on rhyming/phonological awareness/processing (Modules are preceded by a short video explaining the lesson to be learned followed by AI/AI-Generative Online recommendation algorithm) and/or worksheets modules on rhyming that focus on Phonological Awareness/processing skills

Fig. 24F

SoundWise Dx™
Pediatric Neurodevelopmental Assessment
Developed by Pediatricians
6 year old Assessment Guided Treatment flow chart Form A or B

- Start In person Speech/ Language Therapy focusing on improving rhyming/phonological awareness/processing/receptive/expressive language skills.
- Prescriptions for speech and language will be given through SoundWise DX or Pediatrician/provider.
- Multiple SoundWise DX modules will be performed until the child is able to demonstrate proficiency as determined by SoundWise DX computer program AI grader, Pediatrician, or authorized personnel.
- If proficiency is not reached after 3 months,SoundWise DX will administer or give a local referral for an assessment that diagnoses a Specific Learning Disorder with Impairment in Reading (dyslexia). This assessment at the least should include a standardized measure of receptive language (including a cognitive measure if receptive language assessment is a deficit), reading and spelling measures, phonological processing assessments (for example that include but not limited to the CTOPP-2), and simple handwriting assessments. At the same time, a diagnostic assessment for ADHD should be done. If an intellectual disability is suspected, a standardized cognitive measure like an IQ test should also be given. All standardized assessments will be the most current versions of the test available. Results of diagnostic testing will be reviewed by SoundWise DX and/or either an in person licensed psychologist or physician to make the appropriate medical diagnosis. This can be done through SoundWise DX or the child's local care network.

Reading nonsense words:

Reading nonsense words requires the ability to accurately decode or sound out words.

We take into account AI algorithms to recognize, transcribe a child's letter sound/word pronunciation, analyze context/structure where pronunciation varies due to accents/dialects and word/sentence structure comprehension and fluency.

- If a perfect score as determined by SoundWise DX computer program AI grader, pediatrician, or authorized personnel, then recommend the child enrichment with SoundWise DX AI/AI-Generative 6 year old nonsense word/phonological awareness/processing skill modules (Modules are preceded by a short video explaining the lesson to be learned followed by AI/AI-Generative Online recommendation algorithm) and/or worksheets for learning advanced skills
- Concern or Fail: Unable to do 1 to 3 items only (less than 50% wrong on rhyming) then
  - Work on Phonological awareness/processing skills with a caregiver/ teacher using SoundWise DX 6 Year Old Developmental Milestone Information Sheet (DMIS)
  - START SoundWise DX AI/AI-Generative Online 6 year old nonsense word/phonological awareness/phonological processing modules (Modules are preceded by a short video explaining the lesson to be learned followed by AI/AI-Generative Online recommendation algorithm) and/or worksheets that focus on Phonological Awareness/processing skills

Fig. 24G

SoundWise Dx™
Pediatric Neurodevelopmental Assessment
Developed by Pediatricians
6 year old Assessment Guided Treatment flow chart Form A or B

- Multiple SoundWise DX modules will be performed until the child is able to demonstrate proficiency as determined by SoundWise DX computer program AI grader ,Pediatrician, or authorized personnel.
- If unable to pass the skill using the SoundWise DX modules with 3 months of actively working on this skill then include along with modules,
  - Start In person Speech and Language Therapy focusing on improving phonological awareness/ processing/receptive/expressive language skills
  - Prescriptions for speech and language will be given through SoundWise DX or Pediatrician/Provider.
  - Multiple SoundWise DX modules will be performed until the child is able to demonstrate proficiency as determined by SoundWise DX computer program AI grader, Pediatrician, or authorized personnel.

- Fail:If misses 4 or more (50% or greater on rhyming items), then
  - Work on Phonological awareness/processing skills with a caregiver/ teacher using SoundWise DX 6 Year Old Developmental Milestone Information Sheet (DMIS)
  - START SoundWise DX AI/AI-Generative Online 6 year old nonsense word/phonological awareness/processing modules (Modules are preceded by a short video explaining the lesson to be learned followed by AI/AI-Generative Online recommendation algorithm) and/or worksheets that focus on Nonsense words/Phonological Awareness/processing/receptive/expressive skills
  - Start In person Speech and Language Therapy focusing on improving nonsense word/phonological awareness/ processing.
  - Prescriptions for speech and language given by SoundWise or Pediatrician/Provider.
  - Multiple SoundWise DX modules will be performed until the child is able to demonstrate proficiency as determined by SoundWise DX computer program AI grader, Pediatrician, or authorized personnel.
  - If proficiency is not reached after 3 months,SoundWise DX will administer or give a local referral for an assessment that diagnoses a Specific Learning Disorder with Impairment in Reading (dyslexia). This assessment at the least should include a standardized measure of receptive language (including a cognitive measure if receptive language assessment is a deficit), reading and spelling measures, phonological processing assessments (for example that include but not limited to the CTOPP-2), and simple handwriting assessments. At the same time, a diagnostic assessment for ADHD should be done. If an intellectual disability is suspected, a standardized cognitive measure like an IQ test should also be given. All standardized assessments will be the most current versions of the test available. Results of diagnostic testing will be reviewed by SoundWise DX and/or either an in person licensed psychologist or physician to make the appropriate medical diagnosis. This can be done through SoundWise DX or the child's local care network.

Engagement:

Fig. 24H

SoundWise Dx™

Pediatric Neurodevelopmental Assessment

Developed by Pediatricians

6 year old Assessment Guided Treatment flow chart Form A or B

*Any and all diagnoses of psychiatric/behavioral disorders (ADHD, Autism, Anxiety, depression etc, will follow and change accordingly with the most current medical guidelines determined by the latest version of the Diagnostic and Statistical Manual of Mental Disorders which is currently the DSM-V. As new versions are published, SoundWise DX concerns identified and diagnostic criteria will adapt and be changed to match the most current diagnostic criteria.*

Perfect score:

- Able to demonstrate social communication, interaction , eye contact and able to demonstrate joint attention back and forth with assessment tasks. Not showing restrictive and repetitive behaviors, such as flapping their hands, spinning a lot, only interested in lining up toys or objects, sensory issues such as upset with loud noises, and difficulty with change of routine during the assessment.
- Able to sustain attention, not easily distracted, following directions on Assessment tasks.
- Attending the SoundWise DX assessment without crying and worrying about how they are doing with each task.
- Engagement evaluation is determined by SoundWise DX computer program AI grader, pediatrician, or authorized personnel.

A concern or fail for this section:

- Autism Concern:
  - The child has challenges with social communication and interaction. Has poor eye contact, refusal to engage in tasks, and/or lack of joint attention back and forth while doing assessment tasks.
  - The child demonstrates restrictive/repetitive behaviors, interests, and activities such as, but not limited to, flapping hands, spinning, lining up toys/objects, sensory issues (upset by loud noises/smell/touch), and challenges with change of routine during tasks.
- ADHD/ADD/attention deficits: Please note that ADHD diagnosis is made at age 4
  - The child is unable to keep their attention and/or unable to follow directions while completing Assessment without being distracted and/or unable to sit still long enough to complete assessment at age 3 years old, note that a formal diagnosis is not made at age 3, rather only a concern. Children who are inattentive and also exhibit staring spells, need to be evaluated for Absence Seizures. SoundWise DX will offer RX or pediatrician/provider for Neurology referral.
    - Norm values:
      - 3 years old: 6-8 minutes
      - 4 years old: 8-12 minutes
      - 5 and 6 years old: 12-18 minutes
      - 7 and 8 years old: 16-24 minutes
      - 9 and 10 years old: 20-30 minutes
- Anxiety, panic attacks, or Post Traumatic Stress Disorder (PTSD) Concern or Fail:
  - The child is showing emotions of frustration with or without crying and/or demonstrating worry about their performance while completing the assessment.
  - Elevated heart rate and/or blood pressure measured by all digital devices
  - Avoidance behaviors when tasks are hard such as:
    - Child complains or somatic (body) complaints to end or get out of a task like:
      - Headaches
      - Nausea, stomach aches, vomiting
      - Tiredness, yawning, falling asleep
      - Tense posture, clenched shoulders or muscles, clenched teeth
      - Pulling on eyelashes, biting fingers or fingernails

Fig. 24I

SoundWise Dx™
Pediatric Neurodevelopmental Assessment
Developed by Pediatricians
6 year old Assessment Guided Treatment flow chart Form A or B

- Arguing, throwing the materials, leaving the test environment
- Saying they are thirsty, hungry, tired, sleepy, or having to all of a sudden got to go to the bathroom
- Complains of their heart racing
- Child is unable to attempt assessment in part or at all.
- Any other related complaints by the child not listed above.

- Children who do not attempt Assessment will need to to start SoundWise DX AI/AI-Gen engagement modules and a reassessment will be attempted in 1 to 3 months time as per SoundWise DX AI/AI-Gen grader.
- Engagement results are determined by SoundWise DX AI/AI-Gen computer program AI grader, Pediatrician, or authorized personnel.
- Engagement modules cover issues regarding attention, anxiety, autism, or other disorders as discussed below.
  - START SoundWise DX AI/AI-Generative Online 6 year old online Module for lack of engagement (Modules are preceded by a short video explaining the lesson to be learned followed by AI/AI-Generative Online recommendation algorithm) and/or worksheets. The Lack of Engagement modules deliver Speech & Language, Occupational Therapy, Physical Therapy and Behavioral Modification suggestions for building engagement.
  - As the child attends the Lack of Engagement modules, SoundWise DX AI/AI-Gen grader will determine the correct SoundWise DX modules for each individual child.
    - Lack of Engagement SoundWise DX modules include:
      1. Autism diagnostic evaluation through SoundWise DX and/or referral for autism diagnoses through a child's local medical services
      2. Attention Deficit/ADHD behavioral concerns/anxiety
         a. Continue to follow closely, make learning activities fun/engaging, limit activities to short segments.
         b. If severe behavioral issues or anxiety present: referral to child psychologist or for Play Therapy.
         c. Age 6 and older, refer to specific for ADHD module for further recommendations
      3. Modules for other recognized disorders such as post traumatic stress disorder, genetic disorders associated with learning disabilities, environment exposure to lead, fetal alcohol syndrome, Adoption and/or foster care population, proper nutrition, developmental delay, sensory issues, and other situations resulting in childhood developmental delay in need of intervention.
      4. Along with participating in Engagement modules, the following will be provided:
         - Refer for a in-person Speech and Language Evaluation focusing on building strong receptive/expressive language skill
         - Refer for an in person Sensory Integration Focused Occupational Therapy Evaluation focusing on motor integration, oral motor kinesthetics, proprioceptive skills, and sensory regulation..
         - Refer for an in person Physical therapy focusing on building strong gross motor skills.
         - Refer for in person evaluation for Autism
         - Refer for Genetics evaluation
         - Prescriptions for the above services will be provided by SoundWise DX or local health care facility.

Fig. 24J

SoundWise Dx™
Pediatric Neurodevelopmental Assessment
Developed by Pediatricians
6 year old Assessment Guided Treatment flow chart Form A or B

- Specific SoundWise DX modules for Autism, ADHD/ADD, and Anxiety:

1. Autism: Autism presents challenges with social communication and interaction. They do not talk a lot because they are not motivated to socially interact. They have challenges with eye contact and are unable to demonstrate joint attention, not able to play a back and forth game or do SoundWise DX assessment tasks. They show restrictive and repetitive behaviors, such as flapping their hands, spinning a lot, only interested in lining up toys or objects, sensory issues such as being upset with loud noises, wanting to smell things and not wanting to play pretend. Children with Autism also have difficulty with change of routine for example, having a new teacher, or driving a new route home and difficulty changing tasks during the SoundWise DX assessment.
    - Determination of Autism by SoundWise DX computer program AI grader, pediatrician, or authorized personnel will recommend the following:
    - Recommended activities and/or worksheets generated in the modules will address the specific concerns of lack of engagement/ language delay affecting social interaction, high concerns for Autistic Spectrum Disorder (ASD), or ASD confirmed by meeting the diagnostic criteria for ASD as per the most current version of the DSM which is currently the DSM-V. This will includes activities that focus on but or not limited to the following:
        - To strengthen receptive, expressive, and pragmatic language skills
            - Specific games and activities addressing language goals
        - To improve sensory regulation
            - Specific games and activities to decrease sensory triggers whether they be hypo(low) or hyper(high) sensory
            - Recommendation to address sensory seeking behaviors and/or sensory avoidance behaviors
            - Occupational Therapy (OT) like play activities with OT therapy goals addressing visual/motor integration, sensory regulation, visual perceptual skills, executive function, and primitive reflex integration)
        - To improve fine motor skills
            - Specific games and activities to improve any fine motor skills or hand skill ability like but not limited to the following (handwriting, cutting, folding, stringing beads, coloring, drawing, gluing, buttoning, using utensils, etc.
        - To improve gross motor skills
            - Specific games and activities to strengthen gross motor movements that includes focusing on balance, coordination, ball skills (dribbling, throwing,catching, etc.), hand eye coordination, same side and alternating side body movements, body schema activities (proprioceptive, vestibular, tactile, and body awareness)
            - Physical Therapy (PT) therapy like activities with PT gross motor goals
        - To improve social and pragmatic language skills
            - Specific group play therapy along with games and activities promoting opportunity for improved and guided social interaction
                - Group play therapy
                - Applied Behavioral Analysis Therapy
                - Increased peer group interactions.

Fig. 24K

SoundWise Dx™
Pediatric Neurodevelopmental Assessment
Developed by Pediatricians
6 year old Assessment Guided Treatment flow chart Form A or B

- In situations where anxiety or family connections are more calming, the avatar (computer generated face and/or voice used) could be that of a person familiar to the individual) when the assessment or enrichment activities are delivered on the SoundWise DX platform.
- SoundWise DX modules can be used to treat and strengthen skills along with in person therapy especially when waiting for in person therapy. Using SoundWise DX modules will start therapeutic advancement of identified skill deficits while at home when awaiting in person therapies. They can also be used to augment and reinforce the actual future or current therapies in place like medically delivered Speech and Language Therapy, OT, Cognitive Behavioral Therapy, and PT.
- Engagement modules and/or worksheets allow Early Intervention to immediately start while a child awaits for in person evaluation and/or in person autism specific therapy.
- SoundWise DX modules and/or worksheets will improve skills and reassessment will allow progress. Children should continue using the modules and/or worksheets even after starting in-person therapy.
- Referral when indicated per AI/AI generated Algorithm
  - Refer for a in person Speech and Language Evaluation
  - Refer for a in person Sensory Integration Focused Occupational Therapy Evaluation
  - Refer for an in person Diagnostic Evaluation for Autism
  - Refer for in person Child Play Therapy
- Pursue all therapies covered by medical insurance while at the same time caregivers/ teachers work on language skills, social interaction, developmental milestones, and sensory regulation using SoundWise DX 6 Year Old Developmental Milestone Information Sheet (DMIS) for age appropriate activities.
- Recommendations will include prescriptions for in person services generated through SoundWise DX.
- Suggestions to seek specialized diagnostic evaluations when indicated by SoundWise DX AI/AI-Gen Grader will include follow up with the child's primary care medical provider, and specialty referrals.
- As part of the diagnostic process, SoundWise DX will administer and score standardized validated screeners as age appropriate such as but not limited to the MCHAT, ASQ, PEDS Form, Vanderbilts, Denver Developmental assessments, Conners Forms, Scat etc)
- While Autism may be the primary diagnosis or concern, other coexisting conditions like anxiety or ADHD and/or genetic disorders may exist. If a validated screening as discussed above elicits concerns for other disorders, the appropriate referral will be done through SoundWise DX.

2. For Attention Deficit Hyperactivity Disorder Concerns (ADHD/ADD):
   - Behavioral modifications SoundWise DX module for 6 year old Behavioral Basics will be given that focuses tips on a structured environment, making learning activities fun, multisensory activities, and short but repetitive opportunities for learning.
   - If engagement is appropriate, but focus/attention to a task cannot be maintained for the age expected time for this age (12-18 minutes), then refer to SoundWise ADHD/ADD age specific questions and holistic consideration of all factors that can affect attention and sustained focus.

Fig. 24L

SoundWise Dx™
Pediatric Neurodevelopmental Assessment
Developed by Pediatricians
6 year old Assessment Guided Treatment flow chart Form A or B

- Children with ADHD/ADD have a hard time paying attention, daydreaming and often do not seem to listen. They are easily distracted from work and play and often do not pay attention to details/disorganization and do not follow through on directions. Prone to losing a lot of important things/forgetting things and avoids doing things that require mental effort. Having the hyperactivity component makes them prone not being able to stay seated, squirming a lot, talking too much, unable to play quietly and will jump, run and climb when not permitted to do so. They will demonstrate impulsivity, calling out without question being complete, Acts or speaks without thinking, Interrupting others often, trouble taking turns, cannot wait for things and may run onto street without looking out for traffic.
  - SoundWise DX AI/AI Gen grader will administer and score a Vanderbilt screen for parent and teacher if applicable). These screens are diagnostic of ADHD/ADD.
    - Visual attention and focus: SoundWise RX AI/Gen AI computer grader will derive objective and quantitative results for example gaze direction, dwell time, and glance frequency off the assessment site to other objects and locations. While monitoring eye tracking, we will measure where and for how long an individual looks in a certain direction or at a certain target, it is not a measure of actual visual attention However, this information can be used to necessitate further exploration into attention or focus disorders like ADHD/ADD. The SoundWise RX screen eye tracking will be used to assess student attention while taking the test. Just as eye tracking is the go-to method when determining driver distraction via glance target classification it can be used to assess attention to the assessment attention engagement in the test itself, or also suggest more analysis of visual tracking/perception/or processing is warranted.
- When above condition concerns are found, AI/AI-Gen computer program modules and/or worksheets for evaluation and guidance/ for ADHD/ADD will be generated. Further informational sheets on factors that can impact attention will be generated and given to the caregivers.
- Modules for scholastic accommodations such IEP, 504 and not limited to will also be given that can be effectively be used within a child's Individual Educational Plan (IEP) or 504 Plan.
- When formal diagnosis of ADHD for age 6 years old and older has been given, then information regarding evaluation for behavioral modification will be given.
- Starting at age 4 or older, medication for ADHD/ADD when indicated by SoundWise DX AI/AI-Gen and/or caregiver/teacher. Blood pressure. Pulse, EKG rhythm strip will be administered through all digital devices, along with telemedicine visit with SoundWise DX before medication is given.. Pathways towards diagnostic evaluation will be done according to the specific laws in each state.

Fig. 24M

SoundWise Dx™
Pediatric Neurodevelopmental Assessment
Developed by Pediatricians
6 year old Assessment Guided Treatment flow chart Form A or B

- Classroom modifications and accommodation recommendations would be produced via SoundWise DX module via AI/AI-Gen and given via SoundWise DX according to the specific laws in each state.

3. Anxiety:
   - A diagnosis of Anxiety is when a child is worried or scared and it interferes with their everyday activities such as refusing to go to school, playing with friends,especially at recess or at social gatherings, getting to sleep and/or not being able to sleep alone in their bed. They may say their heart is beating too fast, or they have a stomach ache and shaking, maybe having trouble breathing, start to sweat and suddenly are unable to sustain attention and want to find a safe place, like home or a caregiver. See specific symptoms that were listed above in "what constitutes a fail". Anxiety may have been exhibited itself as shyness during the child's early years, or occur after a traumatic event experienced/ witnessed by the child or the child may be a victim of abuse by a caregiver or other.
   - There are 4 types of Anxiety present in children;
     - Social Anxiety-Difficulty playing or being with others, especially in school, will speak softly not wanting to be heard and will not volunteer to raise hand in school or participate in group activities.
     - Separation Anxiety- Unable to separate from the caregiver, wanting to always be in their presence, not wanting to go to school or be on a playdate.
     - Selective Mutism- severe anxiety-speaks at home but not anywhere else. Has early onset.
     - Generalized Anxiety-Strives to be perfect,worries about the past, current events and the future a lot and worries about what may happen in school in their school work or other activities. They may get diagnosed with ADHD, however this child can not pay attention due to worry, rather than attention.
   - The child may demonstrate Anxiety during SoundWise DX by being concerned about getting the assessment tasks correct or simply not speaking. They may cry and turn away and say they are afraid to continue.
   - SoundWise DX AI/Gen-AI will determine through an anxiety algorithm module and/or caregiver/teacher or authorized personnel to start Anxiety SoundWise DX modules as well to start arranged telemedicine visits through SoundWise DX and/or in person therapy.
   - Also the Caregiver/teacher will work on language development, social interaction, and sensory regulation by using SoundWise DX 6 Year Old Developmental Milestone Information Sheet (DMIS) for age appropriate activities.
   - SoundWiseDX will administer and score a diagnostic screen such as PHQ-9/SCARED/Columbia/Hamilton/GAD-7 for Anxiety that is appropriate for age.
   - Based on SoundWiseDX AI/AI-Gen Children will also be started on telemedicine services through SoundWise DX for anxiety.
   - Reasons for indications for medicine management for Anxiety is determined by SoundWise DX AI/AI-Gen, physician, and input from caregiver/teacher. Pulse, Blood Pressure and EKG will be obtained by digital devices and are medically necessary before starting medication. Telemedicine services for anxiety though SoundWise DX must also be initiated and continued while the child is on medication for anxiety.
   - All children diagnosed with Anxiety through SoundWise DX AI/AI-Gen will also be evaluated for ADHD/ADD and/or Autism 4. Low Self Esteem
   - Self esteem should always be monitored closely in a child as this can lead to depression or other mental health disparities in the future.
   - Low self esteem can arise from a variety of reasons.

Fig. 24N

SoundWise Dx™
Pediatric Neurodevelopmental Assessment
Developed by Pediatricians
6 year old Assessment Guided Treatment flow chart Form A or B

- A soundWise DX Module AI/AI-Gen will be given that addresses building self esteem and confidence in a child.
- Telemedicine visits will be recommended via SoundWise DX or their local provider

- Reassessments SoundWise DX:
  - SoundWise DX will offer reassessments (Form B's) after 3 months of module implementation. Initial assessments are Form A.
  - In 3 months or less depending upon the discretion of SoundWise DX AI/AI-Gen computer program AI grader, pediatrician, and/or authorized personnel, the child will retake an assessment
    - If the child is still the same age, they will then take that age years Form B
    - If they have aged up and are now 1 year older, then they will take the next year's assessment Form A.
    - If a child is able to pass some, but not all, or if unable to pass the repeat pediatric assessment, they must follow through with the same algorithm as above until proficiency is determined by SoundWise DX computer program AI grader, pediatrician, or authorized personnel.
    - If the child is able to pass all parts of the new assessment, they should do SoundWise DX enrichment modules based on age group.

Fig. 24O

SoundWise Dx™
Pediatric Neurodevelopmental Assessment
Developed by Pediatricians 6 Year Old Neurodevelopmental Milestone Information Sheet Six year olds tend to be good communicators with both peers and adults. Their language skills and understanding social cues are continuing to improve while their vocabulary is accelerating at a rapid pace. Although they are much better at following directions, they occasionally make mistakes. While they want to be old, they are still little too. Their emotions can still be tender and a little bit tricky. They want to please but they need the adults in their world to be sensitive, especially if they make mistakes. They do not need everything done for them and are very happy to show what they can do independently. When smiling, it is often without their two front teeth!

When parenting a 6 year old, avoid power struggles! Try to give acceptable choices when you can and be firm when you can't. Provide a structured environment, plenty of healthy foods, and a good safe place to play and to work. Remember that six year olds are very active, loving to explore their world phyicially, and wanting your approval. They can run well, climb, and learn to ride a bike. They are also capable of learning and understanding safety rules too.

Six year olds are ready and usually excited to attend school. Most will have a strong language base from which they will use to learn academic subjects. Experienced-based learning is always happening as they continue to learn how to work in groups, gain academic knowledge, follow directions better, and transition to new rules and adjust to new routines.

Very quickly, children learn to adapt and adjust to numerous environments and situations, however, some may have problems with the school routines for a variety of reasons. Recognizing early that a child is struggling in the classroom is very important for their willingness to go to school every day, their self esteem, and over future scholastic success. Most children enjoy learning and going to school. If a child does not, the reasons why should be explored.

When a child is not able to follow directions in the classroom and/or they have trouble with assignments, school can be a distressing and frustrating place. Many of these children that struggle are aware that the difficulty is happening but do not know what to do to help. Not being able to understand directions in the classroom, adapt to changing situations, or respond appropriately to their peers in social situations can be very distressing to a child.

SoundWise DX recognizes the importance of each child being school ready. We recognize and embrace the role that the parent and family relationships play in a child's development and future scholastic success. Parents want to help their children succeed in every situation. SoundWise DX wants to work together with you to help strengthen the foundational skills necessary for your child's overall success. We want children to thrive in school! They should feel both strong and confident in their ability to learn.

Copyright © 2024 All Rights Reserved

Fig. 25A

SoundWise Dx™
Pediatric Neurodevelopmental Assessment
Developed by Pediatricians

What a typical 6 year old should be able to do.

Language Communication Milestones

- Speak in simple but complete sentences wth 5-7 words.
- Retell straightforward stories, recounting events in the correct order.
- Recognize letters and letter-sound matches
- Identifies sounds at the beginning of some words
- Sings songs and rhymes well
- Start to see that some words have more than 1 meaning, like understanding jokes and puns
- Love poems because they recognize word play and repetition
- Understand similar and different
- Should understand concepts of time like (today, tomorrow, yesterday)
- Should understand opposites like (empy/full)
- Has a typical vocabulary ranging from 3,000-10,000 words
- Speech should be clear and always understood by strangers

Important Tip

Limit television and mobile devices no more than 2 hrs per day.

Social Emotional Milestones

- Plays cooperatively with 2-3 children for 20 minutes or more.
- Can wait their turn or wait to have their needs met
- Apologizes for actions they didn't intend
- Pays attention and follows instructions in a group
- Help others
- Explain rules of a game to others.
- Engages in better social problem-solving
- Wants to please others
- Strives to be independent in many tasks
- Seeks new experiences Baby teeth start to fall out around age 6 to be replaced by permanent adult teeth.

Cognitive Milestones

Gross Motor Movement/Physical

Copyright © 2024 All Rights Reserved

Fig. 25B

SoundWise Dx™
Pediatric Neurodevelopmental Assessment
Developed by Pediatricians

| (Learning, Thinking, Problem-Solving) | Milestones |
|---|---|
| • Able to ask question with "Who", "what", "where", "why", "how", "when", and "how many"<br>• Understand number concepts and count to 20<br>• Start to show fast growth in mental abilities<br>• Have vivid imaginations<br>• Love to be read to<br>• Knows right from left<br>• Follow 3 step directions<br>• Attention span should be15-18 minutes<br>• Understand that print is to be read left to right and top to bottom<br>• Attempts to spell words when writing<br>• Able to recognize some words by sight<br>• Able to play board games and take turns<br>• Can tell you their age<br>• Start to understand cause-and-effect relationships<br>• Shows an understanding of right from wrong<br>• Lying, cheating, and stealing are to be expected somewhat at this age. (Kids are figuring out where they fit and what's acceptable) | • Hops on one foot for about 10 feet<br>• Skips on alternate feet across a room<br>• Walk on a balance beam without falling<br>• Runs lightly on toes<br>• Rides a bicycle with or without training wheels<br>• Can swing and climb<br>• Runs very well<br>• Catches a ball reliably<br>• Jumps rope |

Fine Motor Milestones

- Able to print their own first and last name
- Print numbers
- Identify and write both uppercase and lowercase letters
- Tie shoelaces
- Complete bathroom routines without help
- Copy a circle, square, and triangle
- Hold a pencil with a tripod grasp (3 point grasp)
- Color inside the lines
- Draws square & triangle, circle
- Uses glue appropriately
- Complete a 20 piece puzzle
- Dress themselves
- Cathc a ball easily using only their hand Copyright © 2024 All Rights Reserved

Fig. 25C

SoundWise Dx™
Pediatric Neurodevelopmental Assessment
Developed by Pediatricians

Tips for play and learning!

- Make it engaging!
- Use your environment, make it multisensory.
  (touch, feel, say, smell, see, and hear) For example:
  - Listen to the sound of the ocean,bird sounds
  - Feel the softness of your pets fur and roughness of a trees bark
  - Jump into puddles after a rainstorm and celebrate the various sounds of a busy city street.
- Learning is and should be fun!
- Every opportunity to play is an opportunity to learn.
- Keep learning activities around 10-15 minutes but multiple times throughout the day

How to help your child build stronger language skills.

Developing healthy communication skills such as learning to speak, understanding language, and learning to read are key milestones that your child needs to reach so that they enjoy and engage in play, and become successful in school.

Babies learn language through simple exposure by listening and watching you speak to them. They quickly learn how sounds are put together in different ways and have a different meaning. This exposure to sounds is building two major language skills:
1. Receptive language (input) - what you understand.
2. Expressive language (output) - what you can say.

A child's exposure to language starts in utero. As babies, they then start to babble and observe how we speak by looking at our faces and how we move our mouth, lips, and tongue to make sounds. They quickly understand that sounds have meaning and they start to acquire language at an amazing pace. When they are 5-6 years old, they will present to school to learn higher level language skills, like reading, writing, spelling, and math. The strength of your child's early language foundation will directly relate to the ease of their learning, their future academic success, and overall psychological well-being. Help them build a strong foundation for later scholastic and emotional success early. If difficulties arise, try to strengthen these skills as early as possible.

There are lots of simple things you can do that are fun and help build language skills;
- Sings songs, read books, tell stories Copyright © 2024 All Rights Reserved

Fig. 25D

SoundWise Dx™
Pediatric Neurodevelopmental Assessment
Developed by Pediatricians

- Read to your child
    - Build their vocabulary
    - Ask questions about the things you read or talk about
    - Let them use their own imagination and create their own stories too
- Work on identifying objects within their world and building language vocabulary
- Play games with sounds:
    - Like identifying how sounds are different or the same
    - Play rhyming games
    - Play repetition games with sounds
        - Like naming all the words that start with a similar sound
    - Identifying placement of sounds in words
        - "What's the 1st sound, what's the middle sound, what's the last sound in a word?
    - Associate the letters with the sounds but the sounds are more important. Just have fun with figuring out how to play and manipulate sounds like with rhyming. Look in a mirror. Learn that the mouth moves in different ways to make different sounds. Play games where you try to lip-read to guess what sound was made.
    - Let children see your face as you are speaking
        - They need to know how the mouth moves to make different sounds
    - Pick 2-3 sounds and letters and/or numbers to focus on in a week. Play games where you point to or think of things that start with that same sound or identity and count objects with that number.
    - Remember that the sounds are actually more important than the letter in the beginning.
- Talk to your child.
    - TV's and screens are not good substitutes. Limit screen time to 2 hours per day and do not put TV or computer devices in the bedroom
    - Talk about what you are doing as you are doing it. This gives two way to understand the task being taught.
    - Repeat key concepts, especially directional terms. For example: Let's find the BLUE shoes UNDER your bed. Play games like "Simon Says" where practicing directions can be fun.
- Tell children what you are doing and why. Talk, Talk, talk!
- Teach and show at the same time
    - For instance, when introducing new vocabulary say "here is the BRIGHT RED crayon, here is the PALE YELLOW book"
    - Play movement games like jumping UP and jumping DOWN
    - Have fun as learning can be one great adventure and game
    - Children love to move, incorporate movement into exploration of their world Copyright © 2024 All Rights Reserved

Fig. 25E

SoundWise Dx™
Pediatric Neurodevelopmental Assessment
Developed by Pediatricians

- Let your child tell the story in their own words. Their imaginations are entertaining!
- Ask your child questions as you tell a story. See if they are making a mental movie or picture while listening to the books or stories that you read to them.
- Let your child explore and use their imaginations.
- Teach language concepts with games.
    - Play hide & seek or find
    - Play with objects and place them around the room. Then give the child directions to follow with spatial concepts to find the items. For example: Find the BLUE toy ON TOP of the BROWN chair. Find the toy UNDER the table.
    - Focus on one or two words or concepts at a time and then practice multiple times a day to really learn those words or concepts.
- Teach math concepts with games.
    - Quantify/Comparative concepts (small, medium, large, most/least, same/different, young/old, wet/dry, etc.)
    - Play games using blocks to build towers of different sizes and compare.
    - Compare the size of your hands and your child's hands, your shoes to theirs, etc.
    - Play with different numbers of things like food, blocks, or toys. Compare and contrast different amounts so your child starts to learn counting and math concepts.
- Let your child have opportunities to play with other children.
    - Interactive games with both peers and adults allow them to learn about sharing, taking turns and following simple directions.
- Use music as an opportunity to sing, dance together, and express their feelings.
- Allow outside playtime to promote exercise and the understanding of their environment like naming objects around them.
- Exercise can be fun and good for both their brains and their bodies
- Allow them to have sensory experiences like what the wind feels like or what happens when you jump in a puddle of water, smell a flower, press on a squishy object, etc.
- Allowing your child to make choices within the appropriate allowable constraints, such as places to go or what to wear, encourages independence and development of their language skills.
- Encourage affection in your family and reinforce positive behavior. Teach your child that emotions are everyone has a responsibility to control their behavior
- Set limits on behaviors that are not appropriate
- Resolve disagreements and disputes peacefully.
- Children need a structured environment. They also need to feel safe and loved.
- Encourage bedtime routines such as reading to your child.
- Make sure that your child gets enough sleep to wake up well rested.

Copyright © 2024 All Rights Reserved

Fig. 25F

SoundWise Dx™
Pediatric Neurodevelopmental Assessment
Developed by Pediatricians What do sounds have to do with words in print, letters, and reading?

Learn those sounds! Practicing one new sound per week will strengthen your child's ability to eventually sound out words (decode). Decoding enables your child to sound out words so they do not have to guess. Accurate decoding is critically important to future reading success. It is the skill that separates good readers from poor readers.

Whenever you can, point out words wherever you go or in books so that your child recognizes that letters actually mean something. You can point to the print while you read. Play games like finding signs on buildings or street signs, or words on boxes at the supermarket. Reading to your child and pointing out words boosts vocabulary and advances knowledge.

You can teach letters but always teach the sound associated with it too.

Why does all this matter?

A person learns by experience and play. Give your child every opportunity to grow and learn. A strong grasp of language will give your child the ability to thrive in school and later in life. For it is the foundation that you build before 5 years of age that will be the platform from which learning will take place later on. It that foundation did not happen effortlessly it ust be built by practice.

A strong foundation is built using the ability to play with, manipulate, hold onto, and retrieve sounds in words. That critical skill is called "sound processing." It is the skill that "good readers" do well and "poor readers" do not. So help your child accelerate into scholastic success and build a strong language foundation. And remember, those magical ingredients are sounds so play with them and have fun!

Copyright © 2024 All Rights Reserved

Fig. 25G

SoundWise Dx™
Pediatric Neurodevelopmental Assessment
Developed by Pediatricians Parental Questionnaire

Ages 7 & 8 Years: Form A or B

Child: ______________________________ DOB ____________________

Parent Part Completed By: ______________________________

| | | | |
|---|---|---|---|
| 1. Does your child find ways to avoid reading? | □ Yes | □ No | □ Sometimes |
| 2. Does your child mix up sounds in words? | □ Yes | □ No | □ Sometimes |
| 3. Has your child ever had their speech tested? | □ Yes | □ No | |
| 4. Is spelling hard for your child? | □ Yes | □ No | □ Sometimes |
| 5. Does homework take longer than it should? | □ Yes | □ No | □ Sometimes |
| 6. Does your child have a hard time with math word problems? | □ Yes | □ No | □ Sometimes |
| 7. Does your child struggle with multi-step directions? | □ Yes | □ No | □ Sometimes |
| 8. Does anyone in your family struggle with spelling? | □ Yes | □ No | □ Sometimes |
| 9. Does anyone in your family struggle with reading, have dyslexia, or does not read for fun? | □ Yes | □ No | □ Sometimes |
| 10. Does your child enjoy reading? | □ Yes | □ No | □ Sometimes |
| 11. Is it easy for your child to learn new words? | □ Yes | □ No | □ Sometimes |
| 12. Does your child hear well? | □ Yes | □ No | □ Sometimes |
| 13. Can your child tie their shoes? | □ Yes | □ No | □ Sometimes |
| 14. Can your child skip while switching feet? | □ Yes | □ No | □ Sometimes |
| 15. Can your child jump rope? | □ Yes | □ No | □ Sometimes |

Copyright © 2024 All Rights Reserved

Fig. 26

SoundWise Dx™
Pediatric Neurodevelopmental Assessment
Developed by Pediatricians

Age 7 & 8 years: Form A

Name: ______________ □ M □ F DOB:__________ Date:__________

*Administer in a quiet one-on-one setting with limited distractions.*

Fine Motor: *Please have the child do the following:*

| | | |
|---|---|---|
| **Typical three-point pencil grip?** | □ Yes | □ No |
| **Write first name correctly** | □ Yes | □ No |
| **Writes 3 words that have three or four letters in each word** | □ Yes | □ No |
| **Copy a shape** | □ Yes | □ No |
| **Writes numbers 1-10** | □ Yes | □ No |
| **Write the first 10 letters of the abc's in lower case.** *(this should be done in less than 30 seconds)* | □ Yes | □ No |

Phoneme Elision (deletion) (Taking away a sound or sounds)

**Directions: Say, *Let's play a game*.**

**Example: *Say "raindrop". Now say raindrop without saying "drop"* ............................**

**If correct, say, *That's right. Let's try the next one.***

**If incorrect, say. *That's not quite right. Raindrop without saying drop is rain.***

| | | |
|---|---|---|
| *1. Say zipline, now you say zipline without saying "line"* (zip) | □ Yes | □ No |
| 2. *Say headlight, now you say headlight without saying "light"* (head) | □ Yes | □ No |
| *3. Say birthday, now you say birthday without saying "birth"* (day) | □ Yes | □ No |
| *4. Say dream, now you say dream without saying the /d/ sound.* (ream) | □ Yes | □ No |
| *5. Say spell, now you say spell without saying /p/* (sell) | □ Yes | □ No |
| *6. Say track, now you say track with the /r/ sound* (tack) | □ Yes | □ No |
| *7. Say cap, now you say cap with the /c/ sound* (ap) | □ Yes | □ No |
| *8. Say steam, now you say steam without saying /t/* (seam) | □ Yes | □ No |

Copyright © 2024 All Rights Reserved

Fig. 27A

SoundWise Dx™
Pediatric Neurodevelopmental Assessment
Developed by Pediatricians

Age 7 & 8 years: Form A

Reading Single Words *(ask child to read each word)*

| | | |
|---|---|---|
| 1. hurl | ◻ Yes | ◻ No |
| 2. flag | ◻ Yes | ◻ No |
| 3. snail | ◻ Yes | ◻ No |
| 4. tweak | ◻ Yes | ◻ No |
| 5. drank | ◻ Yes | ◻ No |
| 6. best | ◻ Yes | ◻ No |
| 7. frog | ◻ Yes | ◻ No |
| 8. cake | ◻ Yes | ◻ No |

Nonsense Words *(ask child to read each word)*

| | | | | | |
|---|---|---|---|---|---|
| 1. | zeep | ◻ Yes | ◻ No | /z/ /ee/ /p/ | (rhymes with peep) |
| 2. | mrit | ◻ Yes | ◻ No | /m/ /r/ /i/ /t/ | (rhymes with sit) |
| 3. | plack | ◻ Yes | ◻ No | /p/ /l/ /a/ /ck/ | (rhymes with tack) |
| 4. | slest | ◻ Yes | ◻ No | /s/ /l/ /e/ /s/ t/ | (rhymes with best) |
| 5. | grool | ◻ Yes | ◻ No | /g/ /r/ /oo/ /l/ | (rhymes with tool) |
| 6. | breat | ◻ Yes | ◻ No | /b/ /r/ /ee/ /t/ | (rhymes with meet) |
| 7. | zlack | ◻ Yes | ◻ No | /z/ /l/ /a/ /ck/ | (rhymes with tack) |
| 8. | drust | ◻ Yes | ◻ No | /d/ /r/ /u/ /s/ t/ | (rhymes with must) |

Please note the child's demeanor during testing:

| | | | |
|---|---|---|---|
| ◻ Cooperative | ◻ Smiling | ◻ Shy | ◻ Happy and engaged |
| ◻ Uncooperative | ◻ Crying | ◻ Distractible | ◻ English Language Learner |
| ◻ Refuses to Interact | ◻ Tired | ◻ Anxious | ◻ Difficult to motivate |

◻ Attention and ability to focus on task asked was difficult
◻ Other________________________________________

Copyright © 2024 All Rights Reserved

Fig. 27B

SoundWise Dx™
Pediatric Neurodevelopmental Assessment
Developed by Pediatricians

Age 7 & 8 years: Form A

Scoring Yearly vision screening is medically indicated and hearing if necessary

Fine Motor Skills:

- If no misses - strong skills
- If misses 1 go over with parent items child got incorrect
- If miss 2 or more, then work on the skills needed and get occupational therapist referral for pencil grip/drawing/ life skills

Phonemic Elision (Sound Deletion) Skills:

- If no misses - strong skills
- If misses 1-3, give have parent go over phonemic elision with child
- If miss 4 or more (50% or greater), work on the skills refer for speech therapy for phonemic awareness/processing/phonemic elision/along with articulation

Reading Single Words:

- If no misses - no treatment
- If misses 1-3, give encourage parent to read with child and point out words
  If miss 4 or more (50% or greater), work on these skills with a tutor/teacher/librarian to work on learning more words while reading.

Reading Nonsense Word Skills:

- If no misses no treatment
- If misses 1-3, give more opportunities to develop these skills
  If miss 4 or more (50% or greater), then you need to work on these skills at home and speech therapy for nonsense words/phonological awareness/processing.

Engagement:

If any concerns for autism like poor eye contact/lack of joint attention, lack of wanting to engage, and sensory dysregulation refer for Speech, OT, PT and a referral for Autism evaluation

If any concerns for ADHD/ADD, like unable to focus, easily distracted, unable to sustain attention for 16-24 minutes consider speaking to parents about Vanderbilt screen. Children who are inattentive and also exhibit staring spells, need to be evaluated for Absence seizures. SoundWise DX will offer RX or pediatrician/provider for neurology referral.

If there are any concerns about Anxiety, frustration with performance, thinking that they can not do well, crying, saying that they always fail every test,etc. Consider doing SCARED, and Columbia Screen or other screens for anxiety/depression.

Concerns present: ☐ None - Perfect Score

Copyright © 2024 All Rights Reserved

Fig. 27C

SoundWise Dx™
Pediatric Neurodevelopmental Assessment
Developed by Pediatricians

Age 7 & 8 years: Form A

- □ Engagement Concerns (Based of Evaluator's Behavioral Observations)
- □ Attentional Concerns
- □ Fine Motor Concerns
- □ Phonemic Elision (Sound Deletion) Concerns
- □ Reading Sight Word Concerns
- □ Reading Nonsense Word Concerns

Interventional Response:

□ General 7-8 Year Old Milestone Information Sheet
- Provides general understanding of what a 7-8 year should be able to do □ Specific Information Sheet for Opportunity and Development of Individual Skills
- Based upon Neurodevelopmental Foundational Model and Treatment Approach
- Includes Recommended Suggestions for opportunities and activities to grow skills
- Expand Opportunities and Suggestions available through SoundWise DX platform and other recommended sites.
- Increased Academic Focused Instruction on Broad areas of Concern (Engagement, Fine Motor, Phonemic Elision, Reading Sight Words, and Reading Nonsense Words)

Follow up if concerns present: □ 3-6 months later □ Yearly at the next Well Child Visit Copyright © 2024 All Rights Reserved

Fig. 27D

SoundWise Dx™
Pediatric Neurodevelopmental Assessment
Developed by Pediatricians

Ages 7 & 8 years: Form A

Name: ______________________ □ M □ F DOB:____________ Date:_________________

*Have the child write their first name.*

Name: ____________________________________________________

| *Write 3 words with 3 or 4 letters each.* | *Copy the shape.* |
|---|---|
| | 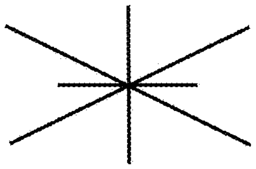 |

*Write numbers one through ten.*

______________________________________________________________

*Write the first 10 letters of the abc's in lower case.*

______________________________________________________________

*Read these words aloud.*

| | |
|---|---|
| hurl | drank |
| flag | best |
| snail | frog |
| tweak | cake |

*Read these nonsense words aloud.*

| | |
|---|---|
| zeep | grool |
| mrit | breat |
| plack | zlack |
| slest | drust |

Copyright © 2024 All Rights Reserved

Fig. 27E

SoundWise Dx™
Pediatric Neurodevelopmental Assessment
Developed by Pediatricians Age 7&8 Form B

Age 7 & 8 years: Form B

Name: ______________________ □ M □ F DOB:____________ Date:________________

*Administer in a quiet one-on-one setting with limited distractions.*
Fine Motor: *Please have the child do the following:*

| | | |
|---|---|---|
| **Typical three-point pencil grip?** | □ Yes | □ No |
| **Write first name correctly.** | □ Yes | □ No |
| **Writes 3 words that have three or four letter in each word** | □ Yes | □ No |
| **Copy a shape** | □ Yes | □ No |
| **Writes numbers 1-10** | □ Yes | □ No |
| **Write the first 10 letters of the abc's in lower case.** *(this should be done in less than 30 seconds)* | □ Yes | □ No |

Phoneme Elision (deletion) (Taking away a sound or sounds)

Directions: Say, *Let's play a game .*
Example: *Say "raindrop". Now say raindrop without saying "drop"* ..........................
If correct, say, *That's right. Let's try the next one.*
If incorrect, say. *That's not quite right. Raindrop without saying drop is rain.*

| | | |
|---|---|---|
| *1. Say doghouse, now you say doghouse without saying "house"* (dog) | □ Yes | □ No |
| *2. Say groundhog, now you say groundhog without saying "hog"* (ground) | □ Yes | □ No |
| *3. Say paintbrush, now you say paintbrush without saying "paint"* (brush) | □ Yes | □ No |
| *4. Say steam, now you say steam without saying the /s/ sound.* (team) | □ Yes | □ No |
| *5. Say drill, now you say drill without saying /r/* (dill) | □ Yes | □ No |
| *6. Say track, now you say track with the /t/ sound* (rack) | □ Yes | □ No |
| *7. Say hat, now you say hat with the /h/ sound* (at) | □ Yes | □ No |
| *8. Say plate, now you say plate without saying /l/* (pate) | □ Yes | □ No |

Copyright © 2024 All Rights Reserved

Fig. 28A

SoundWise Dx™
Pediatric Neurodevelopmental Assessment
Developed by Pediatricians Age 7&8 Form B Age 7 & 8 yrs:Form B

Reading Single Words *(ask child to read each word)*

| | | |
|---|---|---|
| 1. girl | □ Yes | □ No |
| 2. trail | □ Yes | □ No |
| 3. pride | □ Yes | □ No |
| 4. sky | □ Yes | □ No |
| 5. slit | □ Yes | □ No |
| 6. link | □ Yes | □ No |
| 7. three | □ Yes | □ No |
| 8. thank | □ Yes | □ No |

Nonsense Words (ask child to read each word)

| | | | | | |
|---|---|---|---|---|---|
| 1. | gish | □ Yes | □ No | /g/ /i/ /sh/ | (rhymes with dish) |
| 2. | pab | □ Yes | □ No | /p/ /a/ /b/ | (rhymes with cab) |
| 3. | dape | □ Yes | □ No | /d/ /ay /p/ | (rhymes with cape) |
| 4. | bock | □ Yes | □ No | /b/ /o /ck/ | (rhymes with dock) |
| 5. | clat | □ Yes | □ No | /c/ /l/ /a/ /t/ | (rhymes with mat) |
| 6. | wek | □ Yes | □ No | /w/ /e/ /k/ | (rhymes with deck) |
| 7. | moop | □ Yes | □ No | /m/ /oo/ /p/ | (rhymes with loop) |
| 8. | fust | □ Yes | □ No | /f/ /u/ /s/ t/ | (rhymes with must) |

Please note the child's demeanor during testing:

| | | | |
|---|---|---|---|
| □ Cooperative | □ Smiling | □ Shy | □ Happy and engaged |
| □ Uncooperative | □ Crying | □ Distractible | □ English Language Learner |
| □ Refuses to Interact | □ Tired | □ Anxious | □ Difficult to motivate |

□ Other________________________________________

Copyright © 2024 All Rights Reserved

Fig. 28B

SoundWise Dx™
Pediatric Neurodevelopmental Assessment
Developed by Pediatricians Age 7&8 Form B Scoring: Yearly vision screening is medically indicated and hearing if necessary

Fine Motor Skills:

- If no misses - strong skills
- If misses 1 go over with parent items child got incorrect
- If miss 2 or more, then work on the skills needed and get occupational therapist referral for pencil grip/drawing/ life skills

Phonemic Elision (Sound Deletion) Skills:

- If no misses - strong skills
- If misses 1-3, give have parent go over phonemic elision with child
- If miss 4 or more (50% or greater), work on the skills refer for speech therapy for phonemic awareness/processing/phonemic elision/along with articulation

Reading Single Words:

- If no misses - no treatment
- If misses 1-3, give encourage parent to read with child and point out words
  If miss 4 or more (50% or greater), work on these skills with a tutor/teacher/librarian to work on learning more words while reading.

Reading Nonsense Word Skills:

- If no misses no treatment
- If misses 1-3, give more opportunities to develop these skills
  If miss 4 or more (50% or greater), then you need to work on these skills at home and speech therapy for nonsense words/phonological awareness/processing.

Engagement:

If any concerns for autism like poor eye contact/lack of joint attention, lack of wanting to engage, and sensory dysregulation refer for Speech, OT, PT and a referral for Autism evaluation

If any concerns for ADHD/ADD, like unable to focus, easily distracted, unable to sustain attention for 16-24 minutes consider speaking to parents about Vanderbilt screen. Children who are inattentive and also exhibit staring spells, need to be evaluated for Absence seizures. SoundWise DX will offer RX or pediatrician/provider for neurology referral.

If there are any concerns about Anxiety, frustration with performance, thinking that they can not do well, crying, saying that they always fail every test,etc. Consider doing SCARED, and Columbia Screen or other screens for anxiety/depression.

Copyright © 2024 All Rights Reserved

Fig. 28C

SoundWise Dx™
Pediatric Neurodevelopmental Assessment
Developed by Pediatricians Age 7&8 Form B

Concerns present:
- ☐ None - Perfect Score
- ☐ Engagement Concerns (Based of Evaluator's Behavioral Observations)
- ☐ Attentional Concerns
- ☐ Fine Motor Concerns
- ☐ Phonemic Elision (Sound Deletion) Concerns
- ☐ Reading Sight Word Concerns
- ☐ Reading Nonsense Word Concerns

Interventional Response:

☐ General 7-8 Year Old Milestone Information Sheet
- Provides general understanding of what a 7-8 year should be able to do ☐ Specific Information Sheet for Opportunity and Development of Individual Skills
- Based upon Neurodevelopmental Foundational Model and Treatment Approach
- Includes Recommended Suggestions for opportunities and activities to grow skills
- Expand Opportunities and Suggestions available through SoundWise DX platform and other recommended sites.
- Increased Academic Focused Instruction on Broad areas of Concern (Engagement, Fine Motor, Phonemic Elision, Reading Sight Words, and Reading Nonsense Words)

Follow up if concerns present: ☐ 3-6 months later ☐ Yearly at the next Well Child Visit Copyright © 2024 All Rights Reserved

Fig. 28D

SoundWise Dx™
Pediatric Neurodevelopmental Assessment
Developed by Pediatricians

Ages 7 & 8 years: Form B

Name: ____________________ ☐ M ☐ F DOB:____________ Date:________________

Have the child write their first name.

Name: ______________________________________________

| *Write 3 words with 3 or 4 letters each* | *Draw the shape.* |
|---|---|
| | 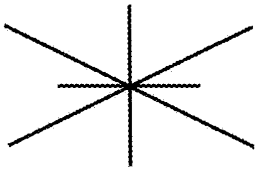 |

*Write numbers one through ten.*

______________________________________________

*Write the first 10 letters of the abc's in lower case.*

______________________________________________

*Read these words aloud.*

| | |
|---|---|
| **girl** | **slit** |
| **trail** | **link** |
| **pride** | **three** |
| **sky** | **thank** |

*Read these nonsense words aloud.*

| | |
|---|---|
| **gish** | **clat** |
| **pab** | **wek** |
| **dape** | **moop** |
| **bock** | **fust** |

Copyright © 2024 All Rights Reserved

Fig. 28E

SoundWise Dx™
Pediatric Neurodevelopmental Assessment
Developed by Pediatricians7/8 year old
7-8 Year Old Assessment Guided Treatment Flow Chart - Form A or B

Vision and Hearing Assessments: should be done on all children yearly

SoundWise DX will perform vision and colorblind testing before every assessment.

SoundWise DX will perform a Vision Snell chart (or any other standardized screen) and a colorblind test (The Ishihara, EnChroma, or any other standardized color blind assessment or screen) before every assessment.) The colorblind tests can be done as early as when a child is able to recognize numbers, shapes, or animals.

*Color blindness (color vision deficiency, or CVD) affects approximately 1 in 12 men (8%) and 1 in 200 women. This is an important thing to know for all children as colors are frequently used on computer academic assessments and inability to discern colors can negatively impact learning.*

*Concern for possible color blindness: If a child misses questions with red and/or green they will be tested for color blindness as soon as they are able to identify the common shapes used in testing books like numbers, shapes, or animals.*

Fine Motor Skills:

SoundWise DX will use AI determination of correct stroke/direction/pressure, speed, accuracy, and skill.

Using hands to do school related tasks. Between 4-9 years of age a child will begin to use the most mature grasp which is the dynamic tripod pencil grip. They will use the tips of their fingers on the writing utensil and hold the utensil at more of an angle rather than vertical.

- If a perfect score on Fine Motor items with correct pencil grip, as determined by SoundWise DX computer program AI grader, pediatrician, or authorized personnel, then recommend the child do enrichment with SoundWise DX AI/AI-Generative occupational therapy modules (Modules are preceded by a short video explaining the lesson to be learned followed by AI/AI-Generative Online recommendation algorithm) and/or worksheets for learning advanced skills.

Fine motor skills listed include, for example,the equivalent of the following (but not limited to) copying shapes and writing numbers,writing words, write name,writing complete ABC's and correct pencil grip (which can be expanded to other skills in the future)

- Fail:unable to do 1 item (< 50% completed incorrectly) is a fail.
  For example if child unable to write first name or copy shape or write 3 words with 3 to 4 letters or write numbers 1-10 or write abc's in less than 30 seconds and/or incorrect (fisted) pencil grip
  - Caregiver/teacher/or authorized personnel will work on drawing with correct pencil grip and drawing, copying, word forming, writing ABC's, and numbers using SoundWise DX 7/8 Year Old Developmental Milestone Information Sheet (DMIS) for guidance.
  - START SoundWise DX AI/AI-Generative Online 7/8 year old Occupational Therapy modules ( Modules are preceded by a short video explaining the lesson to be learned followed by AI/AI-Generative Online recommendation algorithm) and/or worksheets that guides the child perform

Fig. 29A

SoundWise Dx™
Pediatric Neurodevelopmental Assessment
Developed by Pediatricians7/8 year old tasks and development of correct pencil grip with AI grader determining for stroke/direction/pressure/speed, accuracy, and skill.

- Start In person Occupational Therapy for pencil grip/ life skills
- Prescription will be given through SoundWise DX or the patient's Pediatrician/Provider.
- Some children will wear gloves where computer will analyze proper technique with digitized feedback

- Multiple SoundWise DX modules and/or worksheets will be performed until the child is able to demonstrate proficiency or the child is confident to move on to learning advanced skills as determined by an SoundWise DX computer program AI grader, pediatrician, or authorized personnel.

Phoneme Elision ( sound deletion)

Means to take away a sound and is one of the strongest predictors that a child will go on to struggle in reading. It can be tested as early as 4 years old.

We take into account AI algorithms to recognize, transcribe a child's letter sound/word pronunciation, analyze context/structure where pronunciation varies due to accents/dialects and word/sentence structure comprehension and fluency.

- If a perfect score as determined by SoundWise DX computer program AI grader, pediatrician, or authorized personnel, then recommend the child do enrichment with SoundWise DX AI/AI-Generative 7/8 year old phoneme Elision skill modules (Modules are preceded by a short video explaining the lesson to be learned followed by AI/AI-Generative Online recommendation algorithm) and/or worksheets for learning advanced skills
- Concerns or Fail: Unable to do 1 item (less than 50% wrong on phoneme elision) then
  - Work on Phonological awareness/processing/phonemic elision skills with a caregiver/ teacher using SoundWise DX 7/8 Year Old Developmental Milestone Information Sheet (DMIS)
  - START SoundWise DX AI/AI-Generative Online 7/8 year old phoneme elision/ phonemic awareness/processing modules/receptive/expressive speech (Modules are preceded by a short video explaining the lesson to be learned followed by AI/AI-Generative Online recommendation algorithm) and/or worksheets that focus on phoneme Elision/ Phonological Awareness/processing/receptive/expressive language skills
  - Multiple SoundWise DX modules will be performed until the child is able to demonstrate proficiency as determined by SoundWise DX computer program AI grader ,Pediatrician, or authorized personnel.
- If unable to pass the skill using the SoundWise DX modules with 3 months of actively working on this skill then include along with modules,
  - In person Speech/Language Therapy focusing on improving phoneme Elision/phonological awareness/processing/receptive/expressive skills.
  - Prescriptions for speech/language will be given through SoundWise DX or child's Pediatrician/ provider
  - Multiple SoundWise DX modules will be performed until the child is able to demonstrate proficiency as determined by SoundWise DX computer program AI grader, Pediatrician, or authorized personnel.

Fig. 29B

SoundWise Dx™
Pediatric Neurodevelopmental Assessment
Developed by Pediatricians7/8 year old

- Fail: If misses more than 1 (close to or greater than 50% on phoneme elision items), then
  - Caregiver/teacher work on Phonemic elision/phonological awareness/Processing skills using SoundWise DX 7/8 Year Old Developmental Milestone Information Sheet (DMIS)
  - START SoundWise DX AI/AI-Generative Online 7/8 year old for phonemic elision/phonological awareness/processing skills(Modules are preceded by a short video explaining the lesson to be learned followed by AI/AI-Generative Online recommendation algorithm) and/or worksheets modules on phoneme elision/phonemic processing/awareness/receptive/expressive language that focus on Phonological Awareness/processing skills.
  - In person Speech/Language Therapy focusing on improving phoneme elision/phonological awareness/ processing/receptive/expressive language
  - Prescriptions for speech/ language will be given through SoundWise DX or Pediatrician/Provider.
  - Multiple SoundWise DX modules will be performed until the child is able to demonstrate proficiency as determined by SoundWise DX computer program AI grader, Pediatrician, or authorized personnel
  - 
  - If proficiency is not reached after 3 months,SoundWise DX will administer or give a local referral for an assessment that diagnoses a Specific Learning Disorder with Impairment in Reading (dyslexia). This assessment at the least should include a standardized measure of receptive language (including a cognitive measure if receptive language assessment is a deficit), reading and spelling measures, phonological processing assessments (for example that include but not limited to the CTOPP-2), and simple handwriting assessments. At the same time, a diagnostic assessment for ADHD should be done. If an intellectual disability is suspected, a standardized cognitive measure like an IQ test should also be given. All standardized assessments will be the most current versions of the test available. Results of diagnostic testing will be reviewed by SoundWise DX and/or either an in person licensed psychologist or physician to make the appropriate medical diagnosis. This can be done through SoundWise DX or the child's local care network.

Reading nonsense words:

Reading nonsense words requires the ability to accurately decode or sound out words.

We take into account AI algorithms to recognize, transcribe a child's letter sound/word pronunciation, analyze context/structure where pronunciation varies due to accents/dialects and word/sentence structure comprehension and fluency.

Fig. 29C

SoundWise Dx™
Pediatric Neurodevelopmental Assessment
Developed by Pediatricians7/8 year old

- If a perfect score as determined by SoundWise DX computer program AI grader, pediatrician, or authorized personnel, then recommend the child do enrichment with SoundWise DX AI/AI-Generative 7/8 year old nonsense word/phonological awareness skill modules (Modules are preceded by a short video explaining the lesson to be learned followed by AI/AI-Generative Online recommendation algorithm) and/or worksheets for learning advanced skills

- Concern or Fail:Unable to do 1 item only (less than 50% wrong on reading nonsense words) then
  - Work on Phonological Processing/awareness/nonsense word skills with a caregiver/ teacher using SoundWise DX 7/8 Year Old Developmental Milestone Information Sheet (DMIS)
  - START SoundWise DX AI/AI-Generative Online 7/8 year old nonsense word/phonological awareness/phonological processing modules (Modules are preceded by a short video explaining the lesson to be learned followed by AI/AI-Generative Online recommendation algorithm) and/or worksheets that focus on nonsense words/Phonological Awareness/processing/nonsense word/receptive/expressive skills
  - Multiple SoundWise DX modules will be performed until the child is able to demonstrate proficiency as determined by SoundWise DX computer program AI grader ,Pediatrician, or authorized personnel.

- If unable to pass the skill using the SoundWise DX modules with 3 months of actively working on this skill then include along with modules,
    - Start In person Speech and Language Therapy focusing on improving nonsense word/phonological awareness/processing/receptive/expressive language skills
    - Prescriptions for speech and language will be given through SoundWise DX or Pediatrician/Provider.
    - Multiple SoundWise DX modules will be performed until the child is able to demonstrate proficiency as determined by SoundWise DX computer program AI grader, Pediatrician, or authorized personnel.

- Concern or Fail: If misses more than 4 or more (close to or greater than 50% on nonsense word items), then
  - Work on Phonological awareness/processing/nonsense word skills with a caregiver/ teacher using SoundWise DX 7/8 Year Old Developmental Milestone Information Sheet (DMIS)
  - START SoundWise DX AI/AI-Generative Online 7/8 year old nonsense word/phonological awareness/processing modules (Modules are preceded by a short video explaining the lesson to be learned followed by AI/AI-Generative Online recommendation algorithm) and/or worksheets that focus on Phonological Awareness/processing/ nonsense word skills receptive/expressive language skills
  - In person Speech/ Language Therapy focusing on improving nonsense word/phonological awareness/processing/receptive/expressive skills.
  - Prescriptions for speech and language/nonsense word/phonological awareness/processing/receptive/expressive will be given through SoundWise DX or Pediatrician/provider.

Fig. 29D

SoundWise Dx™
Pediatric Neurodevelopmental Assessment
Developed by Pediatricians7/8 year old

- Multiple SoundWise DX modules will be performed until the child is able to demonstrate proficiency as determined by SoundWise DX computer program AI grader, Pediatrician, or authorized personnel.
-

- If proficiency is not reached after 3 months,SoundWise DX will administer or give a local referral for an assessment that diagnoses a Specific Learning Disorder with Impairment in Reading (dyslexia). This assessment at the least should include a standardized measure of receptive language (including a cognitive measure if receptive language assessment is a deficit), reading and spelling measures, phonological processing assessments (for example that include but not limited to the CTOPP-2), and simple handwriting assessments. At the same time, a diagnostic assessment for ADHD should be done. If an intellectual disability is suspected, a standardized cognitive measure like an IQ test should also be given. All standardized assessments will be the most current versions of the test available. Results of diagnostic testing will be reviewed by SoundWise DX and/or either an in person licensed psychologist or physician to make the appropriate medical diagnosis. This can be done through SoundWise DX or the child's local care network.

Reading Real Words:

Reading real words is a visual perceptual skill, as each word is really its own shape or design which comprises the shape of the different letters.The skill of full-word recognition is sight word reading which helps with reading fluency.

- If a perfect score as determined by SoundWise DX computer program AI grader, pediatrician, or authorized personnel, then recommend the child do enrichment with SoundWise DX AI/AI-Generative 7 year old Reading real words modules (Modules are preceded by a short video explaining the lesson to be learned followed by AI/AI-Generative Online recommendation algorithm) and/or worksheets for learning advanced skills

- Failure to do 1 items only (less than 50% wrong on reading single words) then:

- Work on Phonological awareness/processing and reading word skills with a caregiver/ teacher using SoundWise DX 7/8 Year Old Developmental Milestone Information Sheet (DMIS)
  - START SoundWise DX AI/AI-Generative Online 7/8 year old single words/sight word/phonological awareness/phonological processing modules/receptive/expressive (Modules are preceded by a short video explaining the lesson to be learned followed by AI/AI-Generative Online recommendation algorithm) and/or worksheets that focus on Phonological Awareness/processing/reading real word skills
  - Multiple SoundWise DX modules will be performed until the child is able to demonstrate proficiency as determined by SoundWise DX computer program AI grader ,Pediatrician, or authorized personnel.

- If unable to pass the skill using the SoundWise DX modules with 3 months of actively working on this skill then include along with modules,
    - In person Speech and Language Therapy focusing on improving single word/sight word reading/phonological awareness and phonological processing
    - Prescriptions for speech and language will be given through SoundWise DX or though child's healthcare provider

Fig. 29E

SoundWise Dx™
Pediatric Neurodevelopmental Assessment
Developed by Pediatricians7/8 year old

- Multiple SoundWise DX modules will be performed until the child is able to demonstrate proficiency as determined by SoundWise DX computer program AI grader, Pediatrician, or authorized personnel.

- If misses more than 4 ( greater than 50%)
  - Work on single word/sight word reading/Phonological awareness/processing skills with a caregiver/ teacher using SoundWise DX 7/8 Year Old Developmental Milestone Information Sheet (DMIS)
  - START SoundWise DX AI/AI-Generative Online 7/8 year old single word/sight word/phonological awareness/processing/receptive/expressive modules (Modules are preceded by a short video explaining the lesson to be learned followed by AI/AI-Generative Online recommendation algorithm) and/or worksheets that focus on Phonological Awareness/processing/reading single word/slight word skills
  - In person Speech/ Language Therapy focusing on improving single word/sight word/phonological awareness/ processing skills/receptive/expressive skills..
  - Prescriptions for speech and language/nonsense word/phonological awareness will be given through SoundWise DX or Pediatrician/Provider
  - Multiple SoundWise DX modules will be performed until the child is able to demonstrate proficiency as determined by SoundWise DX computer program AI grader, Pediatrician, or authorized personnel.
  - If proficiency is not reached after 3 months,SoundWise DX will administer or give a local referral for an assessment that diagnoses a Specific Learning Disorder with Impairment in Reading (dyslexia). This assessment at the least should include a standardized measure of receptive language (including a cognitive measure if receptive language assessment is a deficit), reading and spelling measures, phonological processing assessments (for example that include but not limited to the CTOPP-2), and simple handwriting assessments. At the same time, a diagnostic assessment for ADHD should be done. If an intellectual disability is suspected, a standardized cognitive measure like an IQ test should also be given. All standardized assessments will be the most current versions of the test available. Results of diagnostic testing will be reviewed by SoundWise DX and/or either an in person licensed psychologist or physician to make the appropriate medical diagnosis. This can be done through SoundWise DX or the child's local care network.

Engagement:

*Any and all diagnoses of psychiatric/behavioral disorders (ADHD, Autism, Anxiety, depression etc, will follow and change accordingly with the most current medical guidelines determined by the latest version of the Diagnostic and Statistical Manual of Mental Disorders which is currently the DSM-V. As new versions are published, SoundWise DX concerns identified and diagnostic criteria will adapt and be changed to match the most current diagnostic criteria.*

Perfect score:

- Able to demonstrate social communication, interaction , eye contact and able to demonstrate joint attention back and forth with assessment tasks. Not showing restrictive and repetitive behaviors, such as flapping their hands, spinning a lot, only

Fig. 29F

SoundWise Dx™
Pediatric Neurodevelopmental Assessment
Developed by Pediatricians7/8 year old interested in lining up toys or objects, sensory issues such as upset with loud noises, and difficulty with change of routine during the assessment.

- Able to sustain attention, not easily distracted, following directions on Assessment tasks.
- Attending the SoundWise DX assessment without crying and worrying about how they are doing with each task.
- Engagement evaluation is determined by SoundWise DX computer program AI grader, pediatrician, or authorized personnel.

A concern or fail for this section:

- Autism Concern:
  - The child has challenges with social communication and interaction. Has poor eye contact, refusal to engage in tasks, and/or lack of joint attention back and forth while doing assessment tasks.
  - The child demonstrates restrictive/repetitive behaviors, interests, and activities such as, but not limited to, flapping hands, spinning, lining up toys/objects, sensory issues (upset by loud noises/smell/touch), and challenges with change of routine during tasks.
- ADHD/ADD/attention deficits:
  - The child is unable to keep their attention and/or unable to follow directions while completing Assessment without being distracted and/or unable to sit still long enough to complete assessment at age 7/8 years old. Children who are inattentive and also exhibit staring spells, need to be evaluated for Absence Seizures. SoundWise DX will offer RX or pediatrician/provider for Neurology referral.
    - Norm values:
      - 3 years old: 6-8 minutes
      - 4 years old: 8-12 minutes
      - 5 and 6 years old: 12-18 minutes
      - 7 and 8 years old: 16-24 minutes
      - 9 and 10 years old: 20-30 minutes
- Anxiety, panic attacks, or Post Traumatic Stress Disorder (PTSD) Concern or Fail:
  - The child is showing emotions of frustration with or without crying and/or demonstrating worry about their performance while completing the assessment.
  - Elevated heart rate and/or blood pressure measured by all digital devices
  - Avoidance behaviors when tasks are hard such as:
    - Child complains or somatic (body) complaints to end or get out of a task like:
      - Headaches
      - Nausea, stomach aches, vomiting
      - Tiredness, yawning, falling asleep
      - Tense posture, clenched shoulders or muscles, clenched teeth
      - Pulling on eyelashes, biting fingers or fingernails
      - Arguing, throwing the materials, leaving the test environment
      - Saying they are thirsty, hungry, tired, sleepy, or having to all of a sudden got to go to the bathroom
      - Complains of their heart racing
      - Child is unable to attempt assessment in part or at all.
      - Any other related complaints by the child not listed above.

- Children who do not attempt Assessment will need to to start SoundWise DX AI/AI-Gen engagement modules and a reassessment will be attempted in 1 to 3 months time as per SoundWise DX AI/AI-Gen grader.

Fig. 29G

SoundWise Dx™
Pediatric Neurodevelopmental Assessment
Developed by Pediatricians7/8 year old

- Engagement results are determined by SoundWise DX AI/AI-Gen computer program AI grader, Pediatrician, or authorized personnel.
- Engagement modules cover issues regarding attention, anxiety, autism, or other disorders as discussed below.
    - START SoundWise DX AI/AI-Generative Online 7/8 year old online Module for lack of engagement (Modules are preceded by a short video explaining the lesson to be learned followed by AI/AI-Generative Online recommendation algorithm) and/or worksheets. The Lack of Engagement modules deliver Speech & Language, Occupational Therapy, Physical Therapy and Behavioral Modification suggestions for building engagement.
    - As the child attends the Lack of Engagement modules, SoundWise DX AI/AI-Gen grader will determine the correct SoundWise DX modules for each individual child.
        - Lack of Engagement SoundWise DX modules include:
            1. Autism diagnostic evaluation through SoundWise DX and/or referral for autism diagnoses through a child's local medical services
            2. Attention Deficit/ADHD behavioral concerns/anxiety
                a. Continue to follow closely, make learning activities fun/engaging, limit activities to short segments.
                b. If severe behavioral issues or anxiety present: referral to child psychologist or for Play Therapy.
                c. Age 4 and older, refer to specific for ADHD module for further recommendations
            3. Modules for other recognized disorders such as post traumatic stress disorder, genetic disorders associated with learning disabilities, environment exposure to lead, fetal alcohol syndrome, Adoption and/or foster care population, proper nutrition, developmental delay, sensory issues, and other situations resulting in childhood developmental delay in need of intervention.
            4. Along with participating in Engagement modules, the following will be provided:
                - Refer for a in-person Speech and Language Evaluation focusing on building strong receptive/expressive language skill
                - Refer for an in person Sensory Integration Focused Occupational Therapy Evaluation focusing on motor integration, oral motor kinesthetics, proprioceptive skills, and sensory regulation..
                - Refer for an in person Physical therapy focusing on building strong gross motor skills.
                - Refer for in person evaluation for Autism
                - Refer for Genetics evaluation
                - Prescriptions for the above services will be provided by SoundWise DX or local health care facility.

- Specific SoundWise DX modules for Autism, ADHD/ADD, and Anxiety:

1. Autism: Autism presents challenges with social communication and interaction. They do not talk a lot because they are not motivated to socially interact. They have challenges with eye contact and are unable to demonstrate joint attention, not able to play a back and forth game or do SoundWise DX assessment tasks. They show restrictive and repetitive behaviors, such as flapping their hands, spinning a lot, only interested in lining up toys or objects, sensory issues such as being upset with loud noises, wanting to smell things and not wanting to play pretend. Children with Autism also have difficulty with change of routine for example, having a new teacher, or

Fig. 29H

SoundWise Dx™
Pediatric Neurodevelopmental Assessment
Developed by Pediatricians7/8 year old driving a new route home and difficulty changing tasks during the SoundWise DX assessment.

- Determination of Autism by SoundWise DX computer program AI grader, pediatrician, or authorized personnel will recommend the following:
- Recommended activities and/or worksheets generated in the modules will address the specific concerns of lack of engagement/ language delay affecting social interaction, high concerns for Autistic Spectrum Disorder (ASD), or ASD confirmed by meeting the diagnostic criteria for ASD as per the most current version of the DSM which is currently the DSM-V. This will includes activities that focus on but or not limited to the following:
  - To strengthen receptive, expressive, and pragmatic language skills
    - Specific games and activities addressing language goals
  - To improve sensory regulation
    - Specific games and activities to decrease sensory triggers whether they be hypo(low) or hyper(high) sensory
    - Recommendation to address sensory seeking behaviors and/or sensory avoidance behaviors
    - Occupational Therapy (OT) like play activities with OT therapy goals addressing visual/motor integration, sensory regulation, visual perceptual skills, executive function, and primitive reflex integration)
  - To improve fine motor skills
    - Specific games and activities to improve any fine motor skills or hand skill ability like but not limited to the following (handwriting, cutting, folding, stringing beads, coloring, drawing, gluing, buttoning, using utensils, etc.
  - To improve gross motor skills
    - Specific games and activities to strengthen gross motor movements that includes focusing on balance, coordination, ball skills (dribbling, throwing,catching, etc.), hand eye coordination, same side and alternating side body movements, body schema activities (proprioceptive, vestibular, tactile, and body awareness)
    - Physical Therapy (PT) therapy like activities with PT gross motor goals
  - To improve social and pragmatic language skills
    - Specific group play therapy along with games and activities promoting opportunity for improved and guided social interaction
      - Group play therapy
      - Applied Behavioral Analysis Therapy
      - Increased peer group interactions.
- In situations where anxiety or family connections are more calming, the avatar (computer generated face and/or voice used) could be that of a person familiar to the individual) when the assessment or enrichment activities are delivered on the SoundWise DX platform.
- SoundWise DX modules can be used to treat and strengthen skills along with in person therapy especially when waiting for in person therapy. Using SoundWise DX modules will start therapeutic advancement of identified skill deficits while at home when awaiting in person therapies. They can also be used to augment and reinforce the actual future or current therapies in place like medically delivered Speech and Language Therapy, OT, Cognitive Behavioral Therapy, and PT.

Fig. 29I

SoundWise Dx™

Pediatric Neurodevelopmental Assessment

Developed by Pediatricians7/8 year old

- Engagement modules and/or worksheets allow Early Intervention to immediately start while a child awaits for in person evaluation and/or in person autism specific therapy.
- SoundWise DX modules and/or worksheets will improve skills and reassessment will allow progress. Children should continue using the modules and/or worksheets even after starting in-person therapy.
- Referral when indicated per AI/AI generated Algorithm
  - Refer for a in person Speech and Language Evaluation
  - Refer for a in person Sensory Integration Focused Occupational Therapy Evaluation
  - Refer for an in person Diagnostic Evaluation for Autism
  - Refer for in person Child Play Therapy

- Pursue all therapies covered by medical insurance while at the same time caregivers/ teachers work on language skills, social interaction, developmental milestones, and sensory regulation using SoundWise DX 7/8 Year Old Developmental Milestone Information Sheet (DMIS) for age appropriate activities.
- Recommendations will include prescriptions for in person services generated through SoundWise DX.
- Suggestions to seek specialized diagnostic evaluations when indicated by SoundWise DX AI/AI-Gen Grader will include follow up with the child's primary care medical provider, and specialty referrals.
- As part of the diagnostic process, SoundWise DX will administer and score standardized validated screeners as age appropriate such as but not limited to the MCHAT, ASQ, PEDS Form, Vanderbilts, Denver Developmental assessments, Conners Forms, Scat etc)
- While Autism may be the primary diagnosis or concern, other coexisting conditions like anxiety or ADHD and/or genetic disorders may exist. If a validated screening as discussed above elicits concerns for other disorders, the appropriate referral will be done through SoundWise DX.

2. For Attention Deficit Hyperactivity Disorder Concerns (ADHD/ADD):
   - Behavioral modifications SoundWise DX module for 7/8 year old Behavioral Basics will be given that focuses tips on a structured environment, making learning activities fun, multisensory activities, and short but repetitive opportunities for learning.
   - If engagement is appropriate, but focus/attention to a task cannot be maintained for the expected time for this age ( 16-24 minutes), then refer to SoundWise ADHD/ADD age specific questions and holistic consideration of all factors that can affect attention and sustained focus.
   - Children with ADHD/ADD have a hard time paying attention, daydreaming and often do not seem to listen. They are easily distracted from work and play and often do not pay attention to details/disorganization and do not follow through on directions. Prone to losing a lot of important things/forgetting things and avoids doing things that require mental effort. Having the hyperactivity component makes them prone not being able to stay seated, squirming a lot, talking too much, unable to play quietly and will jump, run and climb when not permitted to do so. They will demonstrate impulsivity, calling out without question being complete, Acts or speaks without thinking, Interrupting others often, trouble taking turns, cannot wait for things and may run onto street without looking out for traffic.

Fig. 29J

SoundWise Dx™
Pediatric Neurodevelopmental Assessment
Developed by Pediatricians7/8 year old

- SoundWise DX AI/AI Gen grader will administer and score a Vanderbilt screen for parent and teacher if applicable). These screens are diagnostic of ADHD/ADD.

- Visual attention and focus: SoundWise RX AI/Gen AI computer grader will derive objective and quantitative results for example gaze direction, dwell time, and glance frequency off the assessment site to other objects and locations. While monitoring eye tracking, we will measure where and for how long an individual looks in a certain direction or at a certain target, it is not a measure of actual visual attention However, this information can be used to necessitate further exploration into attention or focus disorders like ADHD/ADD. The SoundWise RX screen eye tracking will be used to assess student attention while taking the test. Just as eye tracking is the go-to method when determining driver distraction via glance target classification it can be used to assess attention to the assessment attention engagement in the test itself, or also suggest more analysis of visual tracking/perception/or processing is warranted.

- When above condition concerns are found, AI/AI-Gen computer program modules and/or worksheets for evaluation and guidance/ for ADHD/ADD will be generated. Further informational sheets on factors that can impact attention will be generated and given to the caregivers.
- Modules for scholastic accommodations such IEP, 504 and not limited to will also be given that can be effectively be used within a child's Individual Educational Plan (IEP) or 504 Plan.
- When formal diagnosis of ADHD for age 7/8 years old and older has been given, then information regarding evaluation for behavioral modification will be given.
- Starting at age 7/8 or older, medication for ADHD/ADD when indicated by SoundWise DX AI/AI-Gen and/or caregiver/teacher. Blood pressure. Pulse, EKG rhythm strip will be administered through all digital devices, along with telemedicine visit with SoundWise DX before medication is given.. Pathways towards diagnostic evaluation will be done according to the specific laws in each state.
- Classroom modifications and accommodation recommendations would be produced via SoundWise DX module via AI/AI-Gen and given via SoundWise DX according to the specific laws in each state.

3. Anxiety:
    - A diagnosis of Anxiety is when a child is worried or scared and it interferes with their everyday activities such as refusing to go to school, playing with friends,especially at recess or at social gatherings, getting to sleep and/or not being able to sleep alone in their bed. They may say their heart is beating too fast, or they have a stomach ache and shaking, maybe having trouble breathing, start to sweat and suddenly are unable to sustain attention and want to find a safe place, like home or a caregiver. See specific symptoms that were listed above in "what constitutes a fail". Anxiety may have been exhibited itself as shyness during the child's early years, or occur after a traumatic event experienced/ witnessed by the child or the child may be a victim of abuse by a caregiver or other.

Fig. 29K

SoundWise Dx™
Pediatric Neurodevelopmental Assessment
Developed by Pediatricians7/8 year old

- There are 4 types of Anxiety present in children;
  - Social Anxiety-Difficulty playing or being with others, especially in school, will speak softly not wanting to be heard and will not volunteer to raise hand in school or participate in group activities.
  - Separation Anxiety- Unable to separate from the caregiver, wanting to always be in their presence, not wanting to go to school or be on a playdate.
  - Selective Mutism- severe anxiety-speaks at home but not anywhere else. Has early onset.
  - Generalized Anxiety-Strives to be perfect,worries about the past, current events and the future a lot and worries about what may happen in school in their school work or other activities. They may get diagnosed with ADHD, however this child can not pay attention due to worry, rather than attention.
- The child may demonstrate Anxiety during SoundWise DX by being concerned about getting the assessment tasks correct or simply not speaking. They may cry and turn away and say they are afraid to continue.
- SoundWise DX AI/Gen-AI will determine through an anxiety algorithm module and/or caregiver/teacher or authorized personnel to start Anxiety SoundWise DX modules as well to start arranged telemedicine visits through SoundWise DX and/or in person therapy.
- Also the Caregiver/teacher will work on language development, social interaction, and sensory regulation by using SoundWise DX 7&8 Year Old Developmental Milestone Information Sheet (DMIS) for age appropriate activities.
- SoundWiseDX will administer and score a diagnostic screen such as PHQ-9/SCARED/Columbia/Hamilton/GAD-7 for Anxiety that is appropriate for age.
- Based on SoundWiseDX AI/AI-Gen Children will also be started on telemedicine services through SoundWise DX for anxiety.
- Reasons for indications for medicine management for Anxiety is determined by SoundWise DX AI/AI-Gen, physician, and input from caregiver/teacher. Pulse, Blood Pressure and EKG will be obtained by digital devices and are medically necessary before starting medication. Telemedicine services for anxiety though SoundWise DX must also be initiated and continued while the child is on medication for anxiety.
- All children diagnosed with Anxiety through SoundWise DX AI/AI-Gen will also be evaluated for ADHD/ADD and/or Autism

4. Low Self Esteem

- Self esteem should always be monitored closely in a child as this can lead to depression or other mental health disparities in the future.
- Low self esteem can arise from a variety of reasons.
- A soundWise DX Module AI/AI-Gen will be given that addresses building self esteem and confidence in a child.
- Telemedicine visits will be recommended via SoundWise DX or their local provider
-

- ## Reassessments SoundWise DX:
  - SoundWise DX will offer reassessments (Form B's) after 3 months of module implementation. Initial assessments are Form A.
  - In 3 months or less depending upon the discretion of SoundWise DX AI/AI-Gen computer program AI grader, pediatrician, and/or authorized personnel, the child will retake an assessment
    - If the child is still the same age, they will then take that age years Form B

Fig. 29L

SoundWise Dx™

Pediatric Neurodevelopmental Assessment

Developed by Pediatricians7/8 year old

- If they have aged up and are now 1 year older, then they will take the next year's assessment Form A.
- If a child is able to pass some, but not all, or if unable to pass the repeat pediatric assessment, they must follow through with the same algorithm as above until proficiency is determined by SoundWise DX computer program AI grader, pediatrician, or authorized personnel.
- If the child is able to pass all parts of the new assessment, they should do SoundWise DX enrichment modules based on age group.

Fig. 29M

SoundWise Dx™
Pediatric Neurodevelopmental Assessment
Developed by Pediatricians
7-8 Year Old Neurodevelopmental Milestone Information Sheet Children at this age enjoy their strong language skills and physical development. They start to pick up family responsibilities such as cleaning up after themselves and setting the dinner table for example. As they learn more in school and tackle projects, they develop more questions on new interests and how things work.

They show more independence from parents and family as they look outside their family for activities such as team sports, art classes, and scouts. Thinking about the future and understanding his or her place in the world is important to them. They want to be liked and accepted in school. How they are doing in school and their accomplishments are very important as well as how they do in their after school activities.

What a typical 7 or 8 year old should be able to do.

<u>Language Communication Milestones</u>

- Fully able to explain themselves
- Asks specific questions
- Tend to talk a lot in situations where they are comfortable.
- Pronounce words correctly.
- Are becoming more fluent readers. (fluency is reading accurately and quickly)
- May still have some trouble with basic spelling.
- Have well-developed speech and use correct grammar most of the time.
- Become interested in reading books. For some children, it's a favorite activity.
- Are still working on spelling and grammar in their written work. Their writing is not as advanced as their speech.

<u>Social Emotional Milestones</u>

- Show the ability to get along with others and control their emotions better.
- Develop empathy: i.e.Become more aware of and sensitive to the feelings of others.
- Overcome some fears they had when they were younger but they still can be terrified of the unknown. For example, going to a new school can be a tremendous stress for a 7-year-old. Many children also fear being in trouble with their parents or other adults. In general, they are worried about the opinions of others.
- Form friendships, usually with other children of the same gender.
- Play in larger groups sometimes but they also need time alone.
- Enjoy being around their friends. The opinions of their friends become more important meaning peer pressure may become an issue.
- Gain a sense of security from being involved in regular group activities, such as dance, sports, 4-H or Scouts.
- Are more likely to follow rules they help create.
- Can be impatient. They like immediate gratification and find it hard to wait for things they want.
- Are interested and understand the concept of money.

Copyright © 2024 All Rights Reserved

Fig. 30A

SoundWise Dx™
Pediatric Neurodevelopmental Assessment
Developed by Pediatricians Important Tip Limit television and mobile devices no more than 2 hours per day.

Gross Motor Movement/Physical Milestones

- Their athletic skills are improving as their muscle strength and endurance continue to develop.
- Are getting more coordinated in activities that use the large muscles, such as swimming or climbing.
- Become increasingly skilled in hobbies, sports, and active play.
- Dressing and toileting themselves independently
- Catch a ball more easily using only their hands Cognitive Milestones
(Learning, Thinking, Problem-Solving)

- Have a solid sense of time )able to understands seconds, minutes, days, weeks, and even years)
- Start to prefer a learning style, like hands-on active projects versus quiet independent learning
- Can solve simple math problems using objects (such as counting beads).
- Consider issues and problems using only one factor at a time.
- Know how to count by 2s (2, 4, 6, 8, and so on) and 5s (5, 10, 15, 20, and so on).
- Know what day of the week it is. They don't usually know the full date and year.
- Can read simple sentences.
- Can complete simple single-digit addition and subtraction problems (such as 1 + 8, 7 + 5, 6 - 2, 4 - 3).
- Can tell the difference between right and left.
- Have a black-and-white perspective much of the time. Things are either great or awful, ugly or beautiful, right or wrong. They focus on one trait or idea at a time. This makes it hard for them to understand complex issues.
- Attention span should be16-24 minutes Copyright © 2024 All Rights Reserved

Fig. 30B

SoundWise Dx™
Pediatric Neurodevelopmental Assessment
Developed by Pediatricians Tips for play and learning!

- Learning is and should be fun!
- Every opportunity to play is an opportunity to learn.
- Keep learning activities around 15-20 minutes at a time.
- Practical activities. Look at newspaper articles, notices from school, leaflets/guides in museums, buy books to read or games to play.
- Read together.
- Play Fine Motor Milestones

- Use safety scissors easily.
- Draw a person with 12 parts (by age 7) or 16 parts (by age 8).
- Use a pencil to write their name.
- Tie their shoelaces.
- Draw a diamond shape.
- Writing neatly with 3 fingered grasp and generating movement from fingers (not wrist)
- Writing on lines with good pencil control
- Using knife and fork for soft foods
- Drawing detailed pictures with recognizable objects
- Form letters and numbers correctly (no reversals)
- Building legos Copyright © 2024 All Rights Reserved

Fig. 30C

SoundWise Dx™
Pediatric Neurodevelopmental Assessment
Developed by Pediatricians math games.
- Cook together.

How to help your child build stronger language skills.

Developing healthy communication skills such as learning to speak, understanding language, and learning to read are key milestones that your child needs to reach so that they enjoy and engage in play, and become successful in school.

Language developed as babies learned through simple exposure by listening and watching someone speak to them. They learned how sounds are put together in different ways and have different meanings. This constant exposure to sounds was building the two major language skills:

1. Receptive language (input) - what you understand.
2. Expressive language (output) - what you can say.

A child's exposure to language starts in utero. As babies, they then start to babble and observe how we speak by looking at our faces and how we move our mouth, lips, and tongue to make sounds. They quickly understand that sounds have meaning and they start to acquire language at an amazing pace. When they are 5-6 years old, they will present to school to learn higher level language skills, like reading, writing, spelling, and math. The strength of your child's early language foundation will directly relate to the ease of their learning, their future academic success, and overall psychological well-being. Help them build a strong foundation for later scholastic and emotional success early. If difficulties arise, seek help immediately as foundational skills need to be strengthened before higher level skills are achieved.

Copyright © 2024 All Rights Reserved

Fig. 30D

SoundWise Dx™
Pediatric Neurodevelopmental Assessment
Developed by Pediatricians If your child is having difficulty with reading and/or spelling, it is important to understand why and to work on basic skills before more advanced skills.

There are lots of simple things you can do that are fun and help build language skills:

- Sings songs, read books, tell stories
- Read to your child
    - Build their vocabulary
    - Ask questions about the things you read or talk about
    - Let them use their own imagination and create their own stories too
- Work on identifying objects within their world and building language vocabulary
- Play games with sounds:
    - Like identifying how sounds are different or the same
    - Play rhyming games
    - Play repetition games with sounds
        - Like naming all the words that start with a similar sound
    - Identifying placement of sounds in words
        - "What's the 1st sound, what's the middle sound, what's the last sound in a word?
    - Associate the letters with the sounds but the sounds are more important. Just have fun with figuring out how to play and manipulate sounds like with rhyming. Look in a mirror. Learn that the mouth moves in different ways to make different sounds. Play games where you try to lip-read to guess what sound was made.
    - Let children see your face as you are speaking
        - They need to know how the mouth moves to make different sounds
    - Pick 2-3 sounds and letters and/or numbers to focus on in a week. Play games where you point to or think of things that start with that same sound or identity and count objects with that number.
    - Remember that the sounds are actually more important than the letter in the beginning.
- Talk to your child.
    - TV's and screens are not good substitutes. Limit screen time to 2 hours per day and do not put TV or computer devices in the bedroom
    - Talk about what you are doing as you are doing it. This gives two way to understand the task being taught.
    - Repeat key concepts, especially directional terms. For example: Let's find the BLUE shoes UNDER your bed. Play games like "Simon Says" where practicing directions can be fun.
- Tell children what you are doing and why. Talk, Talk, talk!
- Teach and show at the same time
    - For instance, when introducing new vocabulary say "here is the BRIGHT RED crayon, here is the PALE YELLOW book"

Copyright © 2024 All Rights Reserved

Fig. 30E

SoundWise Dx™
Pediatric Neurodevelopmental Assessment
Developed by Pediatricians

- Have fun as learning can be one great adventure and game
  - Children love to move, incorporate movement into exploration of their world
- Let your child tell the story in their own words. Their imaginations are entertaining!
- Ask your child questions as you tell a story. See if they are making a mental movie or picture while listening to the books or stories that you read to them.
- Let your child explore and use their imaginations.
- Teach language concepts with games.
  - Play hide & seek or find
  - Focus on one or two words or concepts at a time and then practice multiple times a day to really learn those words or concepts.
- Teach math concepts with games.
  - Quantify/Comparative concepts (small, medium, large, most/least, same/different, young/old, wet/dry, etc.)
  - Play games using blocks to build towers of different sizes and compare.
  - Compare the size of your hands and your child's hands, your shoes to theirs, etc.
  - Play with different numbers of things like food, blocks, or toys. Compare and contrast different amounts so your child starts to learn counting and math concepts.
- Let your child have opportunities to play with other children.
  - Interactive games with both peers and adults allow them to learn about sharing, taking turns and following simple directions.
- Use music as an opportunity to sing, dance together, and express their feelings.
- Allow outside playtime to promote exercise and the understanding of their environment like naming objects around them.
- Exercise can be fun and good for both their brains and their bodies
- Allow them to have sensory experiences like what the wind feels like or what happens when you jump in a puddle of water, smell a flower, press on a squishy object, etc. (take a trip to a science museum)
- Allowing your child to make choices within the appropriate allowable constraints.
- Encourage affection in your family and reinforce positive behavior. Teach your child that emotional feelings are allowed but everyone has a responsibility to control their behavior when angry, sad, or upset.
- Set limits on behaviors that are not appropriate
- Resolve disagreements and disputes peacefully.
- Children need a structured environment. They also need to feel safe and loved.
- Encourage bedtime routines such as reading to your child. Limit scree time right before bedtime.
- Make sure that your child gets enough sleep to wake up well rested.

Copyright © 2024 All Rights Reserved

Fig. 30F

SoundWise Dx™
Pediatric Neurodevelopmental Assessment
Developed by Pediatricians What do sounds have to do with words in print, letters, and reading?

Learn those sounds! Practicing one new sound per week will strengthen your child's ability to eventually sound out words (decode). Decoding enables your child to sound out words so they do not have to guess. Accurate decoding is critically important to future reading success. It is the skill that separates good readers from poor readers.

Whenever you can, point out words wherever you go or in books so that your child recognizes that letters actually mean something. You can point to the print while you read. Play games like finding signs on buildings or street signs, or words on boxes at the supermarket. Reading to your child and pointing out words boosts vocabulary and advances knowledge.

You can teach letters but always teach the sound associated with it too.

Why does all this matter?

A person learns by experience and play. Give your child every opportunity to grow and learn. A strong grasp of language will give your child the ability to thrive in school and later in life. For it is the foundation that you build before 5 years of age that will be the platform from which learning will take place later on. It that foundation did not happen effortlessly it must be built by practice.

A strong foundation is built using the ability to play with, manipulate, hold onto, and retrieve sounds in words. That critical skill is called "sound processing." It is the skill that "good readers" do well and "poor readers" do not. So help your child accelerate into scholastic success and build a strong language foundation. And remember, those magical ingredients are sounds so play with them and have fun!

Copyright © 2024 All Rights Reserved

Fig. 30G

SoundWise Dx™
Pediatric Neurodevelopmental Assessment
Developed by Pediatricians Parental Questionnaire

Ages 9 + years: Form A or B

Child: ______________________ DOB ______________

Parent Portion: Completed By: ______________________

| | | | |
|---|---|---|---|
| 1. Is spelling hard for your child? | □ Yes | □ No | □ Sometimes |
| 2. Does your child find ways to avoid reading? | □ Yes | □ No | □ Sometimes |
| 3. Does your child mix up sounds in words? | □ Yes | □ No | □ Sometimes |
| 4. Does homework take longer than it should? | □ Yes | □ No | □ Sometimes |
| 5. Does your child have a hard time with math word problems? | □ Yes | □ No | □ Sometimes |
| 6. Does your child struggle with multi-step directions? | □ Yes | □ No | □ Sometimes |
| 7. Has your child ever had their speech tested? | □ Yes | □ No | |
| 8. Does anyone in your family have a hard time spelling? | □ Yes | □ No | □ Sometimes |
| 9. Does anyone in your family struggle with reading, have dyslexia, or does not read for fun? | □ Yes | □ No | □ Sometimes |
| 11. Does your child enjoy reading? | □ Yes | □ No | □ Sometimes |
| 12. Is it easy for your child to sound out new words? | □ Yes | □ No | □ Sometimes |
| 13. Does your child hear well? | □ Yes | □ No | □ Sometimes |
| 14. Can your child tie their shoes? | □ Yes | □ No | □ Sometimes |
| 15. Does your child enjoy doing physical activities? | □ Yes | □ No | □ Sometimes |
| 16. Does your child have good hygiene and can dress on their own? | □ Yes | □ No | □ Sometimes |

Copyright © 2024 All Rights Reserved

Fig. 31

SoundWise Dx™
Pediatric Neurodevelopmental Assessment
Developed by Pediatricians
Age 9+ years: Form A

Name: ____________________ ☐ M ☐ F DOB:__________ Date:______________

*Administer in a quiet one-on-one setting with limited distractions.*

Fine Motor: *Please have the child do the following:*

| | | |
|---|---|---|
| Typical three-point pencil grip? | ☐ Yes | ☐ No |
| Copies the 3 overlapping circles | ☐ Yes | ☐ No |
| Copies the sentence in under 2 minutes with no errors | ☐ Yes | ☐ No |
| Write first name correctly from memory. | ☐ Yes | ☐ No |
| Write last name correctly from memory. | ☐ Yes | ☐ No |
| Write the lowercase abc's in less than 1 minute without errors. | ☐ Yes | ☐ No |

Phoneme Elision (deletion) (Taking away a sound or sounds)

**Directions: Say, *Let's play a game .***

**Example: *Say "raindrop". Now say raindrop without saying "drop"* ............................**

**If correct, say, *That's right. Let's try the next one.***

**If incorrect, say. *That's not quite right. Raindrop without saying drop is rain.***

| | | |
|---|---|---|
| *1. Say lighthouse, now you say lighthouse without saying "house"* (light) | ☐ Yes | ☐ No |
| *2. Say toothpaste, now you say toothpaste without saying "paste"* (tooth) | ☐ Yes | ☐ No |
| *3. Say skateboard, now you say skateboard without saying "skate"* (board) | ☐ Yes | ☐ No |
| *4. Say steam, now you say steam without saying the /s/ sound.* (team) | ☐ Yes | ☐ No |
| *5. Say drill, now you say drill without saying /r/* (dill) | ☐ Yes | ☐ No |
| *6. Say track, now you say track with the /t/ sound* (rack) | ☐ Yes | ☐ No |
| *7. Say hat, now you say hat with the /h/ sound* (at) | ☐ Yes | ☐ No |
| *8. Say plate, now you say plate without saying /l/* (pate) | ☐ Yes | ☐ No |

**Reading single words *(Have them read these words out loud to you)***

1. myself
2. seven
3. lighting
4. together
5. know
6. sometimes
7. family
8. through

Copyright © 2024 All Rights Reserved

Fig. 32A

SoundWise Dx™
Pediatric Neurodevelopmental Assessment
Developed by Pediatricians
Age 9+ years: Form A

Nonsense Words (ask child to read each word)

| | | | | | |
|---|---|---|---|---|---|
| 1. | glob | □ Yes | □ No | /g/ /l/ /o/ /b/ | (sounds like bob) |
| 2. | bleam | □ Yes | □ No | /b/ /l/ /ee/ /m/ | (sounds like team) |
| 3. | crix | □ Yes | □ No | /c/ /r/ /i/ /x/ | (sounds like trix) |
| 4. | splitten | □ Yes | □ No | /s/ /p/ /l/ /i/ /t/ /n/ | (sounds like mitten) |
| 5. | higgly | □ Yes | □ No | /h/ /i/ /g/ /l/ /ee/ | (sounds like wiggly) |
| 6. | shoop | □ Yes | □ No | /sh /oo/ /p/ | (sounds like hoop) |
| 7. | treen | □ Yes | □ No | /t/ /r/ /ee /n/ | (sounds like green) |
| 8. | strateful | □ Yes | □ No | /s/ /t/ /r/ /ay/ /t/ /f/ /l/ | (sounds like grateful ) |

Please note the the child's demeanor during testing:

□ Cooperative □ Smiling □ Shy □ Happy and engaged
□ Uncooperative □ Crying □ Distractible □ English Language Learner
□ Refuses to Interact □ Tired □ Anxious □ Difficult to motivate
□
Other________________________________________________________________

Copyright © 2024 All Rights Reserved

Fig. 32B

SoundWise Dx™
Pediatric Neurodevelopmental Assessment
Developed by Pediatricians
Age 9+ years: Form A

Scoring Yearly vision screening is medically indicated and hearing if necessary

Fine Motor Skills:

- If no misses - no treatment
- If misses 1 or more, work on pencil grip/drawing/practice handwriting and refer to OT for pencil grip/handwriting/life skills

Phonemic Elision (Sound Deletion) Skills:

- If no misses - no treatment
- If misses 1-3, Parent/tutor/librarian works on skill building with phonemic elision
- If miss 4 or more (50% or greater), Parent/tutor/librarian works on skill building with phonemic elision and refer for speech/language therapy on phonemic awareness/processing/phonemic Elision/receptive/expressive speech

Reading Single Words:

- If no misses - no treatment
- If misses 1-3, Parent/tutor/librarian works on skill building with increasing sight word/vocabulary recognition by reading, discussing what is being read etc
- If miss 4 or more (50% or greater)Parent/tutor/librarian works on skill building with increasing sight word/vocabulary recognition by reading, discussing what is being read etc and consider speech therapist/reading specialist/tutor

Reading Nonsense Word Skills:

- If no misses no treatment
- If misses 1-3, give more opportunities to develop these skills
  If miss 4 or more (50% or greater), then you need to work on these skills at home and speech therapy for nonsense words/phonological awareness/processing.

Engagement:

If any concerns for autism like poor eye contact/lack of joint attention, lack of wanting to engage, and sensory dysregulation refer for Speech, OT, PT and a referral for Autism evaluation

If any concerns for ADHD/ADD, like unable to focus, easily distracted, unable to sustain attention for 20-30 minutes consider speaking to parent about Vanderbilt screen. Children who are inattentive and also exhibit staring spells, need to be evaluated for Absence seizures. SoundWise DX will offer RX or pediatrician/provider for neurology referral.

If there are any concerns about Anxiety, frustration with performance, thinking that they can not do well, crying, saying that they always fail every test,etc. Consider doing SCARED, and Columbia Screen or other screens for anxiety/depression.

Copyright © 2024 All Rights Reserved

Fig. 32C

SoundWise Dx™
Pediatric Neurodevelopmental Assessment
Developed by Pediatricians
Age 9+ years: Form A

Concerns present:
- ☐ None - Perfect Score
- ☐ Engagement Concerns (Based of Evaluator's Behavioral Observations)
- ☐ Attentional Concerns
- ☐ Fine Motor Concerns
- ☐ Phonemic Elision (Sound Deletion) Concerns
- ☐ Reading Sight Word Concerns
- ☐ Reading Nonsense Word Concerns

Interventional Response:

☐ General 9 Year Old Milestone Information Sheet
- Provides general understanding of what a 9 year should be able to do ☐ Specific Information Sheet for Opportunity and Development of Individual Skills
- Based upon Neurodevelopmental Foundational Model and Treatment Approach
- Includes Recommended Suggestions for opportunities and activities to grow skills
- Expand Opportunities and Suggestions available through SoundWise DX platform and other recommended sites.
- Increased Academic Focused Instruction on Broad areas of Concern (Engagement, Fine Motor, Phonemic Elision, Reading Sight Words, and Reading Nonsense Words)

Follow up if concerns present: ☐ 3-6 months later ☐ Yearly at the next Well Child Visit Copyright © 2024 All Rights Reserved

Fig. 32D

SoundWise Dx™
Pediatric Neurodevelopmental Assessment
Developed by Pediatricians

Ages 9+ years: Form A

Name: ____________________ □ M □ F DOB:______________ Date:___________________

Have the child write their first and last name.

Name: ______________________________________________

*Copy the shape.*

*Copy the sentence "The smart brown dog jumps over the mossy rocks":*

______________________________________________

______________________________________________

*Write the a,b,c's in lower case*

______________________________________________

______________________________________________

Copyright © 2024 All Rights Reserved

SoundWise Dx™
Pediatric Neurodevelopmental Assessment
Developed by Pediatricians

Age 9 + years: Form A

Reading single real words *(Have them read these words out loud to you)* myself
seven
lighting
together
know
sometimes
family
through

Nonsense Words *(ask child to read each word)* glob
bleam
crix
splitten
higgly
shoop
treen
striteful

Copyright © 2024 All Rights Reserved

Fig. 32F

SoundWise Dx™
Pediatric Neurodevelopmental Assessment
Developed by Pediatricians 9 year old Form B

Age 9 + years: Form B

Name: ________________________ ☐ M ☐ F DOB:____________ Date:________________

*Administer in a quiet one-on-one setting with limited distractions.*
Fine Motor: *Please have the child do the following:*

| | | |
|---|---|---|
| Typical three-point pencil grip? | ☐ Yes | ☐ No |
| Copies the 3 overlapping circles | ☐ Yes | ☐ No |
| Copies the sentence in under 2 minutes with no errors | ☐ Yes | ☐ No |
| Write their first name correctly from memory. | ☐ Yes | ☐ No |
| Write their last name correctly from memory. | ☐ Yes | ☐ No |
| Write the lowercase abc's in less than 1 minute without errors. | ☐ Yes | ☐ No |

Phoneme Elision (deletion) (Taking away a sound or sounds)

Directions: Say, *Let's play a game .*

Example: *Say "raindrop". Now say raindrop without saying "drop"* ..........................

If correct, say, *That's right. Let's try the next one.*

If incorrect, say. *That's not quite right. Raindrop without saying drop is rain.*

| | | |
|---|---|---|
| *1. Say roadblock, now you say roadblock without saying "block"* (road) | ☐ Yes | ☐ No |
| *2. Say notebook, now you say notebook without saying "note"* (book) | ☐ Yes | ☐ No |
| *3. Say superhero, now you say superhero without saying "super"* (hero) | ☐ Yes | ☐ No |
| *4. Say front, now you say front without saying the /r/ sound.* (font) | ☐ Yes | ☐ No |
| *5. Say pants, now you say pants without saying /t/* (pans) | ☐ Yes | ☐ No |
| *6. Say black, now you say black with the /l/ sound* (back) | ☐ Yes | ☐ No |
| *7. Say sold, now you say sold with the /s/ sound* (old) | ☐ Yes | ☐ No |
| *8. Say brain, now you say brain without saying /b/* (rain) | ☐ Yes | ☐ No |

Reading single words *(Have them read these words out loud to you)*

1. kind
2. eight
3. never
4. laughing
5. space
6. again
7. mountains
8. open

Copyright © 2024 All Rights Reserved

Fig. 33A

SoundWise Dx™
Pediatric Neurodevelopmental Assessment
Developed by Pediatricians

Age 9 + years: Form B

Reading single words *(Have the child read these words out loud to you.)* kind
eight
never
laughing
space
Again
mountains
open

Nonsense Words *(ask child to read each word)* blad
droom
crix
zastly
meast
greech
spretch
faist

Copyright © 2024 All Rights Reserved

Fig. 33B

SoundWise Dx™
Pediatric Neurodevelopmental Assessment
Developed by Pediatricians 9 year old Form B

Age 9+ yrs: Form B

Nonsense Words (ask child to read each word)

| | | | | | |
|---|---|---|---|---|---|
| 1. | blad | ☐ Yes | ☐ No | /b/ /l/ /a/ /d/ | (sounds like glad) |
| 2. | droom | ☐ Yes | ☐ No | /d/ /r/ /oo/ /m/ | (sounds like broom) |
| 3. | crix | ☐ Yes | ☐ No | /c/ /r/ /i/ /x/ | (sounds like trix) |
| 4. | zastly | ☐ Yes | ☐ No | /z/ /a/ /s/ /t/ /l/ /ee/ | (sounds like lastly) |
| 5. | meast | ☐ Yes | ☐ No | /m/ ee/ /s/ /t/ | (sounds like least) |
| 6. | greech | ☐ Yes | ☐ No | /gr /r/ /ee/ /ch/ | (sounds like breech) |
| 7. | spretch | ☐ Yes | ☐ No | /s/ /p/ /r/ /e/ /tch/ | (sounds like fetch) |
| 8. | faist | ☐ Yes | ☐ No | /f/ /ay/ /s/ /t/ | (sounds like waist) |

Please note the the child's demeanor during testing:

| | | | |
|---|---|---|---|
| ☐ Cooperative | ☐ Smiling | ☐ Shy | ☐ Happy and engaged |
| ☐ Uncooperative | ☐ Crying | ☐ Distractible | ☐ English Language Learner |
| ☐ Refuses to Interact | ☐ Tired | ☐ Anxious | ☐ Difficult to motivate |

☐ Other________________________________________

---

Copyright © 2024 All Rights Reserved

Fig. 33C

SoundWise Dx™
Pediatric Neurodevelopmental Assessment
Developed by Pediatricians 9 year old Form B

Scoring Yearly vision screening is medically indicated and hearing if necessary

Fine Motor Skills:

- If no misses - no treatment
- If misses 1 or more, work on pencil grip/drawing/practice handwriting and refer to OT for pencil grip/handwriting/life skills

Phonemic Elision (Sound Deletion) Skills:

- If no misses - no treatment
- If misses 1-3, Parent/tutor/librarian works on skill building with phonemic elision
- If miss 4 or more (50% or greater), Parent/tutor/librarian works on skill building with phonemic elision and refer for speech/language therapy on phonemic awareness/processing/phonemic Elision/receptive/expressive speech

Reading Single Words:

- If no misses - no treatment
- If misses 1-3, Parent/tutor/librarian works on skill building with increasing sight word/vocabulary recognition by reading, discussing what is being read etc
- If miss 4 or more (50% or greater)Parent/tutor/librarian works on skill building with increasing sight word/vocabulary recognition by reading, discussing what is being read etc and consider speech therapist/reading specialist/tutor

Reading Nonsense Word Skills:

- If no misses no treatment
- If misses 1-3, give more opportunities to develop these skills
  If miss 4 or more (50% or greater), then you need to work on these skills at home and speech therapy for nonsense words/phonological awareness/processing.

Engagement:

If any concerns for autism like poor eye contact/lack of joint attention, lack of wanting to engage, and sensory dysregulation refer for Speech, OT, PT and a referral for Autism evaluation

If any concerns for ADHD/ADD, like unable to focus, easily distracted, unable to sustain attention for 20-30 minutes consider speaking to parent about Vanderbilt screen. Children who are inattentive and also exhibit staring spells, need to be evaluated for Absence seizures. SoundWise DX will offer RX or pediatrician/provider for neurology referral.

If there are any concerns about Anxiety, frustration with performance, thinking that they can not do well, crying, saying that they always fail every test,etc. Consider doing SCARED, and Columbia Screen or other screens for anxiety/depression.

Concerns present:
- ☐ None
- ☐ Engagement Concerns
- ☐ Fine Motor Concerns
- ☐ Sound Deletion Concerns
- ☐ Reading Single (Real) Words Concerns
- ☐ Reading Nonsense Words Concerns Copyright © 2024 All Rights Reserved

Fig. 33D

SoundWise Dx™
Pediatric Neurodevelopmental Assessment
Developed by Pediatricians 9 year old Form B

Interventional Response: □ Parent Info & Education Sheet Given with Access to Instructional Videos
□ Increased Academic Focused Instruction on Areas of Concern

Follow up if concerns present: □ mid school year □ end of school year

Copyright © 2024 All Rights Reserved

Fig. 33E

SoundWise Dx™
Pediatric Neurodevelopmental Assessment
Developed by Pediatricians

Age 9+ years: Form B

Name: ______________________ □ M □ F DOB:____________ Date:________________

Write first and last name.

Name: ____________________________________________

*Copy this shape.*

*Copy the sentence on the lines below:*

*"The small white bird flew over the tall tree and landed on the sandy beach.*

______________________________________________

______________________________________________

*Write the a,b,c's in lower case.*

______________________________________________

______________________________________________

Copyright © 2024 All Rights Reserved

SoundWise Dx™
Pediatric Neurodevelopmental Assessment
Developed by Pediatricians 9 year old

9 and Older Assessment Guided Treatment Flow Chart - Form A or B

Vision and Hearing Assessments: should be done on all children yearly.

SoundWise DX will perform vision and colorblind testing before every assessment.

SoundWise DX will perform a Vision Snell chart (or any other standardized screen) and a colorblind test (The Ishihara, EnChroma, or any other standardized color blind assessment or screen) before every assessment.) The colorblind tests can be done as early as when a child is able to recognize numbers, shapes, or animals.

*Color blindness (color vision deficiency, or CVD) affects approximately 1 in 12 men (8%) and 1 in 200 women. This is an important thing to know for all children as colors are frequently used on computer academic assessments and inability to discern colors can negatively impact learning.*

*Concern for possible color blindness: If a child misses questions with red and/or green they will be tested for color blindness as soon as they are able to identify the common shapes used in testing books like numbers, shapes, or animals.*

Fine Motor Skills:

SoundWise DX will use AI determination of correct stroke/direction/pressure, speed, accuracy, and skill.

Using hands to do school related tasks. Between 4-9 years of age a child will begin to use the most mature grasp which is the dynamic tripod pencil grip. They will use the tips of their fingers on the writing utensil and hold the utensil at more of an angle rather than vertical.

- If a perfect score on Fine Motor items with correct pencil grip, as determined by SoundWise DX computer program AI grader, pediatrician, or authorized personnel, then recommend the child to do enrichment with SoundWise DX AI/AI-Generative occupational therapy modules(Modules are preceded by a short video explaining the lesson to be learned followed by AI/AI-Generative Online recommendation algorithm) and/or worksheets for learning advanced skills.

Fine motor skills listed include, for example,the equivalent of the following (but not limited to) copying shapes and writing numbers,writing words, write name,writing complete ABC's and correct pencil grip (which can be expanded to other skills in the future)

Fig. 34A

SoundWise Dx™
Pediatric Neurodevelopmental Assessment
Developed by Pediatricians 9 year old

- Concern or Fail: Unable to do 1 item is a fail Unable to write first and last name,copy shape, copy sentence correctly,write all abc's in less than 1 minute, and other like assignments and/or incorrect (fisted) pencil grip
    - Caregiver/teacher/authorized personnel works with the child on tasks using correct pencil grip using SoundWise DX 9 Year Old Developmental Milestone Information Sheet (DMIS) for guidance.
    - START SoundWise DX AI/AI-Generative Online 9 year old Occupational Therapy modules ( Modules are preceded by a short video explaining the lesson to be learned followed by AI/AI-Generative Online recommendation algorithm) and/or worksheets that guides the child perform tasks and development of correct pencil grip with AI grader determining for stroke/direction/pressure/speed, accuracy, and skill.
    - Start In person Occupational Therapy for pencil grip/drawing/life skills
    - Automatic Prescription will be given through SoundWise DX or Pediatrician/Provider
    - Some children will wear gloves where computer will analyze proper technique with digitized feedback
- Multiple SoundWise DX modules and/or worksheets will be performed until the child is able to demonstrate proficiency or the child is confident to move on to learning advanced skills as determined by an SoundWise DX computer program AI grader, pediatrician, or authorized personnel.

Phoneme Elision ( sound deletion)

Means to take away a sound and is one of the strongest predictors that a child will go on to struggle in reading. It can be tested as early as 4 years old.

We take into account AI algorithms to recognize, transcribe a child's letter sound/word pronunciation, analyze context/structure where pronunciation varies due to accents/dialects and word/sentence structure comprehension and fluency.

- If a perfect score as determined by SoundWise DX computer program AI grader, pediatrician, or authorized personnel, then recommend the child do enrichment with SoundWise DX AI/AI-Generative 9 year old phoneme Elision skill/receptive/expressive language/phonological processing/awareness modules (Modules are preceded by a short video explaining the lesson to be learned followed by AI/AI-Generative Online recommendation algorithm) and/or worksheets for learning advanced skills
- Concern or Fail: Unable to do 1-3 items only (less than 50% wrong on phoneme elision) then:
    - Work on Phonological awareness/processing/phonemic elision/receptive/expressive language skills with a caregiver/

Fig. 34B

SoundWise Dx™
Pediatric Neurodevelopmental Assessment
Developed by Pediatricians 9 year old teacher/authorized personnel using SoundWise DX 9 Year Old Developmental Milestone Information Sheet (DMIS)
- START SoundWise DX AI/AI-Generative Online 9 year old phoneme elision/phonological processing/awareness/receptive/expressive speech/language modules (Modules are preceded by a short video explaining the lesson to be learned followed by AI/AI-Generative Online recommendation algorithm) and/or worksheets that focus on phoneme Elision/ Phonological Awareness/processing/receptive/expressive speech/language skills
- Multiple SoundWise DX modules will be performed until the child is able to demonstrate proficiency as determined by SoundWise DX computer program AI grader ,Pediatrician, or authorized personnel.

- If unable to pass the skill using the SoundWise DX modules with 3 months of actively working on this skill then include along with modules,
  - In person Speech and Language Therapy focusing on improving phoneme Elision/phonological awareness/ processing/receptive/expressive speech/language skills.
  - Prescriptions for speech and language will be given through SoundWise DX or Pediatrician/provider.
  - Multiple SoundWise DX modules will be performed until the child is able to demonstrate proficiency as determined by SoundWise DX computer program AI grader, Pediatrician, or authorized personnel.

- Fail: If misses 4 or more (50% or greater on phoneme elision items), then
  - Caregiver/teacher work on Phoneme elision/Phonological awareness/processing/receptive/expressive skills using SoundWise DX 9 Year Old Developmental Milestone Information Sheet (DMIS)
  - START SoundWise DX AI/AI-Generative Online 9 year old (Modules are preceded by a short video explaining the lesson to be learned followed by AI/AI-Generative Online recommendation algorithm) and/or worksheets modules on phoneme elision/ phonological processing/awareness/receptive/expressive speech/language that focus on Phonological Awareness/processing/phonemic elision skills
  - In person Speech and Language Therapy focusing on improving phoneme elision/phonological awareness/ processing/receptive/expressive speech/language skills
  - Prescriptions for speech and language will be given through SoundWise DX or Pediatrician/Provider..

- Multiple SoundWise DX modules will be performed until the child is able to demonstrate proficiency as determined by SoundWise DX computer program AI grader, Pediatrician, or authorized personnel

- If proficiency is not reached after 3 months,SoundWise DX will administer or give a local referral for an assessment that diagnoses a Specific Learning Disorder with Impairment in Reading (dyslexia). This assessment at the least should include a standardized measure of receptive language (including a cognitive measure if receptive language assessment is a deficit), reading and spelling measures, phonological processing assessments (for example that include but not limited to the CTOPP-2), and simple handwriting assessments. At the same time, a diagnostic assessment

Fig. 34C

SoundWise Dx™
Pediatric Neurodevelopmental Assessment
Developed by Pediatricians 9 year old for ADHD should be done. If an intellectual disability is suspected, a standardized cognitive measure like an IQ test should also be given. All standardized assessments will be the most current versions of the test available. Results of diagnostic testing will be reviewed by SoundWise DX and/or either an in person licensed psychologist or physician to make the appropriate medical diagnosis. This can be done through SoundWise DX or the child's local care network.

Reading Real Words:

Reading real words is a visual perceptual skill, as each word is really its own shape or design which comprises the shape of the different letters.The skill of full-word recognition is sight word reading which helps with reading fluency.

- If a perfect score as determined by SoundWise DX computer program AI grader, pediatrician, or authorized personnel, then recommend the child do enrichment with SoundWise DX AI/AI-Generative 9 year old Reading real words modules (Modules are preceded by a short video explaining the lesson to be learned followed by AI/AI-Generative Online recommendation algorithm) and/or worksheets for learning advanced skills

- Concern or Fail:Unable to do 1-3 items only (less than 50% wrong on reading single words) then:

- Work on Phonological awareness/processing/ reading word skills/receptive/expressive language with a caregiver/ teacher/authorized personnel using SoundWise DX 9 Year Old Developmental Milestone Information Sheet (DMIS)
  - START SoundWise DX AI/AI-Generative Online 9 year old single words/sight word/phonological awareness/ processing/receptive/expressive language modules (Modules are preceded by a short video explaining the lesson to be learned followed by AI/AI-Generative Online recommendation algorithm) and/or worksheets that focus on Phonological Awareness/processing/reading real word skills/receptive/expressive language.
  - Multiple SoundWise DX modules will be performed until the child is able to demonstrate proficiency as determined by SoundWise DX computer program AI grader ,Pediatrician, or authorized personnel.
  - If unable to pass the skill using the SoundWise DX modules with 3 months of actively working on this skill then include along with modules,
    - In person Speech and Language Therapy focusing on improving single word/sight word reading/phonological awareness and phonological processing/receptive/expressive language skills
    - Prescriptions for speech and language will be given through SoundWise DX or though child's healthcare provider
    - Multiple SoundWise DX modules will be performed until the child is able to demonstrate proficiency as determined by SoundWise DX computer program AI grader, Pediatrician, or authorized personnel.

Fig. 34D

SoundWise Dx™
Pediatric Neurodevelopmental Assessment
Developed by Pediatricians 9 year old

- Fail: If misses 4 or more (50% or greater on real word items), then:
  - Work on single word/sight word reading/Phonological awareness/processing/receptive/expressive language skills with a caregiver/ teacher/authorized personnel using SoundWise DX 9 Year Old Developmental Milestone Information Sheet (DMIS)
  - START SoundWise DX AI/AI-Generative Online 9 year old single word/sight word/phonological awareness/receptive/expressive speech/language modules (Modules are preceded by a short video explaining the lesson to be learned followed by AI/AI-Generative Online recommendation algorithm) and/or worksheets that focus on Phonological Awareness/processing/reading real word skills/receptive/expressive language skills
  - In person Speech and Language Therapy focusing on improving single word/sight word/phonological awareness/ processing/receptive/expressive language skills
  - Prescriptions for speech and language will be given through SoundWise DX or Pediatrician/Provider
  - Multiple SoundWise DX modules will be performed until the child is able to demonstrate proficiency as determined by SoundWise DX computer program AI grader, Pediatrician, or authorized personnel.
  - If proficiency is not reached after 3 months,SoundWise DX will administer or give a local referral for an assessment that diagnoses a Specific Learning Disorder with Impairment in Reading (dyslexia). This assessment at the least should include a standardized measure of receptive language (including a cognitive measure if receptive language assessment is a deficit), reading and spelling measures, phonological processing assessments (for example that include but not limited to the CTOPP-2), and simple handwriting assessments. At the same time, a diagnostic assessment for ADHD should be done. If an intellectual disability is suspected, a standardized cognitive measure like an IQ test should also be given. All standardized assessments will be the most current versions of the test available. Results of diagnostic testing will be reviewed by SoundWise DX and/or either an in person licensed psychologist or physician to make the appropriate medical diagnosis. This can be done through SoundWise DX or the child's local care network.

Fig. 34E

SoundWise Dx™
Pediatric Neurodevelopmental Assessment
Developed by Pediatricians 9 year old

Reading nonsense words:

Reading nonsense words requires the ability to accurately decode or sound out words.

We take into account AI algorithms to recognize, transcribe a child's letter sound/word pronunciation, analyze context/structure where pronunciation varies due to accents/dialects and word/sentence structure comprehension and fluency.

- If a perfect score as determined by SoundWise DX computer program AI grader, pediatrician, or authorized personnel, then recommend the child do enrichment with SoundWise DX AI/AI-Generative 9 year old nonsense word/phonological awareness skill modules (Modules are preceded by a short video explaining the lesson to be learned followed by AI/AI-Generative Online recommendation algorithm) and/or worksheets for learning advanced skills

- Concern or Fail: Unable to do 1 to 3 items only (less than 50% wrong on reading nonsense words) then
  - Work on Phonological awareness/processing/nonsense/receptive/expressive language skills with a caregiver/ teacher/authorized personnel using SoundWise DX 9 Year Old Developmental Milestone Information Sheet (DMIS)
  - START SoundWise DX AI/AI-Generative Online 9 year old nonsense word/phonological awareness/ processing/expressive/receptive language skill modules/receptive/expressive speech/language (Modules are preceded by a short video explaining the lesson to be learned followed by AI/AI-Generative Online recommendation algorithm) and/or worksheets that focus on Phonological Awareness/processing/nonsense words/receptive/expressive speech/language skills
  - Multiple SoundWise DX modules will be performed until the child is able to demonstrate proficiency as determined by SoundWise DX computer program AI grader ,Pediatrician, or authorized personnel.

- If unable to pass the skill using the SoundWise DX modules with 3 months of actively working on this skill then include along with modules,
    - In person Speech and Language Therapy focusing on improving nonsenseword/phonologicalawareness/processing/receptive/expressive language skills
    - Prescriptions for speech and language will be given through SoundWise DX or though child's healthcare provider

Fig. 34F

SoundWise Dx™
Pediatric Neurodevelopmental Assessment
Developed by Pediatricians 9 year old

- Multiple SoundWise DX modules will be performed until the child is able to demonstrate proficiency as determined by SoundWise DX computer program AI grader, Pediatrician, or authorized personnel.

- Fail: If misses 4 or more (50% or greater on nonsense word items), then
    - Work on Phonological awareness skills with a caregiver/ teacher/authorized personnel using SoundWise DX 9 Year Old Developmental Milestone Information Sheet (DMIS)
    - START SoundWise DX AI/AI-Generative Online 9 year old nonsense word/phonological awareness/processing/receptive/expressive speech/language modules (Modules are preceded by a short video explaining the lesson to be learned followed by AI/AI-Generative Online recommendation algorithm) and/or worksheets that focus on Phonological Awareness/processing/nonsense words/receptive/expressive speech/language skills
    - In person Speech/ Language Therapy focusing on improving nonsense word/phonological awareness/processing/receptive/expressive speech/language skills
    - Prescriptions for speech and language/nonsense word/phonological awareness will be given through SoundWise DX or Pediatrician/provider.
    - Multiple SoundWise DX modules will be performed until the child is able to demonstrate proficiency as determined by SoundWise DX computer program AI grader, Pediatrician, or authorized personnel.

- If proficiency is not reached after 3 months,SoundWise DX will administer or give a local referral for an assessment that diagnoses a Specific Learning Disorder with Impairment in Reading (dyslexia). This assessment at the least should include a standardized measure of receptive language (including a cognitive measure if receptive language assessment is a deficit), reading and spelling measures, phonological processing assessments (for example that include but not limited to the CTOPP-2), and simple handwriting assessments. At the same time, a diagnostic assessment for ADHD should be done. If an intellectual disability is suspected, a standardized cognitive measure like an IQ test should also be given. All standardized assessments will be the most current versions of the test available. Results of diagnostic testing will be reviewed by SoundWise DX and/or either an in person licensed psychologist or physician to make the appropriate medical diagnosis. This can be done through SoundWise DX or the child's local care network.

Engagement:

*Any and all diagnoses of psychiatric/behavioral disorders (ADHD, Autism, Anxiety, depression etc, will follow and change accordingly with the most current medical guidelines determined by the latest version of the Diagnostic and Statistical Manual of Mental Disorders which is currently the DSM-V. As new versions are published, SoundWise DX concerns identified and diagnostic criteria will adapt and be changed to match the most current diagnostic criteria.*

Fig. 34G

SoundWise Dx™
Pediatric Neurodevelopmental Assessment
Developed by Pediatricians 9 year old

Perfect score:

- Able to demonstrate social communication, interaction , eye contact and able to demonstrate joint attention back and forth with assessment tasks. Not showing restrictive and repetitive behaviors, such as flapping their hands, spinning a lot, only interested in lining up toys or objects, sensory issues such as upset with loud noises, and difficulty with change of routine during the assessment.
- Able to sustain attention, not easily distracted, following directions on Assessment tasks.
- Attending the SoundWise DX assessment without crying and worrying about how they are doing with each task.
- Engagement evaluation is determined by SoundWise DX computer program AI grader, pediatrician, or authorized personnel.

A concern or fail for this section:

- Autism Concern:
  - The child has challenges with social communication and interaction. Has poor eye contact, refusal to engage in tasks, and/or lack of joint attention back and forth while doing assessment tasks.
  - The child demonstrates restrictive/repetitive behaviors, interests, and activities such as, but not limited to, flapping hands, spinning, lining up toys/objects, sensory issues (upset by loud noises/smell/touch), and challenges with change of routine during tasks.
- ADHD/ADD/attention deficits:
  - The child is unable to keep their attention and/or unable to follow directions while completing Assessment without being distracted and/or unable to sit still long enough to complete assessment at age 9 years old, note that a formal diagnosis is not made at age 9, rather only a concern.Children who are inattentive and also exhibit staring spells, need to be evaluated for Absence Seizures. SoundWise DX will offer RX or pediatrician/provider for Neurology referral.
    - Norm values:
      - 3 years old: 6-8 minutes
      - 4 years old: 8-12 minutes
      - 5 and 6 years old: 12-18 minutes
      - 7 and 8 years old: 16-24 minutes
      - 9 and 10 years old: 20-30 minutes
- Anxiety, panic attacks, or Post Traumatic Stress Disorder (PTSD) Concern or Fail:
  - The child is showing emotions of frustration with or without crying and/or demonstrating worry about their performance while completing the assessment.
  - Elevated heart rate and/or blood pressure measured by all digital devices
  - Avoidance behaviors when tasks are hard such as:
    - Child complains or somatic (body) complaints to end or get out of a task like:
      - Headaches
      - Nausea, stomach aches, vomiting
      - Tiredness, yawning, falling asleep
      - Tense posture, clenched shoulders or muscles, clenched teeth
      - Pulling on eyelashes, biting fingers or fingernails
      - Arguing, throwing the materials, leaving the test environment
      - Saying they are thirsty, hungry, tired, sleepy, or having to all of a sudden got to go to the bathroom
      - Complains of their heart racing
      - Child is unable to attempt assessment in part or at all.
      - Any other related complaints by the child not listed above.

Fig. 34H

SoundWise Dx™
Pediatric Neurodevelopmental Assessment
Developed by Pediatricians 9 year old

- Children who do not attempt Assessment will need to to start SoundWise DX AI/AI-Gen engagement modules and a reassessment will be attempted in 1 to 3 months time as per SoundWise DX AI/AI-Gen grader.
- Engagement results are determined by SoundWise DX AI/AI-Gen computer program AI grader, Pediatrician, or authorized personnel.
- Engagement modules cover issues regarding attention, anxiety, autism, or other disorders as discussed below.
  - START SoundWise DX AI/AI-Generative Online 9 year old online Module for lack of engagement (Modules are preceded by a short video explaining the lesson to be learned followed by AI/AI-Generative Online recommendation algorithm) and/or worksheets. The Lack of Engagement modules deliver Speech & Language, Occupational Therapy, Physical Therapy and Behavioral Modification suggestions for building engagement.
  - As the child attends the Lack of Engagement modules, SoundWise DX AI/AI-Gen grader will determine the correct SoundWise DX modules for each individual child.
    - Lack of Engagement SoundWise DX modules include:
      1. Autism diagnostic evaluation through SoundWise DX and/or referral for autism diagnoses through a child's local medical services
      2. Attention Deficit/ADHD behavioral concerns/anxiety
         a. Continue to follow closely, make learning activities fun/engaging, limit activities to short segments.
         b. If severe behavioral issues or anxiety present: referral to child psychologist or for Play Therapy.
         c. Age 4 and older, refer to specific for ADHD module for further recommendations
      3. Modules for other recognized disorders such as post traumatic stress disorder, genetic disorders associated with learning disabilities, environment exposure to lead, fetal alcohol syndrome, Adoption and/or foster care population, proper nutrition, developmental delay, sensory issues, and other situations resulting in childhood developmental delay in need of intervention.
      4. Along with participating in Engagement modules, the following will be provided:
         - Refer for a in-person Speech and Language Evaluation focusing on building strong receptive/expressive language skill
         - Refer for an in person Sensory Integration Focused Occupational Therapy Evaluation focusing on motor integration, oral motor kinesthetics, proprioceptive skills, and sensory regulation..
         - Refer for an in person Physical therapy focusing on building strong gross motor skills.
         - Refer for in person evaluation for Autism
         - Refer for Genetics evaluation
         - Prescriptions for the above services will be provided by SoundWise DX or local health care facility.

- Specific SoundWise DX modules for Autism, ADHD/ADD, and Anxiety:

1. Autism: Autism presents challenges with social communication and interaction. They do not talk a lot because they are not motivated to socially interact. They have challenges with eye contact and are unable to demonstrate joint attention, not able to play a back and forth game or do SoundWise DX assessment tasks. They show restrictive and repetitive behaviors, such as flapping their hands, spinning a lot, only interested in lining up toys or objects, sensory issues such as being upset with loud noises, wanting to smell things and not wanting to play pretend. Children with Autism also have difficulty with change of routine for example, having

Fig. 34I

SoundWise Dx™
Pediatric Neurodevelopmental Assessment
Developed by Pediatricians 9 year old a new teacher, or driving a new route home and difficulty changing tasks during the SoundWise DX assessment.

- Determination of Autism by SoundWise DX computer program AI grader, pediatrician, or authorized personnel will recommend the following:
- Recommended activities and/or worksheets generated in the modules will address the specific concerns of lack of engagement/ language delay affecting social interaction, high concerns for Autistic Spectrum Disorder (ASD), or ASD confirmed by meeting the diagnostic criteria for ASD as per the most current version of the DSM which is currently the DSM-V. This will includes activities that focus on but or not limited to the following:
    - To strengthen receptive, expressive, and pragmatic language skills
        - Specific games and activities addressing language goals
    - To improve sensory regulation
        - Specific games and activities to decrease sensory triggers whether they be hypo(low) or hyper(high) sensory
        - Recommendation to address sensory seeking behaviors and/or sensory avoidance behaviors
        - Occupational Therapy (OT) like play activities with OT therapy goals addressing visual/motor integration, sensory regulation, visual perceptual skills, executive function, and primitive reflex integration)
    - To improve fine motor skills
        - Specific games and activities to improve any fine motor skills or hand skill ability like but not limited to the following (handwriting, cutting, folding, stringing beads, coloring, drawing, gluing, buttoning, using utensils, etc.
    - To improve gross motor skills
        - Specific games and activities to strengthen gross motor movements that includes focusing on balance, coordination, ball skills (dribbling, throwing,catching, etc.), hand eye coordination, same side and alternating side body movements, body schema activities (proprioceptive, vestibular, tactile, and body awareness)
        - Physical Therapy (PT) therapy like activities with PT gross motor goals
    - To improve social and pragmatic language skills
        - Specific group play therapy along with games and activities promoting opportunity for improved and guided social interaction
            - Group play therapy
            - Applied Behavioral Analysis Therapy
            - Increased peer group interactions.
- In situations where anxiety or family connections are more calming, the avatar (computer generated face and/or voice used) could be that of a person familiar to the individual) when the assessment or enrichment activities are delivered on the SoundWise DX platform.
- SoundWise DX modules can be used to treat and strengthen skills along with in person therapy especially when waiting for in person therapy. Using SoundWise DX modules will start therapeutic advancement of identified skill deficits while at home when awaiting in person therapies. They can also be used to augment and reinforce the actual future or current therapies in place like medically delivered Speech and Language Therapy, OT, Cognitive Behavioral Therapy, and PT.
- Engagement modules and/or worksheets allow Early Intervention to immediately start while a child awaits for in person evaluation and/or in person autism specific therapy.

Fig. 34J

SoundWise Dx™
Pediatric Neurodevelopmental Assessment
Developed by Pediatricians 9 year old

- SoundWise DX modules and/or worksheets will improve skills and reassessment will allow progress. Children should continue using the modules and/or worksheets even after starting in-person therapy.
- Referral when indicated per AI/AI generated Algorithm
  - Refer for a in person Speech and Language Evaluation
  - Refer for a in person Sensory Integration Focused Occupational Therapy Evaluation
  - Refer for an in person Diagnostic Evaluation for Autism
  - Refer for in person Child Play Therapy
- Pursue all therapies covered by medical insurance while at the same time caregivers/ teachers work on language skills, social interaction, developmental milestones, and sensory regulation using SoundWise DX 9 Year Old Developmental Milestone Information Sheet (DMIS) for age appropriate activities.
- Recommendations will include prescriptions for in person services generated through SoundWise DX.
- Suggestions to seek specialized diagnostic evaluations when indicated by SoundWise DX AI/AI-Gen Grader will include follow up with the child's primary care medical provider, and specialty referrals.
- As part of the diagnostic process, SoundWise DX will administer and score standardized validated screeners as age appropriate such as but not limited to the MCHAT, ASQ, PEDS Form, Vanderbilts, Denver Developmental assessments, Conners Forms, Scat etc)
- While Autism may be the primary diagnosis or concern, other coexisting conditions like anxiety or ADHD and/or genetic disorders may exist. If a validated screening as discussed above elicits concerns for other disorders, the appropriate referral will be done through SoundWise DX.

2. For Attention Deficit Hyperactivity Disorder Concerns (ADHD/ADD):
   - Behavioral modifications SoundWise DX module for 9 year old Behavioral Basics will be given that focuses tips on a structured environment, making learning activities fun, multisensory activities, and short but repetitive opportunities for learning.
   - If engagement is appropriate, but focus/attention to a task cannot be maintained for the expected time for this age ( 20-30 minutes), then refer to SoundWise ADHD/ADD age specific questions and holistic consideration of all factors that can affect attention and sustained focus.
   - Children with ADHD/ADD have a hard time paying attention, daydreaming and often do not seem to listen. They are easily distracted from work and play and often do not pay attention to details/disorganization and do not follow through on directions. Prone to losing a lot of important things/forgetting things and avoids doing things that require mental effort. Having the hyperactivity component makes them prone not being able to stay seated, squirming a lot, talking too much, unable to play quietly and will jump, run and climb when not permitted to do so. They will demonstrate impulsivity, calling out without question being complete, Acts or speaks without thinking, Interrupting others often, trouble taking turns, cannot wait for things and may run onto street without looking out for traffic.
     - SoundWise DX AI/AI Gen grader will administer and score a Vanderbilt screen for parent and teacher if applicable). These screens are diagnostic of ADHD/ADD.
       - Visual attention and focus: SoundWise RX AI/Gen AI computer grader will derive objective and quantitative

Fig. 34K

SoundWise Dx™
Pediatric Neurodevelopmental Assessment
Developed by Pediatricians 9 year old results for example gaze direction, dwell time, and glance frequency off the assessment site to other objects and locations. While monitoring eye tracking, we will measure where and for how long an individual looks in a certain direction or at a certain target, it is not a measure of actual visual attention However, this information can be used to necessitate further exploration into attention or focus disorders like ADHD/ADD. The SoundWise RX screen eye tracking will be used to assess student attention while taking the test. Just as eye tracking is the go-to method when determining driver distraction via glance target classification it can be used to assess attention to the assessment attention engagement in the test itself, or also suggest more analysis of visual tracking/perception/or processing is warranted.

- When above condition concerns are found, AI/AI-Gen computer program modules and/or worksheets for evaluation and guidance/ for ADHD/ADD will be generated. Further informational sheets on factors that can impact attention will be generated and given to the caregivers.
- Modules for scholastic accommodations such IEP, 504 and not limited to will also be given that can be effectively be used within a child's Individual Educational Plan (IEP) or 504 Plan.
- When formal diagnosis of ADHD for age 9 years old and older has been given, then information regarding evaluation for behavioral modification will be given.
- Starting at age 9 or older, medication for ADHD/ADD when indicated by SoundWise DX AI/AI-Gen and/or caregiver/teacher. Blood pressure. Pulse, EKG rhythm strip will be administered through all digital devices, along with telemedicine visit with SoundWise DX before medication is given.. Pathways towards diagnostic evaluation will be done according to the specific laws in each state.
- Classroom modifications and accommodation recommendations would be produced via SoundWise DX module via AI/AI-Gen and given via SoundWise DX according to the specific laws in each state.

3. Anxiety:
   - A diagnosis of Anxiety is when a child is worried or scared and it interferes with their everyday activities such as refusing to go to school, playing with friends,especially at recess or at social gatherings, getting to sleep and/or not being able to sleep alone in their bed. They may say their heart is beating too fast, or they have a stomach ache and shaking, maybe having trouble breathing, start to sweat and suddenly are unable to sustain attention and want to find a safe place, like home or a caregiver. See specific symptoms that were listed above in "what constitutes a fail". Anxiety may have been exhibited itself as shyness during the child's early years, or occur after a traumatic event experienced/ witnessed by the child or the child may be a victim of abuse by a caregiver or other.
   - There are 4 types of Anxiety present in children;
     - Social Anxiety-Difficulty playing or being with others, especially in school, will speak softly not wanting to be heard and will not volunteer to raise hand in school or participate in group activities.
     - Separation Anxiety- Unable to separate from the caregiver, wanting to always be in their presence, not wanting to go to school or be on a playdate.
     - Selective Mutism- severe anxiety-speaks at home but not anywhere else. Has early onset.
     - Generalized Anxiety-Strives to be perfect,worries about the past, current events and the future a lot and worries about what may happen in school in their school work or

Fig. 34L

SoundWise Dx™
Pediatric Neurodevelopmental Assessment
Developed by Pediatricians 9 year old other activities. They may get diagnosed with ADHD, however this child can not pay attention due to worry, rather than attention.

- The child may demonstrate Anxiety during SoundWise DX by being concerned about getting the assessment tasks correct or simply not speaking. They may cry and turn away and say they are afraid to continue.
- SoundWise DX AI/Gen-AI will determine through an anxiety algorithm module and/or caregiver/teacher or authorized personnel to start Anxiety SoundWise DX modules as well to start arranged telemedicine visits through SoundWise DX and/or in person therapy.
- Also the Caregiver/teacher will work on language development, social interaction, and sensory regulation by using SoundWise DX 9 Year Old Developmental Milestone Information Sheet (DMIS) for age appropriate activities.
- SoundWiseDX will administer and score a diagnostic screen such as PHQ-9/SCARED/Columbia/Hamilton/GAD-7 for Anxiety that is appropriate for age.
- Based on SoundWiseDX AI/AI-Gen Children will also be started on telemedicine services through SoundWise DX for anxiety.
- Reasons for indications for medicine management for Anxiety is determined by SoundWise DX AI/AI-Gen, physician, and input from caregiver/teacher. Pulse, Blood Pressure and EKG will be obtained by digital devices and are medically necessary before starting medication. Telemedicine services for anxiety though SoundWise DX must also be initiated and continued while the child is on medication for anxiety.
- All children diagnosed with Anxiety through SoundWise DX AI/AI-Gen will also be evaluated for ADHD/ADD and/or Autism

4. Low Self Esteem

- Self esteem should always be monitored closely in a child as this can lead to depression or other mental health disparities in the future.
- Low self esteem can arise from a variety of reasons.
- A soundWise DX Module AI/AI-Gen will be given that addresses building self esteem and confidence in a child.
- Telemedicine visits will be recommended via SoundWise DX or their local provider

- Reassessments SoundWise DX:
  - SoundWise DX will offer reassessments (Form B's) after 3 months of module implementation. Initial assessments are Form A.
  - In 3 months or less depending upon the discretion of SoundWise DX AI/AI-Gen computer program AI grader, pediatrician, and/or authorized personnel, the child will retake an assessment
    - If the child is still the same age, they will then take that age years Form B
    - If they have aged up and are now 1 year older, then they will take the next year's assessment Form A.
    - If a child is able to pass some, but not all, or if unable to pass the repeat pediatric assessment, they must follow through with the same algorithm as above until proficiency is determined by SoundWise DX computer program AI grader, pediatrician, or authorized personnel.
    - If the child is able to pass all parts of the new assessment, they should do SoundWise DX enrichment modules based on age group.

Fig. 34M

SoundWise Dx™
Pediatric Neurodevelopmental Assessment
Developed by Pediatricians

9 Years and Older Neurodevelopmental Milestone Information Sheet

A 9 to 10 year old's growing independence from the family is supported by their interests in friends. Healthy friendships are very important to your child's development, but peer pressure can become strong during this time. Children who feel good about themselves are more able to resist negative peer pressure and make better choices for themselves. This is an important time for children to gain a sense of responsibility along with their growing independence. School performance as well as their activities outside of school start to become a big part of their life. Their self esteem is strongly affected by their performance in school and in the activities they participate in.

The physical changes of puberty might be showing by now, especially for girls. Another big change children need to prepare for during this time is starting middle or junior high school.

What a typical 9 or 10 year old should be able to do.

| Language Communication Milestones | Social Emotional Milestones |
|---|---|
| • Have speech patterns that are nearly at an adult level.<br>• Read and enjoy chapter books.<br>• Often read with a goal of learning about something of interest.<br>• Can read and understand a paragraph of complex sentences.<br>• Know that objects have uses and can be grouped into different categories. *(For example, they recognize that a carrot is something to eat and is a type of vegetable)*<br>• Can accomplish increasingly more complex tasks and projects in school, such as book reports. | • Start to form stronger, more complex friendships and peer relationships. It becomes more emotionally important to have friends, especially of the same sex.<br>• Experience more peer pressure.<br>• Become more aware of his or her body as puberty approaches. Body image and eating problems sometimes start around this age. |

Copyright © 2024 All Rights Reserved

Fig. 35A

SoundWise Dx™
Pediatric Neurodevelopmental Assessment
Developed by Pediatricians

- Know the complete date (day of the week, day of the month, month, and year).
- Can name the months of the year in order.

Important Tip

Limit screen time to no more than 2 hours per day except for homework.

Gross Motor Movement/Physical Milestones

- Their athletic skills are improving as their muscle strength and endurance continue to develop.
- Are getting more coordinated in activities that use the large muscles, such as swimming or climbing.
- Become increasingly skilled in hobbies, sports, and active play.
- Dressing and toileting themselves independently
- Catch a ball more easily using only their hands

Fine Motor Milestones

- Enjoy active play, such as bike-riding, swimming, and running games (like "tag").
- Become increasingly interested in team sports.
- Get dressed, brush their hair, brush their teeth, and get ready without any help.
- Use simple tools, such as a hammer, by themselves.
- Like to draw, paint, make jewellery, build models, or do other activities that use their fine motor skills.
- Have learned to write in cursive.

Cognitive Milestones
(Learning, Thinking, Problem-Solving)

- Face more academic challenges at school.
- Become more independent from the family.
- Begin to see the point of view of others more clearly.
- Have an increased attention span usually 20-30 minutes.
- Are skilled in addition and subtraction. They are building skills in multiplication, division, and fractions.
- Learning basic math concepts
- Like organization and planning activities, such as making plans ahead of time with friends.
- Think independently. Most children are improving their decision-making skills Copyright © 2024 All Rights Reserved

Fig. 35B

SoundWise Dx™
Pediatric Neurodevelopmental Assessment
Developed by Pediatricians

| | |
|---|---|
| • Can write simple stories. | |
| | |

Tips for play and learning!

- Learning is and should be fun!
- Every opportunity to play is an opportunity to learn.
- Keep learning activities around 20-30 minutes at a time.
- Practical activities. Look at newspaper articles, notices from school, leaflets/guides in museums, buy books to read or games to play.
- Read together.
- Play math games.
- Cook together.

How to help your child build stronger language skills.

Developing healthy communication skills such as learning to speak, understanding language, and learning to read are key milestones that your child needs to reach so that they enjoy and engage in play, and become successful in school.

Language developed as babies learned through simple exposure by listening and watching someone speak to them. They learned how sounds are put together in different ways and have different meanings. This constant exposure to sounds was building the two major language skills:

1. Receptive language (input) - what you understand.
2. Expressive language (output) - what you can say.

Copyright © 2024 All Rights Reserved

Fig. 35C

SoundWise Dx™
Pediatric Neurodevelopmental Assessment
Developed by Pediatricians A child's exposure to language starts in utero. As babies, they then start to babble and observe how we speak by looking at our faces and how we move our mouth, lips, and tongue to make sounds. They quickly understand that sounds have meaning and they start to acquire language at an amazing pace. When they are 5-6 years old, they will present to school to learn higher level language skills, like reading, writing, spelling, and math. The strength of your child's early language foundation will directly relate to the ease of their learning, their future academic success, and overall psychological well-being. Help them build a strong foundation for later scholastic and emotional success early. If difficulties arise, seek help immediately as foundational skills need to be strengthened before higher level skills are achieved.

If your child is having difficulty with reading and/or spelling, it is important to understand why and to work on basic skills before more advanced skills.

There are lots of simple things you can do that are fun and help build age appropriate scholastic skills:

- Tell stories and have conversations about things
- Read books or have books read to them.. This builds vocabulary
- Ask questions about the things you read or talk about
- Play games with sounds
- If reading fluency, accuracy, or comprehension are issues, seek help quickly
- Talk to your child.
    - TV's and screens are not good substitutes. Limit screen time to 2 hours per day except for homework and do not put TV or computer devices in the bedroom
- Teach children about what you are doing and why. Every opportunity is an opportunity for learning.
- Talk through decision making processes.
- Let you child problems solve and learn how to work and solve problems
- Field trips for active learning are great ways to keep learning fun
- Ask your child questions as you tell a story. See if they are making a mental movie or picture while listening to the books or stories that you read to them.
- Let your child explore and use their imaginations.
- Teach language concepts with games.
    - Play word board games or charades
- Teaching math concepts can be fun
    - Quantify/Comparative concepts (small, medium, large, most/least, same/different, young/old, wet/dry, etc.)
    - Include knowledge of shapes, patterns, measurement, and spatial sense
    - Manipulatives and Hands-On Learning Copyright © 2024 All Rights Reserved

Fig. 35D

SoundWise Dx™
Pediatric Neurodevelopmental Assessment
Developed by Pediatricians

- Use games and puzzles: Introduce math-based board games, puzzles, and apps that make learning math fun and interactive.
  - Real-life applications: Show how math is used in everyday activities like cooking, shopping, and building to make it more relevant and practical.
  - Math-related activities: Engage in activities such as measuring ingredients for recipes, creating patterns with shapes, or building structures using blocks to make math more hands-on and enjoyable.
  - Observe math in nature: Explore how math is present in nature through activities like counting petals on flowers, observing patterns in leaves, or identifying geometric shapes in the environment.
  - Storytelling: Use stories and books that incorporate math concepts to make learning more engaging and relatable.
- Let your child have opportunities to interact with peers
- Allowing your child to make choices within the appropriate allowable constraints.
- Encourage affection in your family and reinforce positive behavior.
- Teach your child that emotional feelings are allowed but everyone has a responsibility to control their behavior when angry, sad, or upset.
- Set limits on behaviors that are not appropriate
- Resolve disagreements and disputes peacefully.
- Make sure that your child gets enough sleep to wake up well rested.

What do sounds have to do with words in print, letters, and reading?

Learn those sounds! Practicing one new sound per week will strengthen your child's ability to eventually sound out words (decode). Decoding enables your child to sound out words so they do not have to guess. Accurate decoding is critically important to future reading success. It is the skill that separates good readers from poor readers.

Whenever you can, point out words wherever you go or in books so that your child recognizes that letters actually mean something. You can point to the print while you read. Play games like finding signs on buildings or street signs, or words on boxes at the supermarket. Reading to your child and pointing out words boosts vocabulary and advances knowledge.

You can teach letters but always teach the sound associated with it too.

Why does all this matter?

Copyright © 2024 All Rights Reserved

Fig. 35E

SoundWise Dx™
Pediatric Neurodevelopmental Assessment
Developed by Pediatricians A person learns by experience and play. Give your child every opportunity to grow and learn. A strong grasp of language will give your child the ability to thrive in school and later in life. For it is the foundation that you build before 5 years of age that will be the platform from which learning will take place later on. If that foundation did not happen effortlessly it must be built by practice.

A strong foundation is built using the ability to play with, manipulate, hold onto, and retrieve sounds in words. That critical skill is called "sound processing." It is the skill that "good readers" do well and "poor readers" do not. So help your child accelerate into scholastic success and build a strong language foundation. And remember, those magical ingredients are sounds so play with them and have fun!

Copyright © 2024 All Rights Reserved

Fig. 35F

SoundWise Dx™
Pediatric Neurodevelopmental Assessment
Developed by Pediatricians 3 year old Assessment Report

Name: ______________________ DOB: ____________

Fine Motor Skills:

If patient, unable to draw line and/or circle. Start OT ☐

If a patient has a fisted pencil grip. Advise parents on a 3 point pencil grip necessary by age 4. Advise Parents ☐

If child attends OT and/or unable to get OT, please reevaluate in 2-3 months

______________________

______________________

Gross Motor Skills:

Patient was unable to do questions #3-6 due to lack of coordination then provide: PT for gross motor skills ☐

______________________

______________________

Receptive Language Skills:

If unable to understand directions or is a 2nd language patient then provide: ST for receptive language delay ☐

If patient attends PT and/or ST, patient must be seen and reevaluated in 2- 3 months

______________________

______________________

Sound Articulation:

If misses 1-3: Advise parents what to do ☐

If misses 4 or greater: Start speech therapy ☐

If patient attends or unable to receive ST, please reevaluate patient in 2-3 months

______________________

______________________

Fig. 36A

SoundWise Dx™
Pediatric Neurodevelopmental Assessment
Developed by Pediatricians 3 year old Assessment Report

Sound Discrimination:

| | | |
|---|---|---|
| If misses 1-3: | Advise parents what to do | ☐ |
| If misses 4 or greater: | Start speech therapy | ☐ |

If patient attends or unable to receive ST, please reevaluate patient in 2-3 months

Behavior/Engagement (how child acts during assessment administration):
If not engaged or upset have patient follow up in 2-3 months to repeat the assessment If not engaged or upset and patient has limited speech, must consider autism and RX must be written for autism evaluation (write CARS or ADOS-2 or STAT assessment must be done)

If not engaged or upset and the patient has normal speech, consider anxiety and have the patient consider submitting a video (to provider) with the child performing some of the skills at home.

When children are unable to focus, easily distracted, unable to sustain attention for 6-8 minutes, consider reevaluation in 3 months If patient stares with no reaction and parents report this behavior at home (stares for 10-15 seconds) throughout the day, consider workup for absence seizures Plan for child: OT, PT, ST services __________ length of time and reevaluate in ____________
Referral written for Early Intervention, private therapy, autism eval, neurologist,developmental, genetics.

Are hearing and vision testing up to date? Yes
☐

Fig. 36B

SoundWise Dx™
Pediatric Neurodevelopmental Assessment
Developed by Pediatricians 4 year old Assessment Report

Name: ______________________________ DOB: ______________

Receptive Language Skills:

If unable to understand directions with > 3 incorrect or
s a 2nd language patent provide ST for: Receptive Language Delay ☐

If gets colors red and green incorrect consider eye exam to rule out color blindness

---

---

Sound Discrimination:

If misses 1-3: Advise parents what to do ☐

If misses 4 or greater : Start speech therapy ☐

---

---

Sound Order Awareness:

If misses 1-3: Advice parents what to do ☐

If misses 4 or greater: Start speech therapy ☐

---

---

Fine Motor Skills:

If patient is unable to draw figure Start OT ☐

If patient has a fisted pencil grip Start OT and show parents 3 point pencil grip ☐

If child can not draw shape Start OT ☐

If child can not trace line within box Advise Parents ☐

If child attends OT and/or unable to get OT, please reevaluate in 2-3 months

---

---

Fig. 37A

SoundWise Dx™
Pediatric Neurodevelopmental Assessment
Developed by Pediatricians 4 year old Assessment Report

Letter name and letter sound identification:

| | | |
|---|---|---|
| If child unable to identify 2-3 letters: | Advise parents | ☐ |
| If child unable to identify > 4 letters: | Advise parents, send note to teacher, and start speech therapy | ☐ |

---

---

Letter identification:

| | | |
|---|---|---|
| If child unable to identify 2-3 letters: | Advise parents | ☐ |
| If child unable to identify > 4 letters: | Advise parents, send note to teacher and start speech therapy | ☐ |

Speech therapy should teach letter sounds first and then matching it with letter identification, phonological awareness, and phonological processing as well as articulation

---

---

Phonemic Ellison (Sound Deletion) Skills:

Word deletions:

| | | |
|---|---|---|
| If misses greater > 2 | Advise parents and send note to teacher | ☐ |
| If misses greater > 3 | Advise parents, send note to teacher and start speech therapy | ☐ |

Sound Deletions:

| | | |
|---|---|---|
| If misses greater > 2 | Advise parents and send note to teacher | ☐ |
| If misses greater > 3 | Advise parents, send note to teacher and start speech therapy | ☐ |

Speech therapy should be written for phonemic elision, articulation, expressive and receptive language, phonological awareness, and phonological processing

---

---

Fig. 37B

SoundWise Dx™
Pediatric Neurodevelopmental Assessment
Developed by Pediatricians 4 year old Assessment Report

Behavior/Engagement (how child acts during assessment administration):
If not engaged or upset have patient follow up in 2-3 months to repeat the assessment If not engaged or upset and patient has limited speech, no eye contact must consider autism and RX must be written for autism evaluation (write CARS or ADOS-2 or STAT assessment must be done)

If not engaged or upset and the patient has normal speech, consider anxiety and have the patient consider submitting a video (to provider) with the child performing some of the skills at home.

When children are unable to focus, easily distracted, unable to sustain attention for 8 -12 minutes, consider speaking to parents about Vanderbilt screen for ADHD/ADD If patient stares with no reaction and parents report this behavior at home (stares for 10-15 seconds) throughout the day, consider workup for absence seizures Plan for child: OT, PT, ST services ____________ length of time and reevaluate in ______________
Referral written for Early Intervention, private therapy, autism eval, neurologist,developmental, genetics.

Are hearing and vision testing up to date? Yes
☐

Fig. 37C

SoundWise Dx™
Pediatric Neurodevelopmental Assessment
Developed by Pediatricians 5 year old Assessment Report

Name: ______________________ DOB: ____________

Receptive Language Skills:
If unable to understand directions with > 3 incorrect or is a 2nd language patient: Start speech therapy for receptive language delay ☐

If gets colors red and green incorrect consider eye exam to rule out color blindness

______________________________

______________________________

Fine Motor Skills:

| | | |
|---|---|---|
| If patient is unable to color circle: | Start OT | ☐ |
| If patient has a fisted pencil grip: | Start OT and show parents 3 point pencil grip | ☐ |
| If child can not copy square | Start OT | ☐ |
| If child can not trace line within box | Advise Parents | ☐ |

If child attends OT or unable to get OT, please reevaluate in 2-3 months

______________________________

______________________________

Letter name and letter sound identification:

| | | |
|---|---|---|
| If child unable to identify 2-3 letters | Advise parents | ☐ |
| If child unable to identify > 4 letters | Advise parents, send note to teacher, and start speech therapy | ☐ |

______________________________

______________________________

Letter identification:

| | | |
|---|---|---|
| If child unable to identify 2-3 letters | Advise parents | ☐ |
| If child unable to identify > 4 letters | Advise parents, send note to teacher, and start speech therapy | |

Fig. 38A

SoundWise Dx™
Pediatric Neurodevelopmental Assessment
Developed by Pediatricians 5 year old Assessment Report Speech therapy should teach letter sounds first and then match sounds to letter identification, phonological awareness, and phonological processing

---

Phonemic Ellison (Sound Deletion) Skills:

Word deletions:

| | | |
|---|---|---|
| If misses greater > 2 | Advise parents and send note to teacher | ☐ |
| If misses greater > 3 | Advise parents, send note to teacher and start speech therapy | ☐ |

Sound Deletions:

| | | |
|---|---|---|
| If misses greater > 2 | Advise parents and send note to teacher | ☐ |
| If misses greater > 3 | Advise parents, send note to teacher and start speech therapy | ☐ |

Speech therapy should be written for phonemic elision, articulation, expressive and receptive language, phonological awareness, and phonological processing

---

Rhyming Exercise:

| | | |
|---|---|---|
| If misses greater > 2 | Advise parents | ☐ |
| If misses greater > 3 | Advise parents how to help, send note to teacher and start speech therapy | ☐ |

---

Behavior/Engagement (how child acts during assessment administration):

If not engaged or upset have patient follow up in 2-3 months to repeat the assessment If not engaged or upset and patient has limited speech, must consider autism and RX must be written for autism evaluation (write CARS or ADOS-2 or STAT assessment must be done)

If not engaged or upset and the patient has normal speech, consider anxiety and have the patient consider submitting a video (to provider) with the child performing some of the skills at home.

Fig. 38B

SoundWise Dx™
Pediatric Neurodevelopmental Assessment
Developed by Pediatricians 5 year old Assessment Report When children are unable to focus, easily distracted, unable to sustain attention for 12-15 minutes, consider speaking to parents about Vanderbilt screen for ADHD/ADD If patient stares with no reaction and parents report this behavior at home (stares for 10-15 seconds) throughout the day, consider workup for absence seizures Plan for child: OT, PT, ST services _________ length of time and reevaluate in ___________
Referral written for Early Intervention, private therapy, autism eval, neurologist, developmental, genetics.

Are hearing and vision testing up to date? Yes
☐

Fig. 38C

SoundWise Dx™
Pediatric Neurodevelopmental Assessment
Developed by Pediatricians 6 year old Assessment Report

Name: ______________________ DOB: ____________

Receptive Language Skills:

If unable to understand directions with > 3 incorrect or is a 2nd language patient: Start speech therapy for receptive language delay ☐

If child gets the colors red and green incorrect consider eye exam to rule out color blindness

---

Fine Motor Skills:

If patient is unable to draw dog or figure with 6+ parts or draw shapes Start OT ☐

If patient has a fisted pencil grip Start OT and show parents 3 point pencil grip ☐

If child can not copy numbers 1-6 Start OT ☐

If child can not write name Advise Parents & OT ☐

If child attends OT or unable to get OT, please reevaluate in 2-3 months

---

Letter name and letter sound identification:

If child unable to identify 2-3 letters Advise parents ☐

If child unable to identify > 4 letters Advise parents, send note to teacher, and start speech therapy ☐

---

Letter identification:

If child unable to identify 2-3 letters Advise parents ☐

If child unable to identify > 4 letters Advise parents, send note to teacher and start speech therapy ☐

Fig. 39A

SoundWise Dx™
Pediatric Neurodevelopmental Assessment
Developed by Pediatricians 6 year old Assessment Report Speech therapy should teach letter sounds first and then match up with letter identification, phonological awareness, and phonological processing

Phonemic Ellison (Sound Deletion) Skills:

Word deletions:

| | | |
|---|---|---|
| If misses greater > 2 | Advise parents and send note to teacher | ☐ |
| If misses greater > 3 | Advise parents, send note to teacher and start speech therapy | ☐ |

Sound Deletions:

| | | |
|---|---|---|
| If misses greater > 2 | Advise parents and send note to teacher | ☐ |
| If misses greater > 3 | Advise parents, send note to teacher and start speech therapy | ☐ |

Speech therapy should be written for phonemic elision, articulation, expressive and receptive language, phonological awareness, and phonological processing

Rhyming Exercise:

| | | |
|---|---|---|
| If misses greater > 2 | Advise parents | ☐ |
| If misses greater > 3 | Advise parents, send note to teacher and start speech therapy | ☐ |

Nonsense Words:

| | | |
|---|---|---|
| If misses greater > 2 | Advise parents | ☐ |
| If misses greater > 3 | Advise parents, send note to teacher and start speech therapy | ☐ |

Speech therapy for nonsense words should indicate phonemic awareness/processing and articulation. Must introduce how to decode words with phonics

Fig. 39B

SoundWise Dx™
Pediatric Neurodevelopmental Assessment
Developed by Pediatricians 6 year old Assessment Report

Behavior/Engagement (how child acts during assessment administration):
If not engaged or upset have patient follow up in 2-3 months to repeat the assessment If not engaged or upset and patient has limited speech, must consider autism and RX must be written for autism evaluation (write CARS or ADOS-2 or STAT assessment must be done)

If not engaged or upset and the patient has normal speech, consider anxiety and have the patient consider submitting a video (to provider) with the child performing some of the skills at home.

When children are unable to focus, easily distracted, unable to sustain attention for 12-15 minutes, consider speaking to parents about Vanderbilt screen for ADHD/ADD.

If patient stares with no reaction and parents report this behavior at home (stares for 10-15 seconds) throughout the day, consider workup for absence seizures Plan for child: OT, PT, ST services _________ length of time and reevaluate in ___________
Referral written for Early Intervention, private therapy, autism eval, neurologist,developmental, genetics.

Are hearing and vision testing up to date? Yes
☐

________________________________________
________________________________________
________________________________________
________________________________________
________________________________________
________________________________________
________________________________________
________________________________________

Fig. 39C

SoundWise Dx™
Pediatric Neurodevelopmental Assessment
Developed by Pediatricians 7-8 year old Assessment Report

Name: ____________________ DOB: __________

Fine Motor Skills:

| | | |
|---|---|---|
| If patient is unable to copy the shape | Start OT | ☐ |
| If patient has a fisted pencil grip | Start OT and show parents 3 point pencil grip | ☐ |
| If child can not copy numbers 1-10 | Start OT | ☐ |
| If child can not write name | Advise Parents & OT | ☐ |
| If child can not write the first 10 letters of the abc's in lowercase | Start OT and work with child at home | ☐ |
| If the child cannot write 3 words that have 3 or 4 letters each | Work with child by reading at home | ☐ |

If child attends OT/ST and unable to get OT/ST, please reevaluate in 2-3 months

______________________________________

______________________________________

Phonemic Ellison (Sound Deletion) Skills:

Word deletions:

| | | |
|---|---|---|
| If misses greater > 2 | Advise parents and send note to teacher | ☐ |
| If misses greater > 3 | Advise parents, send note to teacher and start speech therapy | ☐ |

Sound Deletions:

| | | |
|---|---|---|
| If misses greater > 2 | Advise parents and send note to teacher | ☐ |
| If misses greater > 3 | Advise parents, send note to teacher and start speech therapy | ☐ |

Speech therapy should be written for phonemic elision, articulation, expressive and receptive language, phonological awareness, and phonological processing

______________________________________

______________________________________

Reading Single Words:

| | | |
|---|---|---|
| If misses greater > 2 | Advise parents | ☐ |
| If misses greater > 3 | Advise parents, send note to teacher, | |

Fig. 40A

SoundWise Dx™
Pediatric Neurodevelopmental Assessment
Developed by Pediatricians 7-8 year old Assessment Report and read more with child ☐

A child needs exposure to a new word at least 12 times before they learn a new word.

---

Nonsense Words:

| | | |
|---|---|---|
| If misses greater > 2 | Advise parents | ☐ |
| If misses greater > 3 | Advise parents, send note to teacher and start speech therapy | ☐ |

Speech therapy should work with phonemic awareness/processing, articulation,and learning how to decode a word using phonics.

---

Behavior/Engagement (how child acts during assessment administration):
If not engaged or upset have patient follow up in 2-3 months to repeat the assessment If not engaged or upset and patient has limited speech, must consider autism and RX must be written for autism evaluation (write CARS or ADOS-2 or STAT assessment must be done)

If not engaged or upset and the patient has normal speech, consider anxiety and have the patient consider submitting a video (to provider) with the child performing some of the skills at home.

When children are unable to focus, easily distracted, unable to sustain attention for 16-24 minutes, consider speaking to parents about Vanderbilt screen for ADHD/ADD If patient stares with no reaction and parents report this behavior at home (stares for 10-15 seconds) throughout the day, consider workup for absence seizures Plan for child: OT, PT, ST services __________ length of time and reevaluate in ____________
Referral written for Early Intervention, private therapy, autism eval, neurologist, developmental, genetics, school testing for dyslexia (CTOPP-2) Needs IEP or 504 written for school Are hearing and vision testing up to date?
☐

---

Fig. 40B

SoundWise Dx™
Pediatric Neurodevelopmental Assessment
Developed by Pediatricians 9 year old Assessment Report

Name: ______________________ DOB: ____________

Fine Motor Skills:

If patient is unable to copy the circles — Start OT ☐

If child can not copy the sentence in under 2 minutes with no errors — Start OT ☐

If child can not write their first and last name — Advise parent & start OT ☐

If child can not write the abc's in lower case — Start OT and advise parent ☐

If child attends OT and unable to get OT, please reevaluate in 2-3 months

______________________________

______________________________

Phonemic Ellison (Sound Deletion) Skills:

Word deletions:

| | | |
|---|---|---|
| If misses greater > 2 | Advise parents and send note to teacher | ☐ |
| If misses greater > 3 | Advise parents, send note to teacher and start speech therapy | ☐ |

Sound Deletions:

| | | |
|---|---|---|
| If misses greater > 2 | Advise parents and send note to teacher | ☐ |
| If misses greater > 3 | Advise parents, send note to teacher and start speech therapy | ☐ |

Speech therapy should be written for phonemic elision, articulation, expressive and receptive language, phonological awareness, and phonological processing

______________________________

______________________________

Reading Single Words:

| | | |
|---|---|---|
| If misses greater > 2 | Advise parents | ☐ |
| If misses greater > 3 | Advise parents, send note to teacher and read more often with child | ☐ |

A child needs exposure to a new word at least 12 times before they learn a new word.

______________________________

______________________________

Fig. 41A

SoundWise Dx™
Pediatric Neurodevelopmental Assessment
Developed by Pediatricians 9 year old Assessment Report

Nonsense Words:

| | | |
|---|---|---|
| If misses greater > 2 | Advise parents | ☐ |
| If misses greater > 3 | Advise parents, send note to teacher and start speech therapy | ☐ |

Speech therapy should work with phonemic awareness/processing, articulation,and learning how to decode a word using phonics.

______________________________________________

______________________________________________

Behavior/Engagement (how child acts during assessment administration):
If not engaged or upset have patient follow up in 2-3 months to repeat the assessment If not engaged or upset and patient has limited speech, must consider autism and RX must be written for autism evaluation (write CARS or ADOS-2 or STAT assessment must be done)

If not engaged or upset and the patient has normal speech, consider anxiety and have the the patient submit a video (to the provider) with the child performing some of the skills at home.

When children are unable to focus, easily distracted, unable to sustain attention for 20-30 minutes, consider speaking to parents about the Vanderbilt screen for ADHD/ADD.

If patient stares with no reaction and parents report this behavior at home (stares for 10-15 seconds) throughout the day, consider workup for absence seizures Plan for child: OT, PT, ST services __________ length of time and reevaluate in ____________
Referral written for Early Intervention, private therapy, autism eval, neurologist, developmental, genetics, school testing for dyslexia (CTOPP-2) Needs IEP or 504 written for school Are hearing and vision testing up to date? Yes
☐

______________________________________________

______________________________________________

______________________________________________

______________________________________________

______________________________________________

______________________________________________

______________________________________________

______________________________________________

Fig. 41B

CHILD EVALUATION SYSTEM AND METHOD OF USE

TECHNICAL FIELD

The present disclosure generally relates to systems and methods for diagnosing and treating developmental delay and/or disorders in children, and more particular to systems and methods for the early diagnosis and treatment of children in early childhood to promote at least one of fine motor skills, gross motor skills, sound articulation, and sound discrimination skills, receptive language, expressive language, phonological awareness, phonological processing to prevent reading failure, academic underachievement, color blindness, attentional issues, social emotional dysregulation.

BACKGROUND

Many children with developmental delay and/or other disorders are not recognized or diagnosed until the child is of school age. That is, many developmental delays and/or disorders are not diagnosed until after a child begins school, and usually multiple years after the child begins school. Indeed, in many cases, the child's parents may not be aware that their child may have a developmental delay and/or disorder and therefore do not take any action to identify and/or diagnose and/or seek early intervention to treat the child's delay and/or disorder before the child begins school. In other cases, the child's parents may not be aware of what can be done to diagnose and/or treat a suspected delay and/or disorder and therefore do not take any action to diagnose and/or treat the child's delay and/or disorder before the child begins school. There is a focus on reactive, deficit-driven, 'wait-to-fail' model instead of on the development of preventative approaches. In still other cases, the child's parents may not have the financial means to hire a specialist to diagnose and/or treat a suspected delay and/or disorder and therefore do not take any action to diagnose and/or treat the child's disorder before the child begins school. Every state has early intervention programs that act on a medical provider's prescription to investigate a diagnosis of developmental delay. The wait time for Early intervention to act on this prescription may take up to 3 to 6 months for a diagnosis and for early intervention to start another 3 to 12 months. If a child has Medicaid, most private early intervention sites that a pediatrician may also prescribe as they wait for Early intervention state programs to start is close to nonexistent. Those who have commercial insurance intervention may be provided by private early intervention sites but usually allowed only 1 to 2 months of therapy which is not adequate time to help a child with their delay depending on the severity. In addition, while most state-run early intervention programs focus on under 3 years, at 3 many children who have deficits do not qualify for services due to services are only covered by school board budgets and therefore receive little to no intervention until these deficits become quite large. As a result, a child's delay and/or disorder is often not recognized and/or addressed until after the child begins school and often not until 3$^{rd}$ to 4$^{th}$ grade. At that time, the child's teachers and/or other school staff may observe warning signs that the child has one or more delays and/or disorder and then recommend that a school specialist meet with the child to address the suspected disorder(s). By that time, for example, the child is several grade levels behind in reading and it is difficult to catch up and 75% do not catch up and read at grade level. Of those children, 54% do not attend College. Children who present with speech and language delay are at risk for future reading struggles (dyslexia). Early intervention before school begins is effective at eliminating that risk or lessening it. Those from families who claim English as a second language need early exposure to the English language in order to successfully participate in school in which learning in English is done. Children from an economically disadvantaged background would greatly benefit from exposure before school to the necessary skills needed to successfully perform in school. 67 percent of all fourth graders in the US are reading below grade level and approximately 80% of fourth graders from low socio-economic backgrounds are reading below grade level. Any treatment would therefore only assist the child in significantly reducing reading failure, dyslexia risk, limited exposure to the English language and also those children from disadvantaged back grounds. This program will help every child succeed in school. If only 10 to 20 percent of the population is dyslexic, it does not explain the high 67% of children in 4$^{th}$ grade read below grade level. Looking at the multifactorial reasons for reading and or academic difficulties will help all the children who might potentially struggle from the numerous reasons why.

Even in instances where a child is assessed and/or evaluated at an early stage, parents are not usually informed directly what specifically they need to work on the help their child succeed in school skills until a teacher conference which is given later in the school year and again in the spring when school is almost over. Before beginning school, the methods and/or tests used to evaluate children that are used today focus almost entirely on reading. Most schools presently teach reading by cueing based off contextual language and/or pictorial clues in order to guess what the words are. Guessing is a very inefficient technique and prone to errors. Good readers accurately decode words by manipulating the sounds in words to which over time creates fluent readers. As such, while such methods and/or tests may be somewhat effective in evaluating language, such methods and/or tests fail to evaluate speech, fine and gross motor skills and thus do not evaluate speech and language, fine and gross motor skills simultaneously, nor do they assess the social and emotional regulation required for success in an academic environment. This disclosure describes an improvement over these prior art technologies.

SUMMARY

In one embodiment, in accordance with the principles of the present disclosure, a method for providing evaluation of input data of an individual obtained through administering a worksheet is provided. The method comprises: (a) having the individual draw a line and shape to generate a fine motor skill input data; (b) evaluating the fine motor skill input data against an answer key to generate a fine motor skill evaluation result, wherein the fine motor skill evaluation result is a first determination with respect to the presence or absence of fine motor skill deficiency; Determine the pencil grip if fisted and if so, teach parent or notify teacher to have child work on correct 3 point pencil grip. (c) having the individual do a gross motor skill and receptive language task to generate a gross motor skill input data; (d) evaluating the gross motor skill input data against an answer key to generate a gross motor skill evaluation result, wherein the gross motor skill evaluation result is a first determination with respect to the presence or absence of gross motor skill deficiency; evaluate ability to follow directions to assess receptive language skills and emotional regulation (e) having the individual say a first letter in at least one word to generate a sound articulation input data; (f) evaluating the sound articulation input data against an answer key to generate a sound articulation evaluation result, wherein the sound articulation skill evaluation result is a first determination with respect to the presence or absence of sound articulation deficiency; (g) having the individual determine if one or more letters or words are the same or different to generate a sound discrimination input data; (h) evaluating the sound discrimination input data against an answer key to generate a sound determination evaluation result, wherein the sound determination skill evaluation result is a first determination with respect to the presence or absence of sound determination articulation deficiency; and (i) generating a referral referring the individual for services in areas where the evaluation results were deficient to promote at least one of fine motor skills, gross motor skills, sound articulation, sound discrimination skills receptive language skills, and social emotional development.

In one embodiment, in accordance with the principles of the present disclosure, a method for providing evaluation of input data of an individual obtained through administering a worksheet is provided. The method comprises: (a) having the individual perform a test relating to receptive language skills to generate a receptive language skill input data; (b) evaluating the receptive language skills input data against an answer key to generate a receptive language skills evaluation result, wherein the receptive language skills evaluation result is a first determination with respect to the presence or absence of receptive language deficiency; (c) having the individual perform a test relating to sound discrimination skills to generate a sound discrimination skill input data; (d) evaluating the sound discrimination skill input data against an answer key to generate a sound discrimination skill evaluation result, wherein the sound discrimination skill result is a first determination with respect to the presence or absence of sound discrimination deficiency; (e) having the individual perform a test relating to sound order awareness skills to generate a sound order awareness skill input data; (f) evaluating the sound order awareness skill input data against an answer key to generate a sound order awareness skill evaluation result, wherein the sound order awareness skill evaluation result is a first determination with respect to the presence or absence of sound order awareness deficiency; (g) having the individual perform a test relating to fine motor skills to generate a fine motor skill input data; (h) evaluating the fine motor skill input data against an answer key to generate a fine motor skill evaluation result, wherein the fine motor skill evaluation result is a first determination with respect to the presence or absence of fine motor deficiency; drawing a shape and determining pencil grip (i) having the individual perform a test relating to letter naming and letter sounds to generate a letter naming and letter sound input data; (j) evaluating the letter naming and letter sound input data against an answer key to generate a letter naming and letter sound evaluation result, wherein the letter naming and letter sound evaluation result is a first determination with respect to the presence or absence of letter naming and letter sound deficiency; (k) having the individual perform a test relating to sound deletion to generate a sound deletion input data; (I) evaluating the sound deletion input data against an answer key to generate a sound deletion evaluation result, wherein the sound deletion evaluation result is a first determination with respect to the presence or absence of sound deletion deficiency; and (m) generating a referral referring the individual for services in areas where the evaluation results were deficient to promote at least one of receptive language, sound discrimination, sound order, fine motor, letter naming and letter sound and sound deletion skills, and social and emotional development.

In one embodiment, in accordance with the principles of the present disclosure, a method for providing evaluation of input data of an individual obtained through administering a worksheet is provided. The method comprises: (a) having the individual perform a test relating to receptive language skills to generate a receptive language skill input data; (b) evaluating the receptive language skills input data against an answer key to generate a receptive language skills evaluation result, wherein the receptive language skills evaluation result is a first determination with respect to the presence or absence of receptive language deficiency; (c) having the individual perform a test relating to fine motor skills to generate a fine motor skill input data; (d) evaluating the fine motor pencil grip skill input data against an answer key to generate a fine motor skill evaluation result, wherein the fine motor skill result is a first determination with respect to the presence or absence of fine motor deficiency; (e) having the individual perform a test relating to letter naming and letter sound skills to generate a letter naming and letter sound skill input data; (f) evaluating the letter naming and letter sound skill input data against an answer key to generate a letter naming and letter sound skill evaluation result, wherein the letter naming and letter sound skill evaluation result is a first determination with respect to the presence or absence of letter naming and letter sound deficiency; (g) having the individual perform a test relating to sound deletion to generate a sound deletion input data; (h) evaluating the word deletion and sound deletion input data against an answer key to generate a word deletion and sound deletion evaluation result, wherein the word deletion and sound deletion evaluation result is a first determination with respect to the presence or absence of word deletion and sound deletion deficiency; (i) having the individual perform a test relating to rhyming to generate a rhyming input data; (j) evaluating the rhyming input data against an answer key to generate a rhyming evaluation result, wherein the rhyming evaluation result is a first determination with respect to the presence or absence of rhyming deficiency; and (k) generating a referral referring the individual for services in areas where the evaluation results were deficient to promote at least one of receptive language, fine motor, letter naming and letter sound, word deletion, sound deletion, rhyming skill, and social emotional development or regulation.

In one embodiment, in accordance with the principles of the present disclosure, a method for providing evaluation of input data of an individual obtained through administering a worksheet is provided. The method comprises: (a) having the individual show one or more shapes to generate a receptive language input and color discrimination data; (b) evaluating the receptive language input data against an answer key to generate a receptive language evaluation result and color discrimination, wherein the receptive language evaluation result is a first determination with respect to the presence or absence of receptive language deficiency or color discrimination deficit; (c) having the individual do a fine motor skill to generate a fine motor skill input data; (d) evaluating the fine motor skill input data against an answer key to generate a fine motor skill evaluation result, wherein the fine motor skill evaluation result is a first determination with respect to the presence or absence of fine motor skill deficiency; (e) having the individual say letters and/or sounds to generate a letter/sound input data; (f) evaluating the letter/sound input data against an answer key to generate a letter/sound evaluation result, wherein the letter/sound evaluation result is a first determination with respect to the presence or absence of letter/sound deficiency; (g) having the individual take away sounds and/or letters from a word or words to generate a phoneme input data; (h) evaluating the phoneme input data against an answer key to generate a phoneme evaluation result, wherein the phoneme evaluation result is a first determination with respect to the presence or absence of phoneme deficiency; (i) having the individual perform rhyming exercises to generate a rhyming input data; (j) evaluating the rhyming input data against an answer key to generate a rhyming evaluation result, wherein the rhyming evaluation result is a first determination with respect to the presence or absence of rhyming deficiency; (k) having the individual read nonsense words to generate a nonsense word input data; (I) evaluating the nonsense word input data against an answer key to generate a nonsense word evaluation result, wherein the nonsense word evaluation result is a first determination with respect to the presence or absence of nonsense word deficiency; and (m) generating a referral referring the individual for services in areas where the evaluation results were deficient to promote at least one of receptive language, fine motor, letter/sound, phoneme (phonological processing), rhyming, color discrimination and emotional regulation and engagement and nonsense word skills.

In one embodiment, in accordance with the principles of the present disclosure, a method for providing evaluation of input data of an individual obtained through administering a worksheet is provided. The method comprises: (a) having the individual demonstrate fine motor skills to generate a fine motor skill input data; (b) evaluating the fine motor skill input data against an answer key to generate a fine motor skill evaluation result, wherein the fine motor skill evaluation result is a first determination with respect to the presence or absence of fine motor skill deficiency; (c) having the individual take away a sound or sounds to generate a phoneme elision input data; (d) evaluating the phoneme elision input data against an answer key to generate a phoneme elision evaluation result, wherein the phoneme elision evaluation result is a first determination with respect to the presence or absence of phoneme elision deficiency; (e) having the individual read a single word to generate a single word reading input data; (f) evaluating the single word reading input data against an answer key to generate a single word reading evaluation result, wherein the single word reading evaluation result is a first determination with respect to the presence or absence of single word reading deficiency; (g) having the individual read nonsense words to generate a nonsense word input data; (h) evaluating the nonsense word input data against an answer key to generate a nonsense word evaluation result, wherein the nonsense word evaluation result is a first determination with respect to the presence or absence of nonsense word deficiency; and (i) generating a referral referring the individual for services in areas where the evaluation results were deficient to promote at least one of fine motor, phoneme elision, single word reading, color discrimination, engagement and emotional regulation and nonsense word skills

BRIEF DESCRIPTION OF THE DRAWINGS

The present disclosure will become more readily apparent from the specific description accompanied by the following drawings, in which:

FIG. 1 is one embodiment of a questionnaire used in connection with a first part of a method for evaluating the presence or absence of a delay and/or disorder and/or school readiness, social emotional, fine motor/gross motor in accordance with the principles of the present disclosure;

FIG. 3 is an example of one embodiment of a worksheet used in connection in the first part of the method, in accordance with the principles of the present disclosure;

FIG. 4 is an example of one embodiment of a worksheet used in connection in the first part of the method, in accordance with the principles of the present disclosure;

FIG. 5A is an example of one page of one embodiment of an assessment used in connection with the first part of the method, in accordance with the principles of the present disclosure;

FIG. 5B is an example of one embodiment of another page of the assessment shown in FIG. 5A;

FIG. 6A is an example of one page of one embodiment of an assessment used in connection with the first part of the method, in accordance with the principles of the present disclosure;

FIG. 6B is an example of one embodiment of another page of the assessment shown in FIG. 6A;

FIG. 7A is an example of one page from one embodiment of a milestone information sheet used in connection with the first part of the method, in accordance with the principles of the present disclosure;

FIG. 7B is an example of another page of the milestone information sheet shown in FIG. 7A, in accordance with the principles of the present disclosure;

FIG. 7C is an example of another page of the milestone information sheet shown in FIG. 7A, in accordance with the principles of the present disclosure;

FIG. 7D is an example of another page of the milestone information sheet shown in FIG. 7A, in accordance with the principles of the present disclosure;

FIG. 7E is an example of another page of the milestone information sheet shown in FIG. 7A, in accordance with the principles of the present disclosure;

FIG. 7F is an example of another page of the milestone information sheet shown in FIG. 7A, in accordance with the principles of the present disclosure;

FIG. 7G is an example of one embodiment of another page from the assessment shown in FIG. 7A, in accordance with the principles of the present disclosure;

FIG. 7H is an example of one embodiment of an assessment guided treatment flow chart, in accordance with the principles of the present disclosure;

FIG. 7I is an example of one embodiment of an assessment guided treatment flow chart, in accordance with the principles of the present disclosure;

FIG. 7J is an example of one embodiment of an assessment guided treatment flow chart, in accordance with the principles of the present disclosure;

FIG. 7K is an example of one embodiment of an assessment guided treatment flow chart, in accordance with the principles of the present disclosure;

FIG. 7L is an example of one embodiment of an assessment guided treatment flow chart, in accordance with the principles of the present disclosure;

FIG. 7M is an example of one embodiment of an assessment guided treatment flow chart, in accordance with the principles of the present disclosure;

FIG. 7N is an example of one embodiment of an assessment guided treatment flow chart, in accordance with the principles of the present disclosure;

FIG. 7O is an example of one embodiment of an assessment guided treatment flow chart, in accordance with the principles of the present disclosure;

FIG. 7P is an example of one embodiment of an assessment guided treatment flow chart, in accordance with the principles of the present disclosure;

FIG. 7Q is an example of one embodiment of an assessment guided treatment flow chart, in accordance with the principles of the present disclosure;

FIG. 8 is one embodiment of a questionnaire used in connection with a second part of the method, in accordance with the principles of the present disclosure;

FIG. 9A is an example of one embodiment of a form/document used in connection with the second part of the method, in accordance with the principles of the present disclosure;

FIG. 10A is an example of one embodiment of a form/document used in connection with the second part of the method, in accordance with the principles of the present disclosure;

FIG. 11A is an example of a page from one embodiment of a worksheet used in connection with the second part of the method, in accordance with the principles of the present disclosure;

FIG. 11B is one embodiment of another page from the worksheet shown in FIG. 11A, in accordance with the principles of the present disclosure;

FIG. 11C is one embodiment of another page from the worksheet shown in FIG. 11A, in accordance with the principles of the present disclosure;

FIG. 11D is one embodiment of another page from the worksheet shown in FIG. 11A, in accordance with the principles of the present disclosure;

FIG. 12A is an example of a page from one embodiment of a worksheet used in connection with the second part of the method, in accordance with the principles of the present disclosure;

FIG. 12B is one embodiment of another page from the worksheet shown in FIG. 12A, in accordance with the principles of the present disclosure;

FIG. 12C is one embodiment of another page from the worksheet shown in FIG. 12A, in accordance with the principles of the present disclosure;

FIG. 12D is one embodiment of another page from the worksheet shown in FIG. 12A, in accordance with the principles of the present disclosure;

FIG. 13A is an example of one embodiment of one page of an assessment used in connection with the second part of the method, in accordance with the principles of the present disclosure;

FIG. 13B is an example of one embodiment of another page from the assessment shown in FIG. 13A, in accordance with the principles of the present disclosure;

FIG. 13C is an example of one embodiment of another page from the assessment shown in FIG. 13A, in accordance with the principles of the present disclosure;

FIG. 13D is an example of one embodiment of another page from the assessment shown in FIG. 13A, in accordance with the principles of the present disclosure;

FIG. 13E is an example of one embodiment of another page from the assessment shown in FIG. 13A, in accordance with the principles of the present disclosure;

FIG. 13F is an example of one embodiment of another page from the assessment shown in FIG. 13A, in accordance with the principles of the present disclosure;

FIG. 13G is an example of one embodiment of another page from the assessment shown in FIG. 13A, in accordance with the principles of the present disclosure;

FIG. 13H is an example of one embodiment of another page from the assessment shown in FIG. 13A, in accordance with the principles of the present disclosure;

FIG. 13I is an example of one embodiment of another page from the assessment shown in FIG. 13A, in accordance with the principles of the present disclosure;

FIG. 13J is an example of one embodiment of another page from the assessment shown in FIG. 13A, in accordance with the principles of the present disclosure;

FIG. 13K is an example of one embodiment of another page from the assessment shown in FIG. 13A, in accordance with the principles of the present disclosure;

FIG. 13L is an example of one embodiment of another page from the assessment shown in FIG. 13A, in accordance with the principles of the present disclosure;

FIG. 13M is an example of one embodiment of another page from the assessment shown in FIG. 13A, in accordance with the principles of the present disclosure;

FIG. 13N is an example of one embodiment of another page from the assessment shown in FIG. 13A, in accordance with the principles of the present disclosure;

FIG. 13O is an example of one embodiment of another page from the assessment shown in FIG. 13A, in accordance with the principles of the present disclosure;

FIG. 13P is an example of one embodiment of another page from the assessment shown in FIG. 13A, in accordance with the principles of the present disclosure;

FIG. 14A is one embodiment of an example of one page from a milestone information sheet used in connection with the second part of the method, in accordance with the principles of the present disclosure;

FIG. 14B is an example one embodiment of another page from the milestone information sheet shown in FIG. 14A, in accordance with the principles of the present disclosure;

FIG. 14C is an example one embodiment of another page from the milestone information sheet shown in FIG. 14A, in accordance with the principles of the present disclosure;

FIG. 14D is an example one embodiment of another page from the milestone information sheet shown in FIG. 14A, in accordance with the principles of the present disclosure;

FIG. 14E is an example one embodiment of another page from the milestone information sheet shown in FIG. 14A, in accordance with the principles of the present disclosure;

FIG. 14F is an example one embodiment of another page from the milestone information sheet shown in FIG. 14A, in accordance with the principles of the present disclosure;

FIG. 14G is an example one embodiment of another page from the milestone information sheet shown in FIG. 14A, in accordance with the principles of the present disclosure;

FIG. 15A is one embodiment of a questionnaire used in connection with a third part of the method, in accordance with the principles of the present disclosure;

FIG. 15B is an example of one embodiment of a form/document used in connection with the third part of the method, in accordance with the principles of the present disclosure;

FIG. 15C is an example of one embodiment of a form/document used in connection with the third part of the method, in accordance with the principles of the present disclosure;

FIG. 16A is an example of one embodiment of a form/document used in connection with the third part of the method, in accordance with the principles of the present disclosure;

FIG. 16B is an example of one embodiment of a form/document used in connection with the third part of the method, in accordance with the principles of the present disclosure;

FIG. 17A is an example of one embodiment of one page of an assessment used in connection with the third part of the method, in accordance with the principles of the present disclosure;

FIG. 17B is an example of one embodiment of another page from the assessment shown in FIG. 17A, in accordance with the principles of the present disclosure;

FIG. 17C is an example of one embodiment of another page from the assessment shown in FIG. 17A, in accordance with the principles of the present disclosure;

FIG. 17F is an example of one embodiment of another page from the assessment shown in FIG. 17A, in accordance with the principles of the present disclosure;

FIG. 18A is an example of one embodiment of one page of an assessment used in connection with the third part of the method, in accordance with the principles of the present disclosure;

FIG. 18B is an example of one embodiment of another page from the assessment shown in FIG. 18A, in accordance with the principles of the present disclosure;

FIG. 18C is an example of one embodiment of one page of an assessment used in connection with the third part of the method, in accordance with the principles of the present disclosure;

FIG. 18F is an example of one embodiment of one page of an assessment used in connection with the third part of the method, in accordance with the principles of the present disclosure;

FIG. 19A is an example of one embodiment of one page of an assessment used in connection with the third part of the method, in accordance with the principles of the present disclosure;

FIG. 19B is an example of one embodiment of another page from the assessment shown in FIG. 19A, in accordance with the principles of the present disclosure;

FIG. 19C is an example of one embodiment of another page from the assessment shown in FIG. 19A, in accordance with the principles of the present disclosure;

FIG. 19D is an example of one embodiment of another page from the assessment shown in FIG. 19A, in accordance with the principles of the present disclosure;

FIG. 19E is an example of one embodiment of another page from the assessment shown in FIG. 19A, in accordance with the principles of the present disclosure;

FIG. 19F is an example of one embodiment of another page from the assessment shown in FIG. 19A, in accordance with the principles of the present disclosure;

FIG. 19G is an example of one embodiment of another page from the assessment shown in FIG. 19A, in accordance with the principles of the present disclosure;

FIG. 19H is an example of one embodiment of another page from the assessment shown in FIG. 19A, in accordance with the principles of the present disclosure;

FIG. 19I is an example of one embodiment of another page from the assessment shown in FIG. 19A, in accordance with the principles of the present disclosure;

FIG. 19J is an example of one embodiment of another page from the assessment shown in FIG. 19A, in accordance with the principles of the present disclosure;

FIG. 19K is an example of one embodiment of another page from the assessment shown in FIG. 19A, in accordance with the principles of the present disclosure;

FIG. 19L is an example of one embodiment of another page from the assessment shown in FIG. 19A, in accordance with the principles of the present disclosure;

FIG. 19M is an example of one embodiment of another page from the assessment shown in FIG. 19A, in accordance with the principles of the present disclosure;

FIG. 19N is an example of one embodiment of another page from the assessment shown in FIG. 19A, in accordance with the principles of the present disclosure;

FIG. 20A is one embodiment of an example of one page from a milestone information sheet used in connection with the third part of the method, in accordance with the principles of the present disclosure;

FIG. 20B is an example one embodiment of another page from the milestone information sheet shown in FIG. 20A, in accordance with the principles of the present disclosure;

FIG. 20C is an example one embodiment of another page from the milestone information sheet shown in FIG. 20A, in accordance with the principles of the present disclosure;

FIG. 20D is an example one embodiment of another page from the milestone information sheet shown in FIG. 20A, in accordance with the principles of the present disclosure;

FIG. 20E is an example one embodiment of another page from the milestone information sheet shown in FIG. 20A, in accordance with the principles of the present disclosure;

FIG. 20F is an example one embodiment of another page from the milestone information sheet shown in FIG. 20A, in accordance with the principles of the present disclosure;

FIG. 20G is an example one embodiment of another page from the milestone information sheet shown in FIG. 20A, in accordance with the principles of the present disclosure;

FIG. 21 is one embodiment of a questionnaire used in connection with a fourth part of the method, in accordance with the principles of the present disclosure;

FIG. 22A is an example of one embodiment of one page of a worksheet used in connection with the fourth part of the method, in accordance with the principles of the present disclosure;

FIG. 22B is one embodiment of another page of the worksheet shown in FIG. 22A, in accordance with the principles of the present disclosure;

FIG. 22C is one embodiment of another page of the worksheet shown in FIG. 22A, in accordance with the principles of the present disclosure;

FIG. 22D is one embodiment of another page of the worksheet shown in FIG. 22A, in accordance with the principles of the present disclosure;

FIG. 23H is one embodiment of another page of the worksheet shown in FIG. 23A, in accordance with the principles of the present disclosure;

FIG. 23I is one embodiment of another page of the worksheet shown in FIG. 23A, in accordance with the principles of the present disclosure;

FIG. 24A is an example of one embodiment of one page of an assessment used in connection with the fourth part of the method, in accordance with the principles of the present disclosure;

FIG. 24B is one embodiment of another page of the assessment shown in FIG. 24A, in accordance with the principles of the present disclosure;

FIG. 24C is one embodiment of another page of the assessment shown in FIG. 24A, in accordance with the principles of the present disclosure;

FIG. 24D is one embodiment of another page of the assessment shown in FIG. 24A, in accordance with the principles of the present disclosure;

FIG. 24E is one embodiment of another page of the assessment shown in FIG. 24A, in accordance with the principles of the present disclosure;

FIG. 24F is one embodiment of another page of the assessment shown in FIG. 24A, in accordance with the principles of the present disclosure;

FIG. 24G is one embodiment of another page of the assessment shown in FIG. 24A, in accordance with the principles of the present disclosure;

FIG. 24H is one embodiment of another page of the assessment shown in FIG. 24A, in accordance with the principles of the present disclosure;

FIG. 24I is one embodiment of another page of the assessment shown in FIG. 24A, in accordance with the principles of the present disclosure;

FIG. 24J is one embodiment of another page of the assessment shown in FIG. 24A, in accordance with the principles of the present disclosure;

Figure 2:
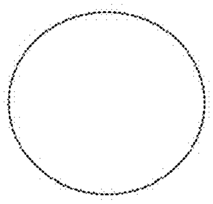
FIG. 2 is an example of one embodiment of a form/document used in connection with the first part of the method, in accordance with the principles of the present disclosure.
Figure 32E:
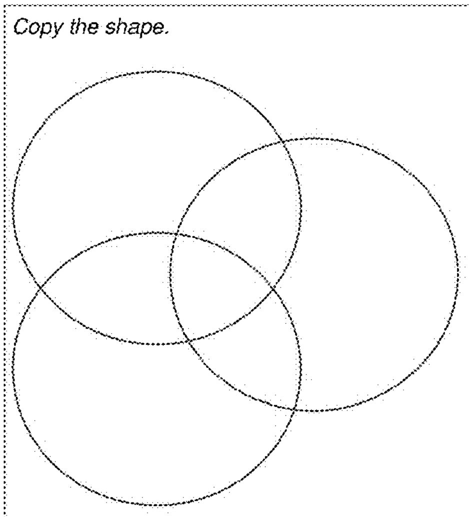
Figure 33F:
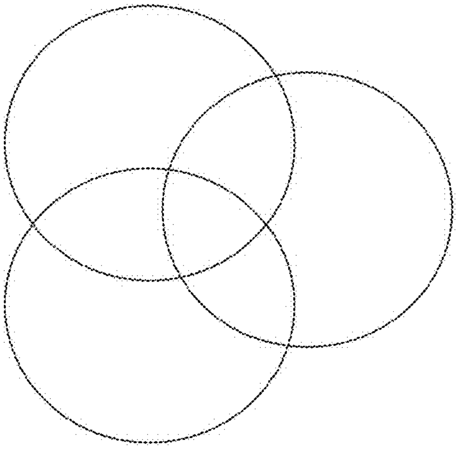

FIG. 24K is one embodiment of another page of the assessment shown in FIG. 24A, in accordance with the principles of the present disclosure;

FIG. 24L is one embodiment of another page of the assessment shown in FIG. 24A, in accordance with the principles of the present disclosure;

FIG. 24M is one embodiment of another page of the assessment shown in FIG. 24A, in accordance with the principles of the present disclosure;

FIG. 24N is one embodiment of another page of the assessment shown in FIG. 24A, in accordance with the principles of the present disclosure;

FIG. 24O is one embodiment of another page of the assessment shown in FIG. 24A, in accordance with the principles of the present disclosure;

FIG. 25A is one embodiment of an example of one page from a milestone information sheet used in connection with the fourth part of the method, in accordance with the principles of the present disclosure;

FIG. 25B is an example one embodiment of another page from the milestone information sheet shown in FIG. 25A, in accordance with the principles of the present disclosure;

FIG. 25C is an example one embodiment of another page from the milestone information sheet shown in FIG. 25A, in accordance with the principles of the present disclosure;

FIG. 25D is an example one embodiment of another page from the milestone information sheet shown in FIG. 25A, in accordance with the principles of the present disclosure;

FIG. 25E is an example one embodiment of another page from the milestone information sheet shown in FIG. 25A, in accordance with the principles of the present disclosure;

FIG. 25F is an example one embodiment of another page from the milestone information sheet shown in FIG. 25A, in accordance with the principles of the present disclosure;

FIG. 25G is an example one embodiment of another page from the milestone information sheet shown in FIG. 25A, in accordance with the principles of the present disclosure;

FIG. 26 is one embodiment of a questionnaire used in connection with a fifth part of the method, in accordance with the principles of the present disclosure;

FIG. 27A is an example of one embodiment of one page of a worksheet used in connection with the fifth part of the method, in accordance with the principles of the present disclosure;

FIG. 27B is one embodiment of another page of the worksheet shown in FIG. 27A, in accordance with the principles of the present disclosure;

FIG. 27C is one embodiment of another page of the worksheet shown in FIG. 27A, in accordance with the principles of the present disclosure;

FIG. 27D is one embodiment of another page of the worksheet shown in FIG. 27A, in accordance with the principles of the present disclosure;

FIG. 27E is one embodiment of another page of the worksheet shown in FIG. 27A, in accordance with the principles of the present disclosure;

FIG. 28A is an example of one embodiment of one page of a worksheet used in connection with the fifth part of the method, in accordance with the principles of the present disclosure;

FIG. 28B is one embodiment of another page of the worksheet shown in FIG. 28A, in accordance with the principles of the present disclosure;

FIG. 28C is one embodiment of another page of the worksheet shown in FIG. 28A, in accordance with the principles of the present disclosure;

FIG. 28D is one embodiment of another page of the worksheet shown in FIG. 28A, in accordance with the principles of the present disclosure;

FIG. 28E is one embodiment of another page of the worksheet shown in FIG. 28A, in accordance with the principles of the present disclosure;

FIG. 29A is one embodiment of one page of an assessment used in connection with the fifth part of the method, in accordance with the principles of the present disclosure;

FIG. 29B is one embodiment of another page of the assessment shown in FIG. 29A, in accordance with the principles of the present disclosure;

FIG. 29C is one embodiment of another page of the assessment shown in FIG. 29A, in accordance with the principles of the present disclosure;

FIG. 29D is one embodiment of another page of the assessment shown in FIG. 29A, in accordance with the principles of the present disclosure;

FIG. 29E is one embodiment of another page of the assessment shown in FIG. 29A, in accordance with the principles of the present disclosure;

FIG. 29F is one embodiment of another page of the assessment shown in FIG. 29A, in accordance with the principles of the present disclosure;

FIG. 29G is one embodiment of another page of the assessment shown in FIG. 29A, in accordance with the principles of the present disclosure;

FIG. 29H is one embodiment of another page of the assessment shown in FIG. 29A, in accordance with the principles of the present disclosure;

FIG. 29I is one embodiment of another page of the assessment shown in FIG. 29A, in accordance with the principles of the present disclosure;

FIG. 29J is one embodiment of another page of the assessment shown in FIG. 29A, in accordance with the principles of the present disclosure;

FIG. 29K is one embodiment of another page of the assessment shown in FIG. 29A, in accordance with the principles of the present disclosure;

FIG. 29L is one embodiment of another page of the assessment shown in FIG. 29A, in accordance with the principles of the present disclosure;

FIG. 29M is one embodiment of another page of the assessment shown in FIG. 29A, in accordance with the principles of the present disclosure;

FIG. 30A is one embodiment of an example of one page from a milestone information sheet used in connection with the fifth part of the method, in accordance with the principles of the present disclosure;

FIG. 30B is an example one embodiment of another page from the milestone information sheet shown in FIG. 30A, in accordance with the principles of the present disclosure;

FIG. 30C is an example one embodiment of another page from the milestone information sheet shown in FIG. 30A, in accordance with the principles of the present disclosure;

FIG. 30D is an example one embodiment of another page from the milestone information sheet shown in FIG. 30A, in accordance with the principles of the present disclosure;

FIG. 30E is an example one embodiment of another page from the milestone information sheet shown in FIG. 30A, in accordance with the principles of the present disclosure;

FIG. 30F is an example one embodiment of another page from the milestone information sheet shown in FIG. 30A, in accordance with the principles of the present disclosure;

FIG. 30G is an example one embodiment of another page from the milestone information sheet shown in FIG. 30A, in accordance with the principles of the present disclosure;

FIG. 31 is one embodiment of a questionnaire used in connection with a sixth part of the method, in accordance with the principles of the present disclosure;

FIG. 32A is an example of one embodiment of one page of a worksheet used in connection with the sixth part of the method, in accordance with the principles of the present disclosure;

FIG. 32B is one embodiment of another page of the worksheet shown in FIG. 32A, in accordance with the principles of the present disclosure;

FIG. 32C is one embodiment of another page of the worksheet shown in FIG. 32A, in accordance with the principles of the present disclosure;

FIG. 32D is one embodiment of another page of the worksheet shown in FIG. 32A, in accordance with the principles of the present disclosure;

FIG. 32E is one embodiment of another page of the worksheet shown in FIG. 32A, in accordance with the principles of the present disclosure;

FIG. 32F is one embodiment of another page of the worksheet shown in FIG. 32A, in accordance with the principles of the present disclosure;

FIG. 33A is an example of one embodiment of one page of a worksheet used in connection with the sixth part of the method, in accordance with the principles of the present disclosure;

FIG. 33B is one embodiment of another page of the worksheet shown in FIG. 33A, in accordance with the principles of the present disclosure;

FIG. 33C is one embodiment of another page of the worksheet shown in FIG. 33A, in accordance with the principles of the present disclosure;

FIG. 33D is one embodiment of another page of the worksheet shown in FIG. 33A, in accordance with the principles of the present disclosure;

FIG. 33E is one embodiment of another page of the worksheet shown in FIG. 33A, in accordance with the principles of the present disclosure;

FIG. 33F is one embodiment of another page of the worksheet shown in FIG. 33A, in accordance with the principles of the present disclosure;

FIG. 34A is one embodiment of one page of an assessment used in connection with the sixth part of the method, in accordance with the principles of the present disclosure;

FIG. 34B is one embodiment of another page of the assessment shown in FIG. 34A, in accordance with the principles of the present disclosure;

FIG. 34C is one embodiment of another page of the assessment shown in FIG. 34A, in accordance with the principles of the present disclosure;

FIG. 34D is one embodiment of another page of the assessment shown in FIG. 34A, in accordance with the principles of the present disclosure;

FIG. 34E is one embodiment of another page of the assessment shown in FIG. 34A, in accordance with the principles of the present disclosure;

FIG. 34F is one embodiment of another page of the assessment shown in FIG. 34A, in accordance with the principles of the present disclosure;

FIG. 34G is one embodiment of another page of the assessment shown in FIG. 34A, in accordance with the principles of the present disclosure;

FIG. 34H is one embodiment of another page of the assessment shown in FIG. 34A, in accordance with the principles of the present disclosure;

FIG. 34I is one embodiment of another page of the assessment shown in FIG. 34A, in accordance with the principles of the present disclosure;

FIG. 34J is one embodiment of another page of the assessment shown in FIG. 34A, in accordance with the principles of the present disclosure;

FIG. 34K is one embodiment of another page of the assessment shown in FIG. 34A, in accordance with the principles of the present disclosure;

FIG. 34L is one embodiment of another page of the assessment shown in FIG. 34A, in accordance with the principles of the present disclosure;

FIG. 34M is one embodiment of another page of the assessment shown in FIG. 34A, in accordance with the principles of the present disclosure;

FIG. 35A is one embodiment of an example of one page from a milestone information sheet used in connection with the sixth part of the method, in accordance with the principles of the present disclosure;

FIG. 35B is an example one embodiment of another page from the milestone information sheet shown in FIG. 35A, in accordance with the principles of the present disclosure;

FIG. 35C is an example one embodiment of another page from the milestone information sheet shown in FIG. 35A, in accordance with the principles of the present disclosure;

FIG. 35D is an example one embodiment of another page from the milestone information sheet shown in FIG. 35A, in accordance with the principles of the present disclosure;

FIG. 35E is an example one embodiment of another page from the milestone information sheet shown in FIG. 35A, in accordance with the principles of the present disclosure;

FIG. 35F is an example one embodiment of another page from the milestone information sheet shown in FIG. 35A, in accordance with the principles of the present disclosure;

FIG. 36A is one page of an assessment report used and/or generated in connection with the first part of the method, in accordance with the principles of the present disclosure;

FIG. 36B is another page of the assessment report shown in FIG. 36A, in accordance with the principles of the present disclosure;

FIG. 37A is one page of an assessment report used and/or generated in connection with the second part of the method, in accordance with the principles of the present disclosure;

FIG. 37B is another page of the assessment report shown in FIG. 37A, in accordance with the principles of the present disclosure;

FIG. 37C is another page of the assessment report shown in FIG. 37A, in accordance with the principles of the present disclosure;

FIG. 38A is one page of an assessment report used and/or generated in connection with the third part of the method, in accordance with the principles of the present disclosure;

FIG. 38B is another page of the assessment report shown in FIG. 38A, in accordance with the principles of the present disclosure;

FIG. 38C is another page of the assessment report shown in FIG. 38A, in accordance with the principles of the present disclosure;

FIG. 39A is one page of an assessment report used and/or generated in connection with the fourth part of the method, in accordance with the principles of the present disclosure;

FIG. 39B is another page of the assessment report shown in FIG. 39A, in accordance with the principles of the present disclosure;

FIG. 39C is another page of the assessment report shown in FIG. 39A, in accordance with the principles of the present disclosure;

FIG. 40A is one page of an assessment report used and/or generated in connection with the fifth part of the method, in accordance with the principles of the present disclosure;

FIG. 40B is another page of the assessment report shown in FIG. 40A, in accordance with the principles of the present disclosure;

FIG. 41A is one page of an assessment report used and/or generated in connection with the sixth part of the method, in accordance with the principles of the present disclosure;

FIG. 41B is another page of the assessment report shown in FIG. 41A, in accordance with the principles of the present disclosure; and Like reference numerals indicate similar parts throughout the figures.

DETAILED DESCRIPTION

The present disclosure may be understood more readily by reference to the following detailed description of the disclosure taken in connection with the accompanying drawing figures, which form a part of this disclosure. It is to be understood that this disclosure is not limited to the specific systems, methods, conditions or parameters described and/or shown herein, and that the terminology used herein is for the purpose of describing particular embodiments by way of example only and is not intended to be limiting of the claimed disclosure.

Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" or "top" and "bottom" are relative and used only in the context to the other and are not necessarily "superior" and "inferior."

Educational (literacy, academic achievement and ability to write with correct pencil grip), neurotypical social emotional learning, sports participation success for all children may be achieved through assessing early childhood development with usage of the system and method of the present disclosure. In particular, the system and method of the present disclosure deliver collaborative actionable skills, personalized, customizable and specific, for each child encompassing and not limited to speech and language, fine and gross motor skills, and social emotional learning.

In some embodiments, the system and method of the present disclosure provide an automated interactive scalable AI based assessment of selected duration (e.g., 15 minutes), scored by AI that can be configured to select personalized, customizable strategies for speech, language, fine and gross motor skills, color blindness, neurotypical social emotional learning. The system and method of the present disclosure can thus be utilized to foster a strong start for reading, social emotional interaction learning, and confidence in sports participation and other extracurricular activities. In some embodiments, the method of the present disclosure can begin when a child is three years old (or younger) and could be made available to pediatricians/medical providers, daycares, preschools, early intervention centers, elementary schools and children homeschooled, caregivers, and parents who want to work with their children in addition to going to school. While it is envisioned that the system and method of the present disclosure may be utilized with all children, that the system and method of the present disclosure may be especially beneficial for children with speech, language difficulties and phonological awareness/processing deficits (dyslexia), English as a second language children; disadvantaged and lack of opportunity; and fine and gross motor skill impairments and those with neurotypical social emotional impairments.

The system and method of the present disclosure are comprehensive by incorporating the critical components of early reading, writing, attention, processing (visual, sensory, auditorily), social emotional learning and motor skills integration simultaneously to identify students at risk. The system and method of the present disclosure are adapted to assure that every child has an appropriate neurodevelopmental course at each age. If they do not, the system and method of the present disclosure can be utilized to prescribe therapeutic treatment to help each child to improve on speech language, fine/gross motor color blindness and vision determination, neurotypical social emotional learning and behavioral regulation.

The system and method of the present disclosure may be utilized to assess children before or while they exhibit problems with speech and language, fine and gross motor, neurotypical social emotional learning in preschool/elementary schools or daycare settings, in pediatrician/provider offices, homeschoolers and for parents who believe their children exhibit developmental delay and are on long waiting list to get intervention or denied services. The system and method of the present disclosure may be utilized in provider offices to identify children during their yearly well child physical exams and when parents and teachers request a closer look at a child's developmental milestones to pick up if they have speech/language, fine/gross motor, neurotypical social emotional and any attention components that may cause a child to be delayed in the school setting including processing visual processing or activity deficits, color blindness, absence seizure, Anxiety, autism risk or emotional dysregulation.

In many instances, a child is not diagnosed and/or treated concerning their neurodevelopmental functional skills or cognitive function attributes until the child is in school or is about to begin school. This typically occurs when the child is approximately between 5 to six years old. A brief screen is done only delivering how their child compares to other children in the school. However, some speech/language disorders, such as, for example, the rise of reading struggles when discovered in early childhood will reduce the risk of future. Delaying treatment often makes the deficiencies or gaps so large that they are often insurmountable. Early intervention by school entry at age 6 prevents or greatly lessens the severity of struggles compared to waiting until a child is 8 years or older. It is therefore beneficial to diagnose and treat the child's language process deficits or phonological awareness deficits as early as possible to provide an opportunity for the child's language processing deficits to be treated and/or remediated by the time the child begins school. When "at risk" beginning readers receive intensive instruction, 56% to 92% of at-risk children across six studies reached the range of average reading ability. Sadly, children are typically not identified or diagnosed with a reading disability until the child is either in 3rd or 4th grade and by that time the child is several grade levels behind in reading and is difficult to catch up to grade level. It is financially very expensive for the parent to hire extra help after school to help the child catch up to grade level and it does cost the school district large amounts of tax dollars as well to help the child read at grade level. This also greatly applies to children from disadvantaged families and those who live in families where English is a second language. Seventy five percent of students who do not read proficiently by third grade never reach reading proficiency in future grades. There is a decrease of likelihood that struggling readers in third grade will attend college compared to their more proficient peers.

The system and method of the present disclosure is groundbreaking in that the system and method of the present disclosure integrate a medical approach together with an educational approach. The system and method of the present disclosure are preventive in that the system and method of the present disclosure prevent struggles or failures from happening instead of addressing them before they occur. When it comes to learning difficulties, we are largely focused on a reactive, deficit-driven, 'wait to fail' model instead of on the development of preventative approaches. The system and method of the present disclosure thus provide an early intervention approach. The system and method of the present disclosure are neurodevelopmental and transformative in the way that system and method of the present disclosure look at addressing early foundational milestone skills first. The system and method of the present disclosure are broad based and multifactorial in that the system and method of the present disclosure look at more than just reading. The system and method of the present disclosure are comprehensive by incorporating critical components of early reading, writing, attention, processing (visual, sensory, auditory), motor skills, and social emotional skills simultaneously to identify students at risk. The system and method of the present disclosure provide assessments and solutions that are based upon neurological (brain) science and the tenets of neuroplasticity (how the brain changes and learns). Best results are seen when the child is given intervention as early as possible. The system and method of the present disclosure is configured to incorporate the Medical-Home model allowing insurance coverage for treatment to be part of the solution. The system and method of the present disclosure are research-based with scientifically proven effectiveness in accordance with the guidelines and recommendations of the American Academy of Pediatrics as both inventors are active members. The system and method of the present disclosure are adapted for a child-centered, collaborative team approach that incorporates an array of adults (parents, teachers, pediatrician, counselors, and occupational, physical and speech therapists) working towards a common goal. The system and method of the present disclosure offer comprehensive solutions that provide customized personalized actionable enrichment plans. The system and method of the present disclosure are innovative in that the system and method of the present disclosure reshape the way school readiness is achieved by looking at multiple skills simultaneously instead of just looking at skills that are for reading. The system and method of the present disclosure are transformative in that early detection and intervention changes lives forever, reduce mental health disparities, build strong self-esteem and reduced absenteeism which is presently an increasingly large problem in the United States post covid pandemic. The system and method of the present disclosure provide universal neurodevelopmental assessments that offer equitable solutions that overcome many barriers like reading failure if risk of dyslexia is not picked up early, lack of access, lack of resources, English 2nd language learners, geographic barriers and high cost of psychoeducational evaluations once failure has occurred. The system and method of the present disclosure are life-changing in that the system and method of the present disclosure provide children, educators, and families the tools and confidence needed to ensure children succeed scholastically, are healthy socially, emotionally and have competence and confidence in their ability to participate in sports, extra activity and thrive in academic life, employment, college and other avenues. The system and method of the present disclosure are adapted to build self-esteem in that a child who is successful in school is not as vulnerable to feelings of shame, failure, inadequacy, anxiety, depression, suicidal ideation, stronger reliance on social services, not completing their education and risk of incarceration in the future. Indeed, 93 million adults in the nation today read at or below basic levels, even though most living-wage jobs require proficient readers.

The system and method of the present disclosure layer foundational life and educational school readiness skills as a basis for scholastic success. The system and method of the present disclosure are adapted to focus on strengthening each foundational skills independently, simultaneously and as early as possible so that all layers can work well together to achieve a stronger and more successful end result. How each and every layer gets connected or integrated together determines how easily, effortlessly, and effectively a specific task can be performed. During early childhood, children develop skills from birth on and when a child is expected to develop which skill has long been studied and documented. Pediatricians study the various milestones specific for each age and during their examination at each well child examination, check for these skills and communicate to the caretakers of the child whether the child's milestones are up to date and if not, what action needs to take to help the child reach the correct milestone. When a child is not asked to demonstrate a skill, and we just rely on parental questionnaires, it is not always effective. A parent may not disclose their child's developmental delay due to fear of labelling culture beliefs, or lack of educational knowledge.

If a child is recommended to get therapy specific for speech, gross motor, fine motor, and/or behavior, then the provider will write a prescription for the specific therapy and send the patient to a state-run early intervention center to confirm the developmental needs of the child and if they agree if the child needs the therapy. If so, then if prescribed by the Pediatrician, the Early Intervention center sets up the therapy necessary for the child to undergo either at the child's home or at a day care facility or school. At the present time, the wait period from after the prescription is received by the Pediatrician to the State-run early intervention center is about 3 to 6 months and the time period to receive intervention is up to 6 to 12 months. A wait time this long in early childhood does not consider the neuroplasticity potential—the ability to build a greater number of connected neurocircuits (almost like building roads or more efficient highway system). Neuroplasticity means "brain change" or "brain learning." The tenets of neuroplasticity are based upon five core principles: 1. Intensity 2. Frequency 3. Specificity (explicit instruction and methodology) 4. Duration 5. Neurodevelopmental hierarchy (i.e., training basic skills before advanced skills). Late identification of a developmental delay in early childhood and receiving intervention late results in the child not being able to catch up in the appropriate timetable compared to peers. Long waits allow fears to continue to increase.

When a child is discovered to have two developmental milestones affected, they require two separate therapists and therefore may not be given simultaneously, and the child will not have a coordinated effort to remediate their developmental delays. With a Pediatrician created interactive Neurodevelopmental assessment, that starts at age 3 years old and younger, the areas of speech/language (receptive, expressive, phonological awareness, fine motor, gross motor, behavioral, challenges, attention, engagement and emotional regulation engagement, and the ability to follow directions can be done based on normative data for each age group based on what has been studied for a neurotypical 3 year old, coexisting condition that mimic attentional disorder like staring spells seizures must be ruled out. The 3-year-old is asked to complete the interactive neurodevelopmental assessment using AI to guide the student and score the assessment. The assessment starts with asking the child to draw a straight line and to copy a circle. We observe the pencil grip and ability to do the two tasks. Although it may be developmental normal for a child to have a fisted pencil grip at this age, we expect that by age 4 years old that they have a three-point (tripod) pencil grip. This gives an opportunity to communicate to the parent or teacher of this child that although this finding is normal, this is your opportunity to work with your child towards a three-point pencil grip expected by age 4 years old. If the child is unable to draw a straight line and circle, we will then present enrichment modules using AI work on the skill of drawing a straight line and circle and other exercise similar to this. The child will then be given different assessments in 2 to 3 months depending on the AI evaluation, (however despite AI assessment we will evaluate no later than 3 months) of the enrichment exercise the child is doing to see if the child is proficient. If in three months the issue persists, then the child will be given more modules to work on this skill and an in-person Occupational therapist prescription will be given to the child to work together with our modules. The child is again evaluated in 3 months' time and further action depending on the score will be taken to help the child with this skill. The next part of the evaluation will be to check for gross motor ability and skill planning along with receptive language. The child is asked to follow directions where they are asked to use the large muscles of their body to demonstrate that they can move appropriately and follow directions by touching their finger to their nose for example. If the child is not able to follow through with these skills, the AI will determine if this is due to child not proficient in the English language. This is asked before the assessment is given and the parent will have the ability to have this part of the assessment given in their primary language to be sure they are able to complete this skill) or if it is due to a receptive language delay or gross motor delay. Also, we will determine if the child is following directions correctly but not fluent in using their hand to point to their nose.

A child not performing well in this skill will need enrichment modules in gross motor tasks and also in following receptive language exercise where they are asked to follow simple commands. In 2 to 3 months' time this will be reevaluated using a similar assessment to be sure this skill has been mastered. The next skill would be to tackle sound articulation. This skill exposes the child to phonological awareness-"Learning how to manipulate the sounds." The child is asked to say the sound of a word, either the first sound, last or middle sound of each word. This skill is fundamental for starting to decode or read as a child must be able to manipulate, play with, hold onto, and retrieve sounds to read or spell well. The child is given several enrichment modules via AI to strengthen this skill and in 2 to 3 months' time will be given another assessment. The next step of this assessment is to assess sound discrimination. The child again is exposed to phonological awareness and is learning to play with sounds. They are asked to listen to three letter sounds said in a row and to determine if all these sounds are the same or different. This is another foundational skill for learning how to decode and later to read which is sound discrimination. The last part of the assessment is to evaluate the child's ability to engage in the assessment and how attentive they are and are they able to communicate back to the AI agent. Depending on the child's demeanor during the assessment, a child may need further evaluation for autism. Children with poor eye contact, lack of joint attention, lack of wanting to engage and sensory deregulation will need modules on simultaneous speech and Occupational therapies while simultaneously participating in our enrichment modules. Physician referral for a prescription for the child to receive urgent in-person speech and Occupational therapy. If the child is able to communicate effectively, able to engage in the assessment but has a staring spell during the assessment for several seconds, then a neurology referral for an EEG will be prescribed to rule out Absence staring spell seizures. If the child is crying and anxious during the assessment, the child will receive enrichment modules to gradually introduce these 3-year-old milestone skills slowly and in 2 to 3 months' time be able to be reevaluated with an assessment again. A questionnaire is given to the parent of the child before the assessment is given that will ask specific questions that will ask the parent about their knowledge of what skills they believe their child knows. It also gives valuable information as to how to help the parent engage in more experience-based learning opportunities. Each parent is given a detailed milestone information packet that will help them understand what a child at each age needs to be able to do and ideas on what they can do to help their child reach their milestones. Whether they answer some of the asks correctly or incorrectly, they are given enrichment modules to improve each day so that they the skills necessary for a 4-year-old child when the next assessment is given.

This novel approach considers all the developmental skills a child should have at a certain age and works on them simultaneously use artificial intelligence to make this scalable and the child is allowed to have this interactive assessment scored immediately and enrichment modules are delivered immediately. What is novel about this approach is it takes into consideration and asks the parent if the child has had a recent hearing and vision test, and through our platform we will be able to deliver a vision test including for color blindness in the older ages and hearing assessment if necessary. We also consider their engagement at the same time and therefore we will not allow a child with suspicion of autism, absence seizure, anxiety and possible attention disorders (ADHD/ADD) to have a delay in diagnosis. We will deliver the necessary enrichment modules to help the child improve and at the same time arrange for a prescription to be given for further evaluation and treatment as necessary. We are providing the necessary foundational developmental skills information needed at age 3 years old and younger building up for the necessary skills needed at age 4 years old and older, etc. We understand that about 67% thirds of our nation's 4th graders are reading below grade level and approximately 80% of fourth graders are from low socioeconomic backgrounds are reading below grade level about 75% of graduating High School students are not proficient in writing. If only 10 to 20 percent of the population are estimated to be dyslexic, then why do an additional 50% or more children struggle to read? The developmental assessments answer these and other reasons why. Each module is interactive and will go at the child's own pace depending on the ability, mood and demeanor of the child that day. The modules are personalized, customized and specific for each child based on the assessment and AI will act as the child's personal tutor. These interactive modules are given every day for short periods of time based on the child's age. The 4-year-old neurodevelopmental assessment starts with a receptive language skill and during this skill we are not only able to see the child's ability to follow directions and be proficient in receptive language skills, but we are also able to see if child knows their shapes and colors. If the child is unable to correctly identify colors and shapes, enrichment modules will be given to teach these skills. If the child is only having trouble with the colors red and green, color blindness tests will be done. Again, the appropriate modules are recommended after the interactive assessment is score for the 4-year-old. The next skill is for sound discrimination as explained above in the 3-year-old assessment, and next sound order awareness where the questions are harder than what a 3-year-old Is expected to know. The next skill is fine motor determination with tasks consistent with what a 4-year-old should perform. Each age level assessment is therefore adjusted for age expected performance. Also, fine motor skills assessment to determine if the child has correct 3-point pencil grip. Added also is the assessment of the ability to identify letters of the alphabet and their sounds. This skill is very important in learning the fundamentals of reading. The next skill is phoneme elision (deletion). This test has a very high positive predictive value for identifying who will later go on to struggle with reading as it is a very sensitive indicator of phonological awareness processing difficulties. Therefore, many critical language skills are addressed together and developed in a coordinated and specific fashion.

Neurodevelopmental skills are built layer upon layer starting with the most basic skills before advanced ones. From infancy, a baby starts to develop these skills in a certain progression and marked by critical milestones for which can be evaluated. For example, with gross motor milestones, an infant first learns to roll over, sit up, and crawl, way before walking and running. To understand sensory regulation based upon a neurodevelopmental model requires an understanding of how an individual regulates themselves within a sensory environment. While touch, smell, taste, sight, sound are senses, so are vestibular (how one responds with respect to their head with gravity), proprioceptive (body position, pressure and force of movements), and interoceptive (understanding the inner working of how a person feels from when they are upset to knowing when they need to go to the restroom). All neurodevelopmental skills integrate together as a child grows, matures, and learns. Learning happens through practice. Learning is the response of the brain to make new connections (new brain wiring in response to explicit learning activities or experiences). This is also called experience-based learning or neuroplasticity. Therefore, every experience from infancy and through childhood is an opportunity for growth. Neurodevelopmental milestones are grouped under different categories such as physical development (gross motor and fine motor), social-emotional and behavioral, cognitive and language.

While every child is different, experts have a clear idea about the range of normal development related to age. When deficits occur, early identification and treatment of deficits is imperative for the development of higher-level skills.

When a child is evaluated using the system and method of the present disclosure, skills of the child are evaluated to determine if the child has any skills that can be performed efficiently, or with "automaticity," meaning you can do it without thinking about how you do it. For example, when learning to "ride a bike" or "drive a car," it was not easy at first. You had to think about every step and how to integrate all those steps together to safely get from destination "A" to destination "B." But now, after a significant amount of practice and repetition, it becomes "neurologic memory." Your brain just knows how to do it without really thinking about it. Learning any new skill basically happens that same way. If a strong foundational platform exists, then all one needs will be the right practice opportunities to learn that skill until automaticity happens. The individual's strengths and weaknesses of their foundational skills will determine the end functional result but practice once those foundational skills are present is critical to end performance. This means that what was once hard and effortful now is quick, easy, and effortless. With that ease will mean that the activity is probably more enjoyable, less anxiety provoking because one does not have to work so hard to do it and one feels more competent in their ability to do it.

The system and method of the present disclosure are designed to help children enjoy and excel in school academically, socially & emotionally and interactively, but not only just with school (the workplace of a child), but also with sports, other extracurricular activities, and subsequently later with the future life skills. The system and method of the present disclosure was designed utilizing Pediatric neurodevelopmental science to provide the tools to not only successfully navigate children throughout their scholastic journey, but also their nonacademic performance like with the physical skills necessary for gym, sports, and other extracurricular activities. This improves their social and emotional well-being, meaning the ability to form relationships with peers, family, and adults. The system and method of the present disclosure are adapted to make learning fun by opening up the world for discovery and giving children strong self-esteem and confidence. Indeed, playing and exploration are some of the greatest ways to learn. Knowing what skills are critically important skills to a child's success are and then incorporating them into everyday play activities for a younger child changes the manner in which children are prepared for school readiness. Giving the parent the information on what skills their children need to improve allows them to be actively involved. Each parent wants the best for their child, and most do not know what their children are expected to know when they enter school. This information is not generally discussed at Pediatrician office well visits and the Pediatrician is usually asked to help the parent when the parent is told by the teacher that the child is falling behind in school. By that time, the child is several grade levels behind in reading and/or fine motor ability. It is important to have this evaluation given by all pediatricians during their well visits. When it is administered by AI, scored by AI and intervention plans are suggested by AI in accordance with the guidelines of the American Academy of Pediatrics, then Pediatricians are able to be the true medical home for each child and will be able to work in conjunction with teachers to give our children the best chance to succeed. When children enter kindergarten, they are given a basic screening test that does not include any testing of motor skills (fine or gross) and the score given to the parent is a percentage of how well their child is doing compared to other children in their classroom, school, county and state. They are not told what they need to work on with their children at home to improve their skills or how to work with them. Parents are only told their child's skills are progressive and instructed ho to help. Only during parent conferences, which happen late in the school year and in the spring when school is almost over, does a discussion happen with the parents.

The system and method of the present disclosure are adapted to make children with weaker skills stronger and to make children with average skills stronger too. This means that if you create the right learning opportunities, every child will have stronger foundations from which to try, achieve, and excel in any endeavor they desire. The system and method of the present disclosure thus can act as a launching pad for learning successes from which each child can become healthy, happy, confident adults with careers they love and are successful at. Having the skills necessary for success in school and beyond reduces mental health disparities and removes the child from being punished for behavioral issues. Children often act out because they do not believe that they belong in school since they do not understand what is going on and others around them. Most children are expelled from the classroom for bad behavior starting at age 4 years old and getting the child to be better at their emotional regulations skills before age 4 years old will help reduce that fact. A lot of children would rather be in trouble than risk public embarrassment of not performing well in school. Also, there is a big problem with children not going to school and the large absentee rate is largely due to children not being able to engage most likely from not having the necessary skills necessary to perform in school and in the playgrounds/recess time. In some embodiments, the system and method of the present disclosure is in accordance with and follows the American Academy of Pediatric guidelines for identification of normal child development at each age and intervention strategies recommended.

The system and method of the present disclosure were designed to recognize that a medical approach is needed in assessing child development. Indeed, children in the elementary school years are in school to "learn to read." If they do not master this skill by the end of the $2^{nd}$ grade, failure is imminent because they are now in school to "read to learn." What starts as a reading gap, becomes an unsurmountable vocabulary and knowledge gap. Academic learning is now very difficult, and gaps can often become so large that they are unable to be closed. 75% of students who do not read proficiently by third grade never reach reading proficiency in future grades. Also, there is a 54% decrease in likelihood that struggling readers in third grade will attend college compared to their more proficient peers. In the United States 93 million adults in the nation today read at or below basic level, even though most living-wage jobs require proficient readers. Approximately ⅓ of all adults cannot read drug labels and low literacy costs the US 230 billion/year in health care costs. The US Department of labor estimates that illiteracy costs American businesses about $225 billion a year in lost productivity. Accordingly, the system and method of the present disclosure provide a medical approach by providing an early identification and early intervention problem solving approach. It means that if you identify a problem or issue early, that provides early intervention and change, then prevention is in the majority of cases possible. For example, you do not have to watch a train derail off a track if there is a way to redirect that train to a different path where a successful and safe arrival is achievable. The system and method of the present disclosure thus prevent a parent from watching the child they love struggle more and more each year as the grade level complexity increases. It is possible to change this trajectory, but it starts with understanding and trusting in "brain science" and knowing that the best outcomes are when you start early. Ideally, this would begin at birth, as it starts with talking to a child, allowing the baby to watch your lips form sounds and the baby soon learns that these sounds have meaning and reading to them. But much more can be done. Indeed, more fun, enjoyable, and bonding activities can be helpful and allowing parents to have this information in front of them in an interactive manner as AI can provide would help parents be able to do more for their children. This is especially also very helpful for day care personnel who are not all trained and not all knowledge in developmental milestones of children. The same goes for preschool teachers and elementary school teachers. 31% of teacher preparation programs devote no course work to reading science. Only 46 percent of undergraduate elementary education programs teach phonemic awareness and usually only a short time is devoted to this subject. The national Reading Panel identified five pillars of reading and only 39% of teacher undergraduate elementary education programs provide instruction in all five components of reading. The five components of reading identified by the national reading panel are 1. Phonemic Awareness is the ability to hear and perceive, identify and manipulate individual sounds (phonemes) in spoken words. 2. Phonics is the relationship between letters and sounds, and how to use this knowledge to decode words. 3. Fluency is the ability to read accurately, quickly and with expression 4. Vocabulary is the knowledge of words and their meaning. 5. Comprehension is the ability to understand and make meaning from what is read. The system and method of the present disclosure can guide children toward activities they need to make them successful with the skill of reading.

The system and method of the present disclosure were designed to recognize that while many of the causes of why a child can go on to struggle scholastically are preventable, some are not. Indeed, while some causes have treatments, others do not. No matter the disorder or condition, early diagnoses and effective intervention generate the best outcomes as earlier diagnosis will allow access to supportive therapies, helpful accommodations, and medical and scholastic supports to be in place.

The system and method of the present disclosure were designed to recognize that children may struggle scholastically, socially and emotionally and in extracurricular activities such as with sports and other activities for many reasons. One reason children may struggle scholastically is lack of opportunity, such as, example, English second language learners, foster care and adoption populations, and socioeconomic conditions affecting access and exposure to learning opportunities. Another reason children may struggle scholastically is attentional issues resulting in lack of adequate engagement/reception of learning instructions and opportunities. For instance, with severe ADHD, even though a child was in the classroom, if they did not adequately receive (attend and focus) on the intervention being given, you must consider that instruction as not to have happened and thus as lack of opportunity. Also, if a child has absence seizures (starring spells) for the moments when they have their seizures, they are unable to attend and listen and therefore will not learn. Thus, they miss bits and pieces of instruction. Children with this disorder may be misdiagnosed with ADHD/ADD. Another reason children may struggle scholastically is language disorders, which are both receptive (input) and expressive (output) or both. These children may not have the ability to understand language in general or have difficulties specifically with phonological awareness. For example, if a language disorder exists, vocabulary and receptive language must be built before reading and listening comprehension at higher levels can take place. Another reason children may struggle scholastically is specific learning disorders, which are sometimes referred to as specific learning disabilities. For example, neuro-developmental disorders that are characterized by a persistent impairment in at least one area, including, for example, impairment in reading (dyslexia), impairment in written expression with or without associated dysgraphia, and impairment in mathematics (dyscalculia). In cases with specific learning disorders or disabilities, they are unexpected and not caused because of a lack of intelligence. Another reason children may struggle scholastically are medical conditions that can impact learning in some way, such as, for example, seizure disorders, some genetic conditions, ADHD, prematurity, cerebral palsy, in utero drug or alcohol exposure, etc. Other reasons children may struggle scholastically is intellectual, such as, for example, cognitive disabilities whether genetic, environmental, or idiopathic. For example, cognitive neuro-developmental disorders are noticed early on with broad developmental delay characterized by intellectual difficulties as well as difficulties in adaptive skills like conceptual, social, and practical areas of living. They are characterized by low IQ scores and low adaptive behavioral functioning across multiple environments (school, home, and community).

The system and method of the present disclosure were designed to recognize that early intervention is important. Indeed, children are in our elementary schools to "learn to read." After the $2^{nd}$ grade, they are in school to "read to learn." If reading is not mastered by the $3^{rd}$ grade, academic gaps grow very quickly. It is important to treat as early as possible because you do not want a reading gap to become an academic gap that is difficult to close. Most children are unable to close that gap. Intervention at any stage is helpful, but the earlier the better. Therefore, it is important to look for and treat all the variables at play early in order to achieve the most successful outcomes. For some, they might just need adequate exposure (reteaching) while attentional focus is present. For others, who are dyslexic with weakness in phonological awareness, they will need explicit instruction to improve phonological awareness skills. For those who are unable to memorize sight words, they might need occupational therapy to help with the visual processing skills required for efficient sight word acquisition. As such, picking the right intervention specifically required by each child, in the most cost-effective and time-saving manner, to accomplish gap closure is very important for each and every child. Indeed, though learning to read may seem effortless, even natural, for some, reading and spelling are complex mental skills involving several different parts of the brain. A weakness in any one of these parts will cause the entire system to slow down and become laborious and frustrating. In order to be effective for all students, reading instruction must address all of the sensory-cognitive skills involved in reading and be informed by the relationship between them as revealed through scientific research.

The system and method of the present disclosure were designed to recognize that reading, writing and spelling are higher level language skills. Indeed, the ability to play and manipulate sounds. Learning to read the sounds is the building block required for language development at its most basic level, which will then affect all higher-level skills like reading. A foundational skill that children need to have before being able to sound words out is to be able to separate spoken words into their individual sounds. Indeed, many struggling readers have extremely poor foundational skills in this area with this being the "crack in the foundation" that makes easy and accurate reading and spelling difficult later on. For some struggling readers, these poor phonological processing skills (processing sounds in words) can prevent future reading success, even when these children are exposed to common place reading instruction as well as phonics programs or even multi-sensory Orton-Gillingham dyslexia methods. If one knows and applies the neurodevelopmental building blocks to assessment and treatment, then age-appropriate tests and interventions can be done to prevent reading and scholastic failure before it occurs. Every test utilized has to be standardized for performance compared to age specific norms. For example, what a kindergartener is expected to do is different than what you would expect an older student to do. The building blocks for foundational language, sensory, emotional regulation, and fine and gross motor skills are critically important and should and can be assessed easily given the right knowledge and tools. Thus, there is nothing random about the tests used which are testing very specific skills based on age expected norms.

In order to understand the complexity of language and why difficulties occur with reading and/or spelling, it is helpful to start at the most basic foundational level and to understand the terms used. The smallest meaningful unit of language is called a phoneme. In English there are 44 different phonemes that are represented by the 26 letters of the alphabet individually or in combination. Phonics instruction involves teaching the relationship between sounds and the letters used to represent them. With respect to spelling, there are hundreds of spelling alternatives that can be used to represent the 44 English phonemes.—Phonological processing (processing sounds in words) is the ability to be aware of, manipulate, and play with different sounds in words. This is the single most important skill that separates a good reader from a poor reader and can be tested for as early as 4 years old. Phonological processing is a combination of visual processing, sound processing, and oral motor movement processing.

While many reading interventions focus on general exposure to literature, phonics memory rules, or the memory of sight words, this is different from building stronger phonological processing. The natural development of phonological awareness skills happens over time and is not the result of rote memorization. Some children need to work many months on this skill depending on the severity of their phonological deficits. If a child has been exposed to previous common school interventions like Whole Language, Balanced Literacy, or even Orton-Gillingham methodology-based interventions and the reading gap has not closed, then the child still has difficulties with phonological processing. These cracks or difficulties in phonological awareness and processing should be tested for and effectively treated. Ideally, this would occur before a child starts school.

Having a child "try harder or just read more" is not an effective solution. Accurate reading is important for reading fluency (quickness and accuracy) and overall comprehension. Filling in unknown words based on contextual skills or guessing are not good alternatives. For many decades, teachers taught reading in elementary school by having children look at pictures or use contextual language to decipher unknown words instead of using their phonological awareness skills to accurately sound out (decode) a word. This method is starting to change, and teachers are beginning to learn how to use awareness and phonics to help children read accurately. This is important because accuracy fuels comprehension as it is a much better methodology than guessing. Developing the skills to accurately decode words is the best solution and should be the goal of any reading instruction and intervention. Early pre-literacy assessments that take a deep look into the separate skills of phonological processing can be very helpful in assessing the root cause of what would become future difficulties. Effective assessments aid to prevent reading failure from ever happening. The system and method of the present disclosure align as a way to focus on finding any weakness early so that reading failure or intervention for that failure does not have to occur.

The system and method of the present disclosure include language assessment portions and later enrichment activities that focus on various factors. One factor that the language assessment portions, and later enrichment activities focus on is strengthening auditory discrimination and phonological awareness. Another factor that the language assessment portions, and later enrichment activities focus on is based upon a neurodevelopmental language model (i.e., understanding how the brain learns simple language foundational skills before more advanced skills). Several brain functions are involved in reading. The visual cortex recognizes printed letters and words, the auditory cortex builds oral world understanding, angular gyrus associates letters with sounds and the frontal lobe produces speech and process meaning. Our methods include language fluency, phonological awareness, orthography, phoneme-grapheme correspondence and fluency in our enrichment modules to develop foundational skills associated with each brain function. There are physiological explanations for why it is critical for children to learn by the third grade. Growth in volume of white matter—(the neural pathways in a child's brain)—between kindergarten and third grade is one of the best predictors of how well a child learns how to read. Therefore, the quality of reading instruction is important and impacts a child's brain white matter development which is the neuropathways that connect areas of the brain. 56% of the variance in reading outcomes can be attributed to the change in volume of white matter during this important critical time in a child's reading trajectory. It is also important to be aware that areas in the brain that control language are remarkably close in proximity and somewhat overlap areas that control sensory and motor movements of the face, tongue, lips and fingers. This is why children with reading struggles like dyslexia often have problems with fine motor control and dysgraphia (difficulty with writing skills) and speech articulation issues due to oral kinesthetic movement difficulties with face and sensation and motor movements of the mouth, tongue and lips. In adult left hemispheric stroke patients (any patients with neurological insult to Broca and Wernicke's areas of the brain) present with expressive and receptive aphasia. Recovery is more successful if they receive therapy in speech/language, fine motor, and gross motor simultaneously. Therefore, in children with reading difficulties, allowing for therapy in speech/language and fine/gross motor simultaneously will allow a more rapid and full recovery which is especially true with children who present with Autism.

Another factor that the language assessment portions, and later enrichment activities focus on is practice in a neuro-rehabilitative model which incorporates the principles of neuroplasticity which means the ability of the brain to make new connections (new brain wiring in response to clear and direct learning activities or experiences). This is also called experience-based learning. Therefore, any program that is based on these specific principles will mean that the intervention is frequent, specific, intensive, based upon neurodevelopmental hierarchy (training basic skills before advanced ones), and occurs for the needed duration so that the child's skills are fully developed, mastered, and able to be performed independently without having to think about how to do it.

With the above considerations in mind, the system and method of the present disclosure include assessing a child as early as possible (using a medical approach) to assess his or her speech and language, fine and gross motor skills to provide a comprehensive analysis that considers various factors, including, for example, whether a skill can be performed with automaticity, whether there are outside reasons why a child may struggle scholastically, whether the child possesses appropriate foundational skills, etc. This allows the system to assess auditory discrimination and phonological awareness skills, neurodevelopmental language skills, experience-based learning skills, etc. In that regard, the system and method of the present disclosure includes administering a plurality of tests to a child relating to speech and language, fine and gross motor skills to assess the child's development and/or school readiness. How the child performs on the tests will determine whether or not the child should seek outside therapy (speech or occupational therapy), which can be recommended using the system and method of the present disclosure. How the child performs on the tests may also be used to assess/evaluate the child for ADHD, autism, anxiety, panic attacks, post-traumatic stress disorder (PTSD), sensor regulation issues depression, absence seizures, low self-esteem, etc.

The following discussion includes a description of a system and method for evaluating and/or assessing developmental disorders and/or school readiness, in accordance with the principles of the present disclosure. Alternate embodiments are also disclosed. Reference will now be made in detail to the exemplary embodiments of the present disclosure, which are illustrated in the accompanying figures. Turning to the FIGS., there are illustrated forms/documents that are used in connection with a system and method for evaluating and/or assessing developmental disorders and/or school readiness.

The system and method of the present disclosure includes a system and method for early evaluation of a child by implementing tests that determine whether the child has adequate speech and language, fine and gross motor skills, or not. That is, the system and method of the present disclosure evaluates a child for the presence or absence of a disorder or condition and/or for school readiness using tests that test the child's language skills, as well as other skills, such as for example, speech, fine and gross motor skills. As discussed in greater detail below, the system of the method of the present disclosure includes several portions or parts that are conducted over several years. For example, the system and method of the present disclosure may begin assessing a child by giving the child a first series of tests in a first part of the method when the child is 3 years old and then may continue periodically (e.g., annually) such that the child is given a second series of tests in a second part of the method when the child is 4 years old, is given a third series of tests in a third part of the test when the child is 5 years old, is given a fourth series of tests in a fourth part of the test when the child is 6 years old, is given a fifth series of tests in a fifth part of the test when the child is 7/8 or years old and is given a sixth series of tests in a sixth part of the test when the child is 9 years old or older. It is believed that early and continued implementation of the system and method of the present disclosure is important for assessing a disorder and treating the disorder effectively. Indeed, if the disorder is not assessed early enough, effective treatment and/or reversal of the disorder may not be possible.

Method

In one embodiment, the method evaluates and/or assesses the presence or absence of a disorder and/or school, sports and emotional social readiness by providing evaluation of input data of an individual, such as, for example, a child. The input data is obtained through administering a worksheet, for example. That is, data concerning the child that is obtained by administering a variety of tests that evaluate speech and language, fine and gross motor skills is recorded on a worksheet, which is evaluated to assess the presence or absence of a disorder and/or school readiness. The evaluation of the worksheet can also be used to determine proper treatment for the child, such as, for example, the need for occupational therapy. The evaluation of the worksheet can further be used to assess/evaluate the child for ADHD, autism, anxiety, panic attacks, post-traumatic stress disorder (PTSD), depression, absence seizures, low self-esteem, etc.

Method—Part One—Year Three

In a first part of the method, which should be administered as early as possible, such as, for example, when the child is approximately 3 years old or younger, the child's parent's is required to fill out a questionnaire that includes various questions about the child. One embodiment of the questionnaire is shown in FIG. 1. As shown in FIG. 1, the questionnaire can include questions about the child's physical abilities, such as, for example, the child's hearing and vision. The questionnaire can also include questions relating to the child's ability to read, write, comprehend information, perform simple tasks, socialize, etc. In some embodiments, the child is required to undergo a Vision Snell chart test and/or a colorblind test (e.g., The Ishihara, EnChroma, or any other standardized color-blind assessment or screen) prior to beginning the first part of the method.

In the first part of the method, tests concerning speech and language, fine and gross motor skills are evaluated the presence or absence of a disorder and/or school readiness ability whether it be in the social, emotional, physical activity (i.e. sports) domain. In particular, in the first part of the method, a first test is administered in which the child has to draw a line or shape, as shown in FIG. 2. The line may be a straight line or a non-straight line, such as, for example, a squiggly line. The shape can be a shape, such as, for example, a circle, square, triangle, etc. The ability of the child to draw the line or shape asked is recorded to generate a fine motor skill input data. The ability of the child to draw the line or shape may be recorded in the worksheet. One embodiment of the worksheet is shown in FIG. 3. Another embodiment of the worksheet is shown in FIG. 4. The fine motor skill input data may include whether or not the child was able to draw the line or shape, how well the child was able to draw the line or shape, etc. In place of or in addition to testing the ability of the child to draw the line or shape, the first test may include a pencil grip test in which the child is required to grip a pencil and the ability to grip the pencil or not and/or the ability to grip the pencil correctly is recorded to generate the fine motor skill input data. For example, if the child uses a fisted grip to grip the pencil, an incorrect pencil grip may be recorded. The ability of the child to grip the pencil may be recorded in the worksheet, as shown in FIG. 4. The fine motor skill input data is evaluated against an answer key to generate a fine motor skill evaluation result. The fine motor skill evaluation result is a first determination with respect to the presence or absence of fine motor skill deficiency. In some embodiments, the fine motor skill evaluation result includes a score, such as, for example, a number score. In some embodiments, the fine motor skill evaluation result includes a written evaluation, such as, for example, words written in sentence or note form that explain what was observed by the practitioner during the first test. In some embodiments, the fine motor skill evaluation result is included in an assessment that evaluates at least each of the tests administered during the first part of the method. One embodiment of the assessment is shown in FIGS. 5A and 5B. Another embodiment of the assessment is shown in FIGS. 6A and 6B. In some embodiments, the first part of the method may be administered when the child is less than 3 years old, such as, for example, when the child is 1 year old, 18 months old, 2 years old, 30 months old, etc. In some embodiments, the child is required to draw both the line and shape in during the first test.

In the first part of the method, a second test is administered in which the child has to do a gross motor skill and receptive language task to generate a gross motor skill input data. The ability of the child to do a gross motor skill and receptive language task may be recorded in the worksheet (FIG. 3 or FIG. 4). In some embodiments, the gross motor skill and receptive language task may include having the child smile, such as, for example, smiling really big. In some embodiments, the gross motor skill and receptive language task may include having the child touch a first finger to his or her nose. In some embodiments, the gross motor skill and receptive language task may include having the child touch a second finger to his or her nose after touching the first finger to his or her nose. In some embodiments, the gross motor skill and receptive language task may include having the child touch a first finger to a second finger. In some embodiments, the gross motor skill and receptive language task may include having the child place both of his or her hands on top of his or her head. The gross motor skill input data is evaluated against an answer key to generate a gross motor skill evaluation result. The gross motor skill evaluation result is a first determination with respect to the presence or absence of gross motor skill deficiency. In some embodiments, the gross motor skill evaluation result is included in the assessment (FIGS. 5A and 5B, or FIGS. 6A and 6B). In some embodiments, the gross motor skill evaluation result uses AI or other software to recognize and/or transcribe the child's letter sound/word pronunciation, analyze context/structure where pronunciation varies due to accents/dialects and word/sentence structure comprehension and fluency.

In the first part of the method, a third test is administered in which the child has to say a first letter in at least one word to generate a sound articulation input data. In particular, the third test evaluates the child's ability to correctly pronounce some English sounds in words that are located at the beginning, middle, or end of a word because the ability to play and manipulate sounds in a word is a foundational building block needed to later read well. The ability of the child to say a first letter in at least one word may be recorded in the worksheet (FIG. 3 or FIG. 4). In some embodiments, having the child say a first letter in at least one word can include the childing saying a first letter in each of a plurality of words to generate the sound articulation input data. The words may include all short words, such as for example, three letter words and/or may include a combination of short words and longer words, such as, for example, three letter words and four-letter words. Alternatively, or in addition to having the child say a first letter in at least one word, the sound articulation input data may be generated by having the child say the sound of a letter or a combination of letters. For example, the sound articulation input data may be generated by having the child say the sound of the letter "M", the letter "T," the letter "H" and/or the letters "EE." The sound articulation input data is evaluated against an answer key to generate a sound articulation evaluation result. The sound articulation skill evaluation result is a first determination with respect to the presence or absence of sound articulation deficiency. In some embodiments, the sound articulation skill evaluation result is included in the assessment (FIGS. 5A and 5B, or FIGS. 6A and 6B).

In the first part of the method, a fourth test is administered in which the child has to determine if one or more letters or words are the same or different to generate a sound discrimination input data. Sound discrimination is the ability to simply tell if sounds are similar or different. Understanding differences in sounds is part of the phonological (sound) awareness which is a skill that must be mastered well to later learn how to accurately decode (sound out) words. Phonological awareness is more than just knowing if sounds are different; it is actually a complicated brain skill of the combined ability of discriminating, manipulating, and changing sounds in words. How you process and understand sounds is what actually makes language meaningful. Phonological processing (the process of understanding sounds in words) is part manipulation and awareness but also the ability to hold on to and retrieve sounds in words. Phonological awareness is the single most important skill that separates good readers from poor readers. Phonological awareness is a combination of visual processing (seeing), auditory processing (hearing), and knowledge of oral mouth movements (feeling). In the fourth test, the child may be required to determine if the sound of the same letter repeated three times sound the same, to determine if the sound of two different letters wherein one of the letters is repeated twice sound the same and/or if the sound of three different letters sound the same. The ability of the child to determine if one or more letters or words are the same or different may be recorded in the worksheet (FIG. 3 or FIG. 4). The sound discrimination input data is evaluated against an answer key to generate a sound determination evaluation result. The sound determination skill evaluation result is a first determination with respect to the presence or absence of sound determination articulation deficiency. In some embodiments, the sound determination skill evaluation result is included in the assessment (FIGS. 5A and 5B, or FIGS. 6A and 6B).

In the first part of the method, a referral is generated referring the individual for services in areas where the evaluation results were deficient to promote at least one of fine motor skills, gross motor skills, sound articulation, and sound discrimination skills. In some embodiments, the assessment (FIGS. 5A and 5B, or FIGS. 6A and 6B), which can include the fine motor skill evaluation result, the gross motor skill evaluation result, the sound articulation evaluation result and/or the sound discrimination evaluation result is evaluated to generate the referral. In particular, if the fine motor skill evaluation result indicates that the child has proficient fine motor skills, the child is not referred for services, such as, for example, occupational therapy to promote advancement in fine motor skills. If, however, the fine motor skill evaluation result indicates that the child is deficient with his or her fine motor skills, the child is referred for services, such as, for example, occupational therapy to promote advancement in fine motor skills. In such cases, the recommended occupational therapy can include focusing on visual motor integration, oral motor kinesthetics, and proprioceptive skills.

Likewise, if the gross motor skill and receptive language evaluation result indicates that the child has proficient gross motor skill and receptive language, the child is not referred for services, such as, for example, occupational therapy to promote advancement in gross motor skill and speech therapy to promote advances in receptive language. If, however, the gross motor skill and receptive language result indicates that the child is deficient with his or her gross motor skill and receptive language, the child is referred for services, such as, for example, occupational therapy to promote advancement in gross motor skill and receptive language. In such cases, the recommended occupational therapy can include tasks to improve following directions, upper extremity movement and coordination, and proprioceptive work. Speech therapy is to strengthen receptive/expressive language skills, etc. In some embodiments, the recommended speech therapy can focus on motor integration, oral motor kinesthetics, and proprioceptive skills. In some embodiments, the recommended occupational therapy can focus on building strong receptive/expressive language skills.

If the sound articulation skill evaluation result indicates that the child has proficient sound articulation skills, the child is not referred for services, such as, for example, Speech therapy to promote advancement in sound articulation skills. If, however, the sound articulation skill evaluation result indicates that the child is deficient with his or her sound articulation skills, the child is referred for services, such as, for example, Speech therapy to promote advancement in sound articulation skills. In such cases, the recommended Speech therapy can include focusing on sound articulation and improving phonological awareness and phonological processing to build the foundational skills needed for reading.

If the sound discrimination skill evaluation result indicates that the child has proficient sound discrimination skills, the child is not referred for services, such as, for example, Speech therapy to promote advancement in sound discrimination skills. If, however, the sound discrimination evaluation result indicates that the child is deficient with his or her sound discrimination skills, the child is referred for services, such as, for example, Speech therapy to promote advancement in sound discrimination skills. In such cases, the recommended Speech therapy can include focusing on phonological processing skills. In some embodiments, the therapy recommendations can include occupational therapy for apraxia in additions to speech and language therapy focusing on improving phonological awareness and phonological processing/sound discrimination/receptive/expressive language.

In some embodiments, the first part of the method includes evaluating the child for ADHD, autism, anxiety, panic attacks, post-traumatic stress disorder (PTSD), depression, absence seizures, low self-esteem, etc. if the evaluation results were deficient to promote at least one of fine motor skills, gross motor skills, sound articulation, and sound discrimination skills. Concerning ADHD if the child is unable to keep their attention and/or unable to follow directions while completing the tests without being distracted and/or is unable to sit still long enough to complete the tests, the evaluation should include an ADHD evaluation. For example, at age 3 the child should be able to sit and attend for 6-8 minutes, at age 4 the child should be able to sit and attend for 8-12 minutes, at ages 5-6 the child should be able to sit and attend for 12-18 minutes, at ages 7-8 the child should be able to sit and attend for 16-24 minutes and at ages 9-10 the child should be able to sit and attend for 20-30 minutes.

The post ADHD evaluation's recommendations can include giving focused tips on a structured environment, making learning activities fun, multisensory activities, and short but repetitive opportunities for learning. If engagement is appropriate, but focus/attention to a task cannot be maintained for the age expected time for the child's age, then the method may refer the child to take a standardized ADHD measure such as the Vanderbilt or others) that includes ADHD/ADD age specific questions and consider all factors that can affect attention and sustained focus. Indeed, children with ADHD/ADD have a hard time paying attention, daydreaming, and often do not seem to listen. They are easily distracted from work and play and often do lack attention to details, are disorganized and do not follow through on directions. They are prone to losing a lot of important things/forgetting things and avoid doing things that require sustained mental effort. Having the hyperactivity component makes them prone not being able to stay seated, squirming a lot, talking too much, unable to play quietly and will jump, run and climb when not permitted to do so. They will demonstrate impulsivity, calling out with answers before the question being complete, acts or speaks without thinking, Interrupting others often, trouble taking turns, cannot wait for things and may run onto street without looking out for traffic. In some embodiments, if the child exhibits signs of ADHD/ADD, the method can be adapted to administer and score a Vanderbilt screen for parent and teacher (if applicable). These screens are diagnostic of ADHD/ADD.

Specific to visual attention and focus, the method can be adapted to derive objective and quantitative results, for example gaze direction, dwell time, and glance frequency off the assessment site to other objects and locations. While monitoring eye tracking, the system will measure where and for how long an individual looks in a certain direction or at a certain target, it is not a measure of actual visual attention. However, this information can be used to necessitate further exploration into attention or focus disorders like ADHD/ADD. The system and method can be further adapted to track and reflex to assess student attention while taking the test. Just as eye tracking is the go-to method when determining driver distraction via glance target classification, it can also be used to assess attention in the test itself. When problems with visual tracked perception processing are found then make in dept analysis optometry is warranted. When the above condition concerns are found, the system and method may be adapted to generate program modules and/or worksheets for evaluation and guidance for ADHD/ADD. It is envisioned that the system and method may also be adapted to generate further informational sheets on factors that can impact attention. These informational sheets can be given to the child's caregivers. Modules for scholastic accommodations such IEP, 504 and not limited to will also be given that can effectively be used within a child's Individual Educational Plan (IEP) or 504 Plan. When formal diagnosis of ADHD has been given, then information regarding evaluation for behavioral modification will be given through the system via the method. The system and method may also be adapted to indicate medication for ADHD/ADD when formal diagnosis of ADHD has been given, as indicated by the system. The system and method may also be adapted to recommend that blood pressure Pulse, EKG rhythm strip be administered through all digital devices, along with a telemedicine visit before medication is given. The system and method may also be adapted to provide classroom modifications and accommodation recommendations.

Concerning autism, the method includes evaluating whether the child has challenges with social communication and interaction, has poor eye contact, refuses to engage in tasks, and/or lacks joint attention back and forth while doing assessment tasks. For example, if the child demonstrates restrictive/repetitive behaviors, interests, and activities such as, but not limited to, flapping hands, spinning, lining up toys/objects, sensory issues (upset by loud noises/smell/touch), and challenges with change of routine during tasks, the evaluation should include an autism evaluation, while awaiting this evaluation. However, treatment must be started with speech and occupational enrichment modules every day until formal in-person Occupational and/or Speech therapy is started. These models should also be continued in conjunction with in-person therapy.

Autism presents challenges with social communication and interaction. Autistic children have speech and language delay and are not motivated to socially interact. They have challenges with eye contact and are unable to demonstrate joint attention, not able to play a back-and-forth game or do various assessment tasks. They show restrictive and repetitive behaviors, such as flapping their hands, spinning a lot, only interested in lining up toys or objects, sensory issues such as being upset with loud noises, wanting to smell things and not wanting to play pretend. Children with Autism also have difficulty with change of routine for example, having a new teacher, or driving a new route home and difficulty changing tasks during an assessment, such as, for example, one or more of the assessments made using the method of the present disclosure.

If the autism evaluation of the present method may recommend activities and/or worksheets that are adapted to address the specific concerns of lack of engagement/language delay affecting social interaction, high concerns for Autistic Spectrum Disorder (ASD), or ASD confirmed. This will include activities that focus on strengthening receptive, expressive, and pragmatic language skills; specific games and activities addressing language goals. To improve sensory regulation, the autism evaluation of the present method may recommend specific games and activities to decrease sensory triggers whether they be hypo (low) or hyper (high) sensory. To address sensory seeking behaviors and/or sensory avoidance behaviors, the autism evaluation may include recommending Occupational Therapy (OT) like play activities with OT therapy goals addressing visual/motor integration, sensory regulation, visual perceptual skills, executive function, and primitive reflex integration. To improve fine motor skills, the autism evaluation of the present method may recommend specific games and activities to improve any fine motor skills or hand skill ability like but not limited to the following (handwriting, cutting, folding, stringing beads, coloring, drawing, gluing, buttoning, using utensils, etc. To improve gross motor skills, the autism evaluation of the present method may recommend specific games and activities to strengthen gross motor movements that include focusing on balance, coordination, ball skills (dribbling, throwing, catching, etc.), hand eye coordination, same side and alternating side body movements, body schema activities (proprioceptive, vestibular, tactile, and body awareness) and/or Physical Therapy (PT) therapy like activities with PT gross motor goals. To improve social and pragmatic language skills, the autism evaluation of the present method may recommend specific group play therapy along with games and activities promoting opportunity for improved and guided social interaction. This can include Group play therapy, Applied Behavioral Analysis Therapy and Increased peer group interactions. In situations where anxiety or family connections are more calming, the method can be adapted to generate an avatar (computer generated face and/or voice used) that could be that of a person familiar to the individual. In some embodiments, one or more of the assessments, evaluations and/or recommendations are delivered to the child via the avatar.

The system and method of the present disclosure can be used to treat and strengthen skills along with in-person therapy especially when waiting for in-person therapy. The system and method of the present disclosure can recommend starting therapeutic advancement of identified skill deficits while at home when awaiting in-person therapies. Such therapeutic advancement can be used to augment and reinforce the actual future or current therapies in place like medically delivered Speech and Language Therapy, OT, Cognitive Behavioral Therapy, and PT. The system and method of the present disclosure can include engagement modules and/or worksheets that allow Early Intervention to immediately start while a child waits for in-person evaluation and/or in-person autism specific therapy. The system and method of the present disclosure can improve skills and reassessment will allow progress. Children should continue using the system and method of the present disclosure even after starting in-person therapy. Referral pursuant to the autism evaluation can include referring the child for an in-person Speech and Language Evaluation, referring the child for an in-person Sensory Integration Focused Occupational Therapy Evaluation, referring the child for an in-person Diagnostic Evaluation for Autism, referring the child for in-person Child Play Therapy.

The system and method of the present disclosure can be adapted to pursue all therapies covered by medical insurance while at the same time caregivers/teachers work on language skills, social interaction, developmental milestones, and sensory regulation using the system and method of the present disclosure for age-appropriate activities. Recommendations will include prescriptions for in-person services generated through the system and method of the present disclosure. Suggestions to seek specialized diagnostic evaluations when indicated by the system and method of the present disclosure will include follow up with the child's primary care medical provider, and specialty referrals. As part of the diagnostic process, the system and method of the present disclosure can be adapted to administer and score standardized validated screeners as age appropriate such as but not limited to the MCHAT, ASQ, PEDS Form, Vanderbilts, Denver Developmental assessments, Conners Forms, Scat, etc. While Autism may be the primary diagnosis or concern, other coexisting conditions like anxiety or ADHD and/or genetic disorders may exist. If a validated screening as discussed above elicits concerns for other disorders, the appropriate referral will be done through the system and method of the present disclosure.

Concerning anxiety, panic attacks, or PTSD, if the child is showing emotions of frustration with or without crying and/or demonstrating worry about their performance while completing the assessment, has an elevated heart rate and/or blood pressure and/or avoids behaviors when tasks are hard such as: complaining to end or get out of a task like, having headaches, having nausea, stomach aches, vomiting, having tiredness, yawning, falling asleep, having a tense posture, clenched shoulders or muscles, clenched teeth, pulling on eyelashes, biting fingers or fingernails, arguing, throwing the materials, leaving the test environment, saying they are thirsty, hungry, tired, sleepy, or having to all of a sudden got to go to the bathroom, complains of their heart racing, is selectively mute, or is unable to attempt to complete the tests in part or at all, the evaluation should include an anxiety, panic attack, or PTSD evaluation.

A diagnosis of Anxiety is when a child is worried or scared and it interferes with their everyday activities such as refusing to go to school, playing with friends, especially at recess or at social gatherings, getting to sleep and/or not being able to sleep alone in their bed. They may say their heart is beating too fast, or they have a stomachache and shaking, maybe having trouble breathing, start to sweat and suddenly are unable to sustain attention and want to find a safe place, like home or a caregiver. Anxiety may have been exhibited itself as shyness during the child's early years or occur after a traumatic event experienced/witnessed by the child or the child may be a victim of abuse by a caregiver or other. There are 4 types of Anxiety present in children. One type of anxiety is Social Anxiety wherein a child displays difficulty playing or being with others, especially in school, will speak softly not wanting to be heard and will not volunteer to raise hand in school or participate in group activities. Another type of anxiety with early onset is Separation Anxiety wherein a child is unable to separate from the caregiver, wanting to always be in their presence, not wanting to go to school or be on a playdate. Another type of anxiety is Selective Mutism—severe anxiety—wherein a child speaks at home but not anywhere else. Another type of anxiety is Generalized Anxiety wherein a child strives to be perfect, worries about the past, current events and the future a lot and worries about what may happen in school in their schoolwork or other activities. They may get diagnosed with ADHD; however, this child cannot pay attention due to worry, rather than attention. The child may demonstrate administration of the present method by being concerned about getting the assessment tasks correct or simply not speaking. They may cry and turn away and say they are afraid to continue FIGS. 7F-7Q provide assessment guided treatment flow charts A and B which provide recommendations for treatment based on the assessments and answers to questions in the 3 year old questionnaire and neurodevelopmental assessments tasks described in FIGS. 1-6.

The system and method of the present disclosure may be configured to determine through an anxiety algorithm module and/or caregiver/teacher or authorized personnel to start Anxiety modules as well to start arranged telemedicine visits through the system and method of the present disclosure and/or in-person therapy. Also, the Caregiver/teacher will work on language development, social interaction, and sensory regulation by using a 3-Year-Old Developmental Milestone Information Sheet (DMIS) of the system and method of the present disclosure for age-appropriate activities. One example of a 3-Year-Old Developmental Milestone Information Sheet is shown in FIGS. 7A-7E. The system and method of the present disclosure may be configured to administer and score a diagnostic screen such as PHQ-9/SCARED/Columbia/Hamilton/GAD-7 for Anxiety that is appropriate for age. Based on the system and method of the present disclosure, Children will also be started on telemedicine services through the system and method of the present disclosure for anxiety.

Reasons for indications for medicine management for Anxiety is determined by the system and method of the present disclosure, physician, and input from caregiver/teacher. Pulse, Blood Pressure and EKG will be obtained by digital devices and are medically necessary before starting medication if indicated. Telemedicine services for anxiety though the system and method of the present disclosure must also be initiated and continued while the child is on medication for anxiety. All children diagnosed with Anxiety through the system and method of the present disclosure will also be evaluated for ADHD/ADD and/or Autism, if indicated.

Concerning low self-esteem, self-esteem should always be monitored closely in a child as this can lead to depression or other mental health disparities in the future. Low self-esteem can arise from a variety of reasons. The system and method of the present disclosure may include one or more modules that address building self-esteem and confidence in a child. Telemedicine visits will be recommended via the system and method of the present disclosure or a local provider. Anxiety will be less when a child can confidently and competently perform what is asked of him.

In the first part of the method, a referral may also generate referring the individual for services in areas where the evaluation results were sufficient to improve the child's skills, even though the child's skills are proficient for his or her age. For example, if the child demonstrates that he or she is able to demonstrate social communication, interaction, eye contact and able to demonstrate joint attention back and forth with assessment tasks, it may be indicative that the child's skills are not deficient, and the child needs to only to continue to build and/or improve his or her skills. Further, not showing restrictive and repetition behaviors, such as flapping their hands, spinning a lot, being only interested in lining up toys or objects, having sensory issue such as being upset with loud noises and difficulty with change of routine may also be indicative that the child's skills are not deficient, and the child needs to only to continue to build and/or improve his or her skills. Indeed, if the child is able to maintain attention, is not easily distracted, follows directions, etc. it may also be indicative that the child's skills are not deficient, and the child needs to only continue to build and/or improve his or her skills. Likewise, if the child is able to complete the tests without crying or worrying about how they are doing on the tests, it may also be indicative that the child's skills are not deficient, and the child needs to only to continue to build and/or improve his or her skills.

In some embodiments, the first part of the method further includes observing behavioral engagement skills of the child throughout the testing process, such as, for example, during the first test, during the second test, during the third test and/or during the fourth test. In some embodiments, the observations made throughout the testing process can include noting the child's demeanor, such as, for example, observations pertaining to whether the child is cooperative, uncooperative, refuses to interact, completed the tests independently, exhibited poor eye contact, smiled, cried, was tired, would not engage, was shy, was distractible, was anxious, needed redirection for completion, was happy and engaged, was an English language learner, was difficult to motivate, etc. In some embodiments, the observations made throughout the testing process are included in the worksheet (FIGS. 3 and 4) and/or are used to generate the referral. In some embodiments, information pertaining to the answers provided in the questionnaire (FIG. 1) is included in the worksheet and/or is used to generate the referral.

Method—Part Two—Year Four

In a second part of the method, which should be administered after the first part of the method discussed above is administered to the child, when the child is approximately 4 years old, the child's parent's is required to fill out a questionnaire that includes various questions about the child. One embodiment of the questionnaire is shown in FIG. 8. As shown in FIG. 8, the questionnaire can include questions about the child's physical abilities, such as, for example, the child's hearing and vision. The questionnaire can also include questions relating to the child's ability to read, write, comprehend information, perform simple tasks, socialize, etc. In some embodiments, the child is required to undergo a Vision Snell chart test and/or a colorblind test (e.g., The Ishihara, EnChroma, or any other standardized color-blind assessment or screen) prior to beginning the second part of the method.

Figure 9B:
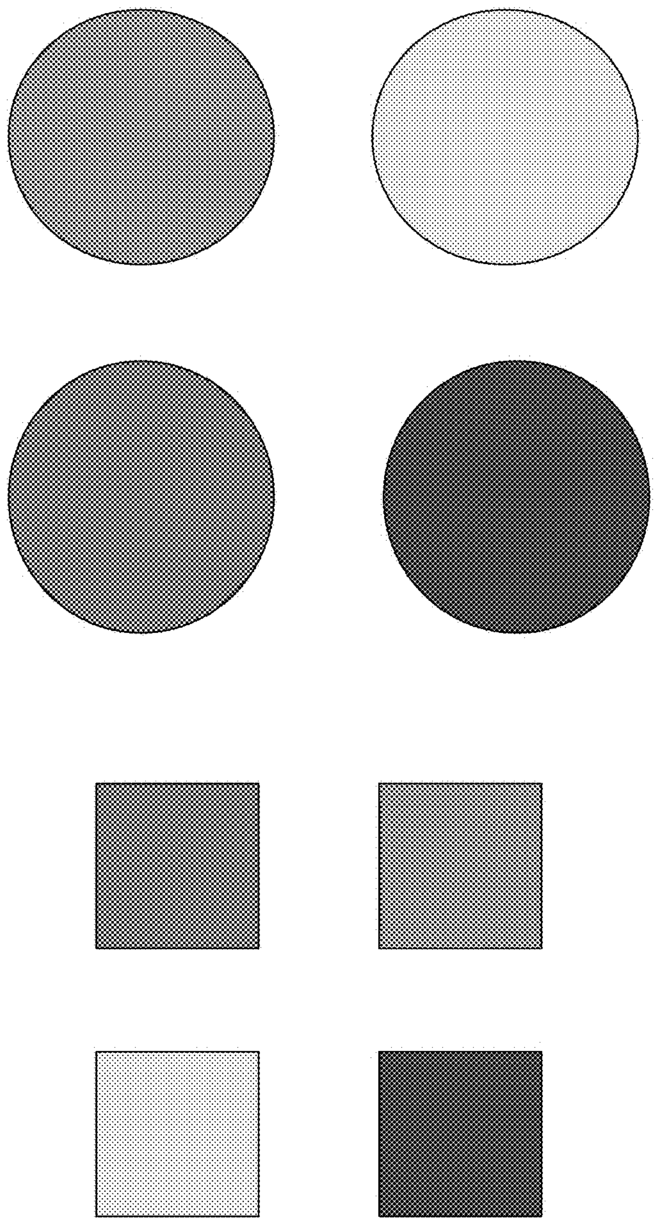
FIG. 9B is one embodiment of a form/document used in connection with form/document shown in FIG. 9A, in accordance with the principles of the present disclosure.
Figure 9C:
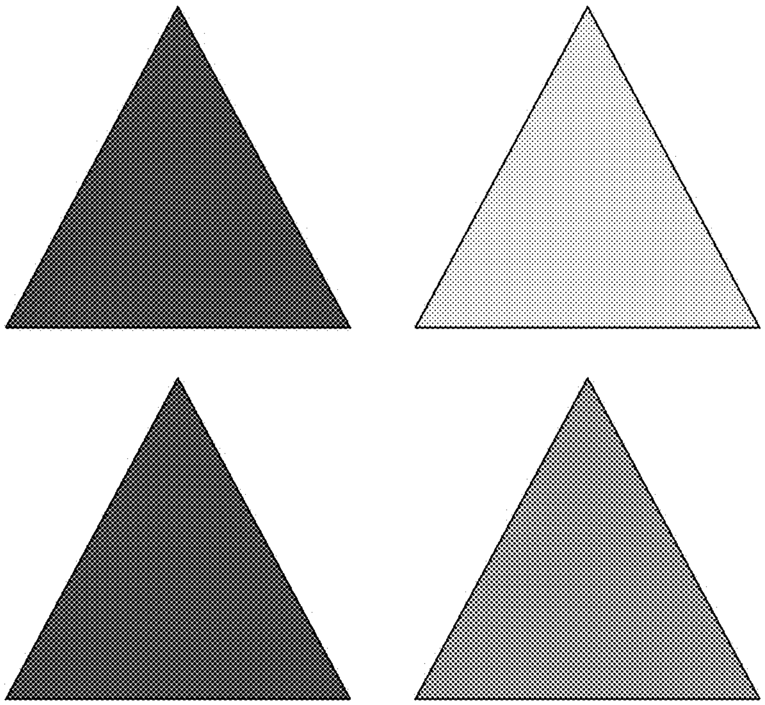
FIG. 9C is one embodiment of a form/document used in connection with form/document shown in FIG. 9A, in accordance with the principles of the present disclosure.
Figure 10B:
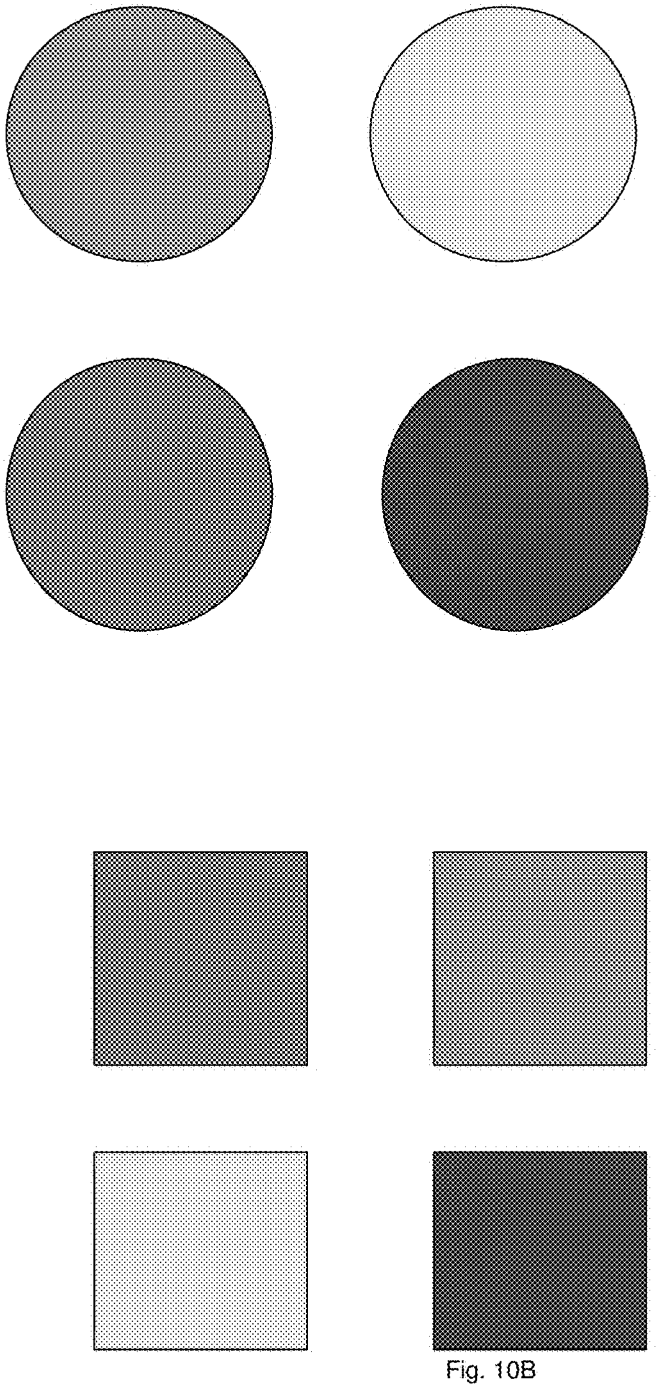
FIG. 10B is one embodiment of a form/document used in connection with form/document shown in FIG. 10A, in accordance with the principles of the present disclosure.
Figure 10C:
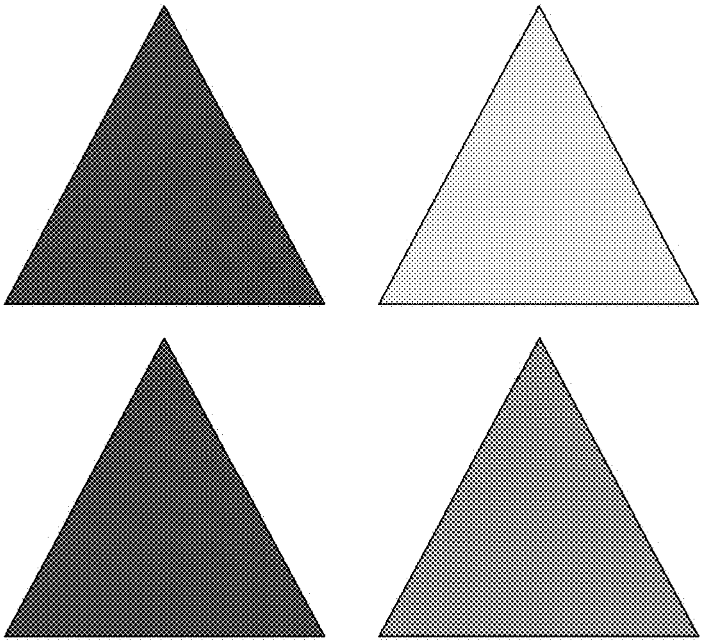
FIG. 10C is one embodiment of a form/document used in connection with form/document shown in FIG. 10A, in accordance with the principles of the present disclosure.
Figure 17D:
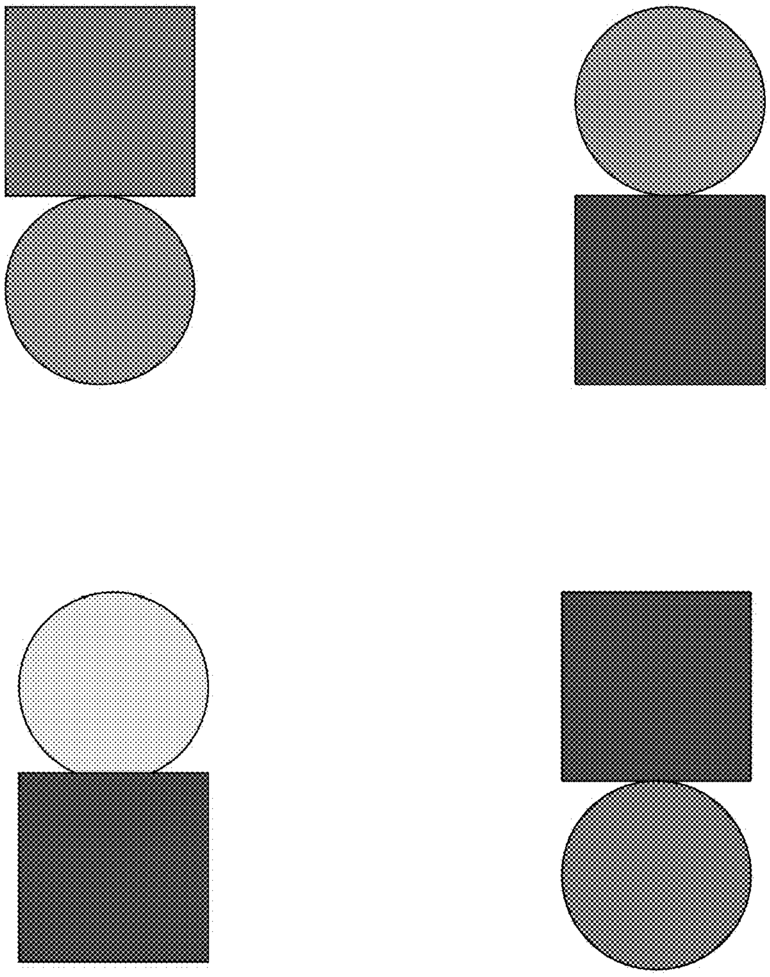
FIG. 17D is an example of one embodiment of another page from the assessment shown in FIG. 17A, in accordance with the principles of the present disclosure.
Figure 17E:
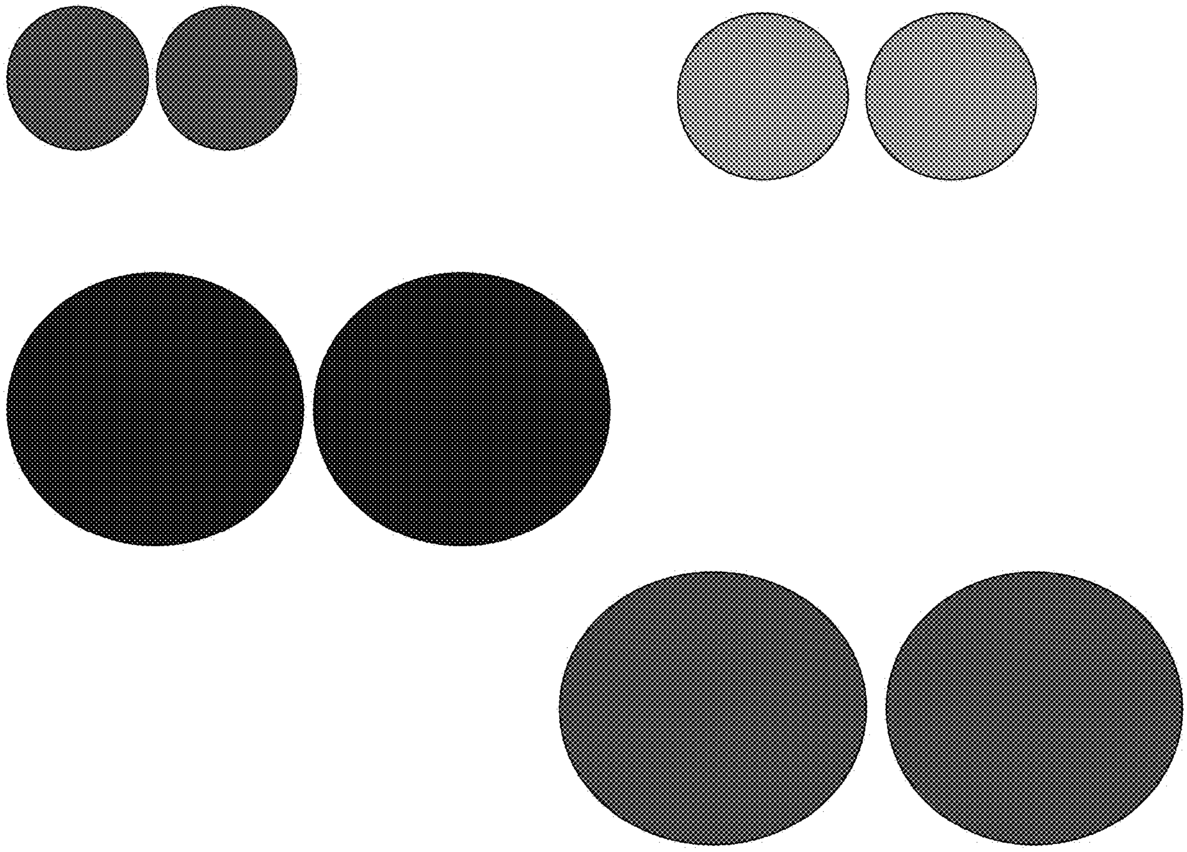
FIG. 17E is an example of one embodiment of another page from the assessment shown in FIG. 17A, in accordance with the principles of the present disclosure.
Figure 18D:
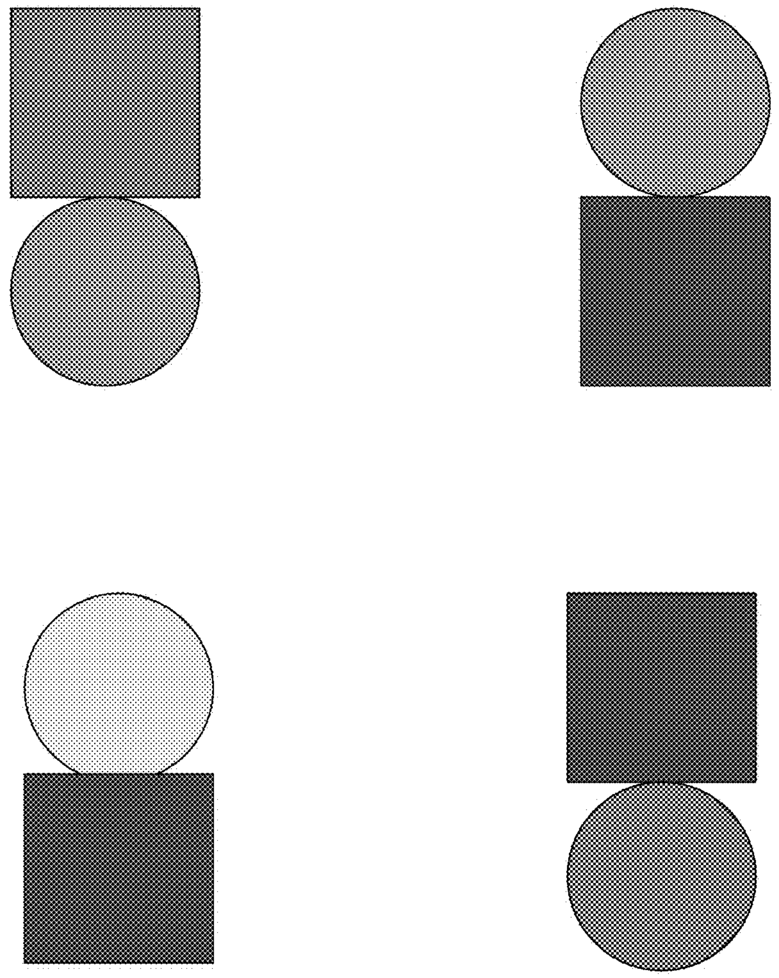
FIG. 18D is an example of one embodiment of one page of an assessment used in connection with the third part of the method, in accordance with the principles of the present disclosure.
Figure 18E:
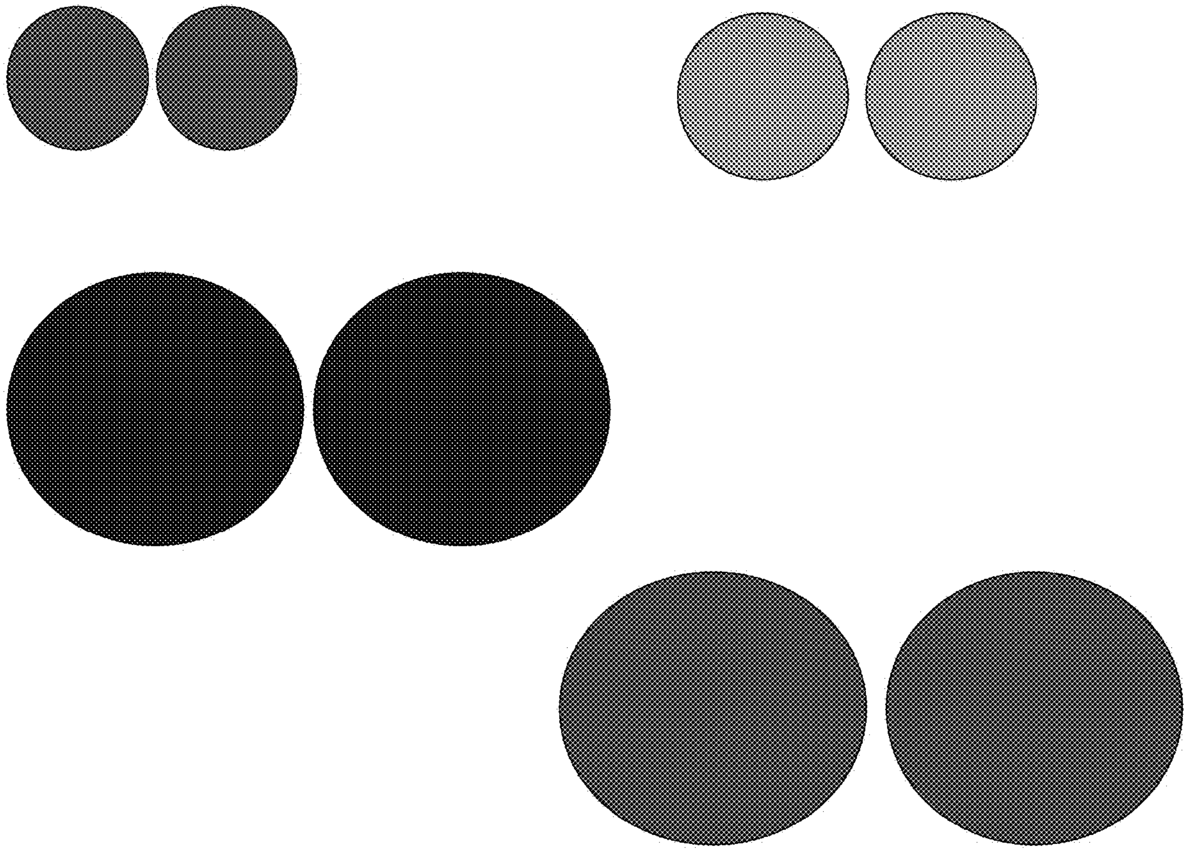
FIG. 18E is an example of one embodiment of one page of an assessment used in connection with the third part of the method, in accordance with the principles of the present disclosure.

In the second part of the method, tests concerning speech and language, fine and gross motor skills are evaluated for the presence or absence of a disorder and/or school readiness. In particular, in the second part of the method, a first test is administered in which the child has to pick a picture that fits best. For example, in some embodiments, the child may be required to draw a cat with three or more parts, as shown in FIG. 9A. In some embodiments, the child may be required to copy a shape, as shown in FIG. 9A. In some embodiments, the child may be required to trace a line within a box, as shown in FIG. 9A. In some embodiments, the child may also be required to show a blue circle; point to a yellow square; show a green square; and/or show a red triangle, as shown in FIGS. 9B and 9C. In other embodiments, the child may be required to draw a dog with three or more parts, as shown in FIG. 10A. In some embodiments, the child may be required to copy a shape, as shown in FIG. 10A. In some embodiments, the child may be required to trace a line within a box, as shown in FIG. 10A. In some embodiments, the child may be required to pick a picture that depicts a red circle; point to a blue square; show a yellow square; and/or show a green triangle, as shown in FIGS. 10B and 10C.

The ability of the child to draw or perform the requested tasks is recorded to generate receptive language input data. The ability of the child to perform one or more of the requested tasks may be recorded in a second worksheet. One embodiment of the second worksheet is shown in FIGS. 11A-11D. Another embodiment of the second worksheet is shown in FIGS. 12A-12D. The receptive language input data may include whether or not the child was able to perform required tasks. The ability of the child to perform the required tasks may be recorded in the second worksheet. The receptive language input data is evaluated against an answer key to generate a receptive language evaluation result. The receptive language evaluation result is another determination with respect to the presence or absence of receptive language deficiency, after the first determination with respect the presence or absence of receptive language deficiency conducted during the first part of the method. In some embodiments, the receptive language evaluation result includes a score, such as, for example, a number score. In some embodiments, the receptive language evaluation result includes a written evaluation, such as, for example, words written in sentence or note form that explain what was observed by the practitioner. In some embodiments, the receptive language result is included in an assessment that evaluates at least each of the tests administered during the second part of the method. One embodiment of the assessment is shown in FIGS. 13A-13Q.

In the second part of the method, a second test is administered in which the child has to do a sound discrimination task to generate a sound discrimination task input data. The ability of the child to do a sound discrimination task may be recorded in the second worksheet (FIGS. 11A-11D or FIGS. 12A-12E). In some embodiments, the sound discrimination task may include having the child say if sounds are the same or different. For example, the child may be required to say if two of the same letters sound different than another letter. In some embodiments, the sound discrimination evaluation result is included in the assessment (FIGS. 11D, or FIGS. 12A-12D). In some embodiments, the sound discrimination evaluation result uses AI or other software to recognize and/or transcribe the child's letter sound/word pronunciation, analyze context/structure where pronunciation varies due to accents/dialects and word/sentence structure comprehension and fluency.

In the second part of the method, a third test is administered in which the child has sound order awareness. The ability with sound order awareness may be recorded in the worksheet (FIGS. 11A-11D or FIGS. 12A-12E as sound order awareness input data. In some embodiments, administering the third test may include asking the child say the first wound in the word "apple"; having the child say the last sound in the word "me"; having the child say the second sound in the word "pin"; having the child say the first sound in the word "bat"; having the child say the first sound in the word "mine"; having the child say the middle sound in the word "pan"; having the child say the last sound in the word "fun"; and/or having the child say the last sound in the word "dog" (FIG. 11A). In some embodiments, administering the third test may include asking the child say the last sound in the word "foot"; having the child say the second sound in the word "feet"; having the child say the first sound in the word "hut"; having the child say the last sound in the word "boat"; having the child say the first sound in the word "blue"; having the child say the first sound in the word "snake"; having the child say the last sound "dog" and/or having the child say the middle sound "cat" (FIG. 12A).

In the second part of the method, a fourth test is administered in which the child has to determine if the child has appropriate fine motor skills. In the fourth test, the child may be required to perform a typical three point pencil grip; to draw a cat with three or more parts; to copy a shape correctly (FIG. 11A); and/or to trace a line within a box; and/or to perform a typical three point pencil grip test; to draw a dog with three or more parts; to copy shapes correctly; and/or to trace a line within a box (FIG. 12A). The ability of the child to perform may be recorded on the worksheet (FIGS. 11A-D or FIGS. 12A-E). The sound order awareness input data is evaluated against an answer key to generate a sound awareness evaluation result. The sound awareness evaluation result is a determination with respect to the presence or absence of sound order awareness foundational skills. In some embodiments, the sound order awareness evaluation result is included in the assessment (FIGS. 13A-13P).

In the second part of the method, a referral is generated referring the individual for services in areas where the evaluation results were deficient to promote at least one of fine receptive language, sound discrimination, sound order awareness and/or fine motor skills. In some embodiments, the assessment (FIGS. 13A-13P), which can include the receptive language result, the sound discrimination result, the sound order awareness result and/or the fine motor skill result is evaluated to generate the referral. In particular, if the fine motor or receptive language result indicates that the child has proficient fine receptive language skills, the child is not referred for services, such as, for example, occupational therapy to promote advancement in fine motor skills. If, however, the fine receptive language result indicates that the child is deficient with his or her fine receptive language skills, the child is referred for services, such as, for example, occupational therapy to promote advancement in fine motor skills.

Likewise, if the sound discrimination evaluation result indicates that the child has proficient sound discrimination, the child is not referred for services, such as, for example, occupational therapy to promote advancement in sound discrimination. If, however, the sound discrimination result indicates that the child is deficient with his or her sound discrimination, the child is referred for services, such as, for example, Speech therapy to promote advancement in sound discrimination.

If the sound order awareness evaluation result indicates that the child has proficient sound order awareness skills, the child is not referred for services, such as, for example, Speech therapy to promote advancement in sound order awareness. If, however, the sound order awareness result indicates that the child is deficient with his or her sound order awareness skills, the child is referred for services, such as, for example, Speech therapy to promote advancement in sound order awareness.

If the receptive language result indicates that the child has proficient receptive language skills, the child is not referred for services, such as, for example, Speech therapy to promote advancement in receptive language skills. If, however, the receptive language result indicates that the child is deficient with his or her receptive language skills, the child is referred for services, such as, for example, Speech therapy to promote advancement in receptive language skills.

In some embodiments, the second part of the method includes evaluating the child for ADHD, autism, anxiety, panic attacks, post-traumatic stress disorder (PTSD), depression, low self-esteem, etc. if the evaluation results in the second part of the method were deficient to promote at least one of fine receptive language, sound discrimination, sound order awareness and/or fine motor skills.

The ADHD evaluation in the second part of the method can include giving focused tips on a structured environment, making learning activities fun, multisensory activities, and short but repetitive opportunities for learning. If engagement is appropriate, but focus/attention to a task cannot be maintained for the age expected time for the child's age, then the method may refer the child to take a test that includes ADHD/ADD age specific questions and consider all factors that can affect attention and sustained focus. In some embodiments, if the child exhibits signs of ADHD/ADD, the method can be adapted to administer and score a Vanderbilt screen for parent and teacher (if applicable). These screens are diagnostic of ADHD/ADD.

Concerning autism, the second part of the method includes evaluating whether the child has challenges with social communication and interaction, has poor eye contact, refuses to engage in tasks, and/or lacks joint attention back and forth while doing assessment tasks. For example, if the child demonstrates restrictive/repetitive behaviors, interests, and activities such as, but not limited to, flapping hands, spinning, lining up toys/objects, sensory issues (upset by loud noises/smell/touch), and challenges with change of routine during tasks, the evaluation should include an autism evaluation.

If the autism evaluation of the present method may recommend activities and/or worksheets that are adapted to address the specific concerns of lack of engagement/language delay affecting social interaction, high concerns for Autistic Spectrum Disorder (ASD), or ASD confirmed. This will include activities that focus on strengthening receptive, expressive, and pragmatic language skills; specific games and activities addressing language goals. To improve sensory regulation, the autism evaluation of the present method may recommend specific games and activities to decrease sensory triggers whether they be hypo (low) or hyper (high) sensory. To address sensory seeking behaviors and/or sensory avoidance behaviors, the autism evaluation may include recommending Occupational Therapy (OT) like play activities with OT therapy goals addressing visual/motor integration, sensory regulation, visual perceptual skills, executive function, and primitive reflex integration.

The system and method of the present disclosure can be used to treat and strengthen skills along with in-person therapy especially when waiting for in-person therapy. The system and method of the present disclosure can recommend starting therapeutic advancement of identified skill deficits while at home when awaiting in-person therapies. Such therapeutic advancement can be used to augment and reinforce the actual future or current therapies in place like medically delivered Speech and Language Therapy, OT, Cognitive Behavioral Therapy, and PT. The system and method of the present disclosure can include engagement modules and/or worksheets that allow Early Intervention to immediately start while a child waits for in-person evaluation and/or in-person autism specific therapy. The system and method of the present disclosure can improve skills and reassessment will allow progress. Children should continue using the system and method of the present disclosure even after starting in-person therapy. Referral pursuant to the autism evaluation can include referring the child for an in-person Speech and Language Evaluation, referring the child for an in-person Sensory Integration Focused Occupational Therapy Evaluation, referring the child for an in-person Diagnostic Evaluation for Autism, referring the child for in-person Child Play Therapy.

Concerning anxiety, panic attacks, or PTSD, if the child is showing emotions of frustration with or without crying and/or demonstrating worry about their performance while completing the assessment, has an elevated heart rate and/or blood pressure and/or avoids behaviors when tasks are hard such as: complaining to end or get out of a task like, having headaches, having nausea, stomach aches, vomiting, having tiredness, yawning, falling asleep, having a tense posture, clenched shoulders or muscles, clenched teeth, pulling on eyelashes, biting fingers or fingernails, arguing, throwing the materials, leaving the test environment, saying they are thirsty, hungry, tired, sleepy, or having to all of a sudden got to go to the bathroom, complains of their heart racing, is selectively mute, or is unable to attempt to complete the tests in part or at all, the evaluation should include an anxiety, panic attack, or PTSD evaluation.

The system and method of the present disclosure may be configured to determine through an anxiety algorithm module and/or caregiver/teacher or authorized personnel to start Anxiety modules as well to start arranged telemedicine visits through the system and method of the present disclosure and/or in-person therapy. Also, the Caregiver/teacher will work on language development, social interaction, and sensory regulation by using a 4-Year-Old Developmental Milestone Information Sheet (DMIS) of the system and method of the present disclosure for age-appropriate activities. One example of a 4-Year-Old Developmental Milestone Information Sheet is shown in FIGS. 14A-14G. The system and method of the present disclosure may be configured to administer and score a diagnostic screen such as PHQ-9/SCARED/Columbia/Hamilton/GAD-7 or others for Anxiety that is appropriate for age. Based on the system and method of the present disclosure, Children will also be started on telemedicine services through the system and method of the present disclosure for anxiety.

Reasons for indications for medicine management for Anxiety is determined by the system and method of the present disclosure, physician, and input from caregiver/teacher. Pulse, Blood Pressure and EKG will be obtained by digital devices and are medically necessary before starting medication. Telemedicine services for anxiety though the system and method of the present disclosure must also be initiated and continued while the child is on medication for anxiety. All children diagnosed with Anxiety through the system and method of the present disclosure will also be evaluated for ADHD/ADD and/or Autism.

Concerning low self-esteem, self-esteem should always be monitored closely in a child as this can lead to depression or other mental health disparities in the future. Low self-esteem can arise from a variety of reasons. The system and method of the present disclosure may include one or more modules that address building self-esteem and confidence in a child. Telemedicine visits will be recommended via the system and method of the present disclosure or a local provider. Anxiety will be less when a child can confidently and competently perform what is asked of them.

In the second part of the method, a referral may also generate referring the individual for services in areas where the evaluation results were sufficient to improve the child's skills, even though the child's skills are proficient for his or her age. For example, if the child demonstrates that he or she is able to demonstrate social communication, interaction, eye contact and able to demonstrate joint attention back and forth with assessment tasks, it may be indicative that the child's skills are not deficient, and the child needs to only to continue to build and/or improve his or her skills. Further, not showing restrictive and repetition behaviors, such as flapping their hands, spinning a lot, being only interested in lining up toys or objects, having sensory issue such as being upset with loud noises and difficulty with change of routine may also be indicative that the child's skills are not deficient, and the child needs to only to continue to build and/or improve his or her skills. Indeed, if the child is able to maintain attention, is not easily distracted, follows directions, etc. it may also be indicative that the child's skills are not deficient, and the child needs to only continue to build and/or improve his or her skills. Likewise, if the child is able to complete the tests without crying or worrying about how they are doing on the tests, it may also be indicative that the child's skills are not deficient, and the child needs to only to continue to build and/or improve his or her skills.

In some embodiments, the second part of the method further includes observing behavioral engagement skills of the child throughout the testing process, such as, for example, during the first test of the second part of the method, during the second test of the second part of the method, during the third test of the second part of the method and/or during the fourth test of the second part of the method. In some embodiments, the observations made throughout the testing process of the second part of the method can include noting the child's demeanor, such as, for example, observations pertaining to whether the child is cooperative, uncooperative, refuses to interact, completed the tests independently, exhibited poor eye contact, smiled, cried, was tired, would not engage, was shy, was distractible, was anxious, needed redirection for completion, was happy and engaged, was an English language learner, was difficult to motivate, etc. In some embodiments, the observations made throughout the testing process of the second part of the method are included in the worksheet (FIGS. 11A-11D or 12A-12E) and/or are used to generate the referral. In some embodiments, information pertaining to the answers provided in the questionnaire of the second part of the method (FIG. 8) is included in the worksheet and/or is used to generate the referral.

Method—Part Three—Year Five

In a third part of the method, which should be administered after the second part of the method discussed above is administered to the child, when the child is approximately 5 years old, the child's parent's is required to fill out a questionnaire that includes various questions about the child. One embodiment of the questionnaire is shown in FIG. 15A. As shown in FIG. 15A, the questionnaire can include questions about the child's physical abilities, such as, for example, the child's hearing and vision. The questionnaire can also include questions relating to the child's ability to read, write, comprehend information, perform simple tasks, socialize, etc. For example, the questionnaire can include questions whether they can understand their child when the child speaks, whether the child is able to rhyme well, whether the child seems to hear OK, whether the child brushes his or her teeth with toothpaste, whether the child mixes up sounds in words, whether the child ever needed ear tubes, whether there is a family history of disorders, etc. (See, FIG. 15A).

In the third part of the method, the child may be required to perform tests relating to receptive language, fine motor and letter naming and letter sound skills. For example, as shown in FIG. 15B, the child may be required to show a green circle on top of a red square, to point to two small red circles, to show the blue triangle inside the yellow circle, to show the pink circle under the dark blue square. The child may also be required to perform a typical three-point pencil grip, color a circle within lines, copy squares and/or draw a line within a rectangle (FIG. 15B). The child may also be required to save various letter names and/or letter sounds (FIG. 15B). In some embodiments, the document shown in FIG. 15B is a worksheet that is used in connection with the third part of the method. For example, the document shown in FIG. 15B may be used as a worksheet to record the child's test results during the third part of the method.

In the third part of the method, tests for perform tests relating to phoneme elision (deletion) and rhyming are performed (FIGS. 16A and 16B) prior to tests for fine motor skills, letter and sound identification skills, phonemic elision (sound deletion) skills (FIGS. 17A-F) and/or receptive language skills, fine motor skills, sound and letter identification skills and phonemic elision skills (FIGS. 18A-F). In some embodiments, the documents shown in FIGS. 16A and 16B can be part of a worksheet that is used in connection with the third part of the method. For example, the documents shown in FIGS. 16A and 16B may be used as worksheets to record the child's test results during the third part of the method. It is envisioned that the results of tests that are recorded in the documents shown in FIGS. 16A and 16B may be used to determine if the child is capable of understanding and following directions. For example, as shown in FIGS. 16A and 16B, the child may be required to play a game in which the child says a word, such as, for example, the word "raindrop," and is then asked to say the word "raindrop" without saying "drop." This may be repeated with other words, as shown in FIGS. 16A and 16B. In some embodiments, the child may be required to say whether or not two words rhyme, as also shown in FIGS. 16A and 16B. The child's behavior may be observed during these tests for considerations such as, for example, whether the child is cooperative, whether the child is uncooperative, whether the child refuses to interact, whether the child completed tasks independently, whether the child exhibited poor eye contact, whether the child smiled, whether the child cried, whether the child appeared tired, whether or not the child would engage, whether the child was shy, whether the child was distractible, whether the child was anxious, whether the child needed redirection to complete tasks, whether the child was happy and engaged, whether the child is an English language learner, whether the child was difficult whether the child's speech was understandable, etc., as shown in FIGS. 16A and 16B.

In the third part of the method, tests for fine motor skills, letter and sound identification skills, phonemic elision (sound deletion) skills (FIG. 17A) and/or receptive language skills, fine motor skills, sound and letter identification skills and phonemic elision skills (FIG. 18A) are evaluated for the presence or absence of a disorder and determination of school readiness. These tests may be administered after the tests discussed in the preceding paragraph and shown in FIGS. 16A and 16B. The ability of the child to perform the requested tasks is recorded to generate input data. The ability of the child to perform one or more of the requested tasks may be recorded in a third worksheet. One embodiment of the third worksheet is shown in FIGS. 17A-17F. Another embodiment of the third worksheet is shown in FIGS. 18A-18F.

The fine motor skill input data may include whether or not the child was able to perform required tasks. The ability of the child to perform the required tasks may be recorded in the third worksheet. The fine motor input data is evaluated against an answer key to generate a fine motor evaluation result. The fine motor evaluation result is another determination with respect to the presence or absence of fine motor deficiency, after the second determination with respect the presence or absence of fine motor conducted during the first and second parts of the method. In some embodiments, the fine motor evaluation result includes a score, such as, for example, a number score. In some embodiments, the fine motor evaluation result includes a written evaluation, such as, for example, words written in sentence or note form that explain what was observed by the practitioner. In some embodiments, the fine motor result is included in an assessment that evaluates at least each of the tests administered during the third part of the method. One embodiment of the assessment is shown in FIGS. 19A-19N.

In the third part of the method, a second test is administered in which the child has to do a letter and sound identification task to generate a letter and sound identification task input data. The ability of the child to do a letter and sound identification task may be recorded in the third worksheet (FIGS. 17A-17F or FIGS. 18A-18F). The letter and sound identification input data are evaluated against an answer key to generate a letter and sound identification evaluation result. The letter and sound identification evaluation result are another determination with respect to the presence or absence of letter and sound identification deficiency, after the second determination with respect the presence or absence of letter and sound identification conducted during the first and second parts of the method. In some embodiments, the letter and sound identification evaluation result include a score, such as, for example, a number score. In some embodiments, the letter and sound identification evaluation result include a written evaluation, such as, for example, words written in sentence or note form that explain what was observed by the practitioner. In some embodiments, the letter and sound identification evaluation result is included in the assessment (FIGS. 19A-19N). In some embodiments, the letter and sound identification evaluation result uses AI or other software to recognize and/or transcribe the child's letter sound/word pronunciation, analyze context/structure where pronunciation varies due to accents/dialects and word/sentence structure comprehension and fluency. In the third part of the method, a third test is administered in which the child has phonemic elision (sound deletion) skills.

In the third part of the method, a third test is administered in which the child has to do a phonemic elision (sound deletion) task to generate a phonemic elision task input data. The ability of the child to do a phonemic elision task may be recorded in the third worksheet (FIGS. 17A-17F or FIGS. 18A-18F). The phonemic elision input data is evaluated against an answer key to generate a phonemic elision evaluation result. The phonemic elision evaluation result is another determination with respect to the presence or absence of phonemic elision deficiency, after the second determination with respect the presence or absence of phonemic elision deficiency conducted during the first and second parts of the method. In some embodiments, the phonemic elision evaluation result includes a score, such as, for example, a number score. In some embodiments, the phonemic elision evaluation result includes a written evaluation, such as, for example, words written in sentence or note form that explain what was observed by the practitioner. In some embodiments, the phonemic elision evaluation result is included in the assessment (FIGS. 19A-19N). In some embodiments, the phonemic elision evaluation result uses AI or other software to recognize and/or transcribe the child's letter sound/word pronunciation, analyze context/structure where pronunciation varies due to accents/dialects and word/sentence structure comprehension and fluency.

In the third part of the method, a fourth test is administered in which the child has to do a rhyming task to generate a rhyming task input data. The ability of the child to do a rhyming task may be recorded in the third worksheet (FIGS. 17A-17F or FIGS. 18A-18F). The rhyming task input data is evaluated against an answer key to generate a rhyming evaluation result. The rhyming evaluation result is another determination with respect to the presence or absence of rhyming deficiency, after the second determination with respect the presence or absence of rhyming deficiency conducted during the first and second parts of the method. Indeed, because rhyming is a phonological awareness skill, the fourth test will test the child's ability to create a repetition of similar sounds in to or more words, which requires the ability to know if the sounds are the same or different. In some embodiments, the rhyming evaluation result includes a score, such as, for example, a number score. In some embodiments, the rhyming evaluation result includes a written evaluation, such as, for example, words written in sentence or note form that explain what was observed by the practitioner. In some embodiments, the rhyming evaluation result is included in the assessment (FIGS. 19A-19N). In some embodiments, the rhyming evaluation result uses AI or other software to recognize and/or transcribe the child's letter sound/word pronunciation, analyze context/structure where pronunciation varies due to accents/dialects and word/sentence structure comprehension and fluency.

In one embodiment of the third part of the method, a fifth test is administered in which the child has to do a receptive language skill task to generate a receptive language skill input data. The ability of the child to do a receptive language skill may be recorded in the third worksheet (FIGS. 18A-18F). The receptive language skill input data is evaluated against an answer key to generate a receptive language skill evaluation result. The receptive language skill evaluation result is another determination with respect to the presence or absence of receptive language skills, after the second determination with respect the presence or absence of receptive language skill deficiency conducted during the first and second parts of the method. In some embodiments, the receptive language skill evaluation result includes a score, such as, for example, a number score. In some embodiments, the receptive language skill evaluation result includes a written evaluation, such as, for example, words written in sentence or note form that explain what was observed by the practitioner. In some embodiments, the receptive language skill evaluation result is included in the assessment (FIGS. 19A-19N). In some embodiments, the receptive language skill evaluation result uses AI or other software to recognize and/or transcribe the child's letter sound/word pronunciation, analyze context/structure where pronunciation varies due to accents/dialects and word/sentence structure comprehension and fluency.

In the third part of the method, a referral is generated referring the individual for services in areas where the evaluation results were deficient to promote at least one of the skills tested in the third part of the method. In some embodiments, the assessment (FIGS. 19A-19N), which can include one or more of the test results in the third part of the method are evaluated to generate the referral. In particular, if the results indicate that the child has proficient fine motor skills, the child is not referred for services, such as, for example, occupational therapy to promote advancement in fine motor skills. If, however, the test results indicate that the child is deficient with his or her fine motor skills, the child is referred for services, such as, for example, occupational therapy to promote advancement in fine motor skills. Likewise, if the results indicate that the child has proficient letter and sound identification skills, the child is not referred for services, such as, for example, Speech therapy to promote advancement in letter and sound identification skills. If, however, the test results indicate that the child is deficient with his or her letter and sound identification skills, the child is referred for services, such as, for example, Speech therapy to promote advancement in letter and sound identification skills. If the results indicate that the child has proficient phonemic elision skills, the child is not referred for services, such as, for example, Speech therapy to promote advancement in phonemic elision skills. If, however, the test results indicate that the child is deficient with his or her phonemic elision skills, the child is referred for services, such as, for example, Speech therapy to promote advancement in phonemic elision skills. If the results indicate that the child has proficient rhyming/phonological awareness skills, the child is not referred for services, such as, for example, Speech therapy to promote advancement in rhyming/phonological awareness skills. If, however, the test results indicate that the child is deficient with his or her rhyming/phonological awareness skills, the child is referred for services, such as, for example, Speech therapy to promote advancement in rhyming/phonological awareness skills. Lastly, if the results indicate that the child has proficient receptive language skills, the child is not referred for services, such as, for example, Speech therapy to promote advancement in receptive language skills. If, however, the test results indicate that the child is deficient with his or her receptive language skills, the child is referred for services, such as, for example, Speech therapy to promote advancement in receptive language skills.

In some embodiments, the third part of the method includes evaluating the child for ADHD, autism, anxiety, panic attacks, post-traumatic stress disorder (PTSD), depression, low self-esteem, etc. if the evaluation results in the third part of the method were deficient to promote at least one of the skills tested in the third part of the method.

The ADHD evaluation in the third part of the method can include giving focused tips on a structured environment, making learning activities fun, multisensory activities, and short but repetitive opportunities for learning. If engagement is appropriate, but focus/attention to a task cannot be maintained for the age expected time for the child's age, then the method may refer the child to take a test that includes ADHD/ADD age specific questions and consider all factors that can affect attention and sustained focus. In some embodiments, if the child exhibits signs of ADHD/ADD, the method can be adapted to administer and score a Vanderbilt screen for parent and teacher (if applicable). These screens are diagnostic of ADHD/ADD. Also, must ask and rule out absence seizures with EEG or another diagnostic device.

Concerning autism, the third part of the method includes evaluating whether the child has challenges with social communication and interaction, has poor eye contact, refuses to engage in tasks, and/or lacks joint attention back and forth while doing assessment tasks. For example, if the child demonstrates restrictive/repetitive behaviors, interests, and activities such as, but not limited to, flapping hands, spinning, lining up toys/objects, sensory issues (upset by loud noises/smell/touch), and challenges with change of routine during tasks, the evaluation should include an autism evaluation, if indicated.

If the autism evaluation of the present method may recommend activities and/or worksheets that are adapted to address the specific concerns of lack of engagement/language delay affecting social interaction, high concerns for Autistic Spectrum Disorder (ASD), or ASD confirmed. This will include activities that focus on strengthening receptive, expressive, and pragmatic language skills; specific games and activities addressing language goals. To improve sensory regulation, the autism evaluation of the present method may recommend specific games and activities to decrease sensory triggers whether they be hypo (low) or hyper (high) sensory. To address sensory seeking behaviors and/or sensory avoidance behaviors, the autism evaluation may include recommending Occupational Therapy (OT) like play activities with OT therapy goals addressing visual/ motor integration, sensory regulation, visual perceptual skills, executive function, and primitive reflex integration.

The system and method of the present disclosure can be used to treat and strengthen skills along with in-person therapy especially when waiting for in-person therapy. The system and method of the present disclosure can recommend starting therapeutic advancement of identified skill deficits while at home when awaiting in-person therapies. Such therapeutic advancement can be used to augment and reinforce the actual future or current therapies in place like medically delivered Speech and Language Therapy, OT, Cognitive Behavioral Therapy, and PT. The system and method of the present disclosure can include engagement modules and/or worksheets that allow Early Intervention to immediately start while a child waits for in-person evaluation and/or in-person autism specific therapy. The system and method of the present disclosure can improve skills and reassessment will allow progress. Children should continue using the system and method of the present disclosure even after starting in-person therapy. Referral pursuant to the autism evaluation can include referring the child for an in-person Speech and Language Evaluation, referring the child for an in-person Sensory Integration Focused Occupational Therapy Evaluation, referring the child for an in-person Diagnostic Evaluation for Autism, referring the child for in-person Child Play Therapy.

Concerning anxiety, panic attacks, or PTSD, if the child is showing emotions of frustration with or without crying and/or demonstrating worry about their performance while completing the assessment, has an elevated heart rate and/or blood pressure and/or avoids behaviors when tasks are hard such as: complaining to end or get out of a task like, having headaches, having nausea, stomach aches, vomiting, having tiredness, yawning, falling asleep, having a tense posture, clenched shoulders or muscles, clenched teeth, pulling on eyelashes, biting fingers or fingernails, arguing, throwing the materials, leaving the test environment, saying they are thirsty, hungry, tired, sleepy, or having to all of a sudden got to go to the bathroom, complains of their heart racing, going selectively mute, or is unable to attempt to complete the tests in part or at all, the evaluation should include an anxiety, panic attack, or PTSD evaluation.

The system and method of the present disclosure may be configured to determine through an anxiety algorithm module and/or caregiver/teacher or authorized personnel to start Anxiety modules as well to start arranged telemedicine visits through the system and method of the present disclosure and/or in-person therapy. Also, the Caregiver/teacher will work on language development, social interaction, and sensory regulation by using a 5-Year-Old Developmental Milestone Information Sheet (DMIS) of the system and method of the present disclosure for age-appropriate activities. One example of a 5-Year-Old Developmental Milestone Information Sheet is shown in FIGS. 20A-20G. The system and method of the present disclosure may be configured to administer and score a diagnostic screen such as PHQ-9/SCARED/Columbia/Hamilton/GAD-7 or others for Anxiety that is appropriate for age. Based on the system and method of the present disclosure, Children will also be started on telemedicine services through the system and method of the present disclosure for anxiety.

Reasons for indications for medicine management for Anxiety is determined by the system and method of the present disclosure, physician, and input from caregiver/teacher. Pulse, Blood Pressure and EKG will be obtained by digital devices and are medically necessary before starting medication. Telemedicine services for anxiety though the system and method of the present disclosure must also be initiated and continued while the child is on medication for anxiety. All children diagnosed with Anxiety through the system and method of the present disclosure will also be evaluated for ADHD/ADD and/or Autism.

Concerning low self-esteem, self-esteem should always be monitored closely in a child as this can lead to depression or other mental health disparities in the future. Low self-esteem can arise from a variety of reasons. The system and method of the present disclosure may include one or more modules that address building self-esteem and confidence in a child. Telemedicine visits will be recommended via the system and method of the present disclosure or a local provider.

In the third part of the method, a referral may also generate referring the individual for services in areas where the evaluation results were sufficient to improve the child's skills, even though the child's skills are proficient for his or her age. For example, if the child demonstrates that he or she is able to demonstrate social communication, interaction, eye contact and able to demonstrate joint attention back and forth with assessment tasks, it may be indicative that the child's skills are not deficient, and the child needs to only to continue to build and/or improve his or her skills. Further, not showing restrictive and repetition behaviors, such as flapping their hands, spinning a lot, being only interested in lining up toys or objects, having sensory issue such as being upset with loud noises and difficulty with change of routine may also be indicative that the child's skills are not deficient, and the child needs to only to continue to build and/or improve his or her skills. Indeed, if the child is able to maintain attention, is not easily distracted, follows directions, etc. it may also be indicative that the child's skills are not deficient, and the child needs to only continue to build and/or improve his or her skills. Likewise, if the child is able to complete the tests without crying or worrying about how they are doing on the tests, it may also be indicative that the child's skills are not deficient, and the child needs to only to continue to build and/or improve his or her skills.

In some embodiments, the third part of the method further includes observing behavioral engagement skills of the child throughout the testing process, such as, for example, during the first test of the third part of the method, during the second test of the third part of the method, during the third test of the third part of the method, during the fourth test of the third part of the method and/or during the fifth test of the third part of the method. In some embodiments, the observations made throughout the testing process of the third part of the method can include noting the child's demeanor, such as, for example, observations pertaining to whether the child is cooperative, uncooperative, refuses to interact, completed the tests independently, exhibited poor eye contact, smiled, cried, was tired, would not engage, was shy, was distractible, was anxious, needed redirection for completion, was happy and engaged, was an English language learner, was difficult to motivate, etc. In some embodiments, the observations made throughout the testing process of the third part of the method are included in the worksheet (FIGS. 17A-17F or 18A-18F) and/or are used to generate the referral. In some embodiments, information pertaining to the answers provided in the questionnaire of the third part of the method (FIG. 16A or 16B) is included in the worksheet and/or is used to generate the referral.

Method—Part Four—Year Six

In a fourth part of the method, which should be administered after the third part of the method discussed above is administered to the child, when the child is approximately 6 years old, the child's parent's is required to fill out a questionnaire that includes various questions about the child. One embodiment of the questionnaire is shown in FIG. 21. As shown in FIG. 21, the questionnaire can include questions about the child's physical abilities, such as, for example, the child's hearing and vision. The questionnaire can also include questions relating to the child's ability to read, write, comprehend information, perform simple tasks, socialize, etc. For example, the questionnaire can include questions whether they can understand their child when the child speaks, whether the child is able to rhyme well, whether the child attends school, whether the child brushes his or her teeth with toothpaste, whether the child mixes up sounds in words, whether the child ever needed ear tubes, whether there is a family history of disorders, etc. (See, FIG. 21).

Figure 22E:
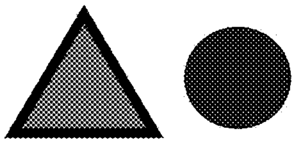
FIG. 22E is one embodiment of another page of the worksheet shown in FIG. 22A, in accordance with the principles of the present disclosure.
Figure 22F:
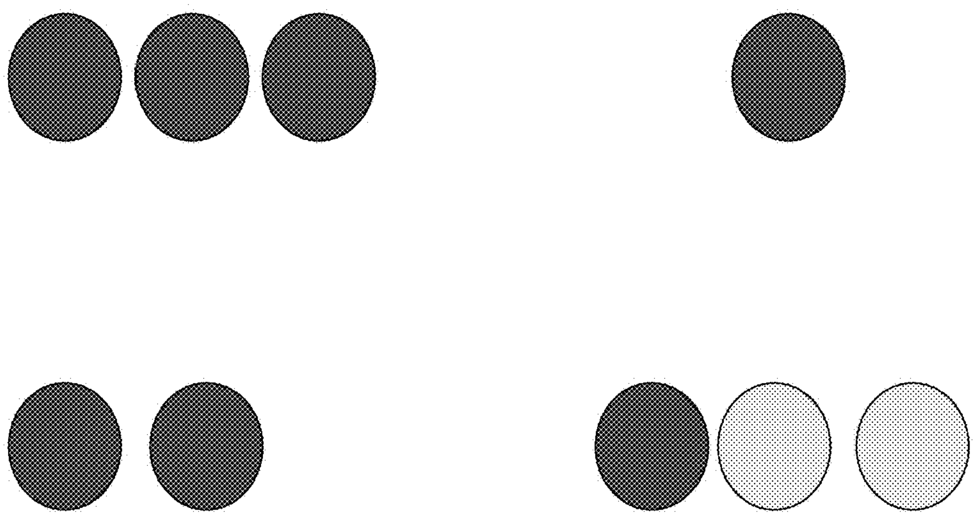
FIG. 22F is one embodiment of another page of the worksheet shown in FIG. 22A, in accordance with the principles of the present disclosure.
Figure 22G:
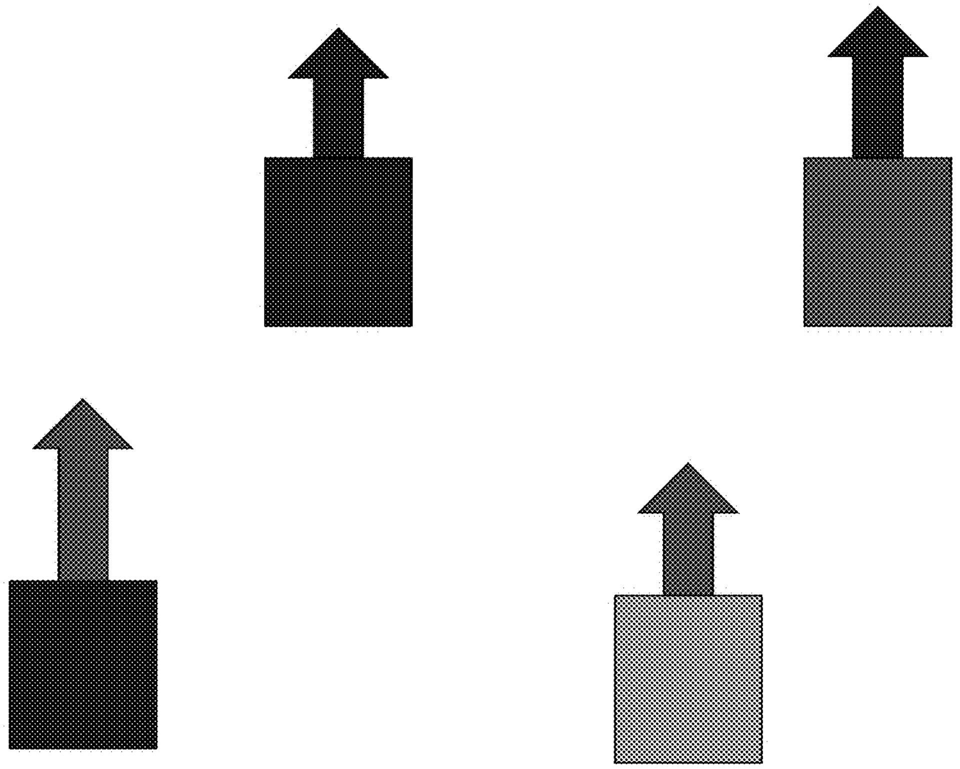
FIG. 22G is one embodiment of another page of the worksheet shown in FIG. 22A, in accordance with the principles of the present disclosure.
Figure 22H:
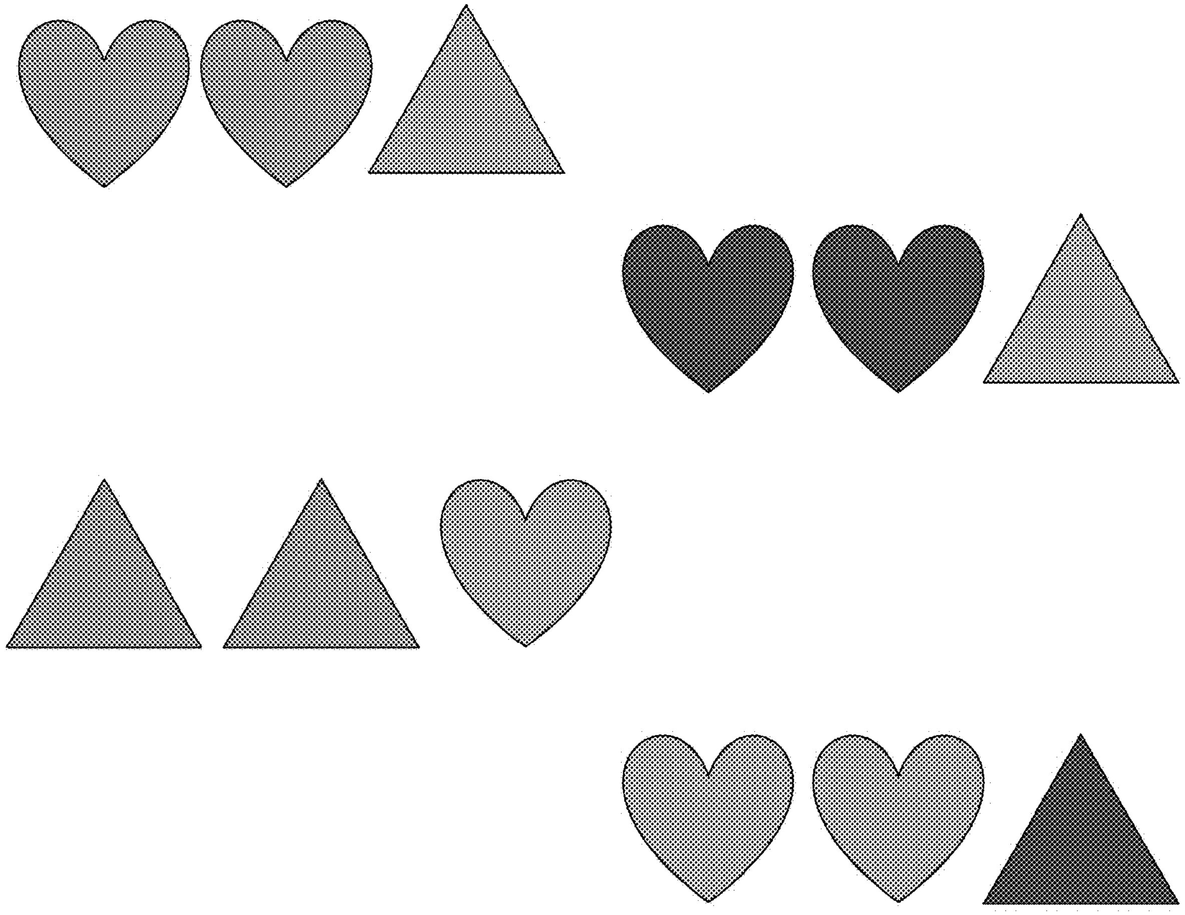
FIG. 22H is one embodiment of another page of the worksheet shown in FIG. 22A, in accordance with the principles of the present disclosure.
Figure 22I:
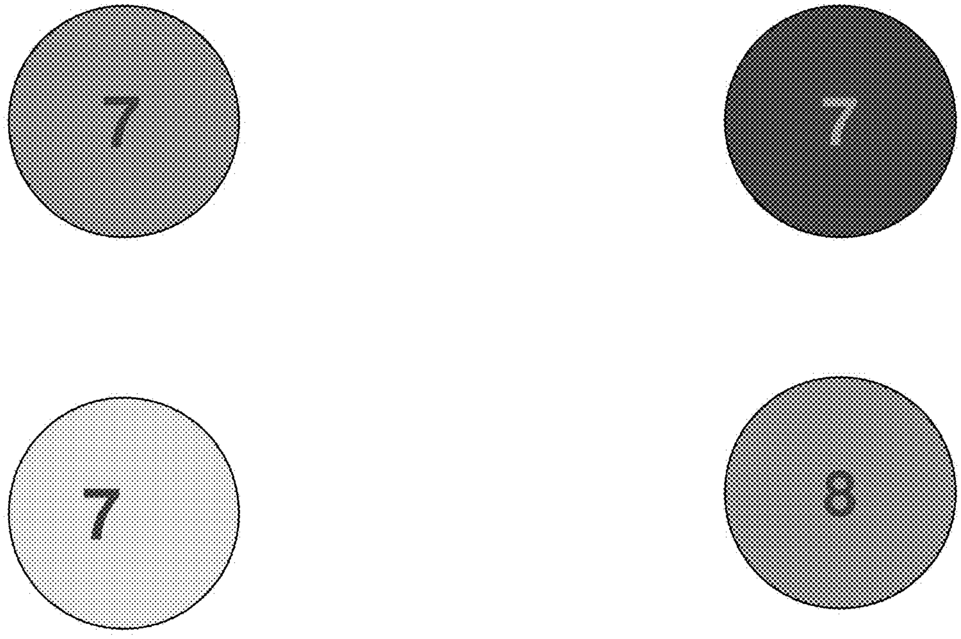
FIG. 22I is one embodiment of another page of the worksheet shown in FIG. 22A, in accordance with the principles of the present disclosure.

In the fourth part of the method, the child may be required to perform tests relating to receptive language, fine motor, letter naming and letter sound, phoneme elision (deletion), rhyming and/or reading skills (See, e.g., FIGS. 22A-22I; and FIGS. 23A-23I. For example, as shown in FIGS. 22A and 22B, the child may be required to show a show three red circles, to show a red arrow on top of a blue square, to show two red hearts and one orange triangle, to show a red number seven inside a yellow circle, etc. The child may also be required to perform a typical three-point pencil grip, draw a dog with six or more body parts, copy numbers one through six, write his or her first name and/or draw a triangle and circle (FIG. 22A). The child may also be required to say various letter names and/or letter sounds and/or perform a game relating to phoneme elision (deletion) similar to that discussed above in which the child is asked to take away a sound or sounds from a word (FIG. 22A). In one embodiment, the child may also be required to perform a rhyming exercise in which the child indicates whether or not two words rhyme (FIG. 22B). In one embodiment, the child may also be required to read nonsense or nonreal words in which the child indicates whether or not the nonsense or nonreal word rhymes with an existing or proper word (FIG. 22B). In some embodiment the document shown in FIGS. 22A-22I and/or the document shown in FIGS. 23A-23I may be used as a worksheet to record results of the tests taken by the child during the fourth part of the method.

Figure 23E:
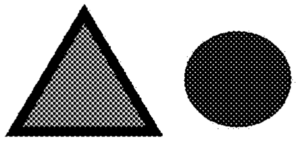
FIG. 23E is one embodiment of another page of the worksheet shown in FIG. 23A, in accordance with the principles of the present disclosure.
Figure 23F:
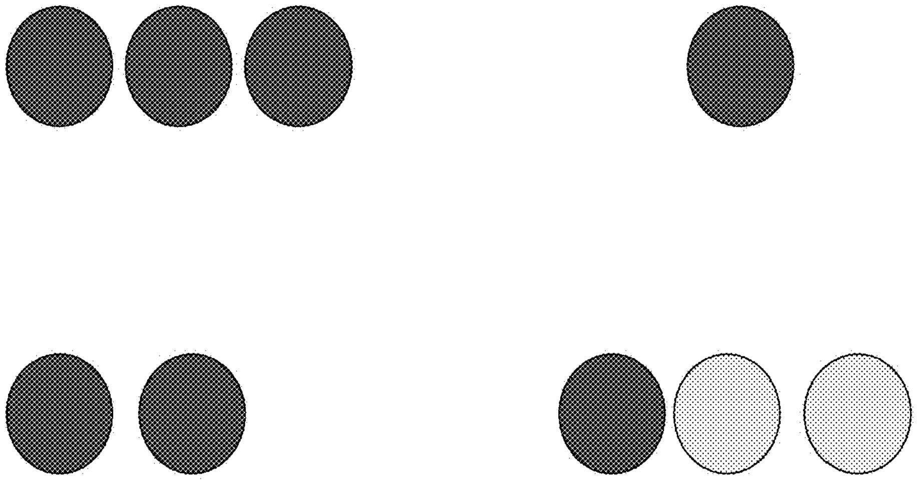
FIG. 23F is one embodiment of another page of the worksheet shown in FIG. 23A, in accordance with the principles of the present disclosure.
Figure 23G:
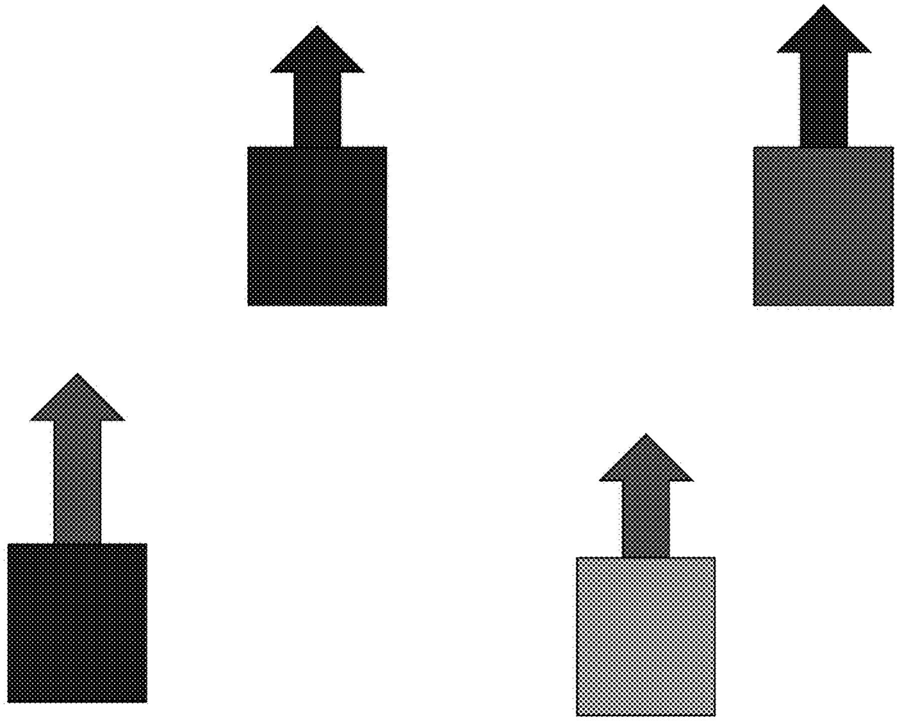
FIG. 23G is one embodiment of another page of the worksheet shown in FIG. 23A, in accordance with the principles of the present disclosure.
Figure 23H:
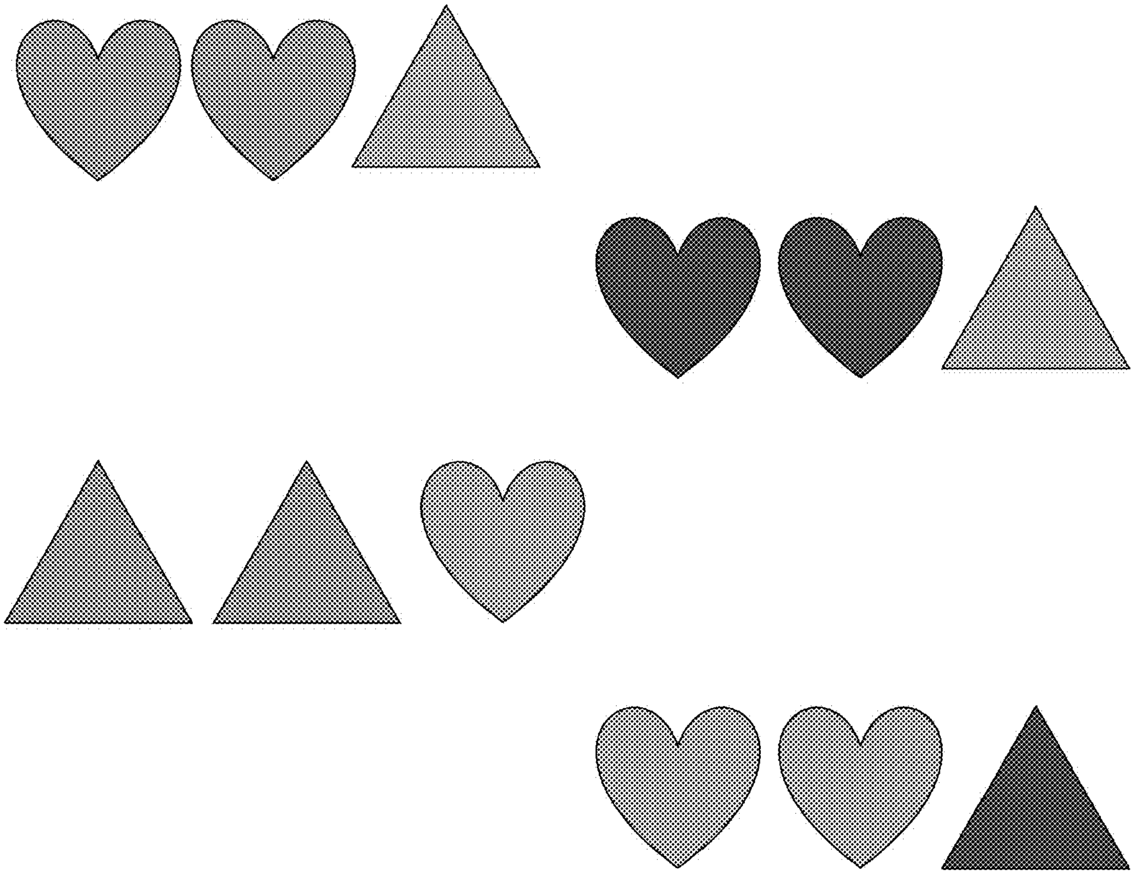
FIG. 23A is an example of one embodiment of one page of a worksheet used in connection with the fourth part of the method, in accordance with the principles of the present disclosure.
FIG. 23B is one embodiment of another page of the worksheet shown in FIG. 23A, in accordance with the principles of the present disclosure.
FIG. 23C is one embodiment of another page of the worksheet shown in FIG. 23A, in accordance with the principles of the present disclosure.
FIG. 23D is one embodiment of another page of the worksheet shown in FIG. 23A, in accordance with the principles of the present disclosure.
Figure 23I:
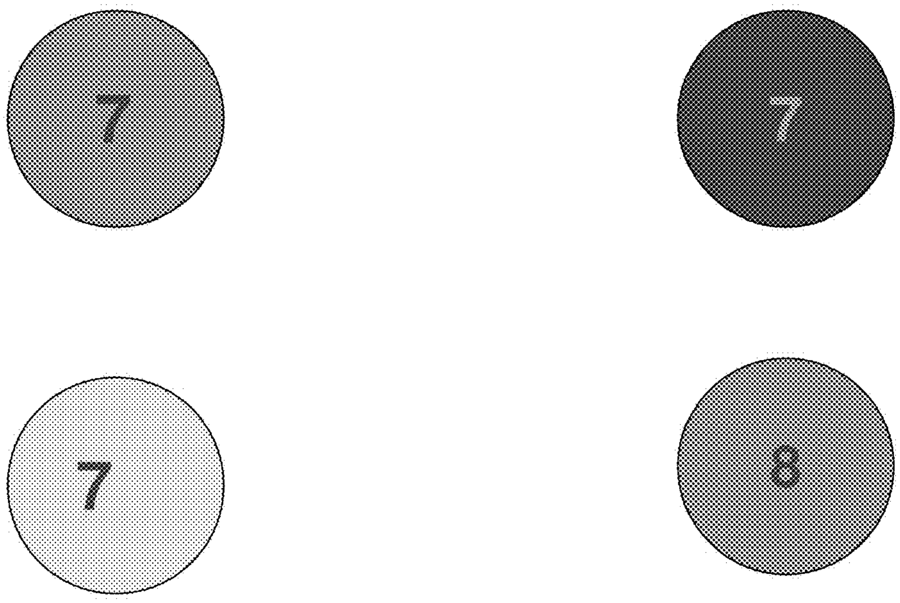

In one embodiment, shown in FIGS. 23A-23I, the child may be required to show a show two red circles, to show a blue arrow on top of a red square, to show two green hearts and one orange triangle, to show a red number seven inside a green circle, etc. The child may also be required to perform a typical three-point pencil grip, draw a dog with six or more body parts, copy numbers one through six, write his or her first name and/or draw a triangle and circle (FIG. 23A). The child may also be required to say various letter names and/or letter sounds and/or perform a game relating to phoneme elision (deletion) similar to that discussed above in which the child is asked to take away a sound or sounds from a word (FIG. 23A). In one embodiment, the child may also be required to perform a rhyming exercise in which the child indicates whether or not two words rhyme (FIG. 23B). In one embodiment, the child may also be required to read nonsense or nonreal words in which the child indicates whether or not the nonsense or nonreal word rhymes with an existing or proper word (FIG. 23B).

In the fourth part of the method, the tests discussed above and shown in FIGS. 22A-22I and/or FIGS. 23A-23I relate to fine motor skills, letter and sound identification skills, phonemic elision (sound deletion) skills and rhyming skills (FIGS. 22C and 22D and/or FIGS. 23C and 23D). The child's behavior may be observed during these tests for considerations such as, for example, whether the child is cooperative, whether the child is uncooperative, whether the child refuses to interact, whether the child completed tasks independently, whether the child exhibited poor eye contact, whether the child smiled, whether the child cried, whether the child appeared tired, whether or not the child would engage, whether the child was shy, whether the child was distractible, whether the child was anxious, whether the child needed redirection to complete tasks, whether the child was happy and engaged, whether the child is an English language learner, whether the child was difficult whether the child's speech was understandable, etc., as shown in FIGS. 22B and 23B.

In the third part of the method, tests for fine motor skills, letter and sound identification skills, phonemic elision (sound deletion) skills and rhyming skills (FIG. 22C) and/or receptive language skills, fine motor skills, sound and letter naming skills, phonemic elision skills and rhyming skills (FIG. 23C) are evaluated for the presence or absence of a disorder and/or school readiness. The ability of the child to perform the requested tasks is recorded to generate input data. The ability of the child to perform one or more of the requested tasks may be recorded in a fourth worksheet. One embodiment of the fourth worksheet is shown in FIGS. 22A-22I. Another embodiment of the fourth worksheet is shown in FIGS. 23A-23I.

The fine motor skill input data may include whether or not the child was able to perform required tasks. The ability of the child to perform the required tasks may be recorded in the fourth worksheet. The fine motor input data is evaluated against an answer key to generate a fine motor evaluation result. The fine motor evaluation result is another determination with respect to the presence or absence of fine motor deficiency, after the third determination with respect the presence or absence of fine motor conducted during the third part of the method. In some embodiments, the fine motor evaluation result includes a score, such as, for example, a number score. In some embodiments, the fine motor evaluation result includes a written evaluation, such as, for example, words written in sentence or note form that explain what was observed by the practitioner. In some embodiments, the fine motor result is included in an assessment that evaluates at least each of the tests administered during the fourth part of the method. One embodiment of the assessment is shown in FIGS. 24A-24O.

In the fourth part of the method, a second test is administered in which the child has to do a letter and sound identification task to generate a letter and sound identification task input data. The ability of the child to do a letter and sound identification task may be recorded in the third worksheet (FIGS. 22A-22I or FIGS. 23A-23I). The letter and sound identification input data is evaluated against an answer key to generate a letter and sound identification evaluation result. The letter and sound identification evaluation result is another determination with respect to the presence or absence of letter and sound identification deficiency, after the second determination with respect the presence or absence of letter and sound identification conducted during the third part of the method. In some embodiments, the letter and sound identification evaluation result include a score, such as, for example, a number score. In some embodiments, the letter and sound identification evaluation result include a written evaluation, such as, for example, words written in sentence or note form that explain what was observed by the practitioner. In some embodiments, the letter and sound identification evaluation result is included in the assessment (FIGS. 24A-24O). In some embodiments, the letter and sound identification evaluation result uses AI or other software to recognize and/or transcribe the child's letter sound/word pronunciation, analyze context/structure where pronunciation varies due to accents/dialects and word/sentence structure comprehension and fluency.

In the fourth part of the method, a third test is administered in which the child has to do a phonemic elision (sound deletion) task to generate a phonemic elision task input data. The ability of the child to do a phonemic elision task may be recorded in the fourth worksheet (FIGS. 22A-22I or FIGS. 23A-23I). The phonemic elision input data is evaluated against an answer key to generate a phonemic elision evaluation result. The phonemic elision evaluation result is another determination with respect to the presence or absence of phonemic elision deficiency, after the second determination with respect the presence or absence of phonemic elision deficiency conducted during the third part of the method. In some embodiments, the phonemic elision evaluation result includes a score, such as, for example, a number score. In some embodiments, the phonemic elision evaluation result includes a written evaluation, such as, for example, words written in sentence or note form that explain what was observed by the practitioner. In some embodiments, the phonemic elision evaluation result is included in the assessment (FIGS. 24A-24O). In some embodiments, the phonemic elision evaluation result uses AI or other software to recognize and/or transcribe the child's letter sound/word pronunciation, analyze context/structure where pronunciation varies due to accents/dialects and word/sentence structure comprehension and fluency.

In the fourth part of the method, a fourth test is administered in which the child has to do a rhyming task to generate a rhyming task input data. The ability of the child to do a rhyming task may be recorded in the third worksheet (FIGS. 22A-22I or FIGS. 23A-23I). The rhyming task input data is evaluated against an answer key to generate a rhyming evaluation result. The rhyming evaluation result is another determination with respect to the presence or absence of rhyming deficiency, after the third determination with respect the presence or absence of rhyming deficiency conducted during the third part of the method. Indeed, because rhyming is a phonological skill, the fourth test will test the child's ability to create a repetition of similar sounds in to or more words, which requires the ability to know if the sounds are the same or different. In some embodiments, the rhyming evaluation result includes a score, such as, for example, a number score. In some embodiments, the rhyming evaluation result includes a written evaluation, such as, for example, words written in sentence or note form that explain what was observed by the practitioner. In some embodiments, the rhyming evaluation result is included in the assessment (FIGS. 24A-24O). In some embodiments, the rhyming evaluation result uses AI or other software to recognize and/or transcribe the child's letter sound/word pronunciation, analyze context/structure where pronunciation varies due to accents/dialects and word/sentence structure comprehension and fluency.

In one embodiment of the fourth part of the method, a fifth test is administered in which the child has to do a nonsense words exercise that compares nonsense words with real words to generate a nonsense word skill input data. The ability of the child to do a nonsense word skill may be recorded in the third worksheet (FIGS. 22A-22I or FIGS. 23A-23I). The nonsense word skill input data is evaluated against an answer key to generate a nonsense word skill evaluation result. The nonsense word skill evaluation result is another determination with respect to the presence or absence of nonsense word skills. In some embodiments, the nonsense word skill evaluation result includes a score, such as, for example, a number score. In some embodiments, the nonsense word skill evaluation result includes a written evaluation, such as, for example, words written in sentence or note form that explain what was observed by the practitioner. In some embodiments, the nonsense word skill evaluation result is included in the assessment (FIGS. 22A-22P). In some embodiments, the nonsense word skill evaluation result uses AI or other software to recognize and/or transcribe the child's letter sound/word pronunciation, analyze context/structure where pronunciation varies due to accents/dialects and word/sentence structure comprehension and fluency.

In the fourth part of the method, a referral is generated referring the individual for services in areas where the evaluation results were deficient to promote at least one of the skills tested in the fourth part of the method. In some embodiments, the assessment (FIGS. 24A-24O), which can include one or more of the test results in the fourth part of the method are evaluated to generate the referral. In particular, if the results indicate that the child has proficient fine motor skills, the child is not referred for services, such as, for example, occupational therapy to promote advancement in fine motor skills. If, however, the test results indicate that the child is deficient with his or her fine motor skills, the child is referred for services, such as, for example, speech therapy to promote advancement in fine motor skills. Likewise, if the results indicate that the child has proficient letter and sound identification skills, the child is not referred for services, such as, for example, occupational therapy to promote advancement in letter and sound identification skills. If, however, the test results indicate that the child is deficient with his or her letter and sound identification skills, the child is referred for services, such as, for example, Speech therapy to promote advancement in letter and sound identification skills. If the results indicate that the child has proficient phonemic elision skills, the child is not referred for services, such as, for example, Speech therapy to promote advancement in phonemic elision skills. If, however, the test results indicate that the child is deficient with his or her phonemic elision skills, the child is referred for services, such as, for example, Speech therapy to promote advancement in phonemic elision skills. If the results indicate that the child has proficient rhyming/phonological awareness skills, the child is not referred for services, such as, for example, Speech therapy to promote advancement in rhyming/phonological awareness skills. If, however, the test results indicate that the child is deficient with his or her rhyming/phonological awareness skills, the child is referred for services, such as, for example, Speech therapy to promote advancement in rhyming/phonological awareness skills. Lastly, if the results indicate that the child has proficient nonsense word skills, the child is not referred for services, such as, for example, speech therapy to promote advancement in nonsense word skills. If, however, the test results indicate that the child is deficient with his or her nonsense word skills, the child is referred for services, such as, for example, Speech therapy to promote advancement in nonsense word skills.

In some embodiments, the fourth part of the method includes evaluating the child for ADHD, autism, anxiety, panic attacks, post-traumatic stress disorder (PTSD), depression, low self-esteem, etc. if the evaluation results in the fourth part of the method were deficient to promote at least one of the skills tested in the fourth part of the method.

The ADHD evaluation in the fourth part of the method can include giving focused tips on a structured environment, making learning activities fun, multisensory activities, and short but repetitive opportunities for learning. If engagement is appropriate, but focus/attention to a task cannot be maintained for the age expected time for the child's age, then the method may refer the child to take a test that includes ADHD/ADD age specific questions and consider all factors that can affect attention and sustained focus. In some embodiments, if the child exhibits signs of ADHD/ADD, the method can be adapted to administer and score a Vanderbilt screen for parent and teacher (if applicable). These screens are diagnostic of ADHD/ADD. Absence seizure must be ruled out by EEG or another medical device.

Concerning autism, the fourth part of the method includes evaluating whether the child has challenges with social communication and interaction, has poor eye contact, refuses to engage in tasks, and/or lacks joint attention back and forth while doing assessment tasks. For example, if the child demonstrates restrictive/repetitive behaviors, interests, and activities such as, but not limited to, flapping hands, spinning, lining up toys/objects, sensory issues (upset by loud noises/smell/touch), and challenges with change of routine during tasks, the evaluation should include an autism evaluation.

If the autism evaluation of the present method may recommend activities and/or worksheets that are adapted to address the specific concerns of lack of engagement/language delay affecting social interaction, high concerns for Autistic Spectrum Disorder (ASD), or ASD confirmed. This will include activities that focus on strengthening receptive, expressive, and pragmatic language skills; specific games and activities addressing language goals. To improve sensory regulation, the autism evaluation of the present method may recommend specific games and activities to decrease sensory triggers whether they be hypo (low) or hyper (high) sensory. To address sensory seeking behaviors and/or sensory avoidance behaviors, the autism evaluation may include recommending Occupational Therapy (OT) like play activities with OT therapy goals addressing visual/motor integration, sensory regulation, visual perceptual skills, executive function, and primitive reflex integration.

The system and method of the present disclosure can be used to treat and strengthen skills along with in-person therapy especially when waiting for in-person therapy. The system and method of the present disclosure can recommend starting therapeutic advancement of identified skill deficits while at home when awaiting in-person therapies. Such therapeutic advancement can be used to augment and reinforce the actual future or current therapies in place like medically delivered Speech and Language Therapy, OT, Cognitive Behavioral Therapy, and PT. The system and method of the present disclosure can include engagement modules and/or worksheets that allow Early Intervention to immediately start while a child waits for in-person evaluation and/or in-person autism specific therapy. The system and method of the present disclosure can improve skills and reassessment will allow progress. Children should continue using the system and method of the present disclosure even after starting in-person therapy. Referral pursuant to the autism evaluation can include referring the child for an in-person Speech and Language Evaluation, referring the child for an in-person Sensory Integration Focused Occupational Therapy Evaluation, referring the child for an in-person Diagnostic Evaluation for Autism, referring the child for in-person Child Play Therapy.

Concerning anxiety, panic attacks, or PTSD, if the child is showing emotions of frustration with or without crying and/or demonstrating worry about their performance while completing the assessment, has an elevated heart rate and/or blood pressure and/or avoids behaviors when tasks are hard such as: complaining to end or get out of a task like, having headaches, having nausea, stomach aches, vomiting, having tiredness, yawning, falling asleep, having a tense posture, clenched shoulders or muscles, clenched teeth, pulling on eyelashes, biting fingers or fingernails, arguing, throwing the materials, leaving the test environment, saying they are thirsty, hungry, tired, sleepy, or having to all of a sudden got to go to the bathroom, complains of their heart racing, goes selectively mute, or is unable to attempt to complete the tests in part or at all, the evaluation should include an anxiety, panic attack, or PTSD evaluation.

The system and method of the present disclosure may be configured to determine through an anxiety algorithm module and/or caregiver/teacher or authorized personnel to start Anxiety modules as well to start arranged telemedicine visits through the system and method of the present disclosure and/or in-person therapy. Also, the Caregiver/teacher will work on language development, social interaction, and sensory regulation by using a 6-Year-Old Developmental Milestone Information Sheet (DMIS) of the system and method of the present disclosure for age-appropriate activities. One example of a 6-Year-Old Developmental Milestone Information Sheet is shown in FIGS. 25A-25G. The system and method of the present disclosure may be configured to administer and score a diagnostic screen such as PHQ-9/SCARED/Columbia/Hamilton/GAD-7 or others for Anxiety that is appropriate for age. Based on the system and method of the present disclosure, Children will also be started on telemedicine services through the system and method of the present disclosure for anxiety.

Reasons for indications for medicine management for Anxiety is determined by the system and method of the present disclosure, physician, and input from caregiver/teacher. Pulse, Blood Pressure and EKG will be obtained by digital devices and are medically necessary before starting medication. Telemedicine services for anxiety though the system and method of the present disclosure must also be initiated and continued while the child is on medication for anxiety. All children diagnosed with Anxiety through the system and method of the present disclosure will also be evaluated for ADHD/ADD and/or Autism, if indicated.

Concerning low self-esteem, self-esteem should always be monitored closely in a child as this can lead to depression or other mental health disparities in the future. Low self-esteem can arise from a variety of reasons. The system and method of the present disclosure may include one or more modules that address building self-esteem and confidence in a child. Telemedicine visits will be recommended via the system and method of the present disclosure or a local provider.

In the fourth part of the method, a referral may also generate referring the individual for services in areas where the evaluation results were sufficient to improve the child's skills, even though the child's skills are proficient for his or her age. For example, if the child demonstrates that he or she is able to demonstrate social communication, interaction, eye contact and able to demonstrate joint attention back and forth with assessment tasks, it may be indicative that the child's skills are not deficient, and the child needs to only to continue to build and/or improve his or her skills. Further, not showing restrictive and repetition behaviors, such as flapping their hands, spinning a lot, being only interested in lining up toys or objects, having sensory issue such as being upset with loud noises and difficulty with change of routine may also be indicative that the child's skills are not deficient, and the child needs to only to continue to build and/or improve his or her skills. Indeed, if the child is able to maintain attention, is not easily distracted, follows directions, etc. it may also be indicative that the child's skills are not deficient, and the child needs to only continue to build and/or improve his or her skills. Likewise, if the child is able to complete the tests without crying or worrying about how they are doing on the tests, it may also be indicative that the child's skills are not deficient, and the child needs to only to continue to build and/or improve his or her skills.

In some embodiments, the fourth part of the method further includes observing behavioral engagement skills of the child throughout the testing process, such as, for example, during the first test of the fourth part of the method, during the second test of the fourth part of the method, during the third test of the fourth part of the method, during the fourth test of the fourth part of the method and/or during the fifth test of the fourth part of the method. In some embodiments, the observations made throughout the testing process of the fourth part of the method can include noting the child's demeanor, such as, for example, observations pertaining to whether the child is cooperative, uncooperative, refuses to interact, completed the tests independently, exhibited poor eye contact, smiled, cried, was tired, would not engage, was shy, was distractible, was anxious, needed redirection for completion, was happy and engaged, was an English language learner, was difficult to motivate, etc. In some embodiments, the observations made throughout the testing process of the fourth part of the method are included in the worksheet (FIGS. 22A-22I or 23A-23I) and/or are used to generate the referral. In some embodiments, information pertaining to the answers provided in the questionnaire of the fourth part of the method (FIG. 21) is included in the worksheet and/or is used to generate the referral.

Method—Part Five—Years Seven and Eight

In a fifth part of the method, which should be administered after the fourth part of the method discussed above is administered to the child, when the child is approximately 7 or 8 years old, the child's parent's is required to fill out a questionnaire that includes various questions about the child. One embodiment of the questionnaire is shown in FIG. 26. As shown in FIG. 26, the questionnaire can include questions about the child's ability to read, ability to spell as well as the child's physical abilities, such as, for example, the child's hearing and vision. The questionnaire can also include questions relating to the child's ability to read, write, comprehend information, perform simple tasks, socialize, etc. For example, the questionnaire can include questions whether they can understand their child when the child speaks, whether the child avoids reading, mixes up sounds in words, has had their speech tested, whether the child has difficulty spelling, whether homework takes the child longer than it should, whether the child has difficulty with math word problems, whether the child struggles with multi-step directions, whether there is a family history of disorders, whether the child enjoys reading, whether it is easy for the child to learn new words, whether the child can tie their own shoes, etc. (See, FIG. 26).

In the fifth part of the method, the child may be required to perform tests relating to fine motor skills, phoneme elision (deletion) skills, rhyming and/or reading skills (See, e.g., FIGS. 27A-27E; and FIGS. 28A-28E. For example, as shown in FIGS. 27A and 28A, the child may be required to perform a typical three-point pencil grip, write his or her first name, write three words that have three or four letters in each word, copy a shape, write numbers 1-10 and/or write the first 10 letters of the ABCs in lower case. In one embodiment, the child may also be required to read one or more single words (FIGS. 27A and 28A). In one embodiment, the child may also be required to read nonsense or nonreal words in which the child indicates whether or not the nonsense or nonreal word rhymes with an existing or proper word (FIGS. 27A and 28A).

In the fifth part of the method, the tests discussed above and shown in FIGS. 27A-22E and/or FIGS. 28A-28E relate to fine motor skills, phonemic elision (sound deletion) skills and reading skills (FIG. 27C and/or FIG. 28C). The child's behavior may be observed during these tests for considerations such as, for example, whether the child is cooperative, whether the child is uncooperative, whether the child refuses to interact, whether the child completed tasks independently, whether the child exhibited poor eye contact, whether the child smiled, whether the child cried, whether the child appeared tired, whether or not the child would engage, whether the child was shy, whether the child was distractible, whether the child was anxious, whether the child needed redirection to complete tasks, whether the child was happy and engaged, whether the child is an English language learner, whether the child was difficult whether the child's speech was understandable, etc., as shown in FIGS. 27B and 28B.

In the fifth part of the method, tests for fine motor skills, phonemic elision (sound deletion) skills and reading skills (FIG. 27C or 28C) are evaluated for the presence or absence of a disorder and/or school readiness. The ability of the child to perform the requested tasks is recorded to generate input data. The ability of the child to perform one or more of the requested tasks may be recorded in a fifth worksheet. One embodiment of the fourth worksheet is shown in FIGS. 27A-27E. Another embodiment of the fifth worksheet is shown in FIGS. 28A-28E.

The fine motor skill input data may include whether or not the child was able to perform required tasks. The ability of the child to perform the required tasks may be recorded in the fifth worksheet. The fine motor input data is evaluated against an answer key to generate a fine motor evaluation result. The fine motor evaluation result is another determination with respect to the presence or absence of fine motor deficiency, after the fourth determination with respect the presence or absence of fine motor conducted during the fourth part of the method. In some embodiments, the fine motor evaluation result includes a score, such as, for example, a number score. In some embodiments, the fine motor evaluation result includes a written evaluation, such as, for example, words written in sentence or note form that explain what was observed by the practitioner. In some embodiments, the fine motor result is included in an assessment that evaluates at least each of the tests administered during the fourth part of the method. One embodiment of the assessment is shown in FIGS. 29A-29M.

In the fifth part of the method, a second test is administered in which the child has to do a phonemic elision (sound deletion) task to generate a phonemic elision task input data. The ability of the child to do a phonemic elision task may be recorded in the fourth worksheet (FIGS. 27A-27E or FIGS. 28A-28E). The phonemic elision input data is evaluated against an answer key to generate a phonemic elision evaluation result. The phonemic elision evaluation result is another determination with respect to the presence or absence of phonemic elision deficiency, after the fourth determination with respect the presence or absence of phonemic elision deficiency conducted during the fourth part of the method. In some embodiments, the phonemic elision evaluation result includes a score, such as, for example, a number score. In some embodiments, the phonemic elision evaluation result includes a written evaluation, such as, for example, words written in sentence or note form that explain what was observed by the practitioner. In some embodiments, the phonemic elision evaluation result is included in the assessment (FIGS. 29A-29M). In some embodiments, the phonemic elision evaluation result uses AI or other software to recognize and/or transcribe the child's letter sound/word pronunciation, analyze context/structure where pronunciation varies due to accents/dialects and word/sentence structure comprehension and fluency.

In the fifth part of the method, a third test is administered in which the child has to read sight words to generate a sight word reading input data. The ability of the child to do a sight word task may be recorded in the third worksheet (FIGS. 27A-27E or FIGS. 28A-28E). The sight word reading input data is evaluated against an answer key to generate a sight word reading evaluation result. The sight word reading evaluation result is a determination with respect to the presence or absence of sight word reading deficiency conducted during the fifth part of the method. In some embodiments, the sight word reading evaluation result includes a score, such as, for example, a number score. In some embodiments, the sight word reading evaluation result includes a written evaluation, such as, for example, words written in sentence or note form that explain what was observed by the practitioner. In some embodiments, the sight word reading evaluation result is included in the assessment (FIGS. 29A-29M). In some embodiments, the sight word reading evaluation result uses AI or other software to recognize and/or transcribe the child's letter sound/word pronunciation, analyze context/structure where pronunciation varies due to accents/dialects and word/sentence structure comprehension and fluency.

In one embodiment of the fifth part of the method, a fourth test is administered in which the child has to do a nonsense words exercise that compares nonsense words with real words to generate a nonsense word skill input data. The ability of the child to do a nonsense word skill may be recorded in the fifth worksheet (FIGS. 27A-27E or FIGS. 28A-28E). The nonsense word skill input data is evaluated against an answer key to generate a nonsense word skill evaluation result. The nonsense word skill evaluation result is another determination with respect to the presence or absence of nonsense word skills. In some embodiments, the nonsense word skill evaluation result includes a score, such as, for example, a number score. In some embodiments, the nonsense word skill evaluation result includes a written evaluation, such as, for example, words written in sentence or note form that explain what was observed by the practitioner. In some embodiments, the nonsense word skill evaluation result is included in the assessment (FIGS. 29A-29M). In some embodiments, the nonsense word skill evaluation result uses AI or other software to recognize and/or transcribe the child's letter sound/word pronunciation, analyze context/structure where pronunciation varies due to accents/dialects and word/sentence structure comprehension and fluency.

In the fifth part of the method, a referral is generated referring the individual for services in areas where the evaluation results were deficient to promote at least one of the skills tested in the fifth part of the method. In some embodiments, the assessment (FIGS. 29A-29M), which can include one or more of the test results in the fifth part of the method are evaluated to generate the referral. In particular, if the results indicate that the child has proficient fine motor skills, the child is not referred for services, such as, for example, occupational therapy to promote advancement in fine motor skills. If, however, the test results indicate that the child is deficient with his or her fine motor skills, the child is referred for services, such as, for example, occupational therapy to promote advancement in fine motor skills. Likewise, if the results indicate that the child has proficient phonemic elision skills, the child is not referred for services, such as, for example, speech therapy to promote advancement in phonemic elision skills. If, however, the test results indicate that the child is deficient with his or her phonemic elision skills, the child is referred for services, such as, for example, Speech therapy to promote advancement in phonemic elision skills. If the results indicate that the child has proficient sight word reading skills, the child is not referred for services, such as, for example, speech therapy to promote advancement in sight word reading skills. If, however, the test results indicate that the child is deficient with his or her sight word reading skills, the child is referred for services, such as, for example, Speech therapy to promote advancement in sight word reading skills. Lastly, if the results indicate that the child has proficient nonsense word skills, the child is not referred for services, such as, for example, Speech therapy to promote advancement in nonsense word skills. If, however, the test results indicate that the child is deficient with his or her nonsense word skills, the child is referred for services, such as, for example, Speech therapy to promote advancement in nonsense word skills.

In some embodiments, the fifth part of the method includes evaluating the child for ADHD, autism, anxiety, panic attacks, post-traumatic stress disorder (PTSD), depression, low self-esteem, etc. if the evaluation results in the fifth part of the method were deficient to promote at least one of the skills tested in the fifth part of the method.

The ADHD evaluation in the fifth part of the method can include giving focused tips on a structured environment, making learning activities fun, multisensory activities, and short but repetitive opportunities for learning. If engagement is appropriate, but focus/attention to a task cannot be maintained for the age expected time for the child's age, then the method may refer the child to take a test that includes ADHD/ADD age specific questions and consider all factors that can affect attention and sustained focus. In some embodiments, if the child exhibits signs of ADHD/ADD, the method can be adapted to administer and score a Vanderbilt screen for parent and teacher (if applicable). These screens are diagnostic of ADHD/ADD. Must rule out absence seizure with EEG or with another medical device.

Concerning autism, the fifth part of the method includes evaluating whether the child has challenges with social communication and interaction, has poor eye contact, refuses to engage in tasks, and/or lacks joint attention back and forth while doing assessment tasks. For example, if the child demonstrates restrictive/repetitive behaviors, interests, and activities such as, but not limited to, flapping hands, spinning, lining up toys/objects, sensory issues (upset by loud noises/smell/touch), and challenges with change of routine during tasks, the evaluation should include an autism evaluation.

If the autism evaluation of the present method may recommend activities and/or worksheets that are adapted to address the specific concerns of lack of engagement/language delay affecting social interaction, high concerns for Autistic Spectrum Disorder (ASD), or ASD confirmed. This will include activities that focus on strengthening receptive, expressive, and pragmatic language skills; specific games and activities addressing language goals. To improve sensory regulation, the autism evaluation of the present method may recommend specific games and activities to decrease sensory triggers whether they be hypo (low) or hyper (high) sensory. To address sensory seeking behaviors and/or sensory avoidance behaviors, the autism evaluation may include recommending Occupational Therapy (OT) like play activities with OT therapy goals addressing visual/motor integration, sensory regulation, visual perceptual skills, executive function, and primitive reflex integration.

The system and method of the present disclosure can be used to treat and strengthen skills along with in-person therapy especially when waiting for in-person therapy. The system and method of the present disclosure can recommend starting therapeutic advancement of identified skill deficits while at home when awaiting in-person therapies. Such therapeutic advancement can be used to augment and reinforce the actual future or current therapies in place like medically delivered Speech and Language Therapy, OT, Cognitive Behavioral Therapy, and PT. The system and method of the present disclosure can include engagement modules and/or worksheets that allow Early Intervention to immediately start while a child waits for in-person evaluation and/or in-person autism specific therapy. The system and method of the present disclosure can improve skills and reassessment will allow progress. Children should continue using the system and method of the present disclosure even after starting in-person therapy. Referral pursuant to the autism evaluation can include referring the child for an in-person Speech and Language Evaluation, referring the child for an in-person Sensory Integration Focused Occupational Therapy Evaluation, referring the child for an in-person Diagnostic Evaluation for Autism, referring the child for in-person Child Play Therapy.

Concerning anxiety, panic attacks, or PTSD, if the child is showing emotions of frustration with or without crying and/or demonstrating worry about their performance while completing the assessment, has an elevated heart rate and/or blood pressure and/or avoids behaviors when tasks are hard such as: complaining to end or get out of a task like, having headaches, having nausea, stomach aches, vomiting, having tiredness, yawning, falling asleep, having a tense posture, clenched shoulders or muscles, clenched teeth, pulling on eyelashes, biting fingers or fingernails, arguing, throwing the materials, leaving the test environment, saying they are thirsty, hungry, tired, sleepy, or having to all of a sudden got to go to the bathroom, complains of their heart racing or is unable to attempt to complete the tests in part or at all, the evaluation should include an anxiety, panic attack, or PTSD evaluation.

The system and method of the present disclosure may be configured to determine through an anxiety algorithm module and/or caregiver/teacher or authorized personnel to start Anxiety modules as well to start arranged telemedicine visits through the system and method of the present disclosure and/or in-person therapy. Also, the Caregiver/teacher will work on language development, social interaction, and sensory regulation by using a 7- and 8-Year-Old Developmental Milestone Information Sheet (DMIS) of the system and method of the present disclosure for age-appropriate activities. One example of a 7- and 8-Year-Old Developmental Milestone Information Sheet is shown in FIGS. 30A-30F. The system and method of the present disclosure may be configured to administer and score a diagnostic screen such as PHQ-9/SCARED/Columbia/Hamilton/GAD-7 or others for Anxiety that is appropriate for age. Based on the system and method of the present disclosure, Children will also be started on telemedicine services through the system and method of the present disclosure for anxiety.

Reasons for indications for medicine management for Anxiety is determined by the system and method of the present disclosure, physician, and input from caregiver/teacher. Pulse, Blood Pressure and EKG will be obtained by digital devices and are medically necessary before starting medication. Telemedicine services for anxiety though the system and method of the present disclosure must also be initiated and continued while the child is on medication for anxiety. All children diagnosed with Anxiety through the system and method of the present disclosure will also be evaluated for ADHD/ADD and/or Autism.

Concerning low self-esteem, self-esteem should always be monitored closely in a child as this can lead to depression or other mental health disparities in the future. Low self-esteem can arise from a variety of reasons. The system and method of the present disclosure may include one or more modules that address building self-esteem and confidence in a child. Telemedicine visits will be recommended via the system and method of the present disclosure or a local provider.

In the fifth part of the method, a referral may also generate referring the individual for services in areas where the evaluation results were sufficient to improve the child's skills, even though the child's skills are proficient for his or her age. For example, if the child demonstrates that he or she is able to demonstrate social communication, interaction, eye contact and able to demonstrate joint attention back and forth with assessment tasks, it may be indicative that the child's skills are not deficient, and the child needs to only to continue to build and/or improve his or her skills. Further, not showing restrictive and repetition behaviors, such as flapping their hands, spinning a lot, being only interested in lining up toys or objects, having sensory issue such as being upset with loud noises and difficulty with change of routine may also be indicative that the child's skills are not deficient, and the child needs to only to continue to build and/or improve his or her skills. Indeed, if the child is able to maintain attention, is not easily distracted, follows directions, etc. it may also be indicative that the child's skills are not deficient, and the child needs to only continue to build and/or improve his or her skills. Likewise, if the child is able to complete the tests without crying or worrying about how they are doing on the tests, it may also be indicative that the child's skills are not deficient, and the child needs to only to continue to build and/or improve his or her skills.

In some embodiments, the fifth part of the method further includes observing behavioral engagement skills of the child throughout the testing process, such as, for example, during the first test of the fifth part of the method, during the second test of the fifth part of the method, during the third test of the fifth part of the method and/or during the fourth test of the fifth part of the method. In some embodiments, the observations made throughout the testing process of the fifth part of the method can include noting the child's demeanor, such as, for example, observations pertaining to whether the child is cooperative, uncooperative, refuses to interact, completed the tests independently, exhibited poor eye contact, smiled, cried, was tired, would not engage, was shy, was distractible, was anxious, needed redirection for completion, was happy and engaged, was an English language learner, was difficult to motivate, etc. In some embodiments, the observations made throughout the testing process of the fifth part of the method are included in the worksheet (FIGS. 27A-27E or 28A-28E) and/or are used to generate the referral. In some embodiments, information pertaining to the answers provided in the questionnaire of the fifth part of the method (FIG. 26) is included in the worksheet and/or is used to generate the referral.

Method—Part Six—Years Nine+

In a sixth part of the method, which should be administered after the fifth part of the method discussed above is administered to the child, when the child is approximately 9 years old or older, the child's parent's is required to fill out a questionnaire that includes various questions about the child. One embodiment of the questionnaire is shown in FIG. 31. As shown in FIG. 31, the questionnaire can include questions about the child's ability to read, ability to spell as well as the child's physical abilities, such as, for example, the child's hearing and vision. The questionnaire can also include questions relating to the child's ability to read, write, comprehend information, perform simple tasks, socialize, etc. For example, the questionnaire can include questions whether they can understand their child when the child speaks, whether the child avoids reading, mixes up sounds in words, has had their speech tested, whether the child has difficulty spelling, whether homework takes the child longer than it should, whether the child has difficulty with math word problems, whether the child struggles with multi-step directions, whether there is a family history of disorders, whether the child enjoys reading, whether it is easy for the child to sound out new words, whether the child can tie their own shoes, etc. (See, FIG. 31).

In the sixth part of the method, the child may be required to perform tests relating to fine motor skills, phoneme elision (deletion) skills, rhyming and/or reading skills (See, e.g., FIGS. 32A-32F; and FIGS. 33A-33E. For example, the child may be required to perform a typical three-point pencil grip, copy three overlapping circles, copy a sentence, write names from memory, write lower case ABC's. In one embodiment, the child may also be required to perform a phoneme elision (deletion) exercise in which the child is to say a word, such as, for example, "raindrop," and the say raindrop without saying "drop," for example. In one embodiment, the child may also be required to read one or more single words. In one embodiment, the child may also be required to read nonsense or nonreal words in which the child indicates whether or not the nonsense or nonreal word rhymes with an existing or proper word.

In the sixth part of the method, the tests discussed above and shown in FIGS. 32A-32F and/or FIGS. 33A-33E relate to fine motor skills, phonemic elision (sound deletion) skills and reading skills. The child's behavior may be observed during these tests for considerations such as, for example, whether the child is cooperative, whether the child is uncooperative, whether the child refuses to interact, whether the child completed tasks independently, whether the child exhibited poor eye contact, whether the child smiled, whether the child cried, whether the child appeared tired, whether or not the child would engage, whether the child was shy, whether the child was distractible, whether the child was anxious, whether the child needed redirection to complete tasks, whether the child was happy and engaged, whether the child is an English language learner, whether the child was difficult whether the child's speech was understandable, etc., as shown in FIGS. 32B and 33B.

In the sixth part of the method, tests for fine motor skills, phonemic elision (sound deletion) skills and reading skills (FIGS. 32C and 32D; or 33B and 33C) are evaluated for the presence or absence of a disorder and/or school readiness. The ability of the child to perform the requested tasks is recorded to generate input data. The ability of the child to perform one or more of the requested tasks may be recorded in a sixth worksheet. One embodiment of the fourth worksheet is shown in FIGS. 32A-32F. Another embodiment of the fifth worksheet is shown in FIGS. 33A-33E.

The fine motor skill input data may include whether or not the child was able to perform required tasks. The ability of the child to perform the required tasks may be recorded in the sixth worksheet. The fine motor input data is evaluated against an answer key to generate a fine motor evaluation result. The fine motor evaluation result is another determination with respect to the presence or absence of fine motor deficiency, after the fifth determination with respect the presence or absence of fine motor conducted during the fifth part of the method. In some embodiments, the fine motor evaluation result includes a score, such as, for example, a number score. In some embodiments, the fine motor evaluation result includes a written evaluation, such as, for example, words written in sentence or note form that explain what was observed by the practitioner. In some embodiments, the fine motor result is included in an assessment that evaluates at least each of the tests administered during the fourth part of the method. One embodiment of the assessment is shown in FIGS. 34A-34M.

In the sixth part of the method, a second test is administered in which the child has to do a phonemic elision (sound deletion) task to generate a phonemic elision task input data. The ability of the child to do a phonemic elision task may be recorded in the fourth worksheet (FIGS. 32A-32F or FIGS. 33A-33E). The phonemic elision input data is evaluated against an answer key to generate a phonemic elision evaluation result. The phonemic elision evaluation result is another determination with respect to the presence or absence of phonemic elision deficiency, after the determination with respect the presence or absence of phonemic elision deficiency conducted during the fifth part of the method. In some embodiments, the phonemic elision evaluation result includes a score, such as, for example, a number score. In some embodiments, the phonemic elision evaluation result includes a written evaluation, such as, for example, words written in sentence or note form that explain what was observed by the practitioner. In some embodiments, the phonemic elision evaluation result is included in the assessment (FIGS. 34A-34M). In some embodiments, the phonemic elision evaluation result uses AI or other software to recognize and/or transcribe the child's letter sound/word pronunciation, analyze context/structure where pronunciation varies due to accents/dialects and word/sentence structure comprehension and fluency.

In the sixth part of the method, a third test is administered in which the child has to read single words, such as, for example, sight words to generate a sight word reading input data. The ability of the child to do a sight word task may be recorded in the third worksheet (FIGS. 32A-32F or FIGS. 33A-33E). The sight word reading input data is evaluated against an answer key to generate a sight word reading evaluation result. The sight word reading evaluation result is a determination with respect to the presence or absence of sight word reading deficiency conducted during the sixth part of the method. In some embodiments, the sight word reading evaluation result includes a score, such as, for example, a number score. In some embodiments, the sight word reading evaluation result includes a written evaluation, such as, for example, words written in sentence or note form that explain what was observed by the practitioner. In some embodiments, the sight word reading evaluation result is included in the assessment (FIGS. 34A-34M). In some embodiments, the sight word reading evaluation result uses AI or other software to recognize and/or transcribe the child's letter sound/word pronunciation, analyze context/structure where pronunciation varies due to accents/dialects and word/sentence structure comprehension and fluency.

In one embodiment of the sixth part of the method, a fourth test is administered in which the child has to do a nonsense words exercise that compares nonsense words with real words to generate a nonsense word skill input data. The ability of the child to do a nonsense word skill may be recorded in the fifth worksheet (FIGS. 32A-32F or FIGS. 33A-33E). The nonsense word skill input data is evaluated against an answer key to generate a nonsense word skill evaluation result. The nonsense word skill evaluation result is another determination with respect to the presence or absence of nonsense word skills. In some embodiments, the nonsense word skill evaluation result includes a score, such as, for example, a number score. In some embodiments, the nonsense word skill evaluation result includes a written evaluation, such as, for example, words written in sentence or note form that explain what was observed by the practitioner. In some embodiments, the nonsense word skill evaluation result is included in the assessment (FIGS. 34A-34M). In some embodiments, the nonsense word skill evaluation result uses AI or other software to recognize and/or transcribe the child's letter sound/word pronunciation, analyze context/structure where pronunciation varies due to accents/dialects and word/sentence structure comprehension and fluency.

In the sixth part of the method, a referral is generated referring the individual for services in areas where the evaluation results were deficient to promote at least one of the skills tested in the fifth part of the method. In some embodiments, the assessment (FIGS. 34A-34M), which can include one or more of the test results in the sixth part of the method are evaluated to generate the referral. In particular, if the results indicate that the child has proficient fine motor skills, the child is not referred for services, such as, for example, occupational therapy to promote advancement in fine motor skills. If, however, the test results indicate that the child is deficient with his or her fine motor skills, the child is referred for services, such as, for example, occupational therapy to promote advancement in fine motor skills. Likewise, if the results indicate that the child has proficient phonemic elision skills, the child is not referred for services, such as, for example, Speech therapy to promote advancement in phonemic elision skills. If, however, the test results indicate that the child is deficient with his or her phonemic elision skills, the child is referred for services, such as, for example, Speech therapy to promote advancement in phonemic elision skills. If the results indicate that the child has proficient sight word reading skills, the child is not referred for services, such as, for example, speech therapy to promote advancement in sight word reading skills. If, however, the test results indicate that the child is deficient with his or her sight word reading skills, the child is referred for services, such as, for example, Speech therapy to promote advancement in sight word reading skills. Lastly, if the results indicate that the child has proficient nonsense word skills, the child is not referred for services, such as, for example, speech therapy to promote advancement in nonsense word skills. If, however, the test results indicate that the child is deficient with his or her nonsense word skills, the child is referred for services, such as, for example, speech therapy to promote advancement in nonsense word skills.

In some embodiments, the sixth part of the method includes evaluating the child for ADHD, autism, anxiety, panic attacks, post-traumatic stress disorder (PTSD), depression, low self-esteem, etc. if the evaluation results in the sixth part of the method were deficient to promote at least one of the skills tested in the sixth part of the method.

The ADHD evaluation in the sixth part of the method can include giving focused tips on a structured environment, making learning activities fun, multisensory activities, and short but repetitive opportunities for learning. If engagement is appropriate, but focus/attention to a task cannot be maintained for the age expected time for the child's age, then the method may refer the child to take a test that includes ADHD/ADD age specific questions and consider all factors that can affect attention and sustained focus. In some embodiments, if the child exhibits signs of ADHD/ADD, the method can be adapted to administer and score a Vanderbilt screen for parent and teacher (if applicable). These screens are diagnostic of ADHD/ADD. Absence seizure will be ruled out with EEG or another medical device.

Concerning autism, the sixth part of the method includes evaluating whether the child has challenges with social communication and interaction, has poor eye contact, refuses to engage in tasks, and/or lacks joint attention back and forth while doing assessment tasks. For example, if the child demonstrates restrictive/repetitive behaviors, interests, and activities such as, but not limited to, flapping hands, spinning, lining up toys/objects, sensory issues (upset by loud noises/smell/touch), and challenges with change of routine during tasks, the evaluation should include an autism evaluation.

If the autism evaluation of the present method may recommend activities and/or worksheets that are adapted to address the specific concerns of lack of engagement/language delay affecting social interaction, high concerns for Autistic Spectrum Disorder (ASD), or ASD confirmed. This will include activities that focus on strengthening receptive, expressive, and pragmatic language skills; specific games and activities addressing language goals. To improve sensory regulation, the autism evaluation of the present method may recommend specific games and activities to decrease sensory triggers whether they be hypo (low) or hyper (high) sensory. To address sensory seeking behaviors and/or sensory avoidance behaviors, the autism evaluation may include recommending Occupational Therapy (OT) like play activities with OT therapy goals addressing visual/motor integration, sensory regulation, visual perceptual skills, executive function, and primitive reflex integration.

The system and method of the present disclosure can be used to treat and strengthen skills along with in-person therapy especially when waiting for in-person therapy. The system and method of the present disclosure can recommend starting therapeutic advancement of identified skill deficits while at home when awaiting in-person therapies. Such therapeutic advancement can be used to augment and reinforce the actual future or current therapies in place like medically delivered Speech and Language Therapy, OT, Cognitive Behavioral Therapy, and PT. The system and method of the present disclosure can include engagement modules and/or worksheets that allow Early Intervention to immediately start while a child waits for in-person evaluation and/or in-person autism specific therapy. The system and method of the present disclosure can improve skills and reassessment will allow progress. Children should continue using the system and method of the present disclosure even after starting in-person therapy. Referral pursuant to the autism evaluation can include referring the child for an in-person Speech and Language Evaluation, referring the child for an in-person Sensory Integration Focused Occupational Therapy Evaluation, referring the child for an in-person Diagnostic Evaluation for Autism, referring the child for in-person Child Play Therapy.

Concerning anxiety, panic attacks, or PTSD, if the child is showing emotions of frustration with or without crying and/or demonstrating worry about their performance while completing the assessment, has an elevated heart rate and/or blood pressure and/or avoids behaviors when tasks are hard such as: complaining to end or get out of a task like, having headaches, having nausea, stomach aches, vomiting, having tiredness, yawning, falling asleep, having a tense posture, clenched shoulders or muscles, clenched teeth, pulling on eyelashes, biting fingers or fingernails, arguing, throwing the materials, leaving the test environment, saying they are thirsty, hungry, tired, sleepy, or having to all of a sudden got to go to the bathroom, complains of their heart racing, goes selectively mute or is unable to attempt to complete the tests in part or at all, the evaluation should include an anxiety, panic attack, or PTSD evaluation.

The system and method of the present disclosure may be configured to determine through an anxiety algorithm module and/or caregiver/teacher or authorized personnel to start Anxiety modules as well to start arranged telemedicine visits through the system and method of the present disclosure and/or in-person therapy. Also, the Caregiver/teacher will work on language development, social interaction, and sensory regulation by using a 9+ Year Old Developmental Milestone Information Sheet (DMIS) of the system and method of the present disclosure for age-appropriate activities. One example of a 9+ Year Old Developmental Milestone Information Sheet is shown in FIGS. 34A-34F. The system and method of the present disclosure may be configured to administer and score a diagnostic screen such as PHQ-9/SCARED/Columbia/Hamilton/GAD-7 for Anxiety that is appropriate for age. Based on the system and method of the present disclosure, Children will also be started on telemedicine services through the system and method of the present disclosure for anxiety.

Reasons for indications for medicine management for Anxiety is determined by the system and method of the present disclosure, physician, and input from caregiver/teacher. Pulse, Blood Pressure and EKG will be obtained by digital devices and are medically necessary before starting medication. Telemedicine services for anxiety though the system and method of the present disclosure must also be initiated and continued while the child is on medication for anxiety. All children diagnosed with Anxiety through the system and method of the present disclosure will also be evaluated for ADHD/ADD and/or Autism, if indicated.

Concerning low self-esteem, self-esteem should always be monitored closely in a child as this can lead to depression or other mental health disparities in the future. Low self-esteem can arise from a variety of reasons. The system and method of the present disclosure may include one or more modules that address building self-esteem and confidence in a child. Telemedicine visits will be recommended via the system and method of the present disclosure or a local provider.

In the sixth part of the method, a referral may also be generated referring the individual for services in areas where the evaluation results were sufficient to improve the child's skills, even though the child's skills are proficient for his or her age. For example, if the child demonstrates that he or she is able to demonstrate social communication, interaction, eye contact and able to demonstrate joint attention back and forth with assessment tasks, it may be indicative that the child's skills are not deficient, and the child needs to only to continue to build and/or improve his or her skills. Further, not showing restrictive and repetition behaviors, such as flapping their hands, spinning a lot, being only interested in lining up toys or objects, having sensory issue such as being upset with loud noises and difficulty with change of routine may also be indicative that the child's skills are not deficient, and the child needs to only to continue to build and/or improve his or her skills. Indeed, if the child is able to maintain attention, is not easily distracted, follows directions, etc. it may also be indicative that the child's skills are not deficient, and the child needs to only continue to build and/or improve his or her skills. Likewise, if the child is able to complete the tests without crying or worrying about how they are doing on the tests, it may also be indicative that the child's skills are not deficient, and the child needs to only to continue to build and/or improve his or her skills.

In some embodiments, the sixth part of the method further includes observing behavioral engagement skills of the child throughout the testing process, such as, for example, during the first test of the sixth part of the method, during the second test of the sixth part of the method, during the third test of the sixth part of the method and/or during the fourth test of the sixth part of the method. In some embodiments, the observations made throughout the testing process of the fifth part of the method can include noting the child's demeanor, such as, for example, observations pertaining to whether the child is cooperative, uncooperative, refuses to interact, completed the tests independently, exhibited poor eye contact, smiled, cried, was tired, would not engage, was shy, was distractible, was anxious, needed redirection for completion, was happy and engaged, was an English language learner, was difficult to motivate, etc. In some embodiments, the observations made throughout the testing process of the sixth part of the method are included in the worksheet (FIGS. 32A-32F or 33A-33E) and/or are used to generate the referral. In some embodiments, information pertaining to the answers provided in the questionnaire of the sixth part of the method (FIG. 31) is included in the worksheet and/or is used to generate the referral.

In some embodiments, one or more of the referrals described above may include an assessment report that refers the child to counseling, for example, based one or more of the evaluation results in a given part of the method. For example, in the first part of the method, the referral in the first part of the method may include an assessment report that assesses fine motor skills, gross motor skills, receptive language skills, sound articulation skills, sound discrimination skills and/or behavior/engagement. One example of an assessment report that can be used in the first step of the method is shown in FIGS. 36A-36B. In the second part of the method, the referral in the second part of the method may include an assessment report that assesses fine motor skills, receptive language skills, sound order awareness skills, sound discrimination skills, letter name and letter sound identification skills, letter identification skills and/or behavior/engagement, and/or social and emotional maturity. One example of an assessment report that can be used in the second step of the method is shown in FIGS. 37A-37B. In the third part of the method, the referral in the third part of the method may include an assessment report that assesses fine motor skills, receptive language skills, phonemic elision (sound deletion) skills, letter name and letter sound identification skills, letter identification skills, rhyming skills, behavior/engagement, and/or social-emotional maturity. One example of an assessment report that can be used in the third step of the method is shown in FIGS. 38A-38C. In the fourth part of the method, the referral in the fourth part of the method may include an assessment report that assesses fine motor skills, receptive language skills, phonemic elision (sound deletion) skills, letter name and letter sound identification skills, letter identification skills, rhyming skills, nonsense word skills, behavior/engagement, and/or social emotional maturity. One example of an assessment report that can be used in the fourth step of the method is shown in FIGS. 39A-39D. In the fifth part of the method, the referral in the fifth part of the method may include an assessment report that assesses fine motor skills, receptive language skills, phonemic elision (sound deletion) skills, letter name and letter sound identification skills, letter identification skills, rhyming skills, nonsense word skills, behavior/engagement and/or social emotional maturity. One example of an assessment report that can be used in the fifth step of the method is shown in FIGS. 40A-40B. In the sixth part of the method, the referral in the sixth part of the method may include an assessment report that assesses fine motor skills, receptive language skills, phonemic elision (sound deletion) skills, letter name and letter sound identification skills, letter identification skills, rhyming skills, nonsense word skills, social emotional maturity and/or behavior/engagement. One example of an assessment report that can be used in the sixth step of the method is shown in FIGS. 41A-41B. The assessments discussed above and shown in FIGS. 36A-41B may be used by a user of the system and method of the present disclosure to submit payments for insurance. For example, the user may use the assessments discussed above and shown in FIGS. 36A-41B to get paid by an insurance company for the tests, evaluations and/or assessments discussed herein.

In some embodiments, the method or methods described above may be executed or carried out by a computing system including a tangible computer-readable storage medium, also described herein as a storage machine, that holds machine-readable instructions executable by a logic machine (i.e. a processor or programmable control device) to provide, implement, perform, and/or enact the above-described methods, processes and/or tasks. When such methods and processes are implemented, the state of the storage machine may be changed to hold different data. For example, the storage machine may include memory devices such as various hard disk drives, CD, or DVD devices. The logic machine may execute machine-readable instructions via one or more physical information and/or logic processing devices. For example, the logic machine may be configured to execute instructions to perform tasks for a computer program. The logic machine may include one or more processors to execute the machine-readable instructions. The computing system may include a display subsystem to display a graphical user interface (GUI), or any visual element of the methods or processes described above. For example, the display subsystem, storage machine, and logic machine may be integrated such that the above method may be executed while visual elements of the disclosed system and/or method are displayed on a display screen for user consumption. The computing system may include an input subsystem that receives user input. The input subsystem may be configured to connect to and receive input from devices such as a mouse, keyboard or gaming controller. For example, a user input may indicate a request that certain task is to be executed by the computing system, such as requesting the computing system to display any of the above-described information or requesting that the user input updates or modifies existing stored information for processing. A communication subsystem may allow the methods described above to be executed or provided over a computer network. For example, the communication subsystem may be configured to enable the computing system to communicate with a plurality of personal computing devices. The communication subsystem may include wired and/or wireless communication devices to facilitate networked communication. The described methods or processes may be executed, provided, or implemented for a user or one or more computing devices via a computer-program product such as via an application programming interface (API).

In connection with the automated and/or computer-enabled versions of the methods discussed herein, in some embodiments, the evaluations conducted in relation to the tests administered during the first, second, third, fourth, fifth and/or sixths parts of the method may be recorded in worksheets, such as, for example, the worksheets shown in FIGS. 3, 4, 11A-D, 12A-D, 22A-I, 23A-J, 27A-E, 28A-E, 32A-F and 33A-F, as discussed above. Information on the worksheets may be input into an electronic device (logic machine) that includes a processor configured to operate AI software. The information that is input from the worksheets into the AI software may be utilized by the AI software to evaluate the information that is input from the worksheets against information captured by the AI software, such as, for example, an answer key. For example, in the first part of the method, the fine motor skill input data may be evaluated by the AI software against an answer key to generate the fine motor skill evaluation result. The fine motor skill evaluation result generated by the AI software may be used by the AI software to generate a referral, such as, for example, a referral to an occupational therapist to help the child with his or her fine motor skills. Likewise, in the first part of the method, the gross motor skill input data may be evaluated by the AI software against an answer key to generate the gross motor skill evaluation result. The gross motor skill evaluation result generated by the AI software may be used by the AI software to generate a referral, such as, for example, a referral to an occupational therapist to help the child with his or her gross motor skills. It is envisioned that the AI software can likewise be used to evaluate sound articulation input data, generate sound articulation evaluation results and provide a referral based on the sound articulation evaluation results; to evaluate sound discrimination input data, generate sound discrimination evaluation results and provide a referral based on the sound discrimination evaluation results; to evaluate receptive language input data, generate receptive language evaluation results and provide a referral based on the receptive language evaluation results; to evaluate sound order awareness input data, generate sound order awareness evaluation results and provide a referral based on the sound order awareness evaluation results; to evaluate letter naming and sound input data, generate letter naming and sound evaluation results and provide a referral based on the letter naming and sound evaluation results; to evaluate sound deletion input data, generate sound deletion results and provide a referral based on the sound deletion evaluation results; to evaluate rhyming input data, generate rhyming results and provide a referral based on the rhyming evaluation results; and to evaluate nonsense words input data, generate nonsense words evaluation results and provide a referral based on the nonsense words evaluation results.

The data used by the AI software to evaluate various input data can come from various sources. In some embodiments, the data used by the AI software to evaluate various input data can come from internet sources. data used by the AI software to evaluate various input data can be limited to what is found on a local area network that is owned and operated by the administrators of the disclosed method, for example. In some embodiments, data used by the AI software to evaluate various input data can come from any source, including, for example, a combination of internet and local area resources.

A portion of the disclosure of this patent document contains material which is subject to (copyright or mask work) protection. The (copyright or mask work) owner has no objection to the facsimile reproduction by anyone of the patent document or the patent disclosure, as it appears in the Patent and Trademark Office patent file or records, but otherwise reserves all (copyright or mask work) rights whatsoever.

It will be understood that various modifications may be made to the embodiments disclosed herein. For example, features of any one embodiment can be combined with features of any other embodiment. Therefore, the above description should not be construed as limiting, but merely as exemplification of the various embodiments. Those skilled in the art will envision other modifications within the scope and spirit of the claims appended hereto.

What is claimed is:

1. A computer-implemented method for monitoring neurodevelopment of an individual, the method comprising: executing a processor to perform the steps of:

(a) causing the processor to instruct an individual to perform speech, language, fine and gross motor skills tasks in a testing process, (b) for a particular task of the tasks, (i) instructing the individual to grip a writing tool to form a grip position to draw a line or shape to generate a fine motor skill input data and store the fine motor skill input data for processing; (ii) instructing the individual to do a gross motor skill and receptive language task to generate a gross motor skill input data and store the gross motor skill input data for processing; (iii) instructing the individual to identify a particular letter and/or say a particular sound in at least one real or nonsense word to generate a sound articulation or a sound deletion input data and store sound articulation input data for processing; and (iv) instructing the individual to determine if one or more sounds individually or in specific combination, letters, or words are the same or different to generate a sound discrimination input data and store sound discrimination input data for processing, (c) communicating with the individual to adjust the grip, recording the grip position into the fine motor skill input data onto a worksheet in the computer, simultaneously recording the gross motor skill receptive language task into the gross motor skill input data, the said letter sound into the sound articulation input data, and the sound discrimination input data onto the worksheet, (d) using the stored input data of the particular task from (b) in the computer to simultaneously evaluating evaluate the worksheet for, the individual's fine motor skill task, the gross motor skill task, sound articulation and sound discrimination to generate a score assessment for each task in 15 minutes, (e) using the score assessment to determine of a proposed treatment protocol for the respective fine motor skill, gross motor skill, sound articulation and sound discrimination, (f) automatically generating a referral, by the computer sending the proposed treatment protocol for the individual to receive comprehensive services to promote at least one of fine motor skills, gross motor skills, sound articulation, and sound discrimination skills, and (g) delivering the referral to the individual or a caregiver of the individual.

2. The method recited in claim 1, further comprising observing behavioral engagement skills of the individual throughout the testing process.

3. The method recited in claim 1, wherein having the individual say specific sounds based upon the particular letter in at least one word to generate the sound articulation input data includes performing a receptive language assessment for the individual.

4. The method recited in claim 1, wherein promoting at least one of fine motor skills, gross motor skills, receptive language, sound articulation, and sound discrimination skills includes performing speech therapy and/or occupational therapy for the individual.

5. The method recited in claim 4, wherein the speech therapy and/or occupational therapy is in-person occupational therapy.

6. The method recited in claim 1, wherein promoting at least one of fine motor skills, gross motor skills, receptive language, sound articulation, and sound discrimination skills includes performing occupational therapy and in-person speech and language therapy for the individual.

7. The method recited in claim 1, wherein promoting at least one of fine motor skills, gross motor skills, receptive language, sound articulation, and sound discrimination skills includes performing speech and language therapy for the individual.

8. The method recited in claim 1, wherein generating the referral includes performing one or more of the assessments selected from the group consisting of an anxiety assessment, an attention deficit/hyperactivity disorder (ADHD) assessment, an autism assessment, and a dyslexia assessment.

9. The method recited in claim 1, wherein the services are conducted using artificial intelligence (AI), pre-recorded programs on-line and/or administered in-person.

10. The method recited in claim 1, wherein the worksheet includes a questionnaire concerning skills of the individual.

* * * * *